(12) United States Patent
Hermann et al.

(10) Patent No.: US 12,024,570 B2
(45) Date of Patent: *Jul. 2, 2024

(54) ANTI-CTLA-4 ANTIBODIES AND USES THEREOF

(71) Applicant: Regeneron Pharmaceuticals, Inc., Tarrytown, NY (US)

(72) Inventors: Aynur Hermann, Jersey City, NJ (US); Ella Ioffe, Bronx, NY (US); Elena Burova, Mount Kisco, NY (US); Gavin Thurston, Briarcliff Manor, NY (US); William Olson, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 280 days.

This patent is subject to a terminal disclaimer.

(21) Appl. No.: 17/070,129

(22) Filed: Oct. 14, 2020

(65) Prior Publication Data

US 2021/0040232 A1 Feb. 11, 2021

Related U.S. Application Data

(63) Continuation of application No. 16/046,551, filed on Jul. 26, 2018, now Pat. No. 10,844,137.

(60) Provisional application No. 62/685,599, filed on Jun. 15, 2018, provisional application No. 62/645,284, filed on Mar. 20, 2018, provisional application No. 62/588,853, filed on Nov. 20, 2017, provisional application No. 62/537,753, filed on Jul. 27, 2017.

(51) Int. Cl.
| | | |
|---|---|---|
| *C07K 16/40* | (2006.01) | |
| *A61K 39/00* | (2006.01) | |
| *A61K 39/395* | (2006.01) | |
| *A61P 35/00* | (2006.01) | |
| *C07K 16/28* | (2006.01) | |
| *C12N 15/62* | (2006.01) | |

(52) U.S. Cl.
CPC ............ *C07K 16/40* (2013.01); *A61K 39/395* (2013.01); *A61P 35/00* (2018.01); *C07K 16/2818* (2013.01); *C12N 15/62* (2013.01); *A61K 2039/507* (2013.01); *A61K 2039/545* (2013.01); *A61K 2300/00* (2013.01); *C07K 16/2809* (2013.01); *C07K 16/2863* (2013.01); *C07K 16/2887* (2013.01); *C07K 2317/21* (2013.01); *C07K 2317/33* (2013.01); *C07K 2317/76* (2013.01); *C07K 2317/92* (2013.01)

(58) Field of Classification Search
None
See application file for complete search history.

(56) References Cited

U.S. PATENT DOCUMENTS 10,844,137 B2 * 11/2020 Hermann ............... C12N 15/62

FOREIGN PATENT DOCUMENTS

| WO | 09/100140 A1 | 8/2009 |
|---|---|---|
| WO | 2012/120125 A1 | 9/2012 |
| WO | 16/130986 A1 | 8/2016 |
| WO | 16/196237 A1 | 12/2016 |
| WO | 17/084078 A1 | 5/2017 |
| WO | 2018/107178 A1 | 6/2018 |

OTHER PUBLICATIONS

U.S. Appl. No. 62/537,753, filed Jul. 27, 2017, Expired.
U.S. Appl. No. 62/588,853, filed Nov. 20, 2017, Expired.
U.S. Appl. No. 62/645,284, filed Mar. 20, 2018, Expired.
U.S. Appl. No. 62/685,599, filed Jun. 15, 2018, Expired.
PCT/US2018/043936, Jul. 26, 2018, WO2019/023482, Expired.
U.S. Appl. No. 16/046,551, filed Jul. 26, 2018, U.S. Pat. No. 10,844,137, Issued.
Burova et al., "Abstract 3824: Antitumor activity of REGN4659, a fully human anti-CTLA-4 monoclonal antibody, against MC38.Ova tumors grown in immunocompetent human CTLA-4 knock-in mice," Cancer Research, Apr. 14, 2018, CP055511537. DOI: 10.1158/1538-7445.AM2018-3824.
Goel et al., "Plasiticty within the Antigen-Combining Site May Manifet as Molecular Mimicry in the Humoral Immune Response," The Journal of Immunology, Inflammasome Reporter Cells; vol. 173: 7358-7367, (2004). [http://www.jimmunol.org/content/173/12/7358].
Hodi et al., "Improved Survival with Ipilimumab in Patients with Metastic Melanoma," New England Journal of Medicine, vol. 363 (No. 8):711-723, (Aug. 19, 2010), XP055015428, DOI: 10.1056/NEJMoa1003466.
Khan et al., "Adjustable Locks and Flexible Keys: Plasticity of Epitope-Paratope Interactions in Germline Antibodies," The Journal of Immunology, vol. 192: 5398-5405 (2014). [http://www.jimmunol.org/content/192/11/5398].
Kirkwood et al., "Phase II Trial of Tremelimumab (CP-675,206) in Patients with Advanced Refractory or Relapsed Melanoma," Clinical Cancer Research, vol. 16 (No. 3): 1042-1048, (Feb. 1, 2010), XP055015424, DOI: 10.1158/1078-0432.CCR-09-2033.
Larkin et al., "Combined Nivolumab and Ipilimumab or Monotherapy in Untreated Melanoma," The New England Journal of Medicine, NEJM, vol. 373 (No. 1):23-34, (Jul. 2, 2015), XP055316141, ISSN: 0028-4793, DOI: 10.1056/NEJMoa1504030.

(Continued)

*Primary Examiner* — Nora M Rooney
(74) *Attorney, Agent, or Firm* — Schwabe, Williamson & Wyatt PC; Aparna Patankar

(57) ABSTRACT

The present invention provides antibodies that bind to cytotoxic T-lymphocyte-associated protein 4 (CTLA-4), and methods of use. In various embodiments of the invention, the antibodies are fully human antibodies that specifically bind to CTLA-4. In some embodiments, the antibodies of the invention are useful for inhibiting or neutralizing CTLA-4 activity, thus providing a means of activating T-cells and/or for treating a disease or disorder such as cancer or viral infection.

21 Claims, 14 Drawing Sheets

Specification includes a Sequence Listing.

(56) References Cited

OTHER PUBLICATIONS

MacCallum et al., "Antibody-antigen Interactions: Contact Analysis and Binding Site Topography," JMB, vol. 262: 732-745 (1996).

Mariuzza et al., "The Structural Basis of Antigen-Antibody Recognition," Ann, Rev. Biophys. Volume 16: 139-159, (1987).

Pascalis et al., "Grafting of "Abbreviated" Complementarity-Determining Regions Containing Specificity-Determining Residues Essential for Ligand Contact to Engineer a Less Immunogenic Humanized Monoclonal Antibody," The Journal of Immunology; 3076-3084 (2002).

Poosarla et al., "Computational De Novo Design of Antibodies Binding to a Peptide With High Affinity," Biotechnology and Bioengineering; vol. 114 No. 6: 1331-1342 (Jun. 2017).

Ribas et al., "Tremelimumab (CP-675,206), a Cytotoxic T Lymphocyte-Associated Antigen 4 Blocking Monoclonal Antibody in Clinical Development for Patients with Cancer," The Oncologist, vol. 12:873-883, (2007); www.TheOncologist.com.

Unt et al., "CTLA-4 Antibodies: New Directions, New Combinations CTLA-4 Antibodies: New Directions, New Combinations," Oncology, vol. 28 (No. 3):1-14, (Nov. 10, 2014), XP055322502.

U.S. Appl. No. 16/046,551, Non-Final Office Action dated Oct. 1, 2019.

U.S. Appl. No. 16/046,551, Notice of Allowance dated Jul. 15, 2020.

WIPO Application No. PCT/US2018/043936, PCT International Search Report and Written Opinion of the International Searching Authority dated Oct. 17, 2018.

\* cited by examiner

ANTI-CTLA-4 ANTIBODIES AND USES THEREOF

CROSS-REFERENCE TO RELATED APPLICATIONS

This application is a continuation of U.S. application Ser. No. 16/046,551, filed Jul. 26, 2018, which claims the benefit under 35 USC § 119(e) of US Provisional Application Nos.: 62/537,753, filed Jul. 27, 2017; 62/588,853, filed Nov. 20, 2017; 62/645,284, filed Mar. 20, 2018; and 62/685,599, filed Jun. 15, 2018. Each of these applications is incorporated herein by reference in its entirety for all purposes.

SEQUENCE LISTING

This application incorporates by reference the Sequence Listing submitted in Computer Readable Form as file 10360US02-Sequence.txt, created on Oct. 14, 2020 and containing 178,058 bytes.

FIELD OF THE INVENTION

The present invention is related to antibodies and antigen-binding fragments of antibodies that specifically bind to the immunomodulatory receptor cytotoxic T-lymphocyte-associated protein 4 (CTLA-4), and therapeutic and diagnostic methods of using those antibodies.

BACKGROUND OF THE INVENTION

Cytotoxic T-lymphocyte-associated protein 4 (CTLA-4; also known as CD152) is a type I transmembrane T cell inhibitory checkpoint receptor expressed on conventional and regulatory T cells. CTLA-4 negatively regulates T cell activation by outcompeting the stimulatory receptor CD28 from binding to its natural ligands, B7-1 (CD80) and B7-2 (CD86). Initial T-cell activation is achieved by stimulating T-cell receptors (TCR) that recognize specific peptides presented by major histocompatibility complex class I or II (MHCI or MHCII) proteins on antigen-presenting cells (APC) (Goldrath et al. 1999, Nature 402: 255-262). An activated TCR in turn initiates a cascade of signaling events, which can be monitored by expression of transfected reporter genes, driven by promoters regulating the expression of various transcription factors such as activator-protein 1 (AP-1), Nuclear Factor of Activated T-cells (NFAT) or Nuclear factor kappa-light-chain-enhancer of activated B cells (NFκB). The T-cell response is then further refined via engagement of co-stimulatory or co-inhibitory receptors expressed either constitutively or inducibly on T-cells such as CD28, CTLA-4 (Cytotoxic T-Lymphocyte-Associated Protein 4), PD-1 (Programmed Cell Death Protein 1), LAG-3 (Lymphocyte-Activation Gene 3) or other molecules (Sharpe et al. 2002, Nat. Rev. Immunol. 2: 116-126).

The co-receptors, CD28 and CTLA-4 compete for the same ligands, CD80 and CD86, expressed on antigen-presenting cells (APC). CTLA-4 binds CD80 and CD86 with a higher affinity than CD28, functions as a decoy and inhibits the activation of CD28 by sequestering away the ligands leading to reduced T-cell activation (Alegre et al. 2001, Nat. Rev. Immunol. 1: 220-228, Walker et al. 2011, Nat. Rev. Immunol. 11: 852-863, and Buchbinder et al., 2016, American Journal of Clinical Oncology, 39:98-106).

BRIEF SUMMARY OF THE INVENTION

The present invention provides antibodies and antigen-binding fragments thereof that bind CTLA-4. The antibodies of the present invention are useful, inter alia, for targeting immune cells expressing CTLA-4, and for modulating CTLA-4 activity. In certain embodiments, the antibodies of the invention are useful for inhibiting or neutralizing CTLA-4 activity and/or for stimulating T cell activation, e.g., under circumstances where T cell-mediated killing is beneficial or desirable. In certain embodiments, the antibodies are useful for inhibiting regulatory T cell function and/or for reactivating exhausted T cells. The anti-CTLA-4 antibodies of the invention, or antigen-binding portions thereof, may be included as part of a multi-specific antigen-binding molecule, for example, to modulate the immune response and/or to target the antibodies to a specific cell type, such as a tumor cell, or an infected cell. The antibodies are useful in treating a disease or disorder such as cancer and viral infection.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, J. Immunol. 164:1925-1933). In certain embodiments, the antibodies may be bispecific.

In a first aspect, the present invention provides isolated recombinant monoclonal antibodies or antigen-binding fragments thereof that bind specifically to CTLA-4. In certain embodiments, the antibodies are fully human.

Exemplary anti-CTLA-4 antibodies of the present invention are listed in Tables 1 and 2 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-CTLA-4 antibodies. Table 2 sets forth the nucleic acid sequence identifiers of the HCVRs, LCVRs, HCDR1, HCDR2 HCDR3, LCDR1, LCDR2 and LCDR3 of the exemplary anti-CTLA-4 antibodies.

The present invention provides antibodies, or antigen-binding fragments thereof, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-CTLA-4 antibodies listed in Table 1. In certain embodiments, the HCVR/LCVR amino acid sequence pair is selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/298, 314/322, 330/338, 346/354, 362/370, 378/386, 394/402, 410/418, 426/434, 442/450, 458/466, 474/482, and 490/498. In certain embodiments, the HCVR/LCVR amino acid sequence pair is selected from one of SEQ ID NOs: 194/202 (e.g., H1H19303P), or 290/298 (e.g., H1H19319P2). In certain embodiments, the present invention provides anti-CTLA-4 antibodies or antigen-binding fragments thereof comprising a HCVR and a LCVR, said HCVR comprising an amino acid sequence listed in Table 1 having up to ten amino acid substitutions, and said LCVR comprising an amino acid sequence listed in Table 1 having up to ten amino acid substitutions. For example, the present invention provides anti-CTLA-4 antibodies or antigen-binding fragments thereof comprising a HCVR and a LCVR, said HCVR comprising an amino acid sequence of SEQ ID NO: 194 having up to ten amino acid substitutions, and said LCVR comprising an amino acid sequence of SEQ ID NO: 202 having up to ten amino acid substitutions. In another exemplary embodiment, the present invention provides anti-CTLA-4 antibodies or antigen-binding fragments thereof comprising a HCVR and a LCVR, said HCVR comprising an amino acid sequence of SEQ ID NO: 194 having at least one amino acid substitution, and said LCVR comprising an amino acid sequence of SEQ ID NO: 202 having at least one amino acid substitution.

The present invention also provides antibodies, or antigen-binding fragments thereof, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-CTLA-4 antibodies listed in Table 1. In certain embodiments, the HCDR3/LCDR3 amino acid sequence pair is selected from the group consisting of SEQ ID NOs: 200/208 (e.g., H1H19303P), and 296/304 (e.g., H1H19319P2).

The present invention also provides antibodies, or antigen-binding fragments thereof, comprising a HCVR and a LCVR, said HCVR comprising HCDR1 comprising an amino acid sequence differing from an amino acid sequence listed in Table 1 by 1 amino acid, HCDR2 comprising an amino acid sequence differing from an amino acid sequence listed in Table 1 by 1 amino acid, and HCDR3 comprising an amino acid sequence differing from an amino acid sequence listed in Table 1 by 1 amino acid. In certain embodiments, the present invention provides antibodies, or antigen-binding fragments thereof, comprising a HCVR and a LCVR, said LCVR comprising LCDR1 comprising an amino acid sequence differing from an amino acid sequence listed in Table 1 by 1 amino acid, LCDR2 comprising an amino acid sequence differing from an amino acid sequence listed in Table 1 by 1 amino acid, and LCDR3 comprising an amino acid sequence differing from an amino acid sequence listed in Table 1 by 1 amino acid. For example, the present invention provides anti-CTLA-4 antibodies, or antigen-binding fragments thereof, comprising a HCVR and a LCVR, said HCVR comprising HCDR1 comprising an amino acid sequence of SEQ ID NO: 196 or an amino acid sequence differing from SEQ ID NO: 196 by 1 amino acid, HCDR2 comprising an amino acid sequence of SEQ ID NO: 198 or an amino acid sequence differing from SEQ ID NO: 198 by 1 amino acid, and HCDR3 comprising an amino acid sequence of SEQ ID NO: 200 or an amino acid sequence differing from SEQ ID NO: 200 by 1 amino acid. In another exemplary embodiment, the present invention provides antibodies, or antigen-binding fragments thereof, comprising a HCVR and a LCVR, said LCVR comprising LCDR1 comprising an amino acid sequence of SEQ ID NO: 204 or an amino acid sequence differing from SEQ ID NO: 204 by 1 amino acid, LCDR2 comprising an amino acid sequence of SEQ ID NO: 206 or an amino acid sequence differing from SEQ ID NO: 206 by 1 amino acid, and LCDR3 comprising an amino acid sequence of SEQ ID NO: 208 or an amino acid sequence differing from SEQ ID NO: 208 by 1 amino acid.

The present invention also provides antibodies, or antigen-binding fragments thereof, comprising a set of six CDRs HCDR1-HCDR2-HCDR3-LCDR1-LCDR2-LCDR3) contained within any of the exemplary anti-CTLA-4 antibodies listed in Table 1. In certain embodiments, the HCDR1-HCDR2-HCDR3-LCDR1-LCDR2-LCDR3 amino acid sequence set is selected from the group consisting of SEQ ID NOs: 196-198-200-204-206-208 (e.g., H1H19303P), and 292-294-296-300-302-304 (e.g., H1H19319P2).

In a related embodiment, the present invention provides antibodies, or antigen-binding fragments thereof, comprising a set of six CDRs HCDR1-HCDR2-HCDR3-LCDR1-LCDR2-LCDR3) contained within an HCVR/LCVR amino acid sequence pair as defined by any of the exemplary anti-CTLA-4 antibodies listed in Table 1. For example, the present invention includes antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 194/202 (e.g., H1H19303P), and 290/298 (e.g., H1H19319P2). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention includes anti-CTLA-4 antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

The present invention includes anti-CTLA-4 antibodies comprising a Fc domain, wherein the Fc domain comprises IgG1 or IgG4 isotype as described elsewhere herein.

The present invention also provides for antibodies and antigen-binding fragments thereof that compete for specific binding to CTLA-4 with an antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

The present invention also provides isolated antibodies and antigen-binding fragments thereof that block CTLA-4 binding to its natural ligands (B7-1/CD80 and B7-2/CD86) In some embodiments, the antibody or antigen-binding fragment thereof that blocks CTLA-4 binding may bind to the same epitope on CTLA-4 as B7-1/CD80 and/or B7-2/CD86 or may bind to a different epitope on CTLA-4 from B7-1/CD80 and/or B7-2/CD86.

The present invention also provides antibodies and antigen-binding fragments thereof that bind specifically to CTLA-4 from human or other species. In certain embodiments, the antibodies may bind to human CTLA-4 and/or to monkey CTLA-4.

The present invention also provides antibodies and antigen-binding fragments thereof that cross-compete for binding to CTLA-4 with a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

The present invention also provides antibodies and antigen-binding fragments thereof that bind to the same epitope as a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1. In certain embodiments, the present invention provides antibodies and antigen-binding fragments thereof that bind to the same epitope as a reference antibody or antigen-binding fragment thereof comprising the CDRs of a HCVR and the CDRs of a LCVR, wherein the HCVR/LCVR amino acid sequence pair has SEQ ID NOs: 194/202.

The present invention also includes anti-CTLA-4 antibodies that interact with one or more amino acids contained within the extracellular domain of human CTLA-4.

In one embodiment, the invention provides a recombinant human monoclonal antibody or antigen-binding fragment that has one or more of the following characteristics: (a) binds specifically to human CTLA-4 and/or cynomolgus CTLA-4; (b) blocks the binding of CTLA-4 to CD80 and/or CD86; (c) blocks CTLA-4-induced T cell down regulation and rescues T cell signaling; and (d) suppresses tumor growth and increases survival in a subject with cancer.

In some embodiments, the antibody or antigen binding fragment thereof may bind specifically to CTLA-4 in an agonist manner, i.e., it may enhance or stimulate CTLA-4 binding and/or activity; in other embodiments, the antibody may bind specifically to CTLA-4 in an antagonist manner, i.e., it may block CTLA-4 from binding to its ligand(s).

In certain embodiments, the antibodies or antigen-binding fragments of the present invention are bispecific comprising a first binding specificity to CTLA-4 and a second binding specificity for a second target epitope. The second target epitope may be another epitope on CTLA-4 or on a different protein. In certain embodiments, the second target epitope may be on a different cell including a different T cell, a B-cell, a tumor cell or a virally infected cell.

In a second aspect, the present invention provides nucleic acid molecules encoding anti-CTLA-4 antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-CTLA-4 antibodies listed in Table 1.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-CTLA-4 antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-CTLA-4 antibody listed in Table 1.

In a related aspect, the present invention provides recombinant expression vectors capable of expressing a polypeptide comprising a heavy or light chain variable region of an anti-CTLA-4 antibody. For example, the present invention includes recombinant expression vectors comprising any of the nucleic acid molecules mentioned above, i.e., nucleic acid molecules encoding any of the HCVR, LCVR, and/or CDR sequences as set forth in Table 1. The present invention also provides recombinant expression vectors capable of expressing a polypeptide comprising a heavy or light chain of an anti-CTLA-4 antibody. For example, the present invention includes recombinant expression vectors comprising any of the nucleic acid molecules mentioned above, i.e., nucleic acid molecules encoding any of the heavy chain or light chain sequences as set forth in Table 1. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

In a third aspect, the present invention provides a pharmaceutical composition comprising a recombinant human antibody or fragment thereof which specifically binds CTLA-4 and a pharmaceutically acceptable carrier. In a related aspect, the invention features a composition which is a combination of an anti-CTLA-4 antibody and a second therapeutic agent. In one embodiment, the second therapeutic agent is any agent that is advantageously combined with an anti-CTLA-4 antibody. Exemplary agents that may be advantageously combined with an anti-CTLA-4 antibody include, without limitation, other agents that bind and/or modulate CTLA-4 signaling (including other antibodies or antigen-binding fragments thereof, etc.) and/or agents which do not directly bind CTLA-4 but nonetheless modulate immune cell activation. Additional combination therapies and co-formulations involving the anti-CTLA-4 antibodies of the present invention are disclosed elsewhere herein.

In a fourth aspect, the invention provides methods to modulate the immune response in a subject, the method comprising administering a therapeutically effective amount of an anti-CTLA-4 antibody or antigen-binding fragment thereof of the invention to the subject in need thereof. In certain embodiments, the invention provides methods to enhance the immune response in a subject, the methods comprising administering to the subject an effective amount of an antibody or fragment thereof of the invention that binds CTLA-4. In one embodiment, the invention provides a method to stimulate or enhance T cell activation in a subject. In certain embodiments, the invention provides methods to rescue T cell activity comprising contacting the T cell with an effective amount of an antibody of the invention such that T cell activity is rescued. In one embodiment, the invention provides methods to inhibit a T regulatory (Treg) cell in a subject, the methods comprising administering a therapeutically effective amount of an antibody or antigen-binding fragment thereof of the invention to the subject in need thereof. In certain embodiments, the subject in need thereof may suffer from a disease or disorder such as cancer or viral infection. In certain embodiments, the present invention provides methods to rescue CTLA-4-mediated inhibition of T cell activity comprising contacting the T cell with an effective amount of an antibody of the present invention.

In a fifth aspect, the invention provides therapeutic methods for treating a disease or disorder such as cancer or viral infection in a subject using an anti-CTLA-4 antibody or antigen-binding portion of an antibody of the invention, wherein the therapeutic methods comprise administering a therapeutically effective amount of a pharmaceutical composition comprising an antibody or fragment of an antibody of the invention to the subject in need thereof. The disorder treated is any disease or condition which is improved, ameliorated, inhibited or prevented by stimulation or inhibition of CTLA-4 activity or signaling. In certain embodiments, the antibody or antigen-binding fragment thereof the invention is administered in combination with a second therapeutic agent to the subject in need thereof. The second therapeutic agent may be selected from the group consisting of an antibody to another T cell co-inhibitor, an antibody to a tumor cell antigen, an antibody to a T cell receptor, an antibody to an epitope on a virally infected cell, a cytotoxic agent, an anti-cancer drug, an anti-viral drug, an anti-inflammatory drug (e.g., corticosteroids), chemotherapeutic agent, radiation therapy, surgery, an immunosuppressant and any other drug or therapy known in the art. In certain embodiments, the second therapeutic agent may be an agent that helps to counteract or reduce any possible side effect(s) associated with an antibody or antigen-binding fragment thereof of the invention, if such side effect(s) should occur.

In certain embodiments, the present invention provides methods for suppressing tumor growth. For example, the present invention provides to suppress tumor growth due to a primary tumor or a metastatic tumor in a subject. In certain embodiments, the present invention provides methods to enhance survival (e.g., progression-free survival or overall survival) of a subject with cancer. Examples of cancer include, but are not limited to, primary and/or recurrent cancer, including blood cancer (e.g., a hematologic malignancy such as lymphoma, myeloma or leukemia), brain cancer (e.g., glioblastoma multiforme), lung cancer (e.g., non-small cell lung cancer, including advanced or metastatic NSCLC), squamous cell carcinoma of head and neck, hepatic cell carcinoma, renal cell carcinoma, melanoma, mesothelioma, ovarian cancer, bladder cancer, breast cancer, bone cancer, colorectal cancer, kidney cancer, esophageal cancer, liver cancer, stomach cancer, pancreatic cancer, skin cancer, cervical cancer, intestinal cancer, prostate cancer, and colon cancer. In certain embodiments, the present invention provides methods for inhibiting or suppressing growth of established tumors. The methods comprise administering to a subject in need thereof a pharmaceutical composition comprising a therapeutically effective amount of an anti-CTLA-4 antibody of the present invention. In certain embodiments, the antibody is administered in combination with a second therapeutic agent selected from the group consisting of a programmed death-1 (PD-1) inhibitor (e.g., an anti-PD-1 antibody such as nivolumab, pembrolizumab or REGN2810), a programmed death-ligand 1 (PD-L1) inhibitor (e.g., an anti-PD-L1 antibody such as atezolizumab, avalumab or durvalumab), a vascular endothelial growth factor (VEGF) antagonist (e.g., aflibercept, bevacizumab), an angiopoietin-2 (Ang2) inhibitor (e.g., an anti-Ang2 antibody such as nesvacumab), a lymphocyte-activation gene 3 (LAG3) inhibitor, a CD20×CD3 bispecific antibody (e.g., REGN1979), a cytotoxin, a chemotherapeutic agent, a cancer vaccine, surgery, and radiation therapy. Additional examples of additional therapies/therapeutic agents that can be used in combination with an anti-CTLA-4 antibody of the invention for use in treating cancer are described elsewhere herein.

The antibody or fragment thereof may be administered subcutaneously, intravenously, intradermally, intraperitoneally, orally, intramuscularly, or intracranially. In certain embodiments, the antibody or fragment thereof is administered locally into the tumor (peritumorally or intratumorally). The antibody or fragment thereof may be administered at a dose of about 0.1 mg/kg of body weight to about 100 mg/kg of body weight of the subject. In certain embodiments, the antibody is administered in an amount of from about 50 mg to about 1000 mg to the subject in need thereof. In some embodiments, the antibody is administered at a dose of from about 25 mg to about 600 mg. In some embodiments, the antibody is administered at a dose of from about 50 mg to about 1200 mg.

The present invention also includes use of an anti-CTLA-4 antibody or antigen-binding fragment thereof of the invention in the manufacture of a medicament for the treatment of a disease or disorder that would benefit from the blockade of CTLA-4 binding and/or signaling such as cancer.

The present invention further includes uses of the antibodies and antigen-binding fragments, or pharmaceutical composition comprising same, (i) in the manufacture of a medicament for treating a disease or disorder that is treatable by antagonizing CTLA-4 (e.g., cancer), and/or (ii) in the treatment of a disease or disorder that is treatable by antagonizing CTLA-4 (e.g., cancer).

In another aspect, the present invention provides a method of treating non-small cell lung cancer (including advanced or metastatic NSCLC) in a subject in need thereof, comprising administering to the subject an anti-CTLA-4 antibody and an anti-PD-1 antibody. In some cases, the anti-CTLA-4 antibody comprises the CDRs of a HCVR comprising the amino acid sequence of SEQ ID NO: 194 and the CDRs of a LCVR comprising the amino acid sequence of SEQ ID NO: 202. In some cases, the anti-CTLA-4 antibody comprises HCDR1-HCDR2-HCDR3-LCDR1-LCDR2-LCDR3 domains, respectively, selected from the group consisting of SEQ ID NOs: 196-198-200-204-206-208. In some cases, the anti-CTLA-4 antibody comprises a HCVR comprising the amino acid sequence of SEQ ID NO: 194, and a LCVR comprising the amino acid sequence of SEQ ID NO: 202. In some cases, the anti-CTLA-4 antibody comprises a human IgG1 heavy chain constant region. In some embodiments, the anti-PD-1 antibody is cemiplimab. The present invention also includes use of such antibodies in the manufacture of a medicament or medicaments for the treatment of cancers (e.g., non-small cell lung cancer, including advanced or metastatic NSCLC).

Other embodiments will become apparent from a review of the ensuing detailed description.

BRIEF DESCRIPTION OF THE FIGURES

FIG. 12 shows the average tumor growth curves in each treatment group. FIG. 13 shows individual tumor volumes in each treatment group as measured on day 21, the last time point when all animals in the study were alive.

DETAILED DESCRIPTION

Figure 1:
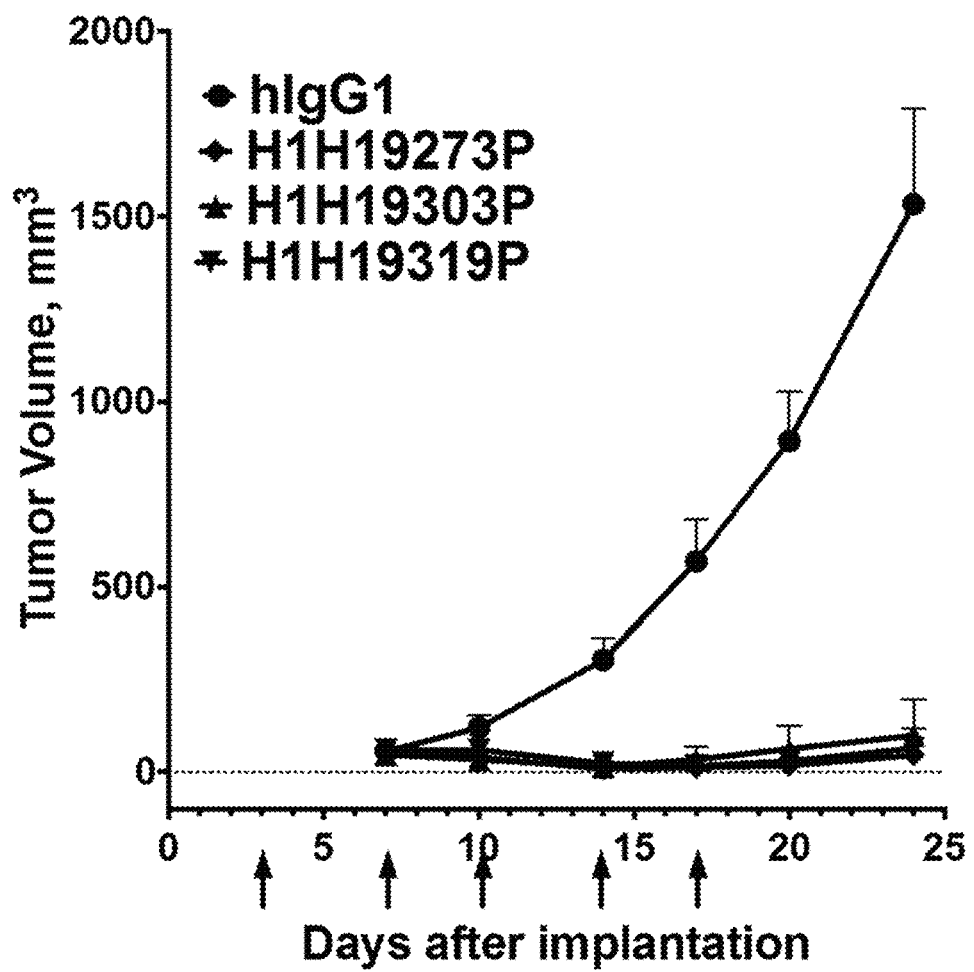
FIG. 1 shows average tumor volumes ($mm^3$+/−SEM) in each treatment group at multiple post-tumor implantation time points for the experiment described in Study (A) in Example 7. CTLA-4$^{hum/hum}$ knock-in mice were implanted SC with MC38.Ova cells ($10^6$ cells/mouse) on day 0 and separated into four treatment groups (9 mice/group). Mice were administered 10 mg/kg of either one of the three lead anti-human CTLA-4 antibodies (H1H19273P, or H1H19303P, or H1H19319) or 10 mg/kg of hIgG1 isotype control intraperitoneally (IP) on days 3, 7, 10, 14 and 17. Tumor volumes were monitored by caliper measurements twice per week for 37 days. Treatment days indicated by arrows.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

The term "CTLA-4" refers to the cytotoxic T-lymphocyte-associated protein 4, an immune checkpoint receptor or T cell co-inhibitor, also known as CD152. The amino acid sequence of full-length human CTLA-4 is provided as SEQ ID NO: 505 (accession number NP_005205.2). The term "CTLA-4" includes recombinant CTLA-4 or a fragment thereof. The term also encompasses CTLA-4 or a fragment thereof coupled to, for example, histidine tag, mouse or human Fc, a signal sequence, or a transmembrane and cytoplasmic domain of CD300a (aa 181-299; accession number NP_009192.2). For example, the term includes sequences discussed in the examples, e.g., comprising a myc-myc-polyhistidine tag at the C-terminus of a full-length CTLA-4, or comprising a mouse Fc (mIgG2a) at the C-terminus of a full-length CTLA-4. Unless specified as being from a non-human species, the term "CTLA-4" means human CTLA-4.

CTLA-4 is a member of the immunoglobulin (Ig) superfamily, and a homolog of CD28, but with greater binding affinity for ligands CD80 and CD86. CTLA-4 is a 223-amino acid type I transmembrane protein containing a V domain, a transmembrane domain, and a cytoplasmic tail that is expressed on activated T cells and regulatory T cells. The CTLA-4 receptor binds to B7-1/CD80 and B7-2/CD86 ligands present on antigen presenting cells (APCs).

As used herein, the term "T cell co-inhibitor" refers to a ligand and/or receptor which modulates the immune response via T cell activation or suppression. The term "T cell co-inhibitor", also known as T cell co-signaling molecule, includes, but is not limited to, programmed death-1 (PD-1), lymphocyte-activation gene 3 (LAG3), B and T lymphocyte attenuator (BTLA), CD-28, 2B4, LY108, T cell immunoglobulin and mucin 3 (TIM3), T cell immunoreceptor with immunoglobulin and ITIM (TIGIT; also known as VSIG9), leucocyte associated immunoglobulin-like receptor 1 (LAIR1; also known as CD305), inducible T cell costimulator (ICOS; also known as CD278), V-domain Ig suppressor of T cell activation (VISTA) and CD160.

The term "antibody", as used herein, is intended to refer to immunoglobulin molecules comprised of four polypeptide chains, two heavy (H) chains and two light (L) chains interconnected by disulfide bonds (i.e., "full antibody molecules"), as well as multimers thereof (e.g. IgM) or antigen-binding fragments thereof. Each heavy chain is comprised of a heavy chain variable region ("HCVR" or "V$_H$") and a heavy chain constant region (comprised of domains C$_H$1, C$_H$2 and C$_H$3). Each light chain is comprised of a light chain variable region ("LCVR or "V$_L$") and a light chain constant region (CO. The V$_H$ and V$_L$ regions can be further subdivided into regions of hypervariability, termed complementarity determining regions (CDR), interspersed with regions that are more conserved, termed framework regions (FR). Each V$_H$ and V$_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human anti-CTLA-4 monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes fully human anti-CTLA-4 monoclonal antibodies comprising variants of any of the HCVR, LCVR, and/or CDR amino acid sequences disclosed herein having one or more conservative substitutions. For example, the present invention includes anti-CTLA-4 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The terms "human antibody" and "fully human antibody," as used herein, are intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the terms "human antibody" and "fully human antibody," as used herein, are not intended to include mAbs in which CDR sequences derived from the germline of another mammalian species (e.g., mouse), have been grafted onto human FR sequences. The terms include antibodies recombinantly produced in a non-human mammal, or in cells of a non-human mammal. The terms are not intended to include antibodies isolated from or generated in a human subject.

The term "recombinant", as used herein, refers to antibodies or antigen-binding fragments thereof of the invention created, expressed, isolated or obtained by technologies or methods known in the art as recombinant DNA technology which include, e.g., DNA splicing and transgenic expression. The term refers to antibodies expressed in a non-human mammal (including transgenic non-human mammals, e.g., transgenic mice), or a cell (e.g., CHO cells) expression system or isolated from a recombinant combinatorial human antibody library.

The term "multi-specific antigen-binding molecules", as used herein refers to bispecific, tri-specific or multi-specific antigen-binding molecules, and antigen-binding fragments thereof. Multi-specific antigen-binding molecules may be specific for different epitopes of one target polypeptide or may contain antigen-binding domains specific for epitopes of more than one target polypeptide. A multi-specific antigen-binding molecule can be a single multifunctional polypeptide, or it can be a multimeric complex of two or more polypeptides that are covalently or non-covalently associated with one another. The term "multi-specific antigen-binding molecules" includes antibodies of the present invention that may be linked to or co-expressed with another functional molecule, e.g., another peptide or protein. For example, an antibody or fragment thereof can be functionally linked (e.g., by chemical coupling, genetic fusion, non-covalent association or otherwise) to one or more other molecular entities, such as a protein or fragment thereof to produce a bi-specific or a multi-specific antigen-binding molecule with a second binding specificity. According to the present invention, the term "multi-specific antigen-binding molecules" also includes bi-specific, tri-specific or multi-specific antibodies or antigen-binding fragments thereof. In certain embodiments, an antibody of the present invention is functionally linked to another antibody or antigen-binding fragment thereof to produce a bispecific antibody with a second binding specificity. Bispecific and multi-specific antibodies of the present invention are described elsewhere herein.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1\times10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to CTLA-4. Moreover, multi-specific antibodies that bind to one domain in CTLA-4 and one or more additional antigens or a bi-specific that binds to two different regions of CTLA-4 are nonetheless considered antibodies that "specifically bind", as used herein.

The term "high affinity" antibody refers to those mAbs having a binding affinity to CTLA-4, expressed as $K_D$, of at least $10^{-8}$ M; preferably $0^{-9}$ M; more preferably $10^{-10}$ M, even more preferably $10^{-11}$ M, even more preferably $10^{-12}$ M, as measured by surface plasmon resonance, e.g., BIACORE™ or solution-affinity ELISA.

By the term "slow off rate", "Koff" or "kd" is meant an antibody that dissociates from CTLA-4, with a rate constant of $1\times10^{-3}$ s$^{-1}$ or less, preferably $1\times10^{-4}$ s$^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to CTLA-4.

In specific embodiments, antibody or antibody fragments of the invention may be conjugated to a moiety such a ligand or a therapeutic moiety ("immunoconjugate"), such as a cytotoxin, a second anti-CTLA-4 antibody, an antibody to a tumor-specific antigen, an anti-cancer drug, or any other therapeutic moiety useful for treating a disease or condition including cancer or viral infection including chronic viral infection.

An "isolated antibody", as used herein, is intended to refer to an antibody that is substantially free of other antibodies (Abs) having different antigenic specificities (e.g., an isolated antibody that specifically binds CTLA-4, or a fragment thereof, is substantially free of Abs that specifically bind antigens other than CTLA-4.

A "blocking antibody" or a "neutralizing antibody", as used herein (or an "antibody that neutralizes CTLA-4 activity" or "antagonist antibody"), is intended to refer to an antibody whose binding to CTLA-4 results in inhibition of at least one biological activity of CTLA-4. For example, an antibody of the invention may prevent or block CTLA-4 binding to CD80 and/or CD86.

An "activating antibody" or an "enhancing antibody", as used herein (or an "agonist antibody"), is intended to refer to an antibody whose binding to CTLA-4 results in increasing or stimulating at least one biological activity of CTLA-4. For example, an antibody of the invention may increase CTLA-4 activity by binding to CTLA-4 in a manner consistent with ligand binding (e.g., CD80 or CD86), resulting in CTLA-4 intracellular signaling.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "cross-competes", as used herein, means an antibody or antigen-binding fragment thereof binds to an antigen and inhibits or blocks the binding of another antibody or antigen-binding fragment thereof. The term also includes competition between two antibodies in both orientations, i.e., a first antibody that binds and blocks binding of second antibody and vice-versa. In certain embodiments, the first antibody and second antibody may bind to the same epitope. Alternatively, the first and second antibodies may bind to different, but overlapping epitopes such that binding of one inhibits or blocks the binding of the second antibody, e.g., via steric hindrance. Cross-competition between antibodies may be measured by methods known in the art, for example, by a real-time, label-free bio-layer interferometry assay. Cross-competition between two antibodies may be expressed as the binding of the second antibody that is less than the background signal due to self-self binding (wherein first and second antibodies is the same antibody). Cross-competition between 2 antibodies may be expressed, for example, as % binding of the second antibody that is less than the baseline self-self background binding (wherein first and second antibodies is the same antibody).

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

Sequence identity can be calculated using an algorithm, for example, the Needleman Wunsch algorithm (Needleman and Wunsch 1970, J. Mol. Biol. 48: 443-453) for global alignment, or the Smith Waterman algorithm (Smith and Waterman 1981, J. Mol. Biol. 147: 195-197) for local alignment. Another preferred algorithm is described by Dufresne et al in Nature Biotechnology in 2002 (vol. 20, pp. 1269-71) and is used in the software GenePAST (GQ Life Sciences, Inc. Boston, MA).

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, preferably a mammal, in need of amelioration, prevention and/or treatment of a disease or disorder such as viral infection, or cancer. The term includes human subjects who have or are at risk of having cancer, metastatic cancer or viral infection.

As used herein, "anti-cancer drug" means any agent useful to treat or ameliorate or inhibit cancer including, but not limited to, cytotoxins and agents such as antimetabolites, alkylating agents, anthracyclines, antibiotics, antimitotic agents, procarbazine, hydroxyurea, asparaginase, corticosteroids, cyclophosphamide, mytotane (O,P'-(DDD)), biologics (e.g., antibodies and interferons) and radioactive agents. As used herein, "a cytotoxin or cytotoxic agent", also refers to a chemotherapeutic agent and means any agent that is detrimental to cells. Examples include Taxol® (paclitaxel), temozolamide, cytochalasin B, gramicidin D, ethidium bromide, emetine, cisplatin, mitomycin, etoposide, tenoposide, vincristine, vinbiastine, coichicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

As used herein, the term "anti-viral drug" refers to any drug or therapy used to treat, prevent, or ameliorate a viral infection in a host subject. The term "anti-viral drug" includes, but is not limited to zidovudine, lamivudine, abacavir, ribavirin, lopinavir, efavirenz, cobicistat, tenofovir, rilpivirine, analgesics and corticosteroids. In the context of the present invention, the viral infections include long-term or chronic infections caused by viruses including, but not limited to, human immunodeficiency virus (HIV), hepatitis B virus (HBV), hepatitis C virus (HCV), human papilloma virus (HPV), lymphocytic choriomeningitis virus (LCMV), and simian immunodeficiency virus (SIV).

As used herein, the term "to enhance immune response", refers to an increase in activity of an immune cell such as T cell or NK cell against a tumor cell or a virally infected cell. In the context of the present invention, the term includes blocking of CTLA-4-mediated inhibition of T cell activity, or rescue or reversal of exhausted state of T cells. It also includes inhibition of regulatory T cell activity. The enhanced immune response, as used in the context of the present invention, results in increased killing of tumor cells and/or inhibition of tumor growth.

The antibodies and antigen-binding fragments of the present invention specifically bind to CTLA-4 and enhance T cell activation. The anti-CTLA-4 antibodies may bind to CTLA-4 with high affinity or with low affinity. In certain embodiments, the antibodies of the present invention may be blocking antibodies wherein the antibodies may bind to CTLA-4 and inhibit CTLA-4 signaling. In some embodiments, the antibodies of the invention block the binding of CTLA-4 to CD80 and/or CD86 and/or stimulate or enhance T cell activation. In some embodiments, the antibodies bind to CTLA-4 and reverse the anergic state of exhausted T cells. In certain embodiments, the antibodies bind to CTLA-4 and inhibit regulatory T cell activity. In some embodiments, the antibodies may be useful for stimulating or enhancing the immune response and/or for treating a subject suffering from cancer, or a viral infection. The antibodies when administered to a subject in need thereof may reduce chronic infection by a virus such as HIV, LCMV or HBV in the subject. They may be used to inhibit the growth of tumor cells in a subject. They may be used alone or as adjunct therapy with other therapeutic moieties or modalities known in the art for treating cancer, or viral infection.

In certain embodiments, the anti-CTLA-4 antibodies may be multi-specific antigen-binding molecules, wherein they comprise a first binding specificity to CTLA-4 and a second binding specificity to an antigen selected from the group consisting of another T cell co-inhibitor, and a different epitope of CTLA-4.

An immunogen comprising any one of the following can be used to generate antibodies to CTLA-4. In certain embodiments, the antibodies of the invention are obtained from mice immunized with a full length, native CTLA-4 (See NCBI accession number NP_005205.2) (SEQ ID NO: 505), or with a recombinant CTLA-4 peptide. Alternatively, CTLA-4 or a fragment thereof may be produced using standard biochemical techniques and used as immunogen.

In certain embodiments, the immunogen is the extracellular domain of CTLA-4. In one embodiment of the invention, the immunogen is a fragment of the extracellular domain of CTLA-4.

In some embodiments, the immunogen may be a recombinant CTLA-4 peptide expressed in *E. coli* or in any other eukaryotic or mammalian cells such as Chinese hamster ovary (CHO) cells.

In certain embodiments, antibodies that bind specifically to CTLA-4 may be prepared using fragments of the above-noted regions, or peptides that extend beyond the designated regions by about 5 to about 20 amino acid residues from either, or both, the N or C terminal ends of the regions described herein. In certain embodiments, any combination of the above-noted regions or fragments thereof may be used in the preparation of CTLA-4 specific antibodies.

The peptides may be modified to include addition or substitution of certain residues for tagging or for purposes of conjugation to carrier molecules, such as, KLH. For example, a cysteine may be added at either the N terminal or C terminal end of a peptide, or a linker sequence may be added to prepare the peptide for conjugation to, for example, KLH for immunization.

Certain anti-CTLA-4 antibodies of the present invention are able to bind to and neutralize the activity of CTLA-4, as determined by in vitro or in vivo assays. The ability of the antibodies of the invention to bind to and neutralize the activity of CTLA-4 may be measured using any standard method known to those skilled in the art, including binding assays, or activity assays, as described herein.

Non-limiting, exemplary in vitro assays for measuring binding activity are illustrated in Examples herein. In Example 3, the binding affinities and kinetic constants of human anti-CTLA-4 antibodies for human and monkey CTLA-4 were determined by surface plasmon resonance or MASS-1. In Example 4, competition sandwich ELISAs were used to assess the ability of the anti-CTLA-4 antibodies to block CTLA-4 protein binding to its natural ligands B7-1 and B7-2. Example 5 describes the binding of the anti-CTLA-4 antibodies to cells expressing CTLA-4. In Example 6, a luciferase assay and an IL-2 release assay were used to determine the ability of anti-CTLA-4 antibodies to activate T cells and rescue IL-2 release.

In certain embodiments, the antibodies of the present invention are able to enhance or stimulate T cell activity in vitro, in a subject with cancer, or in a subject infected with a virus such as LCMV. In certain embodiments, the antibodies of the present invention are used in combination with a second therapeutic agent, such as an antibody to a second T cell co-inhibitor, to enhance the immune response and inhibit tumor growth in a subject.

The antibodies specific for CTLA-4 may contain no additional labels or moieties, or they may contain a label or moiety, e.g., an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In one embodiment, the label may be a radionuclide, a fluorescent dye or a MRI-detectable label. In certain embodiments, such labeled antibodies may be used in diagnostic assays including imaging assays.

Exemplary Embodiments of the Invention

In one aspect, the present invention provides an antibody or antigen-binding fragment thereof that binds human cytotoxic T-lymphocyte-associated protein 4 (CTLA-4) and blocks the interaction between hCTLA-4 and ligands B7-1 and B7-2.

In certain embodiments, the antibody or antigen-binding fragment induces T-cell activation. In some cases, the T-cell is a cytotoxic T-cell. In some cases, the T-cell is a tumor infiltrating lymphocyte.

In certain embodiments, the antibody or antigen-binding fragment binds monkey CTLA-4. In some cases, the antibody or antigen-binding fragment binds monkey CTLA-4 expressing cells with an EC50 of less than 0.5 nM.

In certain embodiments, the antibody or antigen-binding fragment binds hCTLA-4 expressing cells with an EC50 of less than 5 nM, less than 1 nM, or less than 0.5 nM.

In various embodiments, the antibody or antigen-binding fragment is a fully human antibody.

In certain embodiments, the antibody or antigen-binding fragment thereof competes for binding to human CTLA-4 with a reference antibody comprising an HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/298, 314/322, 330/338, 346/354, 362/370, 378/386, 394/402, 410/418, 426/434, 442/450, 458/466, 474/482, and 490/498.

In certain embodiments, the antibody or antigen-binding fragment thereof binds to the same epitope on human CTLA-4 as a reference antibody comprising an HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/298, 314/322, 330/338, 346/354, 362/370, 378/386, 394/402, 410/418, 426/434, 442/450, 458/466, 474/482, and 490/498.

In certain embodiments, the antibody or antigen-binding fragment comprises: (a) the complementarity determining regions (CDRs) of a heavy chain variable region (HCVR) having an amino acid sequence selected from the group consisting of SEQ ID NOs: 2, 18, 34, 50, 66, 82, 98, 114, 130, 146, 162, 178, 194, 210, 226, 242, 258, 274, 290, 306, 314, 330, 346, 362, 378, 394, 410, 426, 442, 458, 474, and 490; and (b) the CDRs of a light chain variable region (LCVR) having an amino acid sequence selected from the group consisting of SEQ ID NOs: 10, 26, 42, 58, 74, 90, 106, 122, 138, 154, 170, 186, 202, 218, 234, 250, 266, 282, 298, 322, 338, 354, 370, 386, 402, 418, 434, 450, 466, 482, and 498.

In certain embodiments, the antibody or antigen-binding fragment comprises the heavy and light chain CDRs of a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/298, 314/322, 330/338, 346/354, 362/370, 378/386, 394/402, 410/418, 426/434, 442/450, 458/466, 474/482, and 490/498.

In certain embodiments, the antibody or antigen-binding fragment comprises HCDR1-HCDR2-HCDR3-LCDR1-LCDR2-LCDR3 domains, respectively, selected from the group consisting of SEQ ID NOs: 4-6-8-12-14-16; 20-22-24-28-30-32; 36-38-40-44-46-48; 52-54-56-60-62-64; 68-70-72-76-78-80; 84-86-88-92-94-96; 100-102-104-108-110-112; 116-118-120-124-126-128; 132-134-136-140-142-144; 148-150-152-156-158-160; 164-166-168-172-174-176; 180-182-184-188-190-192; 196-198-200-204-206-208; 212-214-216-220-222-224; 228-230-232-236-238-240; 244-246-248-252-254-256; 260-262-264-268-270-272; 276-278-280-284-286-288; 292-294-296-300-302-304; 308-310-312-300-302-304; 316-318-320-324-326-328; 332-334-336-340-342-344; 348-350-352-356-358-360; 364-366-368-372-374-376; 380-382-384-388-390-392; 396-398-400-404-406-408; 412-414-416-420-422-424; 428-430-432-436-438-440; 444-446-448-452-454-456; 460-462-464-468-470-472; 476-478-480-484-486-488; and 492-494-496-500-502-504.

In certain embodiments, the antibody or antigen-binding fragment comprises a HCVR/LCVR amino acid sequence pair selected from the group consisting of: SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/298, 314/322, 330/338, 346/354, 362/370, 378/386, 394/402, 410/418, 426/434, 442/450, 458/466, 474/482, and 490/498.

In certain embodiments, the present invention provides an antibody or antigen-binding fragment hereof that is a human, humanized or a chimeric antibody. The antibody or antigen-binding fragment thereof can for instance be an IgG1 or an IgG4 antibody, such as e.g., a human IgG1 or an IgG4 antibody. The constant regions of those antibodies might correspond to wild-type constant regions, or to constant regions into which mutations have been introduced.

In one aspect, the present invention provides a multi-specific antigen-binding molecule comprising a first antigen-binding specificity that binds specifically to CTLA-4 and a second antigen-binding specificity that specifically binds to a second target epitope.

In one aspect, the present invention provides a pharmaceutical composition comprising an anti-CTLA-4 antibody or antigen-binding fragment thereof of any of the above embodiments and a pharmaceutically acceptable carrier or diluent.

In one aspect, the present invention provides isolated polynucleotide molecules and vectors comprising polynucleotide sequences of the antibodies or antigen-binding fragment thereof disclosed herein. In certain embodiments, the present invention provides an isolated polynucleotide molecule and/or a vector comprising a polynucleotide sequence that encodes a HCVR of an antibody as set forth herein. In certain embodiments, the present invention provides an isolated polynucleotide molecule and/or a vector comprising a polynucleotide sequence that encodes a LCVR of an antibody as set forth herein. In certain embodiments, the present invention provides a cell expressing the vectors discussed above or herein.

In one aspect, the present invention provides a method for treating a disease or disorder that is treatable by antagonizing CTLA-4 via administration to a subject in need thereof a therapeutically effective amount of an anti-CTLA-4 antibody or antigen-binding fragment thereof as disclosed herein, or a pharmaceutical composition comprising such antibodies or antigen-binding fragments. In some cases, the disease or disorder is a chronic viral infection caused by a virus selected from the group consisting of human immunodeficiency virus (HIV), hepatitis C virus (HCV), hepatitis B virus (HBV), human papilloma virus (HPV), lymphocytic choriomeningitis virus (LCMV) and simian immunodeficiency virus (SIV). In some cases, the disease or disorder is selected from the group consisting of blood cancer, brain cancer, renal cell cancer, ovarian cancer, bladder cancer, prostate cancer, breast cancer, skin cancer, cervical cancer, kidney cancer, stomach cancer, pancreatic cancer, hepatic cell carcinoma, bone cancer, colon cancer, non-small-cell lung cancer, squamous cell carcinoma of head and neck, colorectal cancer, mesothelioma, B cell lymphoma, and melanoma.

In one aspect, the present invention provides methods of enhancing an immune response in a subject, the method comprising administering a pharmaceutical composition comprising an isolated anti-CTLA-4 antibody or antigen-binding fragment thereof as disclosed herein. In certain embodiments, the present invention provides methods of inhibiting a T-regulatory (Treg) cell in a subject comprising administering a pharmaceutical composition comprising an isolated anti-CTLA-4 antibody or antigen-binding fragment thereof as disclosed herein. In certain embodiments, the present invention provides methods of enhancing T cell activation in a subject, the method comprising administering a pharmaceutical composition comprising an isolated anti-CTLA-4 antibody or antigen-binding fragment thereof as disclosed herein. In certain embodiments, the subject has a disease or disorder selected from the group consisting of blood cancer, brain cancer, renal cell carcinoma (e.g., clear cell renal carcinoma), ovarian cancer, bladder cancer, prostate cancer, breast cancer (e.g., triple negative breast cancer), skin cancer, cervical cancer, stomach cancer, kidney cancer, pancreatic cancer, hepatic cell carcinoma, bone cancer, colon cancer, non-small-cell lung cancer, squamous cell carcinoma of head and neck, colorectal cancer, mesothelioma, lymphoma (e.g., B cell lymphoma, diffuse large B cell lymphoma) and melanoma. In certain embodiments, the subject has a chronic viral infection caused by a virus selected from the group consisting of human immunodeficiency virus (HIV), hepatitis C virus (HCV), hepatitis B virus (HBV), human papilloma virus (HPV), lymphocytic choriomeningitis virus (LCMV) and simian immunodeficiency virus (SIV). In certain embodiments, the anti-CTLA-4 antibody is administered to the subject in combination with a second therapeutic agent selected from the group consisting of a PD-1 inhibitor, a LAG3 inhibitor, an antibody to a tumor specific antigen, an antibody to a virally-infected-cell antigen, a PD-L1 inhibitor, a CD20 inhibitor, a bispecific antibody against CD20 and CD3, a dietary supplement such as an antioxidant, a VEGF antagonist, a cancer vaccine, a chemotherapeutic agent, a cytotoxic agent, surgery, radiation, a NSAID, a corticosteroid, and any other therapy useful for ameliorating at least one symptom associated with the disease or disorder.

In one aspect, the present invention provides methods of inhibiting growth of a tumor or a tumor cell in a subject comprising administering to the subject in need thereof a therapeutically effective amount of an anti-CTLA-4 antibody or antigen-binding fragment thereof as disclosed herein, or a pharmaceutical composition comprising such antibodies or antigen-binding fragments. In certain embodiments, the tumor is primary or recurrent. In certain embodiments, the tumor is an established tumor. In certain embodiments, the subject has metastatic disease and/or has been treated with prior therapy. In certain embodiments, the tumor is present in a subject with a disease or disorder selected from the group consisting of blood cancer, brain cancer, renal cell cancer, ovarian cancer, bladder cancer, prostate cancer, breast cancer, hepatic cell carcinoma, bone cancer, colon cancer, non-small-cell lung cancer, squamous cell carcinoma of head and neck, colorectal cancer, mesothelioma, lymphoma, and melanoma. In certain embodiments, the anti-CTLA-4 antibody or antigen-binding fragment thereof is administered as one or more doses wherein each dose is administered 1 to 12 weeks after the immediately preceding dose. In certain embodiments, the anti-CTLA-4 antibody or antigen-binding fragment thereof is administered at a dose of about 0.1 mg/kg of body weight to about 100 mg/kg of body weight of the subject. In certain embodiments, each dose comprises from about 50 mg to about 1000 mg of the antibody. In certain embodiments, the anti-CTLA-4 antibody is administered to the subject in combination with a second therapeutic agent selected from the group consisting of a PD-1 inhibitor, a LAG3 inhibitor, an antibody to a tumor specific antigen, a PD-L1 inhibitor, a CD20 inhibitor, a bispecific antibody against CD20 and CD3, a dietary supplement such as an antioxidant, a VEGF antagonist, a cancer vaccine, a chemotherapeutic agent, a cytotoxic agent, surgery, radiation, a NSAID, a corticosteroid, and any other therapy useful for ameliorating at least one symptom associated with the disease or disorder. In one embodiment, the second therapeutic agent is a PD-1 inhibitor wherein the PD-1 inhibitor is an antibody or antigen-binding fragment thereof that specifically binds to PD-1. In some embodiments, the PD-1 inhibitor is REGN2810, nivolumab or pembrolizumab. In certain embodiments, the anti-CTLA-4 antibody or antigen-binding fragment thereof is administered subcutaneously, intravenously, intratumorally, peritumorally, intradermally, intraperitoneally, orally, intramuscularly, or intracranially.

In one aspect, the present invention provides methods of rescuing CTLA-4-mediated inhibition of T cell activity comprising contacting the T cell with an anti-CTLA-4 antibody or antigen-binding fragment thereof as disclosed herein. In one embodiment, the T cell is contacted by an anti-CTLA-4 antibody of the present invention in combination with an anti-PD-1 antibody (e.g., REGN2810).

In one aspect, the present invention provides a use of an anti-CTLA-4 antibody or antigen-binding fragment thereof as disclosed herein, or a pharmaceutical composition comprising such antibodies or antigen-binding fragments, in the treatment of a disease or disorder that is treatable by antagonizing CTLA-4. In some cases, the disease or disorder is cancer.

In one aspect, the present invention provides a use of an anti-CTLA-4 antibody or antigen-binding fragment thereof as disclosed herein, or a pharmaceutical composition comprising such antibodies or antigen-binding fragments, in the manufacture of a medicament for treating a disease or disorder that is treatable by antagonizing CTLA-4. In some cases, the disease or disorder is cancer.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to CTLA-4. An antibody fragment may include a Fab fragment, a F(ab')$_2$ fragment, a Fv fragment, a dAb fragment, a fragment containing a CDR, or an isolated CDR. In certain embodiments, the term "antigen-binding fragment" refers to a polypeptide fragment of a multi-specific antigen-binding molecule. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; $V_H$-$C_H2$-$C_H3$; $V_H$-CL; $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-CL. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

Preparation of Human Antibodies

Methods for generating human antibodies in transgenic mice are known in the art. Any such known methods can be used in the context of the present invention to make human antibodies that specifically bind to CTLA-4.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to CTLA-4 are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Bioequivalents

The anti-CTLA-4 antibodies and antibody fragments of the present invention encompass proteins having amino acid sequences that vary from those of the described antibodies, but that retain the ability to bind CTLA-4. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present invention encompass sequences that comprise one or more additions, deletions, or substitutions of nucleotides when compared to the disclosed sequence, but that encode an antibody or antibody fragment that is essentially bioequivalent to an antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-CTLA-4 Antibodies Comprising Fc Variants

According to certain embodiments of the present invention, anti-CTLA-4 antibodies are provided comprising an Fc domain comprising one or more mutations which enhance or diminish antibody binding to the FcRn receptor, e.g., at acidic pH as compared to neutral pH. For example, the present invention includes anti-CTLA-4 antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-CTLA-4 antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). In one embodiment, the present invention includes anti-CTLA-4 antibodies comprising an Fc domain comprising a S108P mutation in the hinge region of IgG4 to promote dimer stabilization. All possible combinations of the foregoing Fc domain mutations, and other mutations within the antibody variable domains disclosed herein, are contemplated within the scope of the present invention.

The present invention also includes anti-CTLA-4 antibodies comprising a chimeric heavy chain constant ($C_H$) region, wherein the chimeric $C_H$ region comprises segments derived from the $C_H$ regions of more than one immunoglobulin isotype. For example, the antibodies of the invention may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., US Patent Publication No. 20140243504, the disclosure of which is hereby incorporated by reference in its entirety).

Biological Characteristics of the Antibodies

In general, the antibodies of the present invention function by binding to CTLA-4. The present invention includes anti-CTLA-4 antibodies and antigen-binding fragments thereof that bind soluble monomeric or dimeric CTLA-4 molecules with high affinity. For example, the present invention includes antibodies and antigen-binding fragments of antibodies that bind dimeric human and monkey CTLA-4 (e.g., at 25° C.) with a $K_D$ of less than about 20 nM as measured by surface plasmon resonance, e.g., using the assay format as defined in Example 3 herein. In certain embodiments, the antibodies or antigen-binding fragments thereof bind monomeric CTLA-4 with a $K_D$ of less than about 10 nM, less than about 5 nM, less than about 2 nM, or less than about 1 nM, as measured by surface plasmon resonance, e.g., using the assay format as defined in Example 3 herein, or a substantially similar assay.

The present invention also includes antibodies and antigen-binding fragments thereof that bind CTLA-4 with a dissociative half-life (t1/2) of greater than about 4 minutes as measured by surface plasmon resonance at 25° C., e.g., using an assay format as defined in Example 3 herein, or a substantially similar assay. In certain embodiments, the antibodies or antigen-binding fragments of the present invention bind CTLA-4 with a t1/2 of greater than about 5 minutes, greater than about 10 minutes, greater than about 15 minutes, greater than about 20 minutes, greater than about 30 minutes, greater than about 40 minutes, greater than about 100 minutes, greater than about 200 minutes, greater than about 300 minutes, or greater than about 500 minutes, as measured by surface plasmon resonance at 25° C., e.g., using an assay format as defined in Example 3 herein (e.g., mAb-capture format), or a substantially similar assay.

The present invention also includes antibodies or antigen-binding fragments thereof that block hCTLA-4 binding to hB7-1 (CD80) and/or hB7-2 (CD86) with an $IC_{50}$ of less than about 320 nM as determined using an Enzyme-linked Immunosorbent Assay (ELISA), e.g., as shown in Example 4, or a substantially similar assay. In certain embodiments, the antibodies or antigen-binding fragments thereof block hCTLA-4 binding to human B7-1 and/or human B7-2 with an $IC_{50}$ less than about 200 nM, less than about 100 nM, less than about 70 nM, less than about 20 nM, less than about 10 nM, less than about 5 nM, less than about 1 nM, or less than about 0.5 nM, as measured by a competition sandwich ELISA, e.g., as defined in Example 4 herein, or a substantially similar assay.

The present invention also includes antibodies or antigen-binding fragment thereof that block binding of hCTLA-4 to human B7-1 and/or human B7-2 by at least 85% as measured by a competition sandwich ELISA, e.g., as defined in Example 4 herein, or a substantially similar assay.

The present invention also includes antibodies or antigen-binding fragments thereof that bind to a human CTLA-4-expressing cell with an $EC_{50}$ less than about 6 nM as measured by an electrochemiluminescence assay as defined in Example 5 herein, or a substantially similar assay. In certain embodiments, the antibodies or antigen-binding fragments thereof bind to a hCTLA-4-expressing cell with an $EC_{50}$ less than about 4 nM, less than about 2 nM, less than about 1 nM, or less than about 0.5 nM, as measured by an electrochemiluminescence assay, e.g., using the assay format in Example 5 herein, or a substantially similar assay. In certain embodiments, the antibodies or antigen-binding fragments thereof bind to a hCTLA-4-expressing cell at a ratio of more than about 10-fold above binding to control cells, at a ratio of more than about 15-fold, or at a ratio of more than about 20-fold above binding to control cells, as measured by an electrochemiluminescence assay, e.g., using the assay format in Example 5 herein, or a substantially similar assay.

The present invention also includes antibodies or antigen-binding fragments thereof that bind to a cynomolgus monkey CTLA-4-expressing cell with an $EC_{50}$ less than about 0.5 nM as measured by an electrochemiluminescence assay as defined in Example 5 herein, or a substantially similar assay. In certain embodiments, the antibodies or antigen-binding fragments thereof bind to a mfCTLA-4-expressing cell with an $EC_{50}$ less than about 0.5 nM, or less than about 0.2 nM, as measured by an electrochemiluminescence assay, e.g., using the assay format as defined in Example 5 herein, or a substantially similar assay.

The present invention also includes antibodies or antigen-binding fragments thereof that block CTLA-4-induced T cell down-regulation (by blocking the CTLA-4/CD80 and CTLA-4/CD86 interactions) with an $EC_{50}$ less than 8 nM as measured by a T cell/APC luciferase reporter assay as defined in Example 6 herein, or a substantially similar assay. In certain embodiments, the antibodies or antigen-binding fragments thereof block CTLA-4-induced T cell down-regulation with an $EC_{50}$ less than about 6 nM, less than about 5 nM, less than about 3 nM, less than about 2.5 nM, or less than about 2 nM, as measured by a T cell/APC luciferase reporter assay, e.g., using the assay format as defined in Example 6 herein, or a substantially similar assay. In certain embodiments, the antibodies or antigen-binding fragments thereof block CTLA-4-induced T cell down-regulation of both human and monkey CTLA-4.

The present invention also includes antibodies or antigen-binding fragments thereof that rescues CTLA-4-mediated inhibition of IL-2 release (by blocking the CTLA-4/CD80 and CTLA-4/CD86 interactions) with an $EC_{50}$ less than about 50 nM as measured by a T cell/APC IL-2 release assay as defined in Example 6 herein, or a substantially similar assay. In certain embodiments, the antibodies or antigen-binding fragments thereof rescues CTLA-4-mediated inhibition of IL-2 release with an $EC_{50}$ less than about 45 nM, less than about 35 nM, less than about 25 nM, or less than about 20 nM, as measured by a T cell/APC IL-2 release assay, e.g., using the assay format as defined in Example 6 herein, or a substantially similar assay. In certain embodiments, the antibodies or antigen-binding fragments thereof block CTLA-4-induced T cell down-regulation and/or CTLA-4-mediated inhibition of IL-2 release for both human and monkey CTLA-4. In certain embodiments, the antibodies or antigen-binding fragments thereof block CTLA-4-induced T cell down-regulation, as demonstrated by IL-2 production, at a rate of from 4 to 6 fold above that observed for an isotype control antibody.

In certain embodiments, the antibodies of the present invention are useful in inhibiting the growth of a tumor or delaying the progression of cancer when administered prophylactically to a subject in need thereof and may increase survival of the subject. For example, the administration of an antibody of the present invention may lead to shrinking of a primary tumor and may prevent metastasis or development of secondary tumors. In certain embodiments, the antibodies of the present invention are useful in inhibiting the growth of a tumor when administered therapeutically to a subject in need thereof and may increase survival of the subject. For example, the administration of a therapeutically effective amount of an antibody of the invention to a subject may lead to shrinking and disappearance of an established tumor in the subject. In certain embodiments, one or more antibodies of the present invention are administered locally (intratumorally or peritumorally) and lead to inhibition of tumor growth in the injected tumor lesion and in distant tumor lesions (abscopal effect).

In various embodiments, the invention provides an isolated recombinant monoclonal antibody or antigen-binding fragment thereof that binds to CTLA-4, wherein the antibody or antigen-binding fragment thereof exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 194, 210, 226, 242, 258, 274, 290, 306, 314, 330, 346, 362, 378, 394, 410, 426, 442, 458, 474, and 490, or a substantially similar sequence thereof having at least 90%, at least 95%, at least 98% or at least 99% sequence identity; (ii) comprises a LCVR having an amino acid sequence selected from the group consisting of SEQ ID NO: 10, 26, 42, 58, 74, 90, 106, 122, 138, 154, 170, 186, 202, 218, 234, 250, 266, 282, 298, 322, 338, 354, 370, 386, 402, 418, 434, 450, 466, 482, and 498, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 24, 40, 56, 72, 88, 104, 120, 136, 152, 168, 184, 200, 216, 232, 248, 264, 280, 296, 312, 320, 336, 352, 368, 384, 400, 416, 432, 448, 464, 480, and 496, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 192, 208, 224, 240, 256, 272, 288, 304, 328, 344, 360, 376, 392, 408, 424, 440, 456, 472, 488, and 504, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 20, 36, 52, 68, 84, 100, 116, 132, 148, 164, 180, 196, 212, 228, 244, 260, 276, 292, 308, 316, 332, 348, 364, 380, 396, 412, 428, 444, 460, 476, and 492, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 70, 86, 102, 118, 134, 150, 166, 182, 198, 214, 230, 246, 262, 278, 294, 310, 318, 334, 350, 366, 382, 398, 414, 430, 446, 462, 478, and 494, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 76, 92, 108, 124, 140, 156, 172, 188, 204, 220, 236, 252, 268, 284, 300, 324, 340, 356, 372, 388, 404, 420, 436, 452, 468, 484, and 500, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 78, 94, 110, 126, 142, 158, 174, 190, 206, 222, 238, 254, 270, 286, 302, 326, 342, 358, 374, 390, 406, 422, 438, 454, 470, 486, and 502, or a substantially similar sequence thereof having at least 90%, at least 95%, at least 98% or at least 99% sequence identity; (v) binds dimeric human and monkey CTLA-4 with a binding dissociation equilibrium constant ($K_D$) of less than about 20 nM as measured in a surface plasmon resonance assay at 25° C.; (vi) binds dimeric human and monkey CTLA-4 with a dissociative half-life (t %) of greater than about 4 minutes as measured in a surface plasmon resonance assay at 25° C.; (vii) blocks hCTLA-4 binding to hB7-1 (CD80) and/or hB7-2 (CD86) with an IC50 of less than about 320 nM as determined using a cell adherence assay; (viii) blocks the binding of hCTLA-4 to human B7-1 and/or human B7-2 by at least 85% as measured by a competition sandwich ELISA; (ix) binds to a human CTLA-4-expressing cell with an EC50 less than about 6 nM as measured by an electochemiluminescence assay; (x) binds to a hCTLA-4-expressing cell at a ratio of more than 10-fold about binding to control cells; (xi) binds to a monkey CTLA-4-expressing cell with an EC50 less than about 0.5 nM as measured by an electochemiluminescence assay; (xii) blocks CTLA-4-induced T cell down regulation with an EC50 less than 8 nM as measured by a T cell/APC luciferase reporter assay; (xiii) blocks CTLA-4-induced T cell down regulation of both human and monkey CTLA-4; (xiv) rescues CTLA-4-mediated inhibition of IL-2 release with $EC_{50}$ less than about 50 nM as determined in a T cell/APC IL-2 release assay; (xv) blocks CTLA-4-induced T cell down-regulation and/or CTLA-4-mediated inhibition of IL-2 release for both human and monkey CTLA-4; (xvi) blocks CTLA-4-induced T cell down-regulation, as demonstrated by IL-2 production, at a rate of from 4 to 6 fold above that observed for an isotype control antibody; (xvii) suppresses tumor growth and increases survival in a subject with cancer, and (xviii) is fully human.

The antibodies of the present invention may possess one or more of the aforementioned biological characteristics, or any combinations thereof. Other biological characteristics of the antibodies of the present invention will be evident to a person of ordinary skill in the art from a review of the present disclosure including the working examples herein.

Species Selectivity and Species Cross-Reactivity

According to certain embodiments of the invention, the anti-CTLA-4 antibodies bind to human CTLA-4 but not to CTLA-4 from other species. Alternatively, the anti-CTLA-4 antibodies of the invention, in certain embodiments, bind to human CTLA-4 and to CTLA-4 from one or more non-human species. For example, the anti-CTLA-4 antibodies of the invention may bind to human CTLA-4 and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee CTLA-4. In certain embodiments, the anti-CTLA-4 antibodies of the invention may bind to human and cynomolgus CTLA-4 with the same affinities or with different affinities, but do not bind to rat and mouse CTLA-4.

Epitope Mapping and Related Technologies

The present invention includes anti-CTLA-4 antibodies which interact with one or more amino acids found within one or more domains of the CTLA-4 molecule including, e.g., an extracellular domain, a transmembrane domain, and a cytoplasmic domain. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within any of the aforementioned domains of the CTLA-4 molecule (e.g. a linear epitope in a domain). Alternatively, the epitope may consist of a plurality of non-contiguous amino acids (or amino acid sequences) located within any or all of the aforementioned domains of the CTLA-4 molecule (e.g. a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, NY). Other methods include alanine scanning mutational analysis, peptide blot analysis (Reineke (2004) Methods Mol. Biol. 248: 443-63), peptide cleavage analysis crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267: 252-259; Engen and Smith (2001) Anal. Chem. 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the invention into groups of antibodies binding different epitopes.

In certain embodiments, the anti-CTLA-4 antibodies or antigen-binding fragments thereof bind an epitope within any one or more of the regions exemplified in CTLA-4, either in natural form, as exemplified in SEQ ID NO: 505, or recombinantly produced, or to a fragment thereof.

The present invention includes anti-CTLA-4 antibodies that bind to the same epitope, or a portion of the epitope, as any of the specific exemplary antibodies described herein in Table 1, or an antibody having the CDR sequences of any of the exemplary antibodies described in Table 1. Likewise, the present invention also includes anti-CTLA-4 antibodies that compete for binding to CTLA-4 or a CTLA-4 fragment with any of the specific exemplary antibodies described herein in Table 1, or an antibody having the CDR sequences of any of the exemplary antibodies described in Table 1. For example, the present invention includes anti-CTLA-4 antibodies that cross-compete for binding to CTLA-4 with one or more antibodies as exemplified herein (e.g., H1H19303P or H1H19319P2).

One can easily determine whether an antibody binds to the same epitope as, or competes for binding with, a reference anti-CTLA-4 antibody by using routine methods known in the art. For example, to determine if a test antibody binds to the same epitope as a reference anti-CTLA-4 antibody of the invention, the reference antibody is allowed to bind to a CTLA-4 protein or peptide under saturating conditions. Next, the ability of a test antibody to bind to the CTLA-4 molecule is assessed. If the test antibody is able to bind to CTLA-4 following saturation binding with the reference anti-CTLA-4 antibody, it can be concluded that the test antibody binds to a different epitope than the reference anti-CTLA-4 antibody. On the other hand, if the test antibody is not able to bind to the CTLA-4 protein following saturation binding with the reference anti-CTLA-4 antibody, then the test antibody may bind to the same epitope as the epitope bound by the reference anti-CTLA-4 antibody of the invention.

To determine if an antibody competes for binding with a reference anti-CTLA-4 antibody, the above-described binding methodology is performed in two orientations: In a first orientation, the reference antibody is allowed to bind to a CTLA-4 protein under saturating conditions followed by assessment of binding of the test antibody to the CTLA-4 molecule. In a second orientation, the test antibody is allowed to bind to a CTLA-4 molecule under saturating conditions followed by assessment of binding of the reference antibody to the CTLA-4 molecule. If, in both orientations, only the first (saturating) antibody is capable of binding to the CTLA-4 molecule, then it is concluded that the test antibody and the reference antibody compete for binding to CTLA-4. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a human anti-CTLA-4 monoclonal antibody conjugated to a therapeutic moiety ("immunoconjugate"), such as a cytotoxin or a chemotherapeutic agent to treat cancer. As used herein, the term "immunoconjugate" refers to an antibody which is chemically or biologically linked to a cytotoxin, a radioactive agent, a cytokine, an interferon, a target or reporter moiety, an enzyme, a toxin, a peptide or protein or a therapeutic agent. The antibody may be linked to the cytotoxin, radioactive agent, cytokine, interferon, target or reporter moiety, enzyme, toxin, peptide or therapeutic agent at any location along the molecule so long as it is able to bind its target. Examples of immunoconjugates include antibody drug conjugates and antibody-toxin fusion proteins. In one embodiment, the agent may be a second different antibody to CTLA-4. In certain embodiments, the antibody may be conjugated to an agent specific for a tumor cell or a virally infected cell. In one embodiment, the antibody is conjugated to an agent specific for a T-cell. The type of therapeutic moiety that may be conjugated to the anti-CTLA-4 antibody and will take into account the condition to be treated and the desired therapeutic effect to be achieved. Examples of suitable agents for forming immunoconjugates are known in the art; see for example, WO 05/103081.

Multi-Specific Antibodies

The antibodies of the present invention may be monospecific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244.

In one aspect, the present invention includes multi-specific antigen-binding molecules or antigen-binding fragments thereof wherein one specificity of an immunoglobulin is specific for the extracellular domain of CTLA-4, or a fragment thereof, and the other specificity of the immunoglobulin is specific for binding outside the extracellular domain of CTLA-4, or a second therapeutic target, or is conjugated to a therapeutic moiety.

Any of the multi-specific antigen-binding molecules of the invention, or variants thereof, may be constructed using standard molecular biological techniques (e.g., recombinant DNA and protein expression technology), as will be known to a person of ordinary skill in the art.

In some embodiments, CTLA-4-specific antibodies are generated in a bi-specific format (a "bi-specific") in which variable regions binding to distinct domains of CTLA-4 are linked together to confer dual-domain specificity within a single binding molecule. Appropriately designed bi-specifics may enhance overall CTLA-4 inhibitory efficacy through increasing both specificity and binding avidity. Variable regions with specificity for individual domains, (e.g., segments of the N-terminal domain), or that can bind to different regions within one domain, are paired on a structural scaffold that allows each region to bind simultaneously to the separate epitopes, or to different regions within one domain. In one example for a bi-specific, heavy chain variable regions ($V_H$) from a binder with specificity for one domain are recombined with light chain variable regions ($V_L$) from a series of binders with specificity for a second domain to identify non-cognate $V_L$ partners that can be paired with an original $V_H$ without disrupting the original specificity for that $V_H$. In this way, a single $V_L$ segment (e.g., $V_L1$) can be combined with two different $V_H$ domains (e.g., $V_H1$ and $V_H2$) to generate a bi-specific comprised of two binding "arms" ($V_H1$-$V_L1$ and $V_H2$-$V_L1$). Use of a single $V_L$ segment reduces the complexity of the system and thereby simplifies and increases efficiency in cloning, expression, and purification processes used to generate the bi-specific (See, for example, U.S. Ser. No. 13/022,759 and US2010/0331527).

Alternatively, antibodies that bind more than one domains and a second target, such as, but not limited to, for example, a second different anti-CTLA-4 antibody, may be prepared in a bi-specific format using techniques described herein, or other techniques known to those skilled in the art. Antibody variable regions binding to distinct regions may be linked together with variable regions that bind to relevant sites on, for example, the extracellular domain of CTLA-4, to confer dual-antigen specificity within a single binding molecule. Appropriately designed bi-specifics of this nature serve a dual function. Variable regions with specificity for the extracellular domain are combined with a variable region with specificity for outside the extracellular domain and are paired on a structural scaffold that allows each variable region to bind to the separate antigens.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mabe bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Administration and Formulations

The invention provides therapeutic compositions comprising the anti-CTLA-4 antibodies or antigen-binding fragments thereof of the present invention. Therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When an antibody of the present invention is used for treating a disease or disorder in an adult patient, or for preventing such a disease, it is advantageous to administer the antibody of the present invention normally at a single dose of about 0.1 to about 60 mg/kg body weight, more preferably about 5 to about 60, about 20 to about 50, about 10 to about 50, about 1 to about 10, or about 0.8 to about 11 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) Science 249: 1527-1533).

The use of nanoparticles to deliver the antibodies of the present invention is also contemplated herein. Antibody-conjugated nanoparticles may be used both for therapeutic and diagnostic applications. Antibody-conjugated nanoparticles and methods of preparation and use are described in detail by Arruebo, M., et al. 2009 ("Antibody-conjugated nanoparticles for biomedical applications" in J. Nanomat. Volume 2009, Article ID 439389, 24 pages, doi: 10.1155/2009/439389), incorporated herein by reference. Nanoparticles may be developed and conjugated to antibodies contained in pharmaceutical compositions to target tumor cells or autoimmune tissue cells or virally infected cells. Nanoparticles for drug delivery have also been described in, for example, U.S. Pat. No. 8,257,740, or U.S. Pat. No. 8,246,995, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intratumoral, peritumoral, intracutaneous, intracranial, intraperitoneal and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L.P.) and the HUMIRA™ Pen (Abbott Labs, Abbott Park, IL), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antibody contained is generally about 5 to about 500 mg per dosage form in a unit dose; especially in the form of injection, it is preferred that the antibody is contained in about 5 to about 100 mg and in about 10 to about 250 mg for the other dosage forms.

Therapeutic Uses of the Antibodies

The antibodies of the invention are useful, inter alia, for the treatment, prevention and/or amelioration of any disease or disorder associated with or mediated by CTLA-4 expression, signaling or activity, or treatable by blocking the interaction between CTLA-4 and the CTLA-4 ligands B7-1/CD80 and/or B7-2/CD86, or otherwise inhibiting CTLA-4 activity and/or signaling. One or more antibodies of the present invention may be administered to relieve or prevent or decrease the severity of one or more of the symptoms or conditions of the disease or disorder. For example, the present invention provides methods for treating cancer (tumor growth inhibition) and/or viral infections by administering an anti-CTLA-4 antibody (or pharmaceutical composition comprising an anti-CTLA-4 antibody) as described herein to a patient in need of such treatment, and anti-CTLA-4 antibodies (or pharmaceutical composition comprising an anti-CTLA-4 antibody) for use in the treatment of cancer (tumor growth inhibition) and/or viral infections. The antibodies of the present invention are useful for the treatment, prevention, and/or amelioration of disease or disorder or condition such as cancer or a viral infection and/or for ameliorating at least one symptom associated with such disease, disorder or condition. In the context of the methods of treatment described herein, the anti-CTLA-4 antibody may be administered as a monotherapy (i.e., as the only therapeutic agent) or in combination with one or more additional therapeutic agents (examples of which are described elsewhere herein).

In some embodiments of the invention, the antibodies described herein are useful for treating subjects suffering from primary or recurrent cancer, including, but not limited to, blood cancer, brain cancer (e.g., glioblastoma multiforme), renal cell carcinoma (e.g., clear cell renal cancer), ovarian cancer, bladder cancer, prostate cancer, breast cancer (e.g., triple negative breast cancer), kidney cancer, cervical cancer, skin cancer, liver cancer, stomach cancer, pancreatic cancer, hepatic cell carcinoma, bone cancer, colon cancer, non-small-cell lung cancer, squamous cell carcinoma of head and neck, colorectal cancer, mesothelioma, and melanoma.

As used herein, the term "blood cancer" includes a hematologic malignancy that affects blood, bone marrow, lymph or lymphatic system. As such, the term includes malignancies of cells from the lymphoid and myeloid cell lineages. The myeloid cell line normally produces granulocytes, erythrocytes, thrombocytes, macrophages, and mast cells; the lymphoid cell line produces B, T, NK and plasma cells. The term, therefore, includes malignancies of the above-mentioned cells, viz. lymphomas, myelomas, lymphoid leukemias and myelogenous leukemias. Examples include, but are not limited to, acute lymphoblastic leukemia, acute myelogenous leukemia, chronic lymphocytic leukemia, chronic myelogenous leukemia, acute monocytic leukemia, Hodgkin's lymphomas, non-Hodgkin's lymphomas (e.g., B cell lymphoma, diffuse large B cell lymphoma), and myeloma (including multiple myeloma).

The antibodies may be used to treat early stage or late-stage symptoms of cancer. In one embodiment, an antibody or fragment thereof of the invention may be used to treat advanced or metastatic cancer. The antibodies are useful in reducing or inhibiting or shrinking tumor growth of both solid tumors and blood cancers. In certain embodiments, treatment with an antibody or antigen-binding fragment thereof of the invention leads to more than 40% regression, more than 50% regression, more than 60% regression, more than 70% regression, more than 80% regression or more than 90% regression of a tumor in a subject. In certain embodiments, the antibodies may be used to prevent relapse of a tumor. In certain embodiments, the antibodies are useful in extending progression-free survival or overall survival in a subject with cancer. In some embodiments, the antibodies are useful in reducing toxicity due to chemotherapy or radiotherapy while maintaining long-term survival in a patient suffering from cancer. In certain embodiments, one or more antibodies of the present invention are injected locally into one or more tumor lesions 9 intratumorally or pertumorally), and lead to inhibition of tumor growth in the injected tumor as well as in one or more adjacent or distant tumors in the subject (abscopal effect).

In certain embodiments, the antibodies of the invention are useful to treat subjects suffering from a chronic viral infection. In some embodiments, the antibodies of the invention are useful in decreasing viral titers in the host and/or rescuing exhausted T cells. In certain embodiments, an antibody or fragment thereof of the invention may be used to treat chronic viral infection by lymphocytic choriomeningitis virus (LCMV). In some embodiments, an antibody or antigen-binding fragment thereof the invention may be administered at a therapeutic dose to a patient with an infection by human immunodeficiency virus (HIV) or human papilloma virus (HPV) or hepatitis B/C virus (HBV/HCV). In a related embodiment, an antibody or antigen-binding fragment thereof of the invention may be used to treat an infection by simian immunodeficiency virus (SIV) in a simian subject such as cynomolgus.

In certain embodiments, a blocking antibody of the present invention may be administered in a therapeutically effective amount to a subject suffering from a cancer or a viral infection.

In certain embodiments, one or more antibodies of the present invention are administered locally into a tumor or near a tumor lesion (intratumorally or pertumorally) in a subject with cancer to minimize systemic exposure and to prevent/ameliorate toxicity due to systemic exposure of the antibody.

It is also contemplated herein to use one or more antibodies of the present invention prophylactically to patients at risk for developing a disease or disorder such as cancer, and viral infection.

In a further embodiment of the invention, the present antibodies are used for the preparation of a pharmaceutical composition for treating patients suffering from cancer, or viral infection. In another embodiment of the invention, the present antibodies are used as adjunct therapy with any other agent or any other therapy known to those skilled in the art useful for treating cancer or viral infection.

Combination Therapies and Formulations

Combination therapies may include an anti-CTLA-4 antibody of the invention and any additional therapeutic agent that may be advantageously combined with an antibody of the invention, or with a biologically active fragment of an antibody of the invention.

The antibodies of the present invention may be combined synergistically with one or more anti-cancer drugs or therapy used to treat or inhibit cancer, including, for example, blood cancer, brain cancer (e.g., glioblastoma multiforme), renal cell carcinoma, ovarian cancer, bladder cancer, prostate cancer, breast cancer, hepatic cell carcinoma, bone cancer, skin cancer, cervical cancer, stomach cancer, kidney cancer, colon cancer, non-small-cell lung cancer, squamous cell carcinoma of head and neck, colorectal cancer, mesothelioma, and melanoma. It is contemplated herein to use anti-CTLA-4 antibodies of the invention in combination with immunostimulatory and/or immunosupportive therapies to inhibit tumor growth, and/or enhance survival of cancer patients. The immunostimulatory therapies include direct immunostimulatory therapies to augment immune cell activity by either "releasing the brake" on suppressed immune cells or "stepping on the gas" to activate an immune response. Examples include targeting other checkpoint receptors, vaccination and adjuvants. The immunosupportive modalities may increase antigenicity of the tumor by promoting immunogenic cell death, inflammation or have other indirect effects that promote an anti-tumor immune response. Examples include radiation, chemotherapy, anti-angiogenic agents, and surgery.

In various embodiments, one or more antibodies of the present invention may be used in combination with a PD-1 inhibitor (e.g., an anti-PD-1 antibody such as nivolumab, pembrolizumab, pidilizumab, BGB-A317 or REGN2810), a PD-L1 inhibitor (e.g., an anti-PD-L1 antibody such as avelumab, atezolizumab, durvalumab, MDX-1105, or REGN3504), a LAG3 inhibitor, a TIM3 inhibitor, a BTLA inhibitor, a TIGIT inhibitor, a CD47 inhibitor, a CD28 inhibitor, a CSF1R inhibitor, a CXCR inhibitor, a CCR4 inhibitor, a CCR8 inhibitor, a CD40 inhibitor, a OX40 inhibitor, a GITR inhibitor, an antagonist of another T cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), a CD20 inhibitor (e.g., an anti-CD20 antibody such as rituximab), an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], a vaccine (e.g., *Bacillus* Calmette-Guerin, a cancer vaccine), an adjuvant to increase antigen presentation (e.g., granulocyte-macrophage colony-stimulating factor), a bispecific antibody (e.g., CD3×CD20 bispecific antibody, or PSMAxCD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, surgery, radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, an antibody-drug conjugate (ADC) (e.g., anti-CD19-DM4 ADC, and anti-DS6-DM4 ADC), an anti-inflammatory drug (e.g., corticosteroids, and non-steroidal anti-inflammatory drugs), a dietary supplement such as anti-oxidants or any other therapy care to treat cancer. In certain embodiments, the anti-CTLA-4 antibodies of the present invention may be used in combination with cancer vaccines including dendritic cell vaccines, oncolytic viruses, tumor cell vaccines, etc. to augment the anti-tumor response. Examples of cancer vaccines that can be used in combination with anti-CTLA-4 antibodies of the present invention include MAGE3 vaccine for melanoma and bladder cancer, MUC1 vaccine for breast cancer, EGFRv3 (e.g., Rindopepimut) for brain cancer (including glioblastoma multiforme), or ALVAC-CEA (for CEA+ cancers).

In certain embodiments, the anti-CTLA-4 antibodies of the invention may be administered in combination with radiation therapy in methods to generate long-term durable anti-tumor responses and/or enhance survival of patients with cancer. In some embodiments, the anti-CTLA-4 antibodies of the invention may be administered prior to, concomitantly or after administering radiation therapy to a cancer patient. For example, radiation therapy may be administered in one or more doses to tumor lesions followed by administration of one or more doses of anti-CTLA-4 antibodies of the invention. In some embodiments, radiation therapy may be administered locally to a tumor lesion to enhance the local immunogenicity of a patient's tumor (adjuvinating radiation) and/or to kill tumor cells (ablative radiation) followed by systemic administration of an anti-CTLA-4 antibody of the invention. For example, intracranial radiation may be administered to a patient with brain cancer (e.g., glioblastoma multiforme) in combination with systemic administration of an anti-CTLA-4 antibody of the invention. In certain embodiments, the anti-CTLA-4 antibodies of the invention may be administered in combination with radiation therapy and a chemotherapeutic agent (e.g., temozolomide) or a VEGF antagonist (e.g., aflibercept). In certain embodiments, the anti-CTLA-4 antibodies of the invention may be administered in combination with radiation therapy and a chemotherapeutic agent (e.g., temozolomide) or a PD-1 inhibitor (e.g., an anti-PD-1 antibody such as REGN2810, nivolumab, or pembrolizumab).

In certain embodiments, the anti-CTLA-4 antibodies of the invention may be administered in combination with one or more anti-viral drugs to treat chronic viral infection caused by LCMV, HIV, HPV, HBV or HCV. Examples of anti-viral drugs include, but are not limited to, zidovudine, lamivudine, abacavir, ribavirin, lopinavir, efavirenz, cobicistat, tenofovir, rilpivirine and corticosteroids.

The additional therapeutically active agent(s)/component(s) may be administered prior to, concurrent with, or after the administration of the anti-CTLA-4 antibody of the present invention. For purposes of the present disclosure, such administration regimens are considered the administration of an anti-CTLA-4 antibody "in combination with" a second therapeutically active component.

The additional therapeutically active component(s) may be administered to a subject prior to administration of an anti-CTLA-4 antibody of the present invention. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an anti-CTLA-4 antibody of the present invention. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of an anti-CTLA-4 antibody of the present invention. "Concurrent" administration, for purposes of the present invention, includes, e.g., administration of an anti-CTLA-4 antibody and an additional therapeutically active component to a subject in a single dosage form (e.g., co-formulated), or in separate dosage forms administered to the subject within about 30 minutes or less of each other. If administered in separate dosage forms, each dosage form may be administered via the same route (e.g., both the anti-CTLA-4 antibody and the additional therapeutically active component may be administered intravenously, subcutaneously, etc.); alternatively, each dosage form may be administered via a different route (e.g., the anti-CTLA-4 antibody may be administered intravenously, and the additional therapeutically active component may be administered subcutaneously). In any event, administering the components in a single dosage from, in separate dosage forms by the same route, or in separate dosage forms by different routes are all considered "concurrent administration," for purposes of the present disclosure. For purposes of the present disclosure, administration of an anti-CTLA-4 antibody "prior to", "concurrent with," or "after" (as those terms are defined herein above) administration of an additional therapeutically active component is considered administration of an anti-CTLA-4 antibody "in combination with" an additional therapeutically active component).

The present invention includes pharmaceutical compositions in which an anti-CTLA-4 antibody of the present invention is co-formulated with one or more of the additional therapeutically active component(s) as described elsewhere herein using a variety of dosage combinations.

In exemplary embodiments in which an anti-CTLA-4 antibody of the invention is administered in combination with a PD-1 inhibitor (e.g., an anti-PD-1 antibody as disclosed in US 2015/0203579, herein incorporated by reference in its entirety), including administration of co-formulations comprising an anti-CTLA-4 antibody and a PD-1 inhibitor, the individual components may be administered to a subject and/or co-formulated using a variety of dosage combinations. Thus, the present invention includes a combination of (i) an anti-CTLA-4 antibody of the invention, and (ii) a PD-1 inhibitor (e.g., an anti-PD-1 antibody as disclosed in US 2015/0203579, herein incorporated by reference in its entirety), for simultaneous, separate and/or sequential use in the treatment of cancer or viral infections. For example, the anti-CTLA-4 antibody and the PD-1 inhibitor (e.g., an anti-PD-1 antibody) each may be administered to a subject and/or contained in a co-formulation in an amount selected from the group consisting of 0.01 mg/kg, 0.02 mg/kg, 0.03 mg/kg, 0.04 mg/kg, 0.05 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg, 5.0 mg/kg, 6.0 mg/kg, 7.0 mg/kg, 8.0 mg/kg, 9.0 mg/kg, and 10.0 mg/kg. In one embodiment, the anti-CTLA-4 antibody and the PD-1 inhibitor (e.g., an anti-PD-1 antibody) each may be administered to a subject and/or contained in a co-formulation in an amount from about 50 mg to about 600 mg, e.g., an amount selected from the group consisting of 50 mg, 100 mg, 200 mg, 250 mg, 300 mg, 350 mg, 400 mg, 450 mg, 500 mg, 550 mg, and 600 mg. The combinations/co-formulations may be administered to a subject according to any of the administration regimens disclosed elsewhere herein, including, e.g., twice a week, once every week, once every 2 weeks, once every 3 weeks, once every month, once every 2 months, once every 3 months, once every 4 months, once every 5 months, once every 6 months, etc. The anti-CTLA-4 antibody of the invention might, for instance, be administered at a dose of about 0.8 to about 11, about 1 to about 10, about 3 to about 10, about 1, about 3 or about 10 mg/kg, simultaneously with an PD-1 inhibitor (e.g. an anti-PD-1 antibody as disclosed in US 2015/0203579) at a dose of about 3 to 5, or about 3.0 mg/kg. The simultaneous administration might for instance occur every 14 days, 21 days or 28 days.

In exemplary embodiments in which an anti-CTLA-4 antibody of the invention is administered in combination with an anti-PD-1 antibody and a VEGF antagonist (e.g., a VEGF trap such as aflibercept), including administration of co-formulations comprising an anti-CTLA-4 antibody, an anti-PD-1 antibody, and a VEGF antagonist, the individual components may be administered to a subject and/or co-formulated using a variety of dosage combinations. For example, the anti-CTLA-4 antibody and/or anti-PD-1 antibody may be administered to a subject and/or contained in a co-formulation in an amount selected from the group consisting of 0.01 mg, 0.02 mg, 0.03 mg, 0.04 mg, 0.05 mg, 0.1 mg, 0.2 mg, 0.3 mg, 0.4 mg, 0.5 mg, 0.6 mg, 0.7 mg, 0.8 mg, 0.9 mg, 1.0 mg, 1.5 mg, 2.0 mg, 2.5 mg, 3.0 mg, 3.5 mg, 4.0 mg, 4.5 mg, 5.0 mg, 6.0 mg, 7.0 mg, 8.0 mg, 9.0 mg, and 10.0 mg; and the VEGF antagonist (e.g., a VEGF trap such as aflibercept) may be administered to the subject and/or contained in a co-formulation in an amount selected from the group consisting of 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg and 3.0 mg. The combinations/co-formulations may be administered to a subject according to any of the administration regimens disclosed elsewhere herein, including, e.g., twice a week, once every week, once every 2 weeks, once every 3 weeks, once every month, once every 2 months, once every 3 months, once every 4 months, once every 5 months, once every 6 months, etc.

Administrative Regimens

According to certain embodiments of the present invention, multiple doses of an anti-CTLA-4 antibody (or a pharmaceutical composition comprising a combination of an anti-CTLA-4 antibody and any of the additional therapeutically active agents mentioned herein) may be administered to a subject over a defined time course. The methods according to this aspect of the invention comprise sequentially administering to a subject multiple doses of an anti-CTLA-4 antibody of the invention. As used herein, "sequentially administering" means that each dose of anti-CTLA-4 antibody is administered to the subject at a different point in time, e.g., on different days separated by a predetermined interval (e.g., hours, days, weeks or months). The present invention includes methods which comprise sequentially administering to the patient a single initial dose of an anti-CTLA-4 antibody, followed by one or more secondary doses of the anti-CTLA-4 antibody, and optionally followed by one or more tertiary doses of the anti-CTLA-4 antibody. The anti-CTLA-4 antibody may be administered at a dose between 0.1 mg/kg to 100 mg/kg body weight of the subject.

The terms "initial dose," "secondary doses," and "tertiary doses," refer to the temporal sequence of administration of the anti-CTLA-4 antibody of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-CTLA-4 antibody, but generally may differ from one another in terms of frequency of administration. In certain embodiments, however, the amount of anti-CTLA-4 antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain embodiments, the amount of anti-CTLA-4 antibody contained in the initial, secondary and/or tertiary doses may be sub-optimal or sub-therapeutic. As used herein, the terms "sub-therapeutic" or "sub-optimal" refer to an antibody dose administered at too low a level to produce a therapeutic effect or below the level necessary to treat a disease such as cancer.

In certain exemplary embodiments of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-CTLA-4 antibody which is administered to a patient prior to the administration of the very next dose in the sequence with no intervening doses.

The methods according to this aspect of the invention may comprise administering to a patient any number of secondary and/or tertiary doses of an anti-CTLA-4 antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antibodies

The anti-CTLA-4 antibodies of the present invention may be used to detect and/or measure CTLA-4 in a sample, e.g., for diagnostic purposes. Some embodiments contemplate the use of one or more antibodies of the present invention in assays to detect a disease or disorder such as cancer, autoimmune disease or viral infection. Exemplary diagnostic assays for CTLA-4 may comprise, e.g., contacting a sample, obtained from a subject (e.g., a patient), with an anti-CTLA-4 antibody of the invention, wherein the anti-CTLA-4 antibody is labeled with a detectable label or reporter molecule or used as a capture ligand to selectively isolate CTLA-4 from subject samples. Alternatively, an unlabeled anti-CTLA-4 antibody can be used in diagnostic applications in combination with a secondary antibody which is itself detectably labeled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure CTLA-4 in a sample include enzyme-linked immunosorbent assay (ELISA), radioimmunoassay (RIA), and fluorescence-activated cell sorting (FACS).

Samples that can be used in CTLA-4 diagnostic assays according to the present invention include any tissue or fluid sample obtainable from a subject, which contains detectable quantities of either CTLA-4 protein, or fragments thereof, under normal or pathological conditions. Generally, levels of CTLA-4 in a particular sample obtained from a healthy patient (e.g., a patient not afflicted with cancer or an autoimmune disease) will be measured to initially establish a baseline, or standard, level of CTLA-4. This baseline level of CTLA-4 can then be compared against the levels of CTLA-4 measured in samples obtained from individuals suspected of having a cancer-related condition, or symptoms associated with such condition.

The antibodies specific for CTLA-4 may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

Aspects of the invention relate to use of the disclosed antibodies as markers for predicting prognosis of cancer or a viral infection in patients. Antibodies of the present invention may be used in diagnostic assays to evaluate prognosis of cancer in a patient and to predict survival.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Generation of Human Antibodies to CTLA-4

Human antibodies to CTLA-4 were generated using either a human CTLA-4 protein (Cat. No.: 7268-CT, R&D Systems) or DNA encoding hCTLA-4 (Accession No: NM_005214.4). The immunogen was administered directly, with an adjuvant to stimulate the immune response, to a VELOCIMMUNE® mouse (i.e., an engineered mouse comprising DNA encoding human Immunoglobulin heavy and kappa light chain variable regions), as described in U.S. Pat. No. 8,502,018 B2. The antibody immune response was monitored by a CTLA-4-specific immunoassay. When a desired immune response was achieved splenocytes were harvested and fused with mouse myeloma cells to preserve their viability and form hybridoma cell lines. The hybridoma cell lines were screened and selected to identify cell lines that produce CTLA-4-specific antibodies. Using this technique, and the immunogen described above, several anti-CTLA-4 chimeric antibodies (i.e., antibodies possessing human variable domains and mouse constant domains) were obtained; exemplary antibodies generated in this manner from the VELOCIMMUNE® mice were designated as H1M20370N, H1M20372N, H1M20393N, H2M20361N, H2M20368N, H2M20369N, H2M20373N, H2M20375N, H2M20379N, H2M20385N, H2M20386N, and H2M20387N.

Anti-CTLA-4 antibodies were also isolated directly from antigen-positive B cells (from either of the immunized mice) without fusion to myeloma cells, as described in U.S. Pat. No. 7,582,298, herein specifically incorporated by reference in its entirety. Using this method, several fully human anti-CTLA-4 antibodies (i.e., antibodies possessing human variable domains and human constant domains) were obtained; exemplary antibodies generated in this manner were designated as follows: H1H19264P, H1H19269P, H1H19273P, H1H19274P, H1H19278P, H1H19279P, H1H19280P, H1H19281P, H1H19283P, H1H19284P, H1H19291P, H1H19294P, H1H19303P, H1H19305P, H1H19307P, H1H19312P, H1H19313P, H1H19314P2, H1H19319P2, and H1H19327P2.

The biological properties of the exemplary antibodies generated in accordance with the methods of this Example are described in detail in the Examples set forth below.

Example 2: Heavy and Light Chain Variable Region Amino Acid and Nucleotide Sequences Table 1 sets forth the amino acid sequence identifiers of the heavy and light chain variable regions and CDRs of selected anti-CTLA-4 antibodies of the invention. The corresponding nucleic acid sequence identifiers are set forth in Table 2.

TABLE 1

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H19264P | 2 | 4 | 6 | 8 | 10 | 12 | 14 | 16 |
| H1H19269P | 18 | 20 | 22 | 24 | 26 | 28 | 30 | 32 |
| H1H19273P | 34 | 36 | 38 | 40 | 42 | 44 | 46 | 48 |
| H1H19274P | 50 | 52 | 54 | 56 | 58 | 60 | 62 | 64 |
| H1H19278P | 66 | 68 | 70 | 72 | 74 | 76 | 78 | 80 |
| H1H19279P | 82 | 84 | 86 | 88 | 90 | 92 | 94 | 96 |
| H1H19280P | 98 | 100 | 102 | 104 | 106 | 108 | 110 | 112 |
| H1H19281P | 114 | 116 | 118 | 120 | 122 | 124 | 126 | 128 |
| H1H19283P | 130 | 132 | 134 | 136 | 138 | 140 | 142 | 144 |
| H1H19284P | 146 | 148 | 150 | 152 | 154 | 156 | 158 | 160 |
| H1H19291P | 162 | 164 | 166 | 168 | 170 | 172 | 174 | 176 |
| H1H19294P | 178 | 180 | 182 | 184 | 186 | 188 | 190 | 192 |
| H1H19303P | 194 | 196 | 198 | 200 | 202 | 204 | 206 | 208 |
| H1H19305P | 210 | 212 | 214 | 216 | 218 | 220 | 222 | 224 |
| H1H19307P | 226 | 228 | 230 | 232 | 234 | 236 | 238 | 240 |
| H1H19312P | 242 | 244 | 246 | 248 | 250 | 252 | 254 | 256 |
| H1H19313P | 258 | 260 | 262 | 264 | 266 | 268 | 270 | 272 |
| H1H19314P2 | 274 | 276 | 278 | 280 | 282 | 284 | 286 | 288 |
| H1H19319P2 | 290 | 292 | 294 | 296 | 298 | 300 | 302 | 304 |
| H1H19327P2 | 306 | 308 | 310 | 312 | 298 | 300 | 302 | 304 |
| H1M20370N | 314 | 316 | 318 | 320 | 322 | 324 | 326 | 328 |
| H1M20372N | 330 | 332 | 334 | 336 | 338 | 340 | 342 | 344 |
| H1M20393N | 346 | 348 | 350 | 352 | 354 | 356 | 358 | 360 |
| H2M20361N | 362 | 364 | 366 | 368 | 370 | 372 | 374 | 376 |
| H2M20368N | 378 | 380 | 382 | 384 | 386 | 388 | 390 | 392 |
| H2M20369N | 394 | 396 | 398 | 400 | 402 | 404 | 406 | 408 |
| H2M20373N | 410 | 412 | 414 | 416 | 418 | 420 | 422 | 424 |
| H2M20375N | 426 | 428 | 430 | 432 | 434 | 436 | 438 | 440 |
| H2M20379N | 442 | 444 | 446 | 448 | 450 | 452 | 454 | 456 |
| H2M20385N | 458 | 460 | 462 | 464 | 466 | 468 | 470 | 472 |
| H2M20386N | 474 | 476 | 478 | 480 | 482 | 484 | 486 | 488 |
| H2M20387N | 490 | 492 | 494 | 496 | 498 | 500 | 502 | 504 |

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H19264P | 1 | 3 | 5 | 7 | 9 | 11 | 13 | 15 |
| H1H19269P | 17 | 19 | 21 | 23 | 25 | 27 | 29 | 31 |
| H1H19273P | 33 | 35 | 37 | 39 | 41 | 43 | 45 | 47 |
| H1H19274P | 49 | 51 | 53 | 55 | 57 | 59 | 61 | 63 |
| H1H19278P | 65 | 67 | 69 | 71 | 73 | 75 | 77 | 79 |
| H1H19279P | 81 | 83 | 85 | 87 | 89 | 91 | 93 | 95 |
| H1H19280P | 97 | 99 | 101 | 103 | 105 | 107 | 109 | 111 |
| H1H19281P | 113 | 115 | 117 | 119 | 121 | 123 | 125 | 127 |
| H1H19283P | 129 | 131 | 133 | 135 | 137 | 139 | 141 | 143 |
| H1H19284P | 145 | 147 | 149 | 151 | 153 | 155 | 157 | 159 |

TABLE 2-continued

| | Nucleic Acid Sequence Identifiers | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H1H19291P | 161 | 163 | 165 | 167 | 169 | 171 | 173 | 175 |
| H1H19294P | 177 | 179 | 181 | 183 | 185 | 187 | 189 | 191 |
| H1H19303P | 193 | 195 | 197 | 199 | 201 | 203 | 205 | 207 |
| H1H19305P | 209 | 211 | 213 | 215 | 217 | 219 | 221 | 223 |
| H1H19307P | 225 | 227 | 229 | 231 | 233 | 235 | 237 | 239 |
| H1H19312P | 241 | 243 | 245 | 247 | 249 | 251 | 253 | 255 |
| H1H19313P | 257 | 259 | 261 | 263 | 265 | 267 | 269 | 271 |
| H1H19314P2 | 273 | 275 | 277 | 279 | 281 | 283 | 285 | 287 |
| H1H19319P2 | 289 | 291 | 293 | 295 | 297 | 299 | 301 | 303 |
| H1H19327P2 | 305 | 307 | 309 | 311 | 297 | 299 | 301 | 303 |
| H1M20370N | 313 | 315 | 317 | 319 | 321 | 323 | 325 | 327 |
| H1M20372N | 329 | 331 | 333 | 335 | 337 | 339 | 341 | 343 |
| H1M20393N | 345 | 347 | 349 | 351 | 353 | 355 | 357 | 359 |
| H2M20361N | 361 | 363 | 365 | 367 | 369 | 371 | 373 | 375 |
| H2M20368N | 377 | 379 | 381 | 383 | 385 | 387 | 389 | 391 |
| H2M20369N | 393 | 395 | 397 | 399 | 401 | 403 | 405 | 407 |
| H2M20373N | 409 | 411 | 413 | 415 | 417 | 419 | 421 | 423 |
| H2M20375N | 425 | 427 | 429 | 431 | 433 | 435 | 437 | 439 |
| H2M20379N | 441 | 443 | 445 | 447 | 449 | 451 | 453 | 455 |
| H2M20385N | 457 | 459 | 461 | 463 | 465 | 467 | 469 | 471 |
| H2M20386N | 473 | 475 | 477 | 479 | 481 | 483 | 485 | 487 |
| H2M20387N | 489 | 491 | 493 | 495 | 497 | 499 | 501 | 503 |

Antibodies are typically referred to herein according to the following nomenclature: Fc prefix (e.g. "H1M," "H4H," etc.), followed by a numerical identifier (e.g. "19264," "20370," etc., as shown in Table 1), followed by a "P," "P2," or "N" suffix. Thus, according to this nomenclature, an antibody may be referred to herein as, e.g., "H1M20370N," "H1H19264P," "H1H19314P2," etc. The H1H prefix on the antibody designations used herein indicates the particular Fc region isotype of the antibody. For example, an "H1H" antibody has a human IgG1 Fc, an "H1M" antibody has a mouse IgG1 Fc, and an "H2M" antibody has a mouse IgG2 Fc (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG1 or a human IgG4, etc.), but in any event, the variable domains (including the CDRs)—which are indicated by the numerical identifiers shown in Table 1—will remain the same, and the binding properties to antigen are expected to be identical or substantially similar regardless of the nature of the Fc domain.

Control Constructs:
Two control constructs (anti-CTLA4 antibodies) were included in the following experiments for comparative purposes:
COMP1: a human anti-CTLA-4 antibody with heavy and light chain variable domains having the amino acid sequences of the corresponding domains of "10D1", as set forth in WO 01/14424 A2 (Bristol Myers Squibb) and produced with a hIgG1 Fc.
COMP2: a human anti-CTLA-4 antibody with heavy and light chain variable domains having the amino acid sequences of the corresponding domains of "11.2.1", as set forth in US 2014/099325 A1 (Pfizer) and produced with a hIgG2 Fc.

Example 3: Surface Plasmon Resonance Derived Binding Affinities and Kinetic Constants of Human Monoclonal Anti-CTLA-4 Antibodies Binding affinities and kinetic constants of human anti-CTLA-4 antibodies were determined by surface plasmon resonance (Biacore 4000 (GE, Pittsburgh, PA) or MASS-1 (Sierra Sensors, Greenville, RI)) at 25° C. (Tables 3 and 4). Antibodies expressed as human IgG1, (i.e., "H1H") were captured onto a CM5 sensor surface (GE) derivatized by amine coupling with a monoclonal mouse-anti-human Fc antibody (GE). Antibodies expressed as mouse IgG1 or mouse IgG2 (i.e., "H1M", "H2M") were captured onto a high-capacity amine sensor surface (Sierra Sensors) derivatized by amine coupling with a polyclonal goat anti-mouse Fc antibody (GE). Various concentrations of soluble human (h) CTLA-4 (SEQ ID NO: 506) or *Macaca fasicularis* (mf) CTLA-4 (SEQ ID NO: 507) proteins expressed with a c-terminus myc-myc-polyhistidine tag (mmh) were injected over the anti-CTLA-4 mAb captured sensor surfaces at a flow rate of 30 or 50 uL/minute. CTLA-4 is a homodimer interconnected by one disulfide bond in the extracellular domain at cysteine residue 157.

All binding studies were performed in a buffer composed of 0.01M HEPES pH 7.4, 0.15M NaCl, 3 mM EDTA, 0.05% v/v Surfactant P20 (HBS-ET running buffer). Association of hCTLA4.mmh or mfCTLA4.mmh to the captured monoclonal antibody was monitored for 4 or 5 min and the dissociation of hCTLA4.mmh or mfCTLA4.mmh in HBS-ET running buffer was monitored for 10 min.

Kinetic association ($k_a$) and dissociation ($k_d$) rate constants were determined by fitting the real-time sensorgrams to a 1:1 binding model using Scrubber 2.0c curve fitting software. Binding equilibrium dissociation constants ($K_D$) and dissociative half-lives (t1/2) were calculated from the kinetic rate constants as:

$$K_D(M) = \frac{kd}{ka}, \text{ and } t1/2 \, (\text{min}) = \frac{\ln(2)}{60 * kd}$$

As shown in Table 3, all the anti-CTLA-4 antibodies of this invention bound to human CTLA-4, many with nanomolar affinity to hCTLA-4.mmh, and displayed cross-reactivity to cynomolgus CTLA-4 protein. Cross reactivity to mouse or rat CTLA-4 protein was not observed (data not shown).

TABLE 3

Biacore binding affinities of human Fc mAbs at 25° C.
Binding at 25 C./ Mab Capture Format

| AbPID | Analyte * | ka (1/Ms) | kd (l/s) | KD (M) | t1/2 (min) |
|---|---|---|---|---|---|
| H1H19264P | hCTLA-4.mmh | 6.04E+04 | 7.31E−04 | 1.21E−08 | 15.8 |
|  | mf CTLA-4.mmh | 4.90E+04 | 9.94E−04 | 2.03E−08 | 11.6 |
| H1H19269P | hCTLA-4.mmh | 3.94E+05 | 4.74E−04 | 1.20E−09 | 24.4 |
|  | mf CTLA-4.mmh | 3.56E+05 | 4.35E−04 | 1.22E−09 | 26.6 |
| H1H19273P | hCTLA-4.mmh | 3.74E+05 | 3.62E−04 | 9.66E−10 | 31.9 |
|  | mf CTLA-4.mmh | 3.62E+05 | 3.46E−04 | 9.56E−10 | 33.4 |
| H1H19274P | hCTLA-4.mmh | 5.30E+05 | 7.60E−04 | 1.43E−09 | 15.2 |
|  | mf CTLA-4.mmh | 5.22E+05 | 4.63E−04 | 8.87E−10 | 25 |
| H1H19278P | hCTLA-4.mmh | 1.79E+05 | 4.02E−04 | 2.25E−09 | 28.8 |
|  | mf CTLA-4.mmh | 1.66E+05 | 1.01E−03 | 6.11E−09 | 11.4 |
| H1H19279P | hCTLA-4.mmh | 3.46E+05 | 2.61E−04 | 7.52E−10 | 44.3 |
|  | mf CTLA-4.mmh | 3.40E+05 | 2.59E−04 | 7.63E−10 | 44.6 |
| H1H19280P | hCTLA-4.mmh | 3.37E+05 | 3.46E−04 | 1.03E−09 | 33.4 |
|  | mf CTLA-4.mmh | 3.20E+05 | 3.09E−04 | 9.64E−10 | 37.4 |
| H1H19281P | hCTLA-4.mmh | 4.84E+05 | 7.41E−04 | 1.53E−09 | 15.6 |
|  | mf CTLA-4.mmh | 4.72E+05 | 1.01E−03 | 2.14E−09 | 11.5 |
| H1H19283P | hCTLA-4.mmh | 2.21E+05 | 8.28E−04 | 3.75E−09 | 14 |
|  | mf CTLA-4.mmh | 2.20E+05 | 6.83E−04 | 3.11E−09 | 16.9 |
| H1H19284P | hCTLA-4.mmh | 1.48E+05 | 3.69E−04 | 2.49E−09 | 31.3 |
|  | mf CTLA-4.mmh | 1.94E+05 | 3.05E−04 | 1.57E−09 | 37.9 |
| H1H19291P | hCTLA-4.mmh | 8.88E+04 | 1.23E−03 | 1.38E−08 | 9.4 |
|  | mf CTLA-4.mmh | 9.31E+04 | 1.21E−03 | 1.30E−08 | 9.6 |
| H1H19294P | hCTLA-4.mmh | 2.85E+05 | 3.23E−04 | 1.13E−09 | 35.7 |
|  | mf CTLA-4.mmh | 2.63E+05 | 2.69E−04 | 1.02E−09 | 43 |
| H1H19303P | hCTLA-4.mmh | 1.21E+05 | 1.99E−03 | 1.64E−08 | 5.8 |
|  | mf CTLA-4.mmh | 1.56E+05 | 2.45E−03 | 1.57E−08 | 4.7 |
| H1H19305P | hCTLA-4.mmh | 2.89E+05 | 1.21E−03 | 4.19E−09 | 9.5 |
|  | mf CTLA-4.mmh | 2.84E+05 | 9.02E−04 | 3.18E−09 | 12.8 |
| H1H19307P | hCTLA-4.mmh | 2.17E+05 | 2.84E−04 | 1.31E−09 | 40.6 |
|  | mf CTLA-4.mmh | 2.09E+05 | 2.92E−04 | 1.40E−09 | 39.5 |
| H1H19312P | hCTLA-4.mmh | 3.20E+05 | 1.05E−03 | 3.29E−09 | 11 |
|  | mf CTLA-4.mmh | 3.33E+05 | 7.60E−04 | 2.28E−09 | 15.2 |
| H1H19313P | hCTLA-4.mmh | 4.89E+05 | 7.58E−04 | 1.55E−09 | 15.2 |
|  | mf CTLA-4.mmh | 4.75E+05 | 4.64E−04 | 9.76E−10 | 24.9 |
| H1H19314P2 | hCTLA-4.mmh | 1.15E+05 | 1.13E−03 | 9.87E−09 | 10.2 |
|  | mf CTLA-4.mmh | 1.07E+05 | 9.13E−04 | 8.57E−09 | 12.6 |
| H1H19319P2 | hCTLA-4.mmh | 1.43E+05 | 1.46E−03 | 1.02E−08 | 7.9 |
|  | mf CTLA-4.mmh | 2.03E+05 | 2.61E−03 | 1.29E−08 | 4.4 |
| H1H19327P2 | hCTLA-4.mmh | 8.81E+03 | 5.85E−04 | 6.63E−08 | 19.8 |
|  | mf CTLA-4.mmh | 1.88E+05 | 1.17E−02 | 6.24E−08 | 1 |
| H1H20361N | hCTLA-4.mmh | 6.21E+04 | 1.99E−03 | 3.21E−08 | 5.8 |
|  | mf CTLA-4.mmh | ND | ND | ND | ND |
| H1H20361N2 | hCTLA-4.mmh | 5.39E+04 | 2.51E−03 | 4.65E−08 | 4.6 |
|  | mf CTLA-4.mmh | ND | ND | ND | ND |
| H1H20370N | hCTLA-4.mmh | 1.72E+05 | 5.88E−04 | 3.43E−09 | 19.6 |
|  | mf CTLA-4.mmh | ND | ND | ND | ND |
| H1H20370N2 | hCTLA-4.mmh | 5.13E+04 | 1.21E−03 | 2.36E−08 | 9.5 |
|  | mf CTLA-4.mmh | ND | ND | ND | ND |
| H1H20372N | hCTLA-4.mmh | 8.05E+04 | 3.67E−04 | 4.55E−09 | 31.5 |
|  | mf CTLA-4.mmh | ND | ND | ND | ND |
| H1H20373N | hCTLA-4.mmh | 5.23E+05 | 4.01E−04 | 7.66E−10 | 28.8 |
|  | mf CTLA-4.mmh | ND | ND | ND | ND |
| H1H20375N | hCTLA-4.mmh | 4.19E+04 | 2.79E−03 | 6.65E−08 | 4.1 |
|  | mf CTLA-4.mmh | ND | ND | ND | ND |
| H1H20380N2 | hCTLA-4.mmh | 1.37E+06 | 3.20E−04 | 2.33E−10 | 36.2 |
|  | mf CTLA-4.mmh | ND | ND | ND | ND |
| H1H20386N | hCTLA-4.mmh | 1.85E+05 | 1.94E−03 | 1.05E−08 | 6 |
|  | mf CTLA-4.mmh | ND | ND | ND | ND |
| H1H20386N2 | hCTLA-4.mmh | 1.35E+05 | 1.68E−03 | 1.24E−08 | 6.9 |
|  | mf CTLA-4.mmh | ND | ND | ND | ND |

* h and mf CTLA-4 mmh proteins were flown over mAb-captured surfaces at concentrations ranging from 0.37 nM to 90 nM in 3-fold dilutions;
ND = Not Determined

Example 4: Anti-CTLA-4 Antibodies Block the Interaction Between Human CTLA-4 and its Natural Ligands, B7-1 and B7-2

CTLA-4 (cytotoxic T-lymphocyte-associated protein 4) is a type I transmembrane T cell inhibitory checkpoint receptor expressed on conventional and regulatory T cells. CTLA-4 negatively regulates T cell activation by outcompeting the stimulatory receptor CD28 from binding to its natural ligands, B7-1 (CD80) and B7-2 (CD86). In this example, the ability of anti-CTLA-4 antibodies to block CTLA-4 protein binding to plate-bound B7-1 and B7-2 was assessed using competition sandwich Enzyme-linked Immunosorbent Assays (ELISA). Various concentrations of anti-CTLA-4 antibody were pre-mixed with a constant amount of dimeric CTLA-4 protein and the reduction of the CTLA-4 binding to the plate immobilized B7-1 or B7-2, due to the presence of the antibody, was monitored.

Briefly, assays were performed using the following procedure: Human B7-1 and B7-2 proteins, expressed with c-terminal human IgG1 and 6×Histidine (hIgG1-6×His; R&D Systems, Minneapolis, MN) were separately coated at 2 μg/mL in PBS on a 96-well microtiter plate overnight (ON) at 4° C. Nonspecific binding sites were subsequently blocked using a 0.5% (w/v) solution of BSA in PBS. Separately, a constant amount of 200 pM or 400 pM of recombinant hCTLA-4-mFc protein (human CTLA-4 extracellular domain expressed with a c-terminal Fc portion of mouse IgG2a, SEQ ID NO: 508) was added to serially diluted anti-CTLA-4 antibodies, or solutions with no antibody present. In this example, anti-CTLA-4 antibody doses ranged from 1.7 pM to a maximum of either 100 nM or 1.0 uM. Next, after 1 h at room temperature (RT), antibody-protein complexes with 200 pM constant concentration of hCTLA-4-mFc protein were transferred to microtiter plates coated with hB7-1-hIgG1-6His, and antibody-protein complexes with 400 pM constant concentration of hCTLA-4-mFc were transferred to hB7-2-hIgG1-6His coated plates. After a subsequent 1 h incubation at RT, wells were washed, and plate-bound hCTLA-4-mFc was detected with anti-mouse Fcγ-fragment specific goat polyclonal antibodies conjugated with horseradish peroxidase (HRP) (JacksonImmunoResearch, West Grove, PA). Plates were developed using TMB substrate solution (BD Biosciences, San Jose, CA) according to manufacturer's instructions and absorbance was measured at 450 nm on a Victor plate reader (PerkinElmer™, Waltham, MA).

All data analysis was performed using a sigmoidal dose-response model within Prism™ software (GraphPad, LaJolla, CA). Calculations were performed as follows: $IC_{50}$, defined as the concentration of antibody required to reduce 50% of hCTLA-4 binding to hB7-1 or B7-2, was used as an indicator of blocking potency. Percent blockade at maximum concentration of the antibody tested (100 nM or 1.0 uM) was calculated as the ability of antibodies to block the binding of 200 pM or 400 pM of hCTLA-4-mFc to hB7-1 or hB7-2, respectively, relative to the baseline of the assay. The binding signal of samples with 200 pM or 400 pM of hCTLA-4-mFc in the absence of antibody was referenced as 100% binding or 0% blocking; and the baseline signal of the sample buffer without hCTLA-4-mFc or antibody was referenced as 0% binding or 100% blocking.

As the results in Table 4 show, the anti-CTLA-4 antibodies of this invention display a wide range of ability to block the binding of human CTLA-4 to its natural ligands, B7-1 or B7-2. Exemplary antibodies H1H19273P and H1H19313P potently block the binding of CTLA-4 to B7-1 or B7-2 with picomolar $IC_{50}$ values and with percent blockade of ~100% at 1.0 uM maximum antibody concentration. Several antibodies, such as H1H20373N were stronger blockers of CTLA-4 binding to B7-2 than B7-1, while some antibodies showed minimal blocking ability of either ligand (H1H19314P2).

TABLE 4

Anti-CTLA-4 Antibodies Block the Binding of hCTLA-4 to ligands hB7-1 or hB7-2

| | Ab blocking of 200 pM hCTLA-4-mFc binding to plate-coated hB7-1/CD80-hIgG1-6His | | Ab blocking of 400pM hCTLA-4-mFc binding to plate-coated hB7-2/CD86-hIgG1-6His | |
|---|---|---|---|---|
| | Maximum Ab concentration: 100 nM | | | |
| AbPID | $IC_{50}$ (M) | % Blockade | $IC_{50}$ (M) | % Blockade |
| Blocking ability of Human Fc anti-CTLA-4 antibodies | | | | |
| H1H19264P | — | 8 | — | 43 |
| H1H19269P | 1.0E−10 | 98 | 1.9E−10* | 100 |
| H1H19274P | 1.3E−10 | 99 | 2.5E−10 | 100 |
| H1H19278P | 3.2E−10 | 99 | 5.4E−10 | 100 |
| H1H19279P | 2.1E−10 | 97 | 2.2E−10 | 100 |
| H1H19280P | 1.1E−10 | 99 | 2.0E−10 | 100 |
| H1H19281P | 9.4E−11* | 99 | 1.9E−10* | 100 |
| H1H19283P | 9.7E−09 | 96 | 1.2E−09 | 99 |
| H1H19284P | 1.7E−10 | 98 | 3.1E−10 | 99 |
| H1H19291P | 2.0E−09 | 98 | 2.5E−09 | 99 |
| H1H19294P | 1.5E−10 | 99 | 2.5E−10 | 99 |
| H1H19305P | 1.9E−10 | 98 | 3.6E−10 | 99 |
| H1H19307P | 1.8E−10 | 99 | 2.9E−10 | 99 |
| H1H19312P | 2.0E−10 | 97 | 5.1E−10 | 99 |
| H1H19314P2 | — | 0 | — | 7 |
| H1H19327P2 | — | 7 | — | 38 |
| H1H19273P | 2.5E−10 | 98 | 5.4E−10 | 98 |
| H1H19303P | 1.8E−07 | 90 | 3.9E−08 | 97 |
| H1H19313P | 4.0E−10 | 98 | 7.7E−10 | 99 |
| H1H19319P2 | 3.2E−07 | 85 | 4.3E−08 | 97 |

TABLE 4-continued

Anti-CTLA-4 Antibodies Block the Binding of hCTLA-4 to ligands hB7-1 or hB7-2

| | Ab blocking of 200 pM hCTLA-4-mFc binding to plate-coated hB7-1/CD80-hIgG1-6His | | Ab blocking of 400pM hCTLA-4-mFc binding to plate-coated hB7-2/CD86-hIgG1-6His | |
|---|---|---|---|---|
| | Maximum Ab concentration: 100 nM | | | |
| AbPID | $IC_{50}$ (M) | % Blockade | $IC_{50}$ (M) | % Blockade |
| H1H20370N | 8.6E−10 | 95 | 9.9E−10 | 96 |
| H1H20370N2 | 1.1E−08 | 85 | 9.8E−09 | 92 |
| H1H20372N | 2.5E−09 | 98 | 9.9E−10 | 98 |
| H1H20361N | 6.9E−08 | 73 | 6.5E−08 | 82 |
| H1H20361N2 | 1.2E−07 | 53 | 1.1E−07 | 70 |
| H1H20373N | — | 22 | 3.4E−08 | 91 |
| H1H20375N | — | 13 | — | 29 |
| H1H20380N2 | 5.0E−10 | 98 | 3.8E−10 | 98 |
| H1H20386N | 1.8E−08 | 94 | 7.7E−09 | 96 |
| H1H20386N2 | INC | 59 | 1.7E−07 | 87 |
| Controls | | | | |
| mIgG2a Isotype | — | −6 | — | 1 |
| hIgG1 Isotype | — | 15 | — | 14 |

Negative Max % Blocking (ie −8) indicates an increase of hCTLA-4 binding detected in the presence of antibody.
(—) indicates $IC_{50}$ values not quantitative for antibodies blocking <50% at the highest concentration tested.
(INC): inconclusive: sigmoidal binding curve was not fitted by Prism™ software to calculate $IC_{50}$ value.
(*) Indicates $IC_{50}$ value below the theoretical bottom of assay (0.1 × $10^{-09}$ M for hCTLA-4 binding to hB7-1/CD80, or 0.2 × $10^{-09}$ M for hCTLA-4 binding to hB7-2/CD86)

Example 5: Anti-CTLA-4 Antibodies Display Specific and Potent Binding to Human CTLA-4 Engineered Cell Lines In this example, the ability of anti-human (h) CTLA-4 antibodies to bind specifically to human-CTLA-4 expressing cell lines was determined using electrochemiluminescence (ECL) based detection.

Briefly, mouse embryonic fibroblast cells isolated from Velocimmune® mice (VI-fibroblasts) were stably transfected with human CTLA-4 (amino acids M1-N223, NCBI Accession #NM_005214.4). The non-transfected VI-fibroblast cells have no detectable expression of CTLA-4 by fluorescence activated cell sorting (FACS) and were included as binding controls. Additionally, a reporter T cell line generated by transducing immortal human Jurkat T-cells (ATCC, Manassas, VA) with an NFAT-Luc lentivirus reporter (Qiagen, Germantown, MD) and h, m or mf CTLA-4 chimeric constructs was also assessed in this assay. The chimeric constructs comprised the extracellular domain of either hCTLA-4 (aa 1-161; accession number NP_005205.2), mouse CTLA-4 (ms CTLA-4, amino acids 1-161, accession number NM_009843.4) or mf CTLA-4 (aa from 1-161; accession number XP 005574071.1) fused to the trans-membrane and cytoplasmic domain of hCD300a (aa 181-299; accession number NP_009192.2).

Approximately 2.0×10⁴ VI-fibroblast/hCTLA-4 cells or 1.0×10⁴ Jurkat/NFAT chimera cells were seeded separately onto 96-well carbon electrode plates (MULTI-ARRAY high bind plate, Meso Scale Discovery (MSD; Rockville, MD)) and incubated for 1 hour (h) at 37° C. Nonspecific binding sites were blocked by 2% BSA (w/v) in PBS for 1 hour at room temperature (RT). Serial dilutions of anti-CTLA-4 or isotype control antibodies, ranging from 1.7 pM to 150 nM, or buffer containing no-antibody was added to plate-bound cells for 1 h, RT. Plates were then washed to remove unbound antibodies using an AquaMax2000 plate washer with a cell washing head (MDS Analytical Technologies, Sunnyvale, CA). The plate-bound antibodies were detected with either SULFO-TAG™-conjugated goat polyclonal anti-human IgG antibody specific for heavy and light chains (Jackson Immunoresearch, West Grove, PA) or a SULFO-TAG™-conjugated goat polyclonal anti-mouse IgG antibody specific for Fcγ fragment (Jackson Immunoresearch) for 1 h, RT.

After washes, plates were developed with Read Buffer (MSD) according to manufacturer's recommended procedure and luminescent signals were recorded with a SECTOR Imager 600 (MSD). Luminescence intensity, measured in relative light units (RLU), was recorded to indicate the binding intensity of each antibody at the range of concentrations. The ratio of signal detected with 0.4 nM or 0.6 nM antibody binding to the CTLA-4 engineered cells compared to parental cells at the same concentration was reported as an indication of specificity of CTLA-4 binding.

In addition, direct binding signals (RLU) were analyzed as a function of the antibody concentration and the data were fitted with a sigmoidal (four-parameter logistic) dose-response model using GraphPad Prism™ software (GraphPad, LaJolla, CA). The $EC_{50}$ value, defined as the concentration of antibody at which 50% of the maximal binding signal is detected, was determined to indicate binding potency to CTLA-4 engineered cells.

As the results in Table 5 show, a majority of the anti-CTLA-4 antibodies of this invention bound specifically to the hCTLA-4 engineered cell lines. Several exemplary antibodies, such as H1H19303P and H1H19280P bound with picomolar $EC_{50}$ values and with ratios 20-23-fold above binding to control cell lines.

A selection of antibodies were further assessed for cross reactivity to mouse and cynomolgus monkey engineered cell lines. As the results in Table 6 show, anti-CTLA-4 antibodies H1H19303P, H1H19273P, H1H19319P2 and H1H19319P potently bind to Jurkat/NFAT Luc/human and cynomolgus CTLA-4/hCD300 chimera cell lines, with picomolar EC50 values. No cross-reactivity to mouse CTLA-4 chimera cells was observed.

TABLE 5

Anti-CTLA-4 Antibodies Specifically Bind to Cell Lines Engineered to Express Human CTLA-4

| Ab PID | Cell Binding Potency to VI-fibroblast/hCTLA-4, EC50 (M) | Ratio of RLU Signal binding to VI fibroblast/hCTLA-4 relative to parental VI-fibroblast Ratio at 0.4 nM Ab concentration |
|---|---|---|
| Cell Binding Properties of Human Fc anti-CTLA-4 antibodies | | |
| H1H19264P | NB | 1 |
| H1H19269P (*) | 4.0E−10 | 15 |
| H1H19273P | INC | 11 |
| H1H19274P (*) | 3.9E−10 | 18 |
| H1H19278P | 2.2E−10 | 19 |
| H1H19279P | 2.4E−10 | 18 |
| H1H19280P | 1.3E−09 | 15 |
| H1H19281P | 7.5E−11 | 23 |
| H1H19283P | 7.9E−10 | 7 |
| H1H19284P | INC | 7 |
| H1H19291P | INC | 5 |
| H1H19294P | 6.8E−10 | 10 |
| H1H19303P (*) | 2.1E−10 | 20 |
| H1H19305P (*) | 8.4E−10 | 12 |
| H1H19307P | 3.7E−09 | 7 |
| H1H19312P (*) | 7.0E−10 | 14 |
| H1H19313P (*) | 1.6E−10 | 11 |
| H1H19314P2 (*) | 3.4E−09 | 8 |
| H1H19319P2 | 2.4E−10 | 16 |
| H1H19327P2 | 2.9E−10 | 16 |
| CONTROLS | | |
| hIgG1 Isotype Control | NB | 1 |
| Cell binding properties of Hybridoma CTLA-4 antibodies (H1M, H2M) | | |
| | | Ratio at 0.6 nM Ab concentration |
| H1M20370N | 2.2E−10 | 23 |
| H1M20372N | 8.8E−10 | 14 |
| H1M20393N (*) | 7.3E−09 | 12 |
| H2M20361N | 3.2E−10 | 19 |
| H2M20368N | 2.6E−10 | 25 |
| H2M20369N | 9.0E−10 | 18 |
| H2M20373N | 6.2E−11 | 22 |
| H2M20375N | 1.9E−10 | 18 |
| H2M20379N | 9.2E−11 | 28 |
| H2M20380N | 1.2E−10 | 28 |
| H2M20385N | 5.5E−09 | 8 |
| H2M20386N | INC | 3 |
| H2M20387N | INC | 3 |
| CONTROLS | | |
| COMP1 | INC | 11 |
| mIgG2 Isotype Control | NB | 1 |

NB = non-binder; antibodies with a binding ratio of less than 3 were classified as non-binders
(*) RLU value for highest two antibody concentrations were excluded to calculate EC50 values.
INC = inconclusive, GraphPad Prism ™ cannot fit 4 parameters sigmoidal curve for EC50 value calculation, but antibody specifically bound to CTLA-4 expressing cells with ratios 3-fold or greater above the parental cells.

TABLE 6

Selected Anti-CTLA-4 antibodies Display Specificity of Binding to Engineered Jurkat Human and Monkey Cell Lines

| | Potency of cell binding on Jurkat/NFAT Luc / CTLA-4 | | Ratio of RLU Signal binding to Jurkat/NFAT Luc / CTLA-4 hC300a Chimera for binding to Jurkat/NFAT Luc/cl.3C7 | | |
|---|---|---|---|---|---|
| | hCD300a Chimera, EC50 (M) | | | mf CTLA-4 | |
| Ab PID | hCTLA-4 | mf CTLA-4 | hCTLA-4 0.4 nM | 0.4 nM | ms CTLA-4 0.4 nM |
| H1H19303P (*) | 2.9E−10 | 1.1E−10 | 13 | 17 | 1 |
| H1H19273P (*) | 5.2E−10 | 2.2E−10 | 14 | 20 | 1 |
| H1H19319P2 (*) | 2.8E−10 | 1.7E−10 | 13 | 15 | 1 |
| H1H19313P (*) | 1.1E−10 | 1.4E−10 | 16 | 25 | 1 |
| CONTROLS | | | | | |
| COMP1 | INC | INC | 6 | 8 | 1 |
| hIgG1 Isotype Control | NB | NB | 1 | 1 | 1 |

Monkey = *Macaca fascicularis*.

NB = non-binder; antibodies with a binding ratio of less than 3 were classified as non-binders (*) RLU value for highest two antibody concentrations were excluded to calculate EC50 values.

INC = inconclusive, GraphPad Prism ™ cannot fit 4 parameters sigmoidal curve for EC50 value calculation, but antibody specifically bound to CTLA-4 expressing cells with ratios 3-fold or greater above the parental cells.

Example 6: Anti-CTLA-4 Antibodies Induce T-Cell Activation in Engineered Reporter T-Cell/APC Bioassay Systems In this example, T-cell/Antigen Presenting Cell (APC)-based luciferase reporter bioassays were developed to evaluate the effects of blocking CTLA-4/CD80 or CTLA-4/CD86 interaction and T-cell activation. In one bioassay format, the effect of anti-CTLA-4 antibody administration on the T-cell/APC system was assessed by measuring luciferase activity. In a second assay, the ability of anti-CTLA-4 antibodies to induce Interleukin (IL)-2 release was assessed.

As described in the examples above, the anti-CTLA-4 antibodies tested in this example demonstrated binding to human and cynomolgus monkey (*Macaca fasciularis*) CTLA-4 via surface plasmon resonance (SPR) and exhibited specific and potent binding to cell lines engineered to express human CTLA-4. These selected CTLA-4 antibodies were also previously shown to block the binding of CTLA-4 to B7-1 (CD80) and B7-2 (CD86).

Background

T-cell activation is achieved by stimulating T-cell receptors (TCR) that recognize specific peptides presented by major histocompatibility complex class I or II (MHCI or MHCII) proteins on antigen-presenting cells (APC) (Goldrath et al. 1999). An activated TCR in turn initiates a cascade of signaling events, which can be monitored by reporter genes, driven by various transcription factors such as activator-protein 1 (AP-1), Nuclear Factor of Activated T-cells (NFAT) or Nuclear factor kappa-light-chain-enhancer of activated B cells (NFκB). The T-cell response is then further refined via engagement of co-receptors expressed either constitutively or inducible on T-cells such as CD28, CTLA-4 (Cytotoxic T-Lymphocyte-Associated Protein 4), PD-1 (Programmed Cell Death Protein 1), LAG-3 (Lymphocyte-Activation Gene 3) or other molecules (Sharpe et al. 2002). The co-receptors, CD28 and CTLA-4 compete for the same ligands, CD80 and CD86 expressed on antigen-presenting cells (APC) to which CTLA-4 has a higher affinity than CD28. CTLA-4 functions as a decoy and inhibits the activation of CD28 by sequestering away the ligands leading to reduced T-cell activation. (Alegre et al. 2001 and Walker et al. 2011).

NFAT-Luciferase Activity

Cell line engineering: Reporter T-cells were engineered by transducing immortal human Jurkat T-cells (ATCC), which endogenously express a TCR and CD28 on the cell surface, with an NFAT-Luc lentivirus reporter (Qiagen, Rockville, MD) as per manufacturer's instructions. The lentivirus encodes the firefly luciferase gene under the control of a minimal CMV (Cytomegalovirus) promoter and tandem repeats of the NFAT transcriptional response element (TRE) and a puromycin resistance gene.

After antibiotic selection and single cloning, the Jurkat/NFAT-Luc clonal line 3C7 (Jurkat/NFAT-Luc cl.3C7) was transduced with lentiviral encoding human (h) or monkey (mf—*Macaca fascicularis*) CTLA-4 chimeric proteins. The chimeric construct comprises the extracellular domain of hCTLA-4 (aa 1-161; accession number NP_005205.2) or mfCTLA-4 (aa from 1-161; accession number XP_005574071.1) fused to the trans-membrane and cytoplasmic domain of hCD300a (aa 181-299; accession number NP_009192.2). CD300a is found on immune cells and transmits inhibitory signals via its immuno-receptor tyrosine based inhibition motifs (ITIM) (DeBell et al. 2012). The resulting stable T-cell lines, Jurkat/NFAT-Luc/hCTLA-4-hCD300a and Jurkat/NFAT-Luc/mfCTLA-4-hCD300a, were selected and maintained in RPMI+10% FBS+penicillin+streptomycin+glutamine supplemented with 500 μg/mL G418 and 1 μg/mL puromycin.

Human Raji B-cells (ATCC, Manassas, VA), which endogenously express CD20, Fc gamma receptors (FcγR), CD80 and CD86 on the cell surface, were used as APC cells in the luciferase-based bioassay. Raji cells were maintained in RPMI+10% FBS+penicillin+streptomycin+glutamine supplemented with HEPES and sodium pyruvate.

T-cell/APC stimulation: Reporter T-cells are stimulated via a T-cell activating anti-CD20×CD3 bispecific antibody (REGN2281), which targets CD3 expressed on Jurkat T-cells and CD20 on Raji B-cells. The bispecific mode of binding of REGN2281 leads to an increase of the NFAT coupled reporter gene, luciferase, in the Jurkat/NFAT-Luc T-cells.

In Jurkat/NFAT-Luc/CTLA-hCD300a chimera cells however, maximal activation of the reporter gene with REGN2281 is attenuated due to inhibitory signaling transmitted by the interaction of CTLA-4-hCD300a chimeric receptors with its ligands, CD80/CD86, expressed on Raji cells. In this bioassay, anti-CTLA-4 antibodies blocking the CTLA-4/CD80 and CD86 axis would, in theory, rescue NFAT-Luc activity in the Jurkat reporter cells by disabling the inhibitory signal delivered via the CD300a tail of the chimeric CTLA-4 protein.

In this assay format, anti-CTLA-4 antibodies could simultaneously induce an agonistic signal in Jurkats, triggered by the anchoring of the antibody Fc to FcγR on Raji cells. The blocking of FcγR with saturating levels of IgG molecules or FcγR specific antibodies can reduce the agonistic effect of CTLA-4 antibodies. Therefore, an Fc block step was included in the assay to inhibit the binding of CTLA-4 mabs to FcγR on Raji cells.

Luciferase Assay: 24 h prior to screening, $5 \times 10^5$ reporter T-cells and $7.5 \times 10^5$ Raji APCs were cultured in assay medium (RPMI1640 supplemented with 10% FBS and penicillin+streptomycin+glutamine (PSG)). The following day, anti-CTLA-4 antibodies and isotype matched negative controls (serially diluted 1:3; dose-range 15 pM to 100 nM) were tested in the presence of 100 pM REGN2281 and 10 nM of Fc Block or 10 nM of a human IgG4 isotype control to occupy endogenous FcγRIIb receptors on Raji cells. Serially diluted antibodies were added to corresponding wells in 96 well white flat bottom plates (Nunc/Thermo Fisher, Pittsburgh, PA) containing a fixed concentration of 100 pM REGN2281/10 nM Fc Block or 100 pM REGN2281/10 nM hIgG4 isotype control. Reporter T-cells and Raji APCs were re-suspended at $2 \times 10^6$/mL and T-cells were first added to plates with a final concentration $5 \times 10^4$ cells/well. Plates were incubated for 15-30 minutes at 37° C./5% $CO_2$, followed by the addition of Raji cells with a final concentration of $5 \times 10^4$ cells/well. Samples were incubated for another 4-6 h at 37° C./5% $CO_2$, before the addition of 100 μL ONE-Glo™ (Promega, Madison WI) to detect NFAT-Luc activity. The emitted light was captured in relative light units (RLU) on the multilabel plate reader Victor (PerkinElmer, Waltham, MA). All serial dilutions were tested in duplicates.

The $EC_{50}$ values of CTLA-4 antibodies were determined from a four-parameter logistic equation over a 10-point dose-response curve using GraphPad Prism software (GraphPad, La Jolla, CA). Fold induction was calculated by normalizing the relative RLU values of each sample to the mean of samples containing no CTLA-4 antibody, which was set to 1.

Results: As recorded in Table 7, no increase in reporter gene activity (luciferase) was observed when anti-CTLA-4 antibodies were added to parental Jurkat/NFAT-Luc cl 3C7 cells plus Raji APCs, in the presence of REGN2281+/−Fc block. However, increasing luciferase activity was recorded when anti-CTLA-4 antibodies were added to the Jurkat/NFAT-Luc/h and mf CTLA-4/hCD300 chimera cell lines/Raji APC system, in the presence of REGN2281+/−Fc block. In this bioassay format, anti-CTLA-4 antibodies block the interaction of CTLA-4 on the Jurkat reporter cells with CD80/CD86 expressed endogenously on Raji cells, leading to the induction of the luciferase protein. The anti-CTLA-4 antibodies tested in this assay increase luciferase activity, with maximal values observed in the presence of Fc block, with $EC_{50}$s ranging from 1.77 nM to 7.67 nM. As shown in Table 7, H1H19303P performed better than comparators 1 and 2 as tested.

CTLA-4 T-Cell/APC Human Interleukin 2 (hIL-2) Release Assay

Cell line engineering: The Jurkat/NFAT-Luc clonal line 3C7 (as described above) was transduced with in house made lentiviral sup encoding hCTLA-4 full length protein (accession number NP_005205.2). The resulting stable T-cell line (Jurkat/NFAT-Luc/hCTLA-4 wt) was sorted for high expression by flow cytometry and maintained in RPMI+10% FBS+PSG supplemented with 500 µg/mL G418 and 1 µg/mL puromycin.

Human Embryonic Kidney (HEK) 293 cells (ATCC) were transfected with human CD20 and used for the transduction with lentiviral sups to overexpress hCD80 (aa 1-288; accession number NP_005182.1) or hCD86 (aa 1-329; accession number NP_787058.4) fused to green fluorescent protein (GFP; aa 2-240; accession number WP_031943942.1) with a 4×G4S linker between. After single cloning by limiting dilution, the following resulting clonal lines were generated: HEK293/hCD20/hCD80-GFP clone 1F4 and HEK293/hCD20/hCD86-GFP clone 4G5. Cell lines were maintained in DME+10% FBS+PSG+non-essential-amino-acids (NEAA, Irvine Scientific, Santa Ana, CA) supplemented with 500 µg/mL G418.

T-cell/APC stimulation: Engineered T-cells are stimulated via a T-cell activating bispecific antibody REGN2281, as described above. Binding of REGN2281 to CD3 leads to the clustering of CD3 subunits in complex with the TCR and activates the T-cell, which in turn releases hIL-2. The release of IL-2 can be further mounted by CD28 interaction with its ligands, CD80 or CD86 located on the engineered HEK293 cells. The maximal activation of Jurkat/NFAT-Luc/hCTLA-4 cells is attenuated, due to the competition of CTLA-4 with CD28 for the binding of the ligands CD80/CD86 on HEK293 cells (Carreno et al. 2000).

In this bioassay, antibodies blocking the CTLA-4/CD80 or CD86 interaction would rescue the IL-2 release in engineered Jurkat cells by disabling the inhibitory CTLA-4 arm.

IL-2 release Assay: 24 h prior to screening, engineered T-cells were cultured to $5 \times 10^5$ cells/mL in assay medium (RPMI1640+10% FBS+PSG). The following day, HEK293 cells were washed with D-PBS (Irvine Scientific), detached with trypsin (Specialty Media) and blocked with assay medium. Next, HEK293 cells were treated with assay medium containing 50 µg/mL of Mitomycin C to arrest cell growth, for 1 h at 37° C./5% $CO_2$. Cells were subsequently washed thoroughly with assay medium to remove free Mitomycin C.

The anti-CTLA-4 antibodies and their isotype controls were serially diluted 1:3 in assay medium, with a 10-point dilution ranging from 15 pM to 100 nM. Serially diluted antibodies were added to corresponding wells in a 96 well round bottom plates (Nunc) containing a fixed concentration of 300 pM REGN2281. Reporter T-cells were added to plates with a final concentration $1 \times 10^5$ cells/well. Plates were incubated for 15-30 min at 37° C./5% $CO_2$, followed by the addition of HEK293 cells with a final concentration of $2.5 \times 10^3$ cells/well. Plates were incubated for 72 h at 37° C./5% $CO_2$ and supernatants were collected and used for IL-2 measurements. IL-2 levels were measured using the AlphaLISA kit (PerkinElmer) according to manufacturer's protocol. The measurements were acquired on the multilabel plate reader Envision (PerkinElmer). All serial dilutions were tested in duplicates.

The $EC_{50}$ values of the CTLA-4 mAbs were determined from a four-parameter logistic equation over a 10-point dose-response curve using GraphPad Prism. The fold induction was calculated by normalizing the relative IL-2 values of each sample to the samples containing no anti-CTLA-4 antibody. Table 9 shows the fold induction reached at 100 nM and the calculated $EC_{50}$ values reached in the hIL-2 release assay.

Results: As the results in Table 8 show, the anti-CTLA-4 antibodies tested in this assay induce IL-2 production in the Jurkat/NFAT-Luc/CTLA-4 chimera//Raji APC system. At 100 nM concentration, anti-CTLA-4 antibodies induce IL-2 production with fold activities ranging from 4 to 6× above that observed in the assay system using CTLA-4 negative reporter T-cells. As shown in Table 8, H1H19303P performed better than comparators 1 and 2 as tested.

Summary

In summary, selected anti-CTLA-4 antibodies were tested in two engineered T cell/10360US02 APC bioassay systems designed to assess the activity of the antibodies on T-cell activation. In one format, anti-CTLA-4 antibodies activated T-cells as measured by an increase in NFAT-Luciferase activity, indicating that the antibodies block the interaction between CTLA-4 and ligands CD80 and CD86. In a second format, the anti-CTLA-4 antibodies induced production of IL-2, indicating that anti-CTLA-4 antibodies can block the CTLA-4/CD80 and CTLA-4/CD86 interaction, thereby rescuing IL-2 release.

TABLE 7

EC$_{50}$ of CTLA-4 mabs in CTLA-4 T-cell/APC luciferase assay

| | Assay System | | | | | |
|---|---|---|---|---|---|---|
| | T cell: Parental Jurkat/NFATLuc cl.3C7 [M] APC: Raji | | T cell: Jurkat/NFAT-Luc hCTLA-44/hCD300 [M] APC: Raji | | T cell: Jurkat/NFAT-Luc mfCTLA-4/hCD300 [M] APC: Raji | |
| Antibody 100 nM | −Fc Block | +Fc Block | −Fc Block | +Fc Block | −Fc Block | +Fc Block |
| H1H19273P | — | — | 2.74E−09 | 3.83E−09 | 3.05E−09 | 1.83E−09 |
| H1H19291P | — | — | 2.36E−09 | 3.92E−09 | — | 7.67E−09 |
| H1H19313P | — | — | 1.69E−09 | 3.47E−09 | 1.34E−09 | 1.84E−09 |
| H1H19303P | — | — | 1.61E−09 | 1.73E−09 | 1.28E−09 | 1.77E−09 |
| H1H19319P2 | — | — | 2.47E−09 | 4.18E−09 | — | 4.91E−09 |
| H1H19327P2 | — | — | 4.20E−09 | 5.49E−09 | — | 5.76E−09 |
| COMP1 | — | — | 3.20E−09 | 3.30E−09 | — | 3.00E−09 |
| COMP2 | — | — | 1.97E−09 | 2.07E−09 | 1.11E−09 | 1.70E−09 |
| hIgG1 Isotype | — | — | — | — | — | — |
| hIgG2 Isotype | — | — | — | — | — | — |

(—) indicates EC$_{50}$ values could not be determined from the fitted curve

TABLE 8

Fold induction at 100 nM CTLA-4 mabs and EC$_{50}$ of CTLA-4 mabs in CTLA-4 T-cell/APC IL-2 release assay

| | Assay System | | | | | |
|---|---|---|---|---|---|---|
| | T cell: Parental Jurkat/NFATLuc cl.3C7 APC: HEK293/hCD20 | | T cell: Jurkat/NFAT-Luc hCTLA-44/hCD300 APC: HEK293/hCD20/hCD80 | | T cell: Jurkat/NFAT-Luc mfCTLA-4/hCD300 APC: HEK293/hCD20/hCD86 | |
| Antibody 100 nM | EC50 [M] | Fold at 100 nM | EC50 [M] | Fold at 100 nM | EC50 [M] | Fold at 100 nM |
| H1H19273P | — | 0.9 | 3.33E−08 | 5.1 | 1.14E−08 | 6.5 |
| H1H19303P | — | 1.1 | 4.09E−08 | 5.4 | 4.09E−08 | 4.4 |
| H1H19313P | — | 0.9 | 2.19E−08 | 5.7 | 2.19E−08 | 6.1 |
| H1H19319P2 | — | 1.6 | 1.56E−08 | 4.2 | 1.56E−08 | 6.4 |
| COMP1 | — | 1.3 | 1.83E−08 | 4.1 | 4.63E−08 | 6.3 |
| COMP2 | — | 0.9 | 1.17E−08 | 5.0 | 9.71E−08 | 5.0 |
| hIgG1 Isotype | — | 1.2 | — | 0.8 | — | 1.1 |
| hIgG2 Isotype | — | 0.8 | — | 1.0 | — | 1.0 |

(—) indicates EC$_{50}$ values could not be determined from the fitted curve

Example 7: Efficacy of Anti-CTLA-4 Antibodies Against Tumors

This Example describes the anti-tumor efficacy of exemplary anti-CTLA-4 antibodies of the invention against MC38.Ova tumors grown in mice humanized for the CTLA-4 gene.

Human CTLA-4$^{hum/hum}$ knock-in mice were engineered on a C57BL/6 strain background using VelociGene™ technology, wherein the mice express a chimeric protein comprising the human CTLA-4 extracellular domain fused to mouse CTLA-4 transmembrane and cytoplasmic domains from the endogenous Ctla4 locus (Valenzuela et al 2003; Nat. Biotechnol. 21: 652-659). The MC38.Ova cell line was engineered by stable lentiviral transduction of MC38 cells to express transmembrane chicken ovalbumin antigen (Ova).

Study (A)
CTLA-4$^{hum/hum}$ knock-in mice were implanted subcutaneously (SC) with MC38.Ova cells (10$^6$ cells/mouse) on day 0 and received 10 mg/kg of either H1H19273P, or H1H19303P, or H1H19319 or 10 mg/kg of hIgG1 isotype control IP on days 3, 7, 10, 14 and 17. Tumor volumes and tumor-free animals were monitored for up to 37 days.

Figure 2:
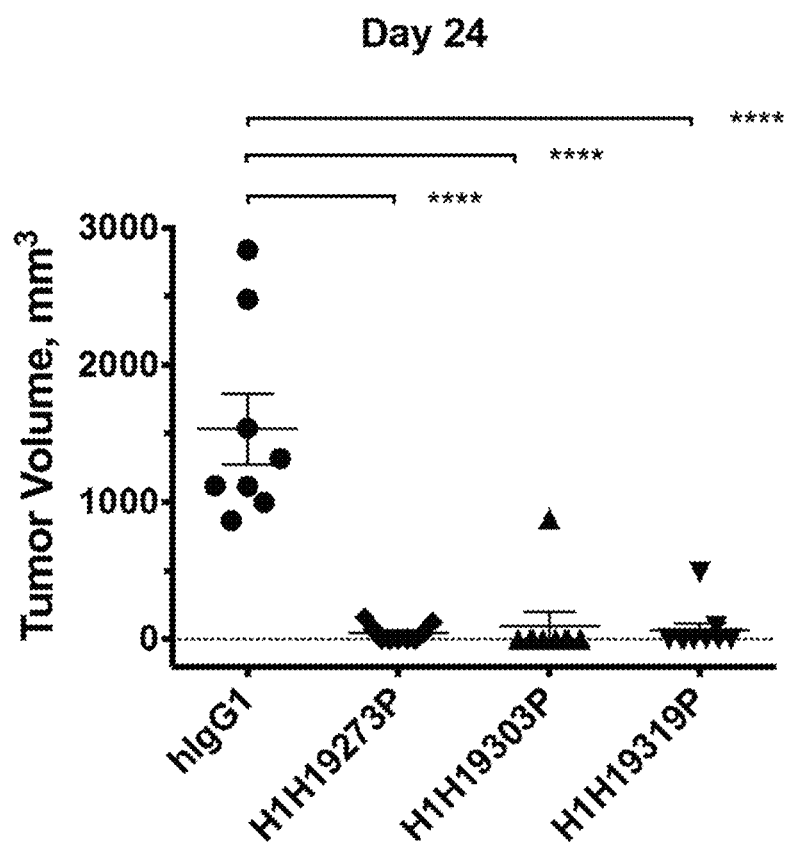
FIG. 2 shows individual tumor volumes at day 24 for the experiment described in Study (A) in Example 7. Day 24 was the last time point in the study when all animals in all groups were alive. Statistical significance was determined by one-way ANOVA with Dunnett's multiple comparisons post-test (****$p<0.0001$).

All three anti-CTLA-4 antibodies showed partial tumor growth inhibition tested at 10 mg/kg compared to treatment with isotype control (FIG. 1). Treatment with H1H19303P resulted in 8 out of 9 (89%) mice tumor-free in 10 mg/kg dose group by day 24 (FIG. 2). Treatments with either H1H19319P or H1H19273P were similarly efficacious, resulting in complete tumor growth inhibition in 7 out of 9 mice (78%) and 5 out of 9 mice (56%) respectively by day 24. None of the animals was tumor-free in the isotype control treated group at day 24. Tumor volumes at day 24 were significantly smaller (p<0.0001) for each anti-CTLA-4 antibody treatment group compared to the group administered the isotype control.

Figure 3:
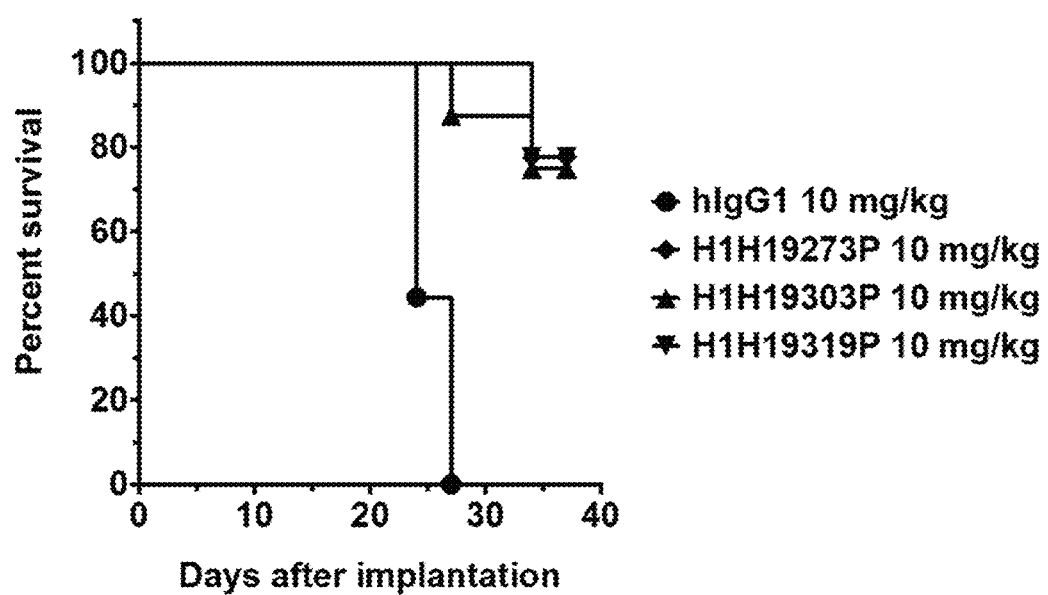
FIG. 3 shows Kaplan-Meier survival curves for the experiment described in Study (A) in Example 7.

Mice observed to be tumor-free at day 24 were monitored for 37 days post-implantation. The survival rate was significantly higher in mice treated with either of anti-human CTLA-4 antibodies (p<0.0001) compared to mice administered an isotype control (FIG. 3). No tumor recurrence was observed in all tumor-free mice from anti-CTLA-4 antibody groups. No evidence of body weight loss was observed as a result of antibody treatment.

In summary, treatment with each of the three anti-human CTLA-4 antibodies (H1H19273P, H1H19303P, and H1H19319) resulted in reduced tumor growth, improved tumor clearance and improved survival compared to isotype control. Efficacy of each of the three anti-human CTLA-4 antibodies in this model was comparable.

Study (B)

The exemplary anti-CTLA-4 antibody used for this study is a fully human antibody that binds specifically to human CTLA-4 and comprises HCDR1-HCDR2-HCDR3-LCDR1-LCDR2-LCDR3 of SEQ ID NOs: 196-198-200-204-206-208 and HCVR/LCVR of SEQ ID Nos: 194/202 (also known as H1H19303P). The full-length heavy chain amino acid sequence of H1H19303P (also known as REGN4659) is shown in SEQ ID NO: 509, and the full-length light chain amino acid sequence of H1H19303P is shown in SEQ ID NO: 510 (Table 9).

TABLE 9

Amino acid sequences of H1H19303P

| Ab region | Amino acid sequence |
|---|---|
| HCVR | SEQ ID NO: 194<br>EVQLVESGGGLVQPGGSLRLSCAASGFTFSNYEMSWVRQAP<br>GKGLEWVSSIRTSGTTKYYADSMKGRFTISRDNAKNSLYLQ<br>MNSLRAEDTAVYYCAGGGTFLHYWGQGTLVTVSS |
| LCVR | SEQ ID NO: 202<br>DIQMTQSPSSVSASVGDRVTITCRASQGIASYLAWYQQKPG<br>KAPKLLIYAASSLQTGVPSRFSGSGYGTDFTLTISSLQPED<br>FATYYCQQAKSFPMYTFGQGTKLEIK |
| HCDR1 | SEQ ID NO: 196<br>GFTFSNYE |
| HCDR2 | SEQ ID NO: 198<br>IRTSGTTK |
| HCDR3 | SEQ ID NO: 200<br>AGGGTFLHY |
| LCDR1 | SEQ ID NO: 204<br>QGIASY |
| LCDR2 | SEQ ID NO: 206<br>AAS |
| LCDR3 | SEQ ID NO: 208<br>QQAKSFPMYT |
| HC | SEQ ID NO: 509<br>*EVQLVESGGGLVQPGGSLRLSCAASGFTFSNYEMSWVRQA<br>PGKGLEWVSSIRTSGTTKYYADSMKGRFTISRDNAKNSLYL<br>QMNSLRAEDTAVYYCAGGGTFLHYWGQGTLVTVSSASTKGP<br>SVFPLAPSSKSTSGGTAALGCLVKDYFPEPVTVSWNSGALT<br>SGVHTFPAVLQSSGLYSLSSVVTVPSSSLGTQTYICNVNHK<br>PSNTKVDKKVEPKSCDKTHTCPPCPAPELLGGPSVFLFPPK<br>PKDTLMISRTPEVTCVVVDVSHEDPEVKFNWYVDGVEVHNA<br>KTKPREEQYNSTYRVVSVLTVLHQDWLNGKEYKCKVSNKAL<br>PAPIEKTISKAKGQPREPQVYTLPPSRDELTKNQVSLTCLV<br>KGFYPSDIAVEWESNGQPENNYKTTPPVLDSDGSFFLYSKL<br>TVDKSRWQQGNVFSCSVMHEALHNHYTQKSLSLSPGK |
| LC | SEQ ID NO: 510<br>*DIQMTQSPSSVSASVGDRVTITCRASQGIASYLAWYQQKP<br>GKAPKLLIYAASSLQTGVPSRFSGSGYGTDFTLTISSLQPE<br>DFATYYCQQAKSFPMYTFGQGTKLEIKRTVAAPSVFIFPPS<br>DEQLKSGTASVVCLLNNFYPREAKVQWKVDNALQSGNSQES<br>VTEQDSKDSTYSLSSTLTLSKADYEKHKVYACEVTHQGLSS<br>PVTKSFNRGEC |

*the underlined sequence is the variable region

Administration and Analysis of Anti-Tumor Activity of Anti-CTLA-4 Antibodies

The anti-tumor activity of H1H19303P was tested at different doses in MC38.Ova tumor-bearing CTLA-4$^{hum/hum}$ knock-in mice. A hIgG1 isotype control was included as a negative control. CTLA-4$^{hum/hum}$ knock-in mice were implanted SC in the hind flank with $1\times10^6$ MC38.Ova cells on day 0 and separated into four treatment groups (Table 10). Mice were administered H1H19303P, or a hIgG1 isotype control IP on days 3, 6, 9, 13 and 16. Tumor volumes were measured by caliper twice per week for 37 days. Tumor-bearing mice were sacrificed with $CO_2$ either at day 37 or at the following endpoints: tumor volumes >2000 mm$^3$ or tumor ulceration. Tumor-free mice were followed for up to 107 days for a survival study.

TABLE 10

Dosing scheme for efficacy study in CTLA-4$^{hum/hum}$ knock-in mice implanted with MC38.Ova Cells

| Treatment Groups | Dose | No. of Mice/ Group | Route of Administration | Dosing Schedule | Bleed Schedule$^a$ |
|---|---|---|---|---|---|
| H1H19303P | 2 mg/kg | 8 | IP | Days 3, 6, 9, 13, and 16 | Days −2, 6, 13, 20 |
| H1H19303P | 5 mg/kg | 8 | | | |
| H1H19303P | 10 mg/kg | 8 | | | |
| hIgG1 Isotype Control | 10 mg/kg | 7 | | | |

$^a$Serum samples were analyzed for antibody levels by ELISA. Samples collected at days 6, 13, and 20 were analyzed for the 10 mg/kg H1H19303P and hIgG1 control groups, and samples collected at days 6 and 20 were analyzed for the 2 mg/kg and 5 mg/kg dose groups for H1H19303P.

Blood samples were collected from the submandibular vein two days before the start of the experiment (day −2) and two hours before antibody administration on days 6, 13 and 20. Serum samples were frozen and stored for subsequent measurements of serum antibody levels.

Statistical analysis was performed using GraphPad Prism software (Version 6). Statistical significance for differences in tumor volumes between animal groups was determined by one-way ANOVA with Dunnett's multiple comparisons post-hoc test. Statistical significance for tumor-free survival was determined by log-rank (Mantel-Cox) test. To determine whether each group was significantly different from the control group, the two group Mantel-Cox analysis was run with the significance level ($\alpha$=0.05) adjusted for number of comparisons (k=6) using the Bonferroni method ($\alpha_{adjusted}$=0.05/6).

Serum Concentration of Total Human IgG Antibody

The serum concentration of total H1H19303P and hIgG1 isotype control antibody was determined using a sandwich ELISA specific for the detection of human Fcγ. Serum samples collected at days 6, 13, and 20 were analyzed for the 10 mg/kg H1H19303P and hIgG1 control groups, and samples collected at days 6 and 20 were analyzed for the 2 mg/kg and 5 mg/kg dose groups for H1H19303P. Briefly, goat anti-human Fcγ polyclonal antibody at 1 µg/mL in PBS was passively adsorbed to a microtiter plate overnight at 4° C. followed by a nonspecific binding block with 5% BSA in PBS. The standard used for calibration in this assay was H1H19303P, or isotype control antibody at concentrations ranging from 2.7 to 350 ng/mL (1:2 serial dilution). Serial dilutions of standards and serum samples were prepared in dilution buffer (0.5% BSA in PBS). Samples were then added to the anti-hFcγ-coated plate (100 μL/well) and incubated for 1 hour at room temperature. Subsequently, plate-captured human IgG antibodies were detected using 160 ng/mL of an HRP-conjugated anti-hFcγ polyclonal antibody in dilution buffer. The chromogenic HRP-substrate, 3,3′,5,5′-tetramethylbenzidine (TMB) was used to detect HRP activity, and the resultant $OD_{450}$ was read on a Perkin Elmer Victor X4 Multimode Plate Reader. The lowest concentration of standard (H1H19303P, or isotype control antibody) used for calibration (2.7 ng/mL) was within the dynamic range of the assay and was defined as this assay's LLOQ. Data were analyzed by non-linear regression using Graph-Pad Prism software. Average concentrations from 2 replicate experiments were used for analysis.

Serum Concentration of Mouse Anti-Human Antibodies

Anti-H1H19303P or anti-IgG1 control antibody mouse IgG titers were determined using a sandwich ELISA specific for the detection of each of the antibodies injected. Serum samples collected at days 6, 13, and 20 were analyzed for the 10 mg/kg H1H19303P and hIgG1 control groups, and samples collected at days 6 and 20 were analyzed for the 2 mg/kg and 5 mg/kg dose groups for H1H19303P. Briefly, H1H19303P or anti-IgG1 control antibody at 1 μg/mL in PBS were passively adsorbed to a microtiter plate overnight at 4° C. followed by a nonspecific binding block with 5% bovine serum albumin (BSA) in PBS. Serial dilutions of serum samples were prepared in dilution buffer (0.5% BSA in PBS) starting from 1:500. Therefore, the corresponding dilution factor (500) was defined as the assay's lower limit of detection (LOD). Samples were then added to the H1H19303P or anti-IgG1 control antibody-coated plates (100 μL/well) and incubated 16-18 hours at 4° C. Wells with addition of dilution buffer only were included to determine the assay background. Subsequently, plate-captured mouse IgG was detected using horseradish peroxidase (HRP)-conjugated goat anti-mouse Fcγ polyclonal antibody at 40 ng/mL. The chromogenic HRP-substrate, TMB was used to detect HRP activity, and the resultant optical density at 450 nm ($OD_{450}$) was read on a Perkin Elmer Victor X4 Multimode Plate Reader. Data of binding signal versus dilution factor were analyzed by non-linear regression using Graph-Pad Prism software and titers were calculated. The MAHA titer was defined as the calculated dilution factor of the serum sample corresponding to a binding signal equivalent to twice the background signal of the assay.

Results

CTLA-4$^{hum/hum}$ knock-in mice were implanted SC with MC38.Ova cells on day 0 and received 2, 5, or 10 mg/kg H1H19303P or 10 mg/kg hIgG1 isotype control IP on days 3, 6, 9, 13 and 16. Tumor volumes were monitored for 37 days, and tumor-free animals were monitored for up to 107 days.

Figure 4:
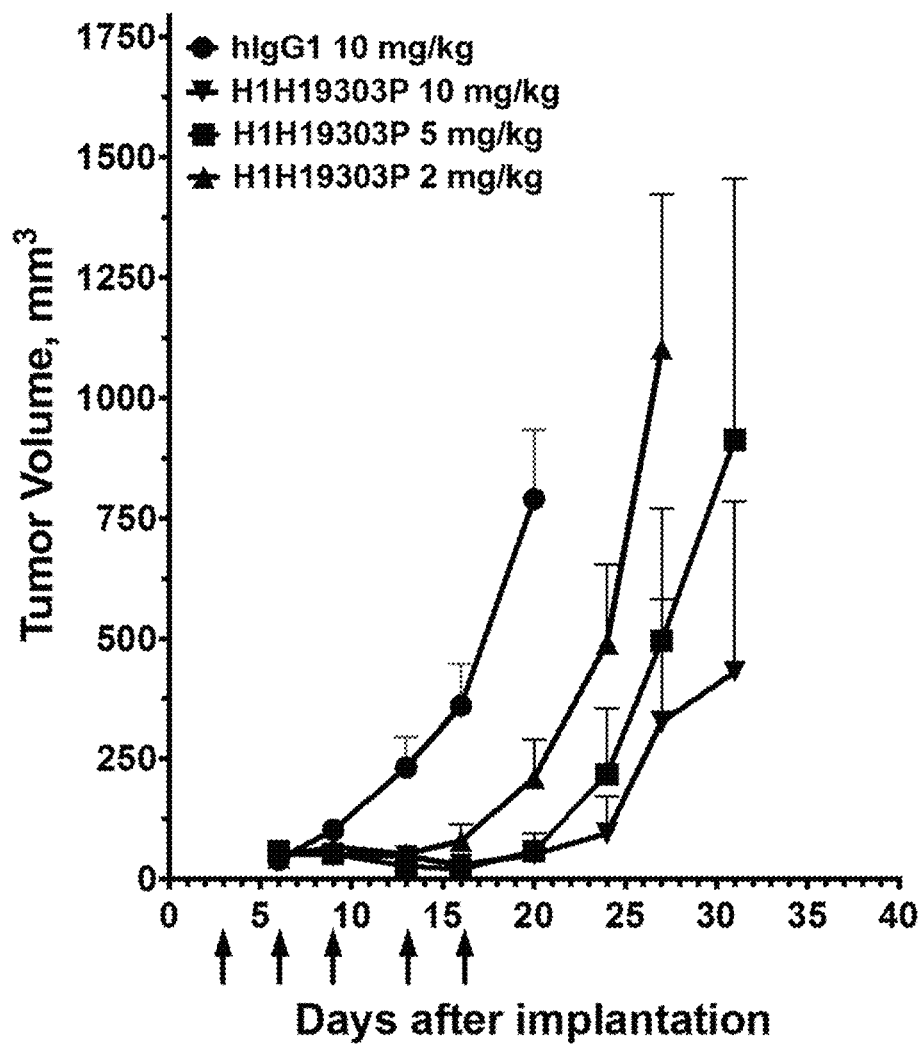
FIG. 4 shows average tumor volumes (mm³+/−SEM) in each treatment group at multiple post-tumor implantation time points for the experiment described in Study (B) in Example 7. CTLA-4$^{hum/hum}$ knock-in mice were administered anti-CTLA-4 antibody H1H19303P or an hIgG1 isotype control IP on days 3, 6, 9, 13 and 16. Tumor volumes were monitored by caliper measurements twice per week for 37 days. Treatment days are indicated by arrows.
Figure 5:
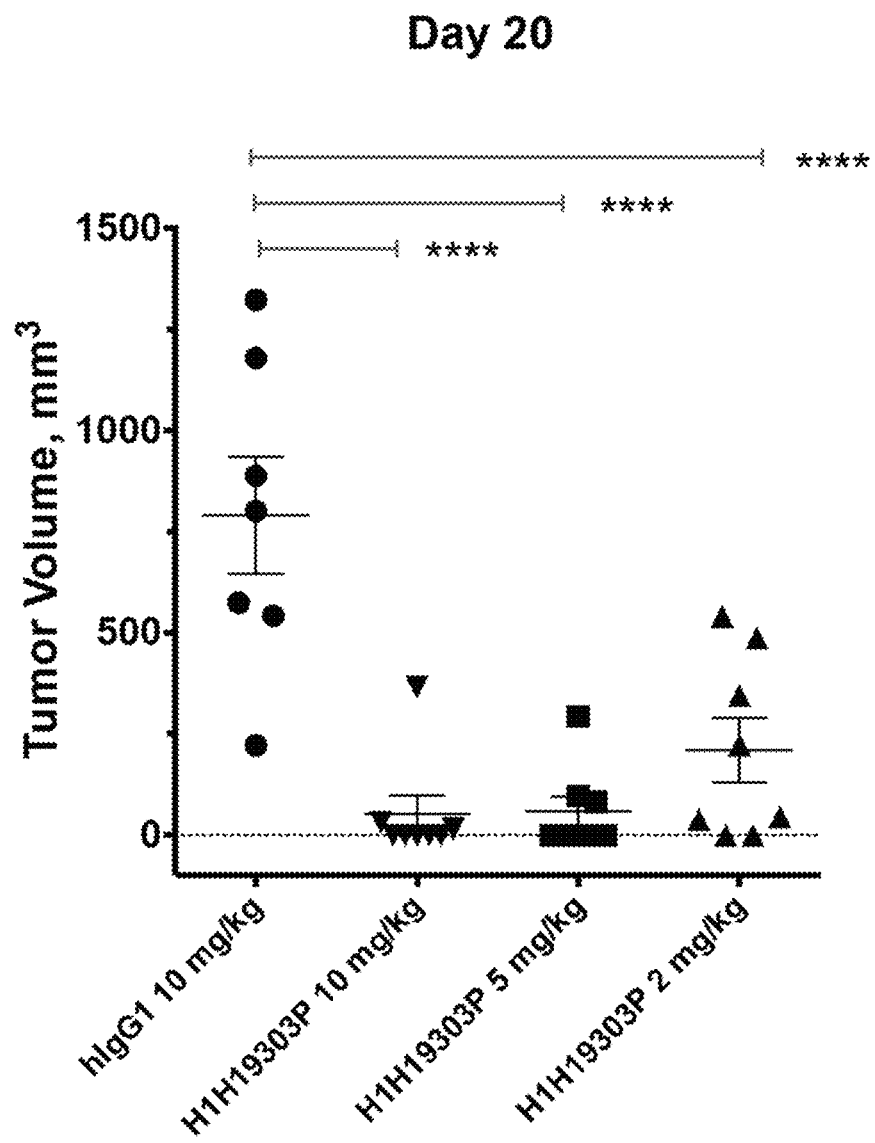
FIG. 5 shows individual tumor volumes at day 20 for the experiment described in Study (B) in Example 7. Statistical significance was determined by one-way ANOVA with Dunnett's multiple comparisons post-test (****p<0.0001).

H1H19303P showed partial tumor growth inhibition at all doses tested (FIG. 4) compared to treatment with isotype control. Treatment with H1H19303P resulted in 5 out of 8 (63%) mice tumor-free in both the 5 mg/kg and 10 mg/kg dose groups and 2 out of 8 (25%) mice tumor-free in the 2 mg/kg dose group by day 20. Tumor volumes at day 20 were significantly smaller (p<0.0001) for H1H19303P treatment groups compared to the group administered the isotype control (FIG. 5).

Figure 6:
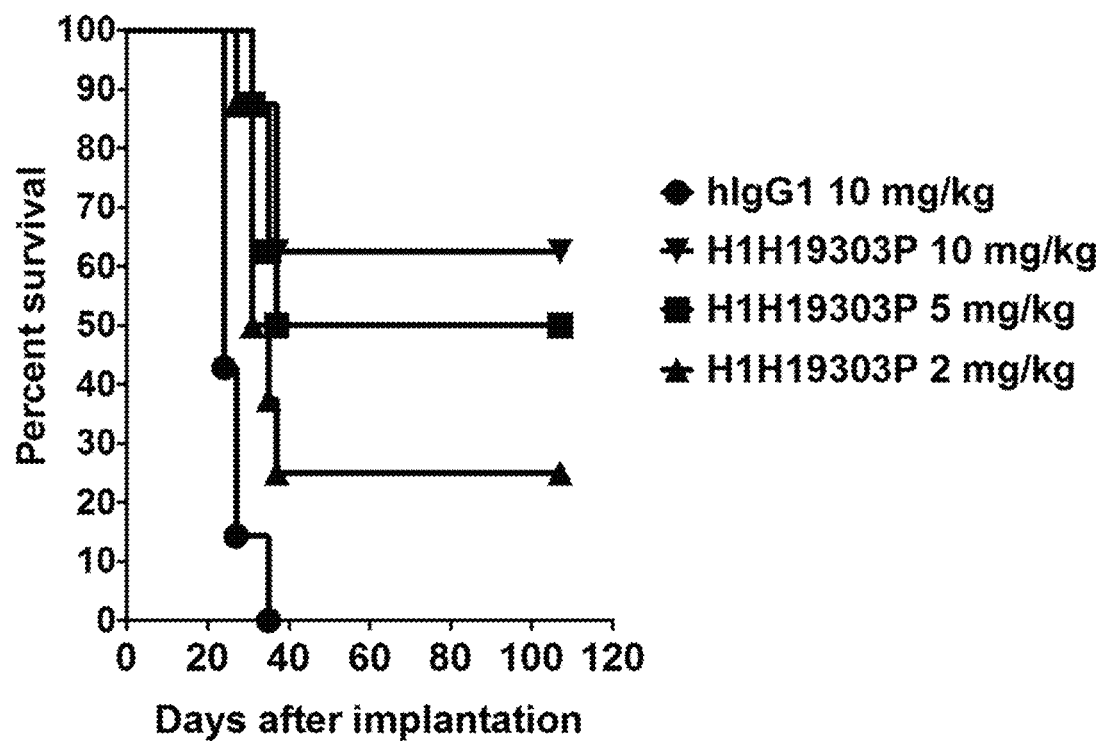
FIG. 6 shows Kaplan-Meier survival curves for the experiment described in Study (B) in Example 7.

Mice observed to be tumor-free at day 20 were monitored for up to 107 days post-implantation. The survival rate was significantly higher in mice treated with H1H19303P (p<0.0001) compared to mice administered an isotype control (FIG. 6). No tumor recurrence was observed in 24 out of 25 tumor-free mice from all dose groups. No evidence of body weight loss was observed as a result of antibody treatment.

In summary, prophylactic treatment with H1H19303P significantly reduced tumor growth in a dose-dependent manner, improved tumor clearance and improved survival compared to isotype control.

Evaluation of Serum Antibody Concentrations and MAHA by ELISA

Figure 7:
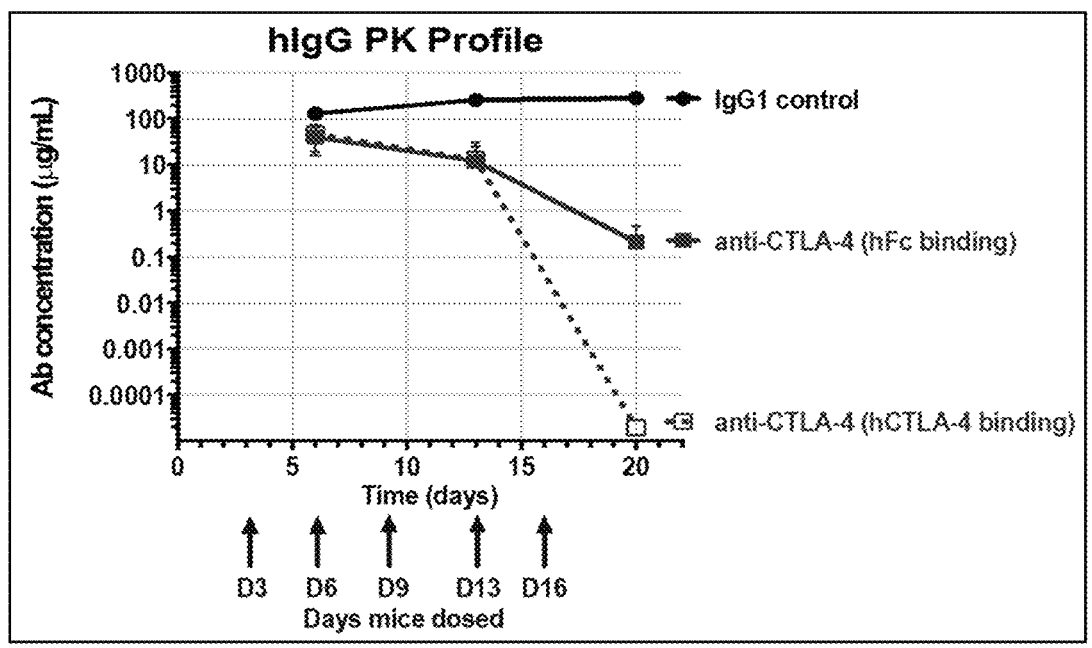
FIG. 7 shows the concentration of total H1H19303P and hIgG1 isotype control antibody in serum, as described in Study (B) in Example 7.
Figure 8:
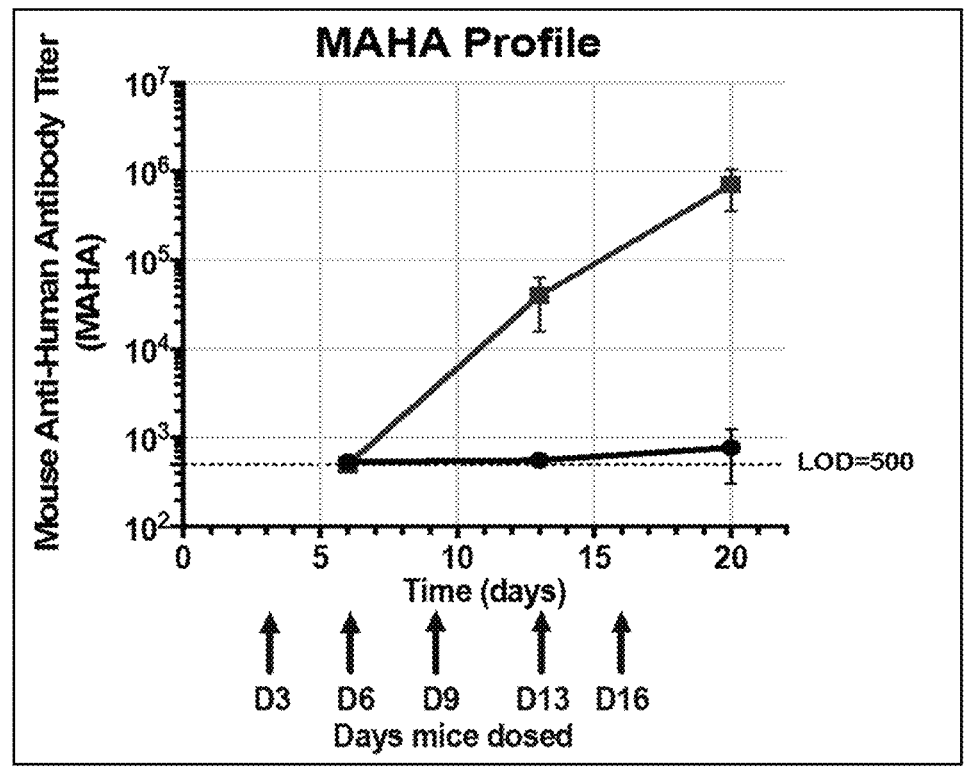
FIG. 8 shows the concentration of mouse anti-human antibodies (MAHA) against H1H19303P (■) or isotype control (●), as described in Study (B) in Example 7.

Serum samples collected on days 6, 13 and 20 were analyzed for concentrations of H1H19303P and isotype control, as well as for MAHA titers using ELISA. The concentration of H1H19303P and hIgG1 isotype control antibody in serum was determined using a sandwich ELISA specific for the detection of human IgG (FIG. 7). Specific mouse IgG titers to H1H19303P or IgG1 control antibody were determined using a sandwich ELISA specific for the detection of each antibody (FIG. 8).

At day 6, H1H19303P and isotype control were detected in serum at all doses tested, with average serum concentrations of 39.8±24, 33.5±8.9, and 10.4±2.9 observed for the 10, 5, and 2 mg/kg doses of H1H19303P, respectively (Table 11).

TABLE 11

Serum concentrations of H1H19303P and isotype control

| Dose | Antibody Administered | Average Serum Concentration (μg/mL)$^a$ | | |
|---|---|---|---|---|
| | | Day 6 | Day 13 | Day 20 |
| 10 mg/kg | H1H19303P | 39.8 ± 24 | 12.0 ± 13 | 0.21 ± 0.254 |
| | Isotype Control | 130 ± 10.4 | 255 ± 43.4 | 279 ± 64.4 |
| 5 mg/kg | H1H19303P | 33.5 ± 8.9 | NT | ≤LLOQ |
| 2 mg/kg | H1H19303P | 10.4 ± 2.9 | NT | ≤LLOQ |

$^a$Data shown are average serum concentrations with standard deviation.
NT: Not tested;
LLOQ: Lower limit of quantification

TABLE 12

Average titer of mouse anti- H1H19303P and anti-isotype control antibodies

| Dose | Antibody Administered | Average Titer$^a$ | | |
|---|---|---|---|---|
| | | Day 6 | Day 13 | Day 20 |
| 10 mg/kg | H1H19303P | ≤LOD | 39831 ± 24087 | 711076 ± 352075 |
| | hIgG1 Control | ≤LOD | ≤LOD | 564 ± 658 |
| 5 mg/kg | H1H19303P | ≤LOD | NT | 779150 ± 514583 |
| 2 mg/kg | H1H19303P | ≤LOD | NT | 878074 ± 409564 |

$^a$Data shown are average titers with standard deviation.
NT: Not tested;
LOD: Limit of detection After day 6, reductions in serum concentrations were observed for H1H19303P for all dose groups by day 20, despite additional administration of antibody at days 6, 9, 13, and 16 (Table 11). Rapid antibody clearance was observed compared to isotype control for the 10 mg/kg dose groups. The reduction in serum concentrations of H1H19303P are likely attributed to the development of MAHA (FIG. 8, Table 12). MAHA titers were observed at all time-points measured after day 6 for all doses of H1H19303P. However, MAHA titers for isotype control were at the limit of detection at all time-points tested.

Conclusion

Intraperitoneal administration of H1H19303P at doses of 10 mg/kg, 5 mg/kg or 2 mg/kg resulted in reduction of tumor growth, improved tumor clearance, and improved survival compared to hIgG1 control in CTLA-4$^{hum/hum}$ knock-in mice implanted with MC38.Ova tumor cells. Serum concentrations of H1H19303P decreased over time, corresponding with development of anti-H1H19303P MAHA at timepoints after day 6.

Example 8: Efficacy of the Combination Treatment with Anti-Mouse CTLA-4 Antibodies and Anti-Human PD-1 Antibodies (REGN2810) in PD-1$^{hum/hum}$ Knock-in Mice Bearing MC38.Ova Tumor This Example describes the anti-tumor efficacy of an anti-CTLA-4 antibody in combination with an anti-PD-1 antibody in mice humanized for the PD-1 gene. The anti-PD-1 antibody used in this study is REGN2810 (also known as cemiplimab), and is described in U.S. Pat. No. 9,987,500 as H4H7798N. PD-1$^{hum/hum}$ knock-in mice have been described in US Patent Application Publication US2015/0203579.

Figure 9:
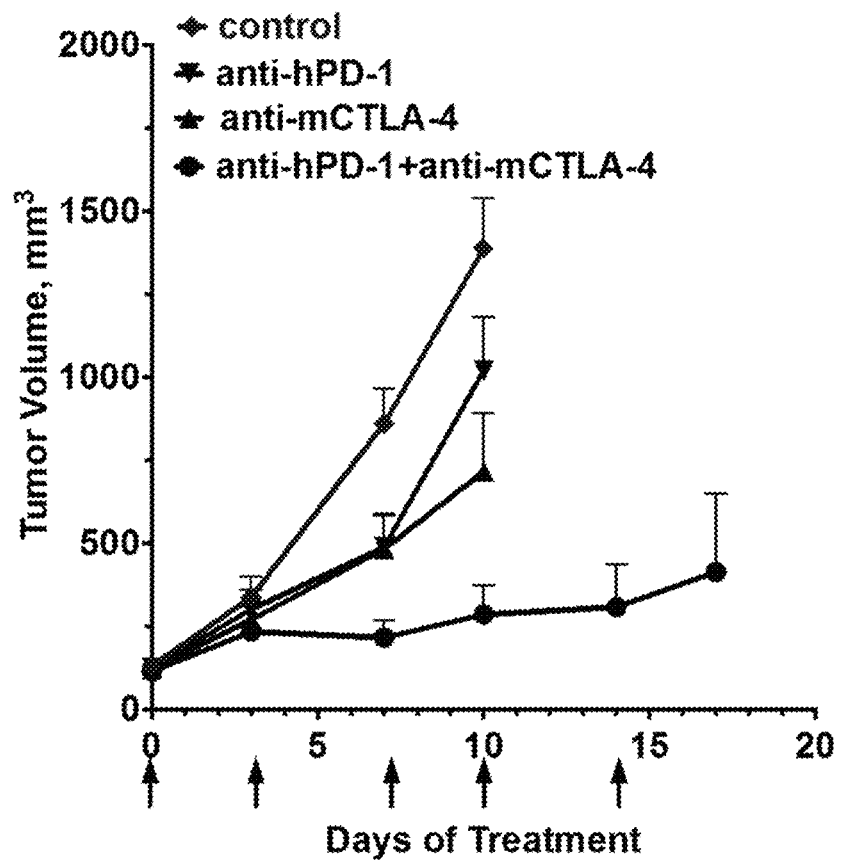
FIG. 9 shows average tumor volumes (mm³+/−SEM) in each treatment group at multiple post-tumor implantation time points for the experiment described in Example 8. Treatment days are indicated by arrows.
Figure 10:
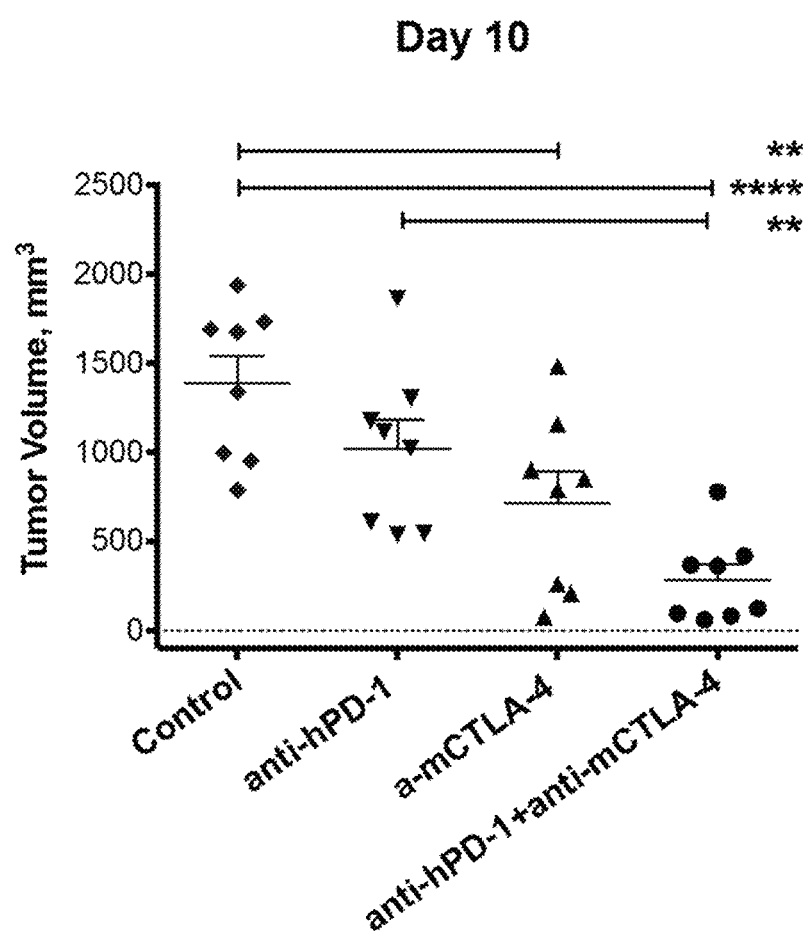
FIG. 10 shows individual tumor volumes at day 10 after treatment initiation, as described in Example 8.
Figure 11:
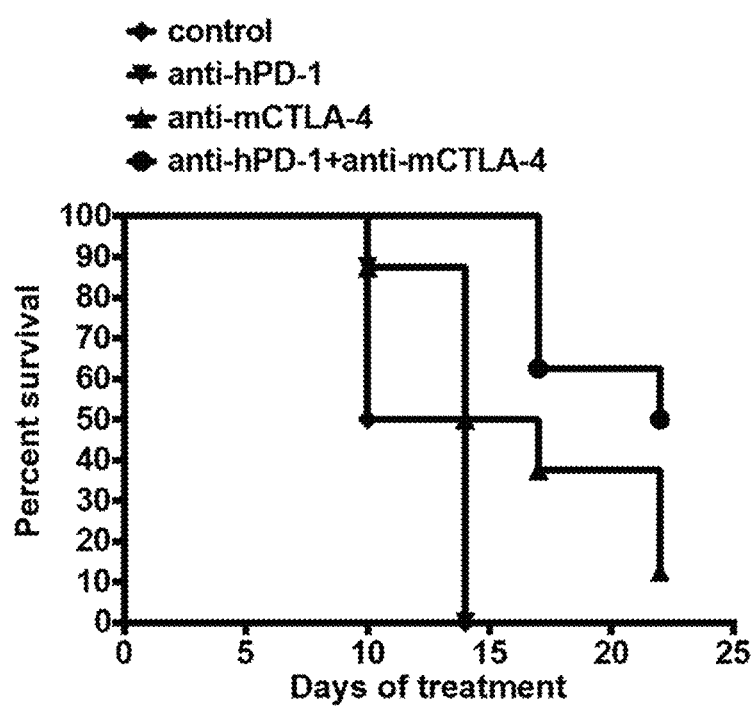
FIG. 11 shows Kaplan-Meier survival curves for the experiment described in Example 8.

PD-1$^{hum/hum}$ knock-in mice were implanted subcutaneously with MC38.Ova cells (5×10$^5$ cells/mouse). Mice were randomized into 4 treatment groups when mean tumor size reached 100 mm$^3$ (day 0 of treatment). Mice were administered 10 mg/kg of either isotype control antibody, an anti-mouse CTLA-4-mIgG2a antibody (clone 9D9), anti-human PD-1 antibody (REGN2810) or a combination of anti-mouse CTLA-4 and anti-human PD-1 antibodies (10 mg/kg+10 mg/kg) IP on days 0, 3, 7, 10 and 14. Tumor volumes and tumor-free animals were monitored for up to 22 days. Tumor volumes were monitored by caliper measurements twice per week for 22 days. Monotherapy with anti-CTLA-4 antibodies or anti-PD-1 antibodies showed partial tumor growth inhibition tested at 10 mg/kg compared to treatment with isotype control (FIG. 9). Individual tumor volumes at day 10 after treatment initiation (FIG. 10) were used for statistical analysis, as this was the last time point in the study where all animals in all groups were alive. Statistical significance was determined by one-way ANOVA with Dunnett's multiple comparisons post-test (p<0.01, p<0.0001). Combination of anti-CTLA-4 and anti-PD-1 antibodies treatment resulted in more efficacious tumor growth inhibition compared to monotherapy with either antibody with statistically significant smaller tumors at day 10 in a combo treated group than in an anti-PD-1 treated group (p<0.0001, FIG. 10). One out of eight animals in anti-CTLA-4 treatment group and 2 out of eight animals in a combo treated group became tumor-free by day 22. Treatment with a combination of anti-CTLA-4 and anti-PD-1 antibodies also resulted in a significant difference in animal survival rate compared to control group (Mantel-Cox test, **p<0.0001, FIG. 11). No evidence of body weight loss was observed as a result of antibody treatment.

In summary, treatment with a combination of anti-mCTLA-4 and anti-PD-1 (REGN2810) antibodies resulted in reduced tumor growth and improved survival compared to monotherapy with either antibody.

Example 9: Anti-Tumor Efficacy of REGN4659 Treatment in Established MC38.Ova Tumor Model in Human CTLA-4$^{hum/hum}$ Mice Experimental Design Sixty CTLA-4$^{hum/hum}$ mice were subcutaneously implanted with 5×10$^5$ MC38.Ova cells in the flank on day 0. On day 10, thirty mice with average tumor volume of 100 mm$^3$ were selected and randomized into 3 treatment groups (N=10/group). On days 10, 13 and 17 mice were dosed with antibodies as follows: group 1, hIgG1 isotype control Ab (REGN1932) at 25 mg/kg; group 2, anti-hCTLA-4 Ab (REGN4659; H1H19303P) at 25 mg/kg; group 3, anti-hCTLA-4 Ab (REGN4659; H1H19303P) at 10 mg/kg.

All antibodies were administered by IP injection. Tumor volumes were monitored by caliper measurements for the duration of the experiment (27 days).

Results

Figure 12:
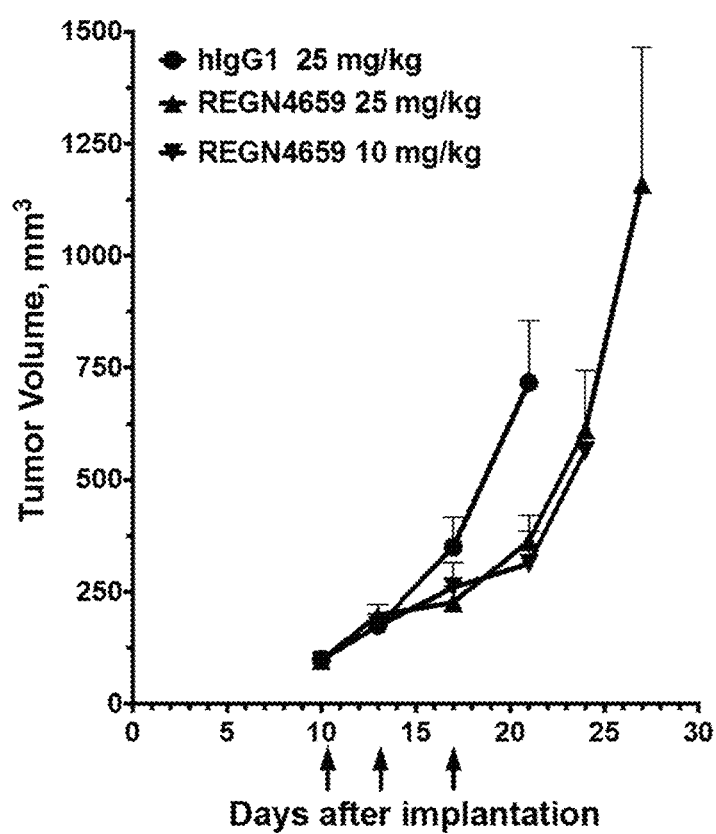
FIGS. 12 and 13 show that H1H19303P (also known as REGN4659) delays growth of established tumors in CTLA-4$^{hum/hum}$ mice. Mice were engrafted sc into the flank with Mc38.Ova cells (5×10^5 cells/mouse), randomized into treatment groups on day 10 when tumor volumes reached 100 mm^3, and REGN4659 (25 mg/kg, 10 mg/kg, n=10) or the isotype control Ab (25 mg/kg, n=10) were administered on days 10,13,17 and tumor volumes were monitored until day 27.

REGN4569 treatment of established MC38.Ova tumors resulted in partial tumor growth inhibition (FIG. 12).

Figure 13:
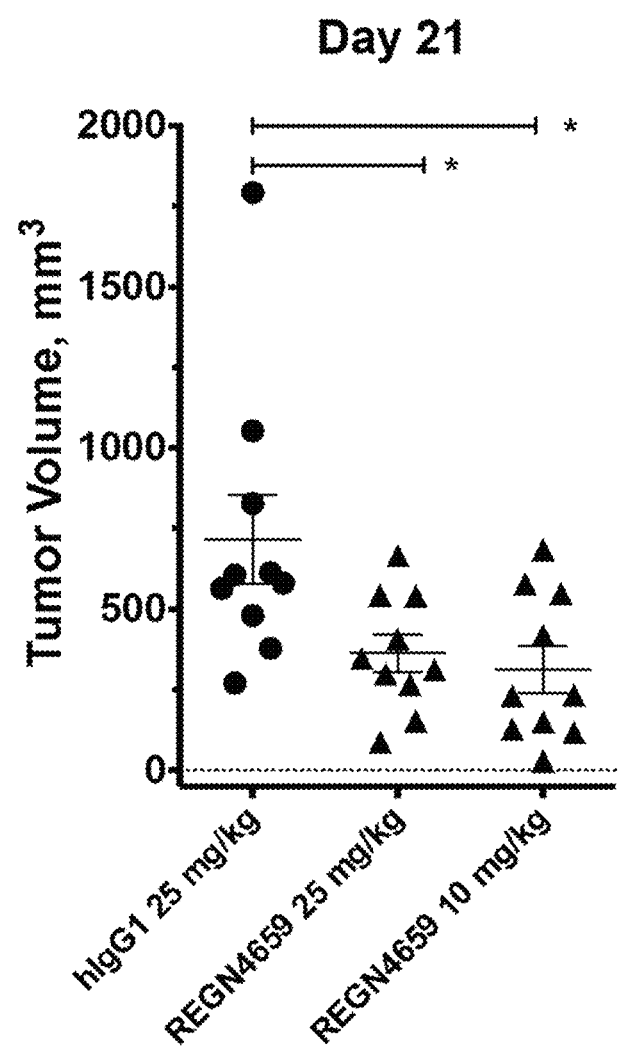

REGN4659 monotherapy was similarly efficacious at both doses, 10 mg/kg and at 25 mg/kg, in reducing tumor growth (FIG. 13).

One-way analysis of variance (ANOVA) with Tukey's multiple comparison post-test revealed a significant difference in mean tumor volumes between each REGN4569 monotherapy group and hIgG1 isotype control group (p<0.05) at day 21, the last day when the animals in all treated groups were alive (FIG. 13).

Example 10: Analysis of Intratumoral and Peripheral T Cells After REGN4659 Treatment of Established Subcutaneous MC38.Ova Tumors in CTLA-4$^{hum/hum}$ Mice Experimental Design Forty CTLA-4$^{hum/hum}$ mice were subcutaneously implanted with 5×10$^5$ MC38.Ova cells in the flank on day 0. On day 10, twenty mice with average tumor volume of 100 mm$^3$ were selected and randomized into 2 treatment groups (N=10/group). On days 10 and 13 mice were dosed with antibodies as follows: group 1, hIgG1 isotype control Ab (REGN1932) at 25 mg/kg; group 2, anti-hCTLA-4 Ab (REGN4659; H1H19303P) at 25 mg/kg. All antibodies were administered by IP injection. Tumor volumes were monitored by caliper measurements. On day 17, when tumors reached 355+/−35 mm$^3$ (mean+/−SEM) in hIgG1 group and 180+/−43 mm$^3$ (mean+/−SEM) in REGN4659 treated group, all mice were sacrificed. Tumors and spleens were harvested for lymphocyte analysis by flow cytometry. Single cells suspensions of tumors and spleens were prepared. Cells were treated with 24G.2 (Bioxcell), which blocks Fc binding to FcgRIIb and FcgRIII, and subsequently stained for viability with LIVE/DEAD™ Fixable Aqua Dead Cell dye (Invitrogen) and then with a cocktail of antibodies against CD45 (clone 30-F11; Biolegend), C90.2 (clone 30-H12; Biolegend), CD8 (clone 53-6.7; Biolegend), CD4 (GK1.5; Biolegend), CD11b (cloneM1/70; Biolegend) and human CTLA-4 (clone BN13, BD). For intracellular staining, samples were fixed, permeabilized, and stained with antibodies to FoxP3 (clone FJK-16s, Invitrogen) and human CTLA-4. Samples were then analyzed on a FACS Canto flow cytometer (BD).

Results

Figure 14:
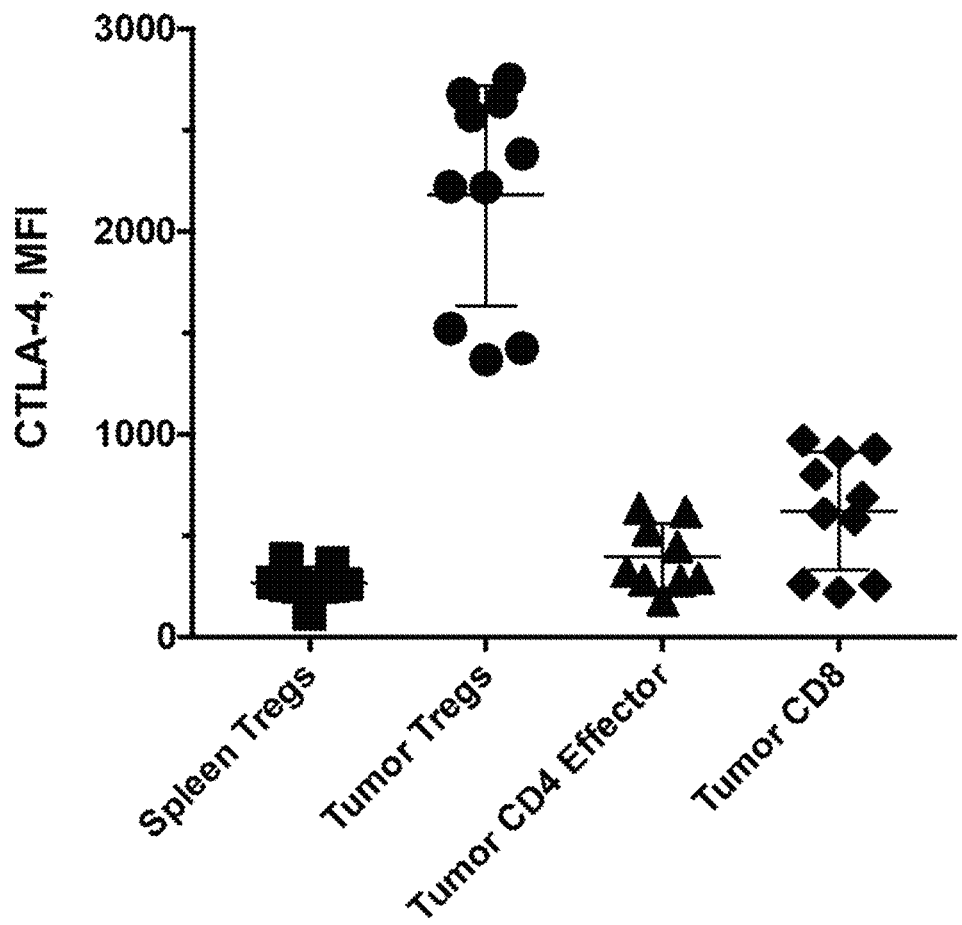
FIG. 14 shows mean fluorescent intensity (MFI) of total (surface and intracellular) human CTLA-4 expression on intratumoral and splenic Tregs and T effector cells in tumor bearing CTLA-4$^{hum/hum}$ mice treated with hIgG1 control antibody. Expression of CTLA-4 on splenic CD8$^+$ and CD4$^+$ effector cells was indistinguishable from the isotype control staining (MFI=0) and is not shown.

T-cell subsets were analyzed in tumors and spleens of MC38.Ova tumor bearing mice at day 17 after implantation and REGN4659 antibody treatment. Assessment of Teff and Treg population at the tumor site and in the periphery in the spleens showed that REGN4659, which possesses hIgG1 isotype (SEQ ID NO: 509 is the full-length heavy chain amino acid sequence of H1H19303P, also known as REGN4659), mediates reduction of Tregs in the tumor site after just two administrations of therapeutic antibody in MC38.Ova tumor bearing CTLA-4$^{hum/hum}$ mice (Table 12). Expansion of CD4$^+$ effector cells and CD8$^+$ cells at the tumor site is observed whereas treatment with REGN4659 expanded Tregs in the spleens. These data show that REGN4659 promotes anti-tumor activity in MC38.Ova tumor model in CTLA-4$^{hum/hum}$ mice by selectively reducing intratumoral Tregs along with activation of intratumoral effector T cells. The different outcome of REGN4659 on intratumoral Treg numbers compared to splenic Tregs or T effector cells could be attributed to differences in the expression levels of CTLA-4. To answer this question, CTLA-4 expression level (surface and intracellular) on T-cells was measured by FACS from the hIgG1 control treated group. The expression of total CTLA-4 on intratumoral Tregs was about 3 times higher than on intratumoral CD8$^+$ and CD4$^+$ effector cells and about 8 times higher than on Tregs from spleen (FIG. 14). This difference in expression may explain selective loss of tumor Tregs by FcgR dependent mechanism, given high binding affinity of antibodies with human IgG1 constant region to murine Fcg receptors.

TABLE 13

CTLA-4 blockade with REGN4659 expands intratumoral CD4+effector and CD8+cells, but reduces Tregs.

| | Tumor | | |
|---|---|---|---|
| | CD4+ Effector () | CD4+ Treg () | CD8+ (**) |
| hIgG1 | 2.12 ± 0.72 | 56.82 ± 5.14 | 6.12 ± 0.64 |
| REGN4659 | 5.83 ± 0.87 | 35.38 ± 3.08 | 11.83 ± 1.49 |

TABLE 13-continued

CTLA-4 blockade with REGN4659 expands intratumoral CD4+effector and CD8+cells, but reduces Tregs.

| | Spleen | | |
|---|---|---|---|
| | CD4+Effector (*) | CD4+ Treg () | CD8+ |
| hIgG1 | 10.11 ± 1.33 | 30.6 ± 1.60 | 8.73 ± 0.74 |
| REGN4659 | 14.67 ± 0.78 | 40.4 ± 0.93 | 6.99 ± 0.52 |

Table 13 shows the percentage of CD45$^+$ cells that are CD4$^+$FoxP3$^-$ (CD4$^+$effector), percentage of CD45$^+$ that are CD8$^+$ and percentage of CD4$^+$ cells that are FoxP3$^+$ (CD4$^+$Treg). Unpaired T-test analysis revealed significant difference in CD4$^+$ effector, CD8$^+$, CD4$^+$Tregs in tumors and in CD4$^+$effector and CD4$^+$ Tregs in spleens between REGN4659 group and isotype control treated group (p <0.005, * p <0.001).

Example 11: Changes in T Cell Function and Overall Systemic Immune Activation in Spleens of Tumor Bearing Mice Treated with REGN4659

Experimental Design

Twenty CTLA-4$^{hum/hum}$ mice were subcutaneously implanted with 5×10$^5$ MC38.Ova cells in the flank on day 0 and randomized into 2 treatment groups (N=9/group). On days 3, 7, 11, 14 and 17 mice were dosed either with hIgG1 isotype control Ab (REGN1932) at 10 mg/kg or with anti-hCTLA-4 Ab (REGN4659; H1H19303P) at 10 mg/kg. All antibodies were administered by IP injection. Tumor volumes were monitored by caliper measurements. Mice were sacrificed starting from day 24 (when tumor grew too big) to day 37 (end of the experiment). In REGN4659 group, 8 out of 9 mice became tumor free, while in the control group none of the mice was tumor free at day 24. Expression levels of murine genes (normalized to murine cyclophilin B RNA expression) was measured by Taqman real-time PCR. Unpaired t-test showed statistically significant increase in relative levels of FoxP3, CD3e, Perforin, IFNg, TNFa, PD-L1, PD-L2 in REGN4659 group compared to isotype control group.

Results

Taqman analysis of spleens of REGN4659-treated mice revealed increased transcript levels for FoxP3, CD3e, Perforin, IFNg, TNFa, PD-L1, PD-L2, suggesting increase in T cells effector function and overall immune-enhancing function of REGN4659. The expression levels of the murine genes (normalized to murine cyclophilin B RNA expression) is shown in Table 14. Unpaired t-test showed statistically significant increase in relative levels of FoxP3, CD3e, Perforin, IFNg, TNFa, PD-L1 and PD-L2 in REGN4659 group compared to isotype control group.

TABLE 14

REGN4659 therapy enhanced adaptive immune responses in vivo.

| | FOXP3 (*) | CD3ε (*) | Perforin (*) | IFNγ (*) | TNFα (***) | PD-L1 (*) | PD-L2 (***) |
|---|---|---|---|---|---|---|---|
| hIgG1 | 3.12 ± 0.54 | 2.72 ± 0.39 | 2.46 ± 0.35 | 0.962 ± 0.16 | 1.98 ± 0.34 | 2.81 ± 0.59 | 1.98 ± 0.30 |
| REGN 4659 | 9.15 ± 1.28 | 11.48 ± 1.57 | 10.65 ± 1.45 | 4.33 ± 0.61 | 6.42 ± 0.88 | 5.33 ± 0.61 | 7.46 ± 1.02 |

Reported average ± SEM; Unpaired t test, two-tailed; *p < 0.05, p ≤ 1.01, *p ≤ 1.001.

Example 12: Human Clinical Trial of Anti-CTLA-4 Antibody (REGN4659) in Combination with Cemiplimab (Anti-PD-1 Antibody) in the Treatment of Patients with Advanced or Metastatic Non-Small Cell Lung Cancer This study is an open-label, phase I, first-in-human (FIH) study evaluating REGN4659 (i.e., H1H19303P of Examples 1-7 and 9-11) alone, high dose cemiplimab alone (cohort C), and the combination of REGN4659 with cemiplimab in the treatment of advanced or metastatic non-small cell lung cancer (NSCLC). The study comprises both a dose escalation phase and a dose expansion phase.

Cemiplimab (REGN2810; Example 8) is a high-affinity, fully human, hinge-stabilized IgG4P antibody directed to the PD-1 receptor that potently blocks the interaction of PD-1 with its ligands, PD-L1 and PD-L2.

Study Objectives

The primary objective of the dose escalation phase is to assess safety, tolerability, and pharmacokinetics (PK) of REGN4659 alone, high-dose cemiplimab alone, and the combination of REGN4659 with cemiplimab in treatment-experienced patients with non-small cell lung cancer (NSCLC). The primary objectives of the dose expansion phase are to assess preliminary anti-tumor activity of the combination of REGN4659 with cemiplimab as measured by the objective response rate (ORR) in anti-PD-1/PD-L1 immunotherapy experienced NSCLC patients, and to assess the safety, tolerability, and PK of REGN4659 and cemiplimab in anti-PD-1/PD-L1 immunotherapy experienced NSCLC patients.

The secondary objectives of the study are (i) to assess preliminary anti-tumor activity of high-dose cemiplimab monotherapy and the combination of REGN4659 with cemiplimab as measured by the ORR in treatment-experienced patients with NSCLC in the dose escalation phase, (ii) to assess anti-tumor activity of REGN4659 with cemiplimab via multiple criteria during dose escalation and expansion, and (iii) to assess systemic pharmacodynamic effects of REGN4659 and cemiplimab, measured by the changes in peripheral blood biomarkers of T-cell activation, including ICOS+CD4 T-cells.

Study Design

This study is an open-label, phase I, first-in-human (FIH) study evaluating REGN4659 alone, high-dose cemiplimab alone (cohort C), and the combination of REGN4659 with cemiplimab in the treatment of advanced or metastatic NSCLC. There are 2 phases of this study: a dose escalation phase in treatment-experienced patients (prior chemotherapy and/or anti-PD-1/PD-L1 immunotherapy) with NSCLC, and a dose expansion phase in anti-PD-1/PD-L1 immunotherapy experienced patients with NSCLC.

The study comprises a screening period of up to 28 days (day −28 to day −1), followed by up to seventeen 42-day treatment cycles (for up to 102 weeks of treatment), and a 24-week follow-up period. A patient will receive treatment until the 102-week treatment period is complete, or until unequivocal disease progression, unacceptable toxicity, withdrawal of consent, or until another study withdrawal criterion is met. After a minimum of 24 weeks of treatment, patients with confirmed complete response (CR) may elect to discontinue treatment and continue with all relevant study assessments. In dose escalation, tumor biopsies are expected to be performed unless medically contraindicated. Tumor biopsies are mandatory as part of the dose expansion cohorts. For patients who experience a response and subsequently progress, a tumor biopsy at the time of progression will be requested but is not required.

Patients who progress within 6 months after completing the treatment period for CR, partial response (PR), or stable disease (SD) after meeting study-defined criteria and continuing with defined visits are allowed to resume study treatment following reconfirmation of relevant study eligibility criteria. Patients can receive up to 102 weeks of additional therapy. The resumed dose and drug(s) should generally be the same as the patient originally received or a dose level chosen for the expansion cohort(s) following discussion between the sponsor and investigator.

Patients in cohort C who tolerate 2 doses of cemiplimab (1050 mg Q3W), but who subsequently demonstrate PD, will have the option of adding the highest combination dose of cemiplimab and REGN4659 safely administered up to that point in an attempt to seek a response using combined CTLA-4 and PD-1 blockade.

Dose Escalation: Eight dose escalation cohorts are planned. Three dose levels of REGN4659 (25, 75, and 250 mg intravenous [IV] fixed dose) will be investigated at various schedules every 3, 6, and 12 weeks (Q3W, Q6W, Q12W) in combination with cemiplimab at 2 dose levels (350 and 1050 mg IV fixed dose) administered Q3W. Prior to beginning combination cohorts with 1050 mg of cemiplimab, a cohort of 1050 mg of cemiplimab Q3W monotherapy will be investigated (cohort C). For dose escalation cohorts designated with an asterisk (cohorts 1*, 2*, and 4*), a single lead-in dose of REGN4659 monotherapy will precede combination therapy by 3 weeks to assess safety of REGN4649 prior to combination with cemiplimab. Six of the 8 cohorts (1*, C, 2*, 2, 3, and 4*) will be used for dose-limiting toxicity (DLT) evaluation. In addition to the DLT-evaluable cohorts, 2 additional dose cohorts (5 and 6) will each enroll 6 patients for safety and PK/pharmacodynamics evaluation. Cohorts 5 and 6 will be enrolled after tolerability of cohorts 2 and 3 are established, respectively. The dose combinations in cohorts 5 and 6 are potentially of interest even if higher dose intensities of REGN4659 (cohorts 2 and 3) are tolerable. However, these cohorts will not require DLT evaluation if cohorts 2 and 3 are tolerable due to the lower exposures of REGN4659 in cohorts 5 and 6. Except for cohort C where 6 patients will be enrolled, a minimum of 3 patients in each dose cohort will be required to be evaluable for DLT. To maximize the efficiency of the phase 1 dose escalation while maintaining patient safety, 4 patients will be enrolled in each dose cohort (except cohort C), in case a patient discontinues prior to being evaluable for DLT. Cohorts 3 and 6 (combination cohorts with high dose cemiplimab) will not be initiated until all 6 patients in cohort C have completed the DLT period. Dose escalation will proceed through dose cohorts until a maximum tolerated dose (MTD) of the combination is attained or all dose cohorts have been tested. However, even prior to completion of dose escalation, dose cohort(s) may be selected for expansion once tolerability and pharmacodynamic activity are evaluated for any cohort.

Dose-Limiting Toxicities: In addition to the inability to administer (due to study drug toxicity) dose #2 within the window, a DLT will be considered upon occurrence of the following study toxicities with the exception of events that are deemed clearly related to disease progression or intercurrent illness:

Non-Hematologic Toxicity:
(i) Grade ≥2 uveitis (considered as a potential irAE);
(ii) Aspartate aminotransferase (AST) or alanine aminotransferase (ALT) >5 times upper limit of normal (ULN) and/or total bilirubin >3 times ULN. For patients with liver metastases, AST, ALT and/or total bilirubin >2× baseline value if grade 2 at baseline; and
(iii) Any grade nonhematologic toxicity, including irAEs (as defined by experience with other immunomodulatory drugs, with the exception of the following:
   (a) Grade 3 nausea, vomiting, or diarrhea unless persistent (>72 hours duration) despite maximal supportive care measures, as prescribed by the treating physician; and
   (b) Grade ≥3 laboratory abnormalities that are considered clinically insignificant and do not meet criteria for an adverse event (AE).

Hematologic Toxicity:
(i) Grade 4 neutropenia lasting more than 7 days;
(ii) Grade 4 thrombocytopenia;
(iii) Grade 3 thrombocytopenia with bleeding;
(iv) Grade febrile neutropenia (fever 38.5° C. with absolute neutrophil count <1.0×10$^9$/L) or grade neutropenia with documented infection;
(v) Grade 4 anemia; and
(vi) Grade 3 anemia lasting longer than 7 days or requiring transfusion.

If safety issues develop in an individual cohort subsequent to the DLT evaluation, enrollment may be paused after a discussion between the investigators and the sponsor has occurred. Safety issues triggering a pause could include early or late safety events.

Dose Expansion: Dose cohort(s) may be selected for expansion once tolerability and pharmacodynamics activity (including but not limited to an increase in peripheral ICOS+ T-cells) are evaluated for any cohort except for cohort C, which will not be expanded. Dose expansion cohort(s) will enroll anti-PD-1/PD-L1 immunotherapy-experienced patients with NSCLC who have progressed while receiving anti-PD-1/PD-L1 therapy to determine the tolerability and activity of combination therapy in this population. Up to 3 separate dose regimens will be selected for dose expansion to identify the optimal combination regimen in patients with NSCLC. The expansion cohort(s) will enroll a maximum of 27 patients each based upon a Simon 2-stage design. If safety issues develop in an individual expansion cohort, enrollment may be paused after a discussion between the investigators and the sponsor has occurred. Safety issues triggering a pause could include early or late safety events.

Study Duration

The duration of the study is approximately 102 weeks, not including the screening or follow-up periods.

Population

Sample Size: Up to approximately 53 adult patients are expected to be enrolled during dose escalation and up to 3 expansion cohorts to a maximum of 27 patients in each cohort are expected to be enrolled during dose expansion at up to approximately 15 sites in the United States. The total number of patients enrolled will depend upon observed DLTs during dose escalation, PK/pharmacodynamics analyses, the number of expansion cohorts opened, and the efficacy in stage 1 of the Simon 2-stage expansion cohorts.

Target Population: The target population for this study is men and women ≥18 years of age diagnosed with unresectable stage IIIB or stage IV squamous or non-squamous NSCLC.

Inclusion Criteria: A patient must meet the following criteria to be eligible for inclusion in the study:

1. Men and women ≥18 years of age;
2. Patients with histologically or cytologically documented squamous or non-squamous NSCLC with unresectable stage IIIB or stage IV disease;
3. Dose escalation (except cohort C): Treatment-experienced patients who have received no more than 3 lines of systemic therapy including no more than 2 lines of cytotoxic chemotherapy, and for whom no available therapy is expected to convey clinical benefit. Patients who have received prior PD-1/PD-L1 immunotherapy must not have permanently discontinued due to a treatment-related AE. Patients with targetable mutations (including epidermal growth factor receptor [EGFR], ALK, and ROS1) are permitted during dose escalation but must have additionally received at least 1 line of targeted therapy.
  a. NOTE: 1) Adjuvant or neoadjuvant chemotherapy or immunotherapy (after surgery and/or radiation therapy) OR 2) definitive chemoradiation therapy with or without subsequent immunotherapy for stage III disease is permissible and not included when evaluating line of therapy in patients who developed recurrent or metastatic disease more than 6 months after completing therapy;
4. Dose escalation cohort C: Anti-PD-1/PD-L1 naïve patients who have received 1 to 2 prior lines of cytotoxic chemotherapy including a platinum doublet-containing regimen. Patients with targetable mutations (including EGFR, ALK, and ROS1) are permitted during dose escalation but must have additionally received at least 1 line of targeted therapy.
  a. NOTE: 1) Adjuvant or neoadjuvant chemotherapy OR 2) definitive chemoradiation therapy for stage III disease is permissible and not included when evaluating line of therapy in patients who developed recurrent or metastatic disease more than 6 months after completing therapy;
5. Expansion cohort(s): Anti-PD-1/PD-L1 experienced patients who have progressed while receiving therapy or within 6 months of stopping therapy for stage III or IV disease. Patients must not have permanently discontinued anti-PD-1/PD-L1 therapy due to treatment related AE. Patients must have received one line of anti-PD-1/PD-L1 immunotherapy. Patients may also have received one line of chemotherapy. Prior combination chemotherapy and immunotherapy is permissible as long as no additional line/s of either therapy has been received except as described in the note below.
  a. NOTE: 1) Adjuvant or neoadjuvant chemotherapy or immunotherapy (after surgery and/or radiation therapy) OR 2) definitive chemoradiation therapy with or without subsequent immunotherapy for stage III disease is permissible and not included when evaluating line of therapy in patients who developed recurrent or metastatic disease more than 6 months after completing therapy;
6. Archival or newly obtained formalin-fixed tumor tissue which has not previously been irradiated;
7. Expansion cohort(s): At least 1 radiographically measurable lesion by computed tomography (CT) or magnetic resonance imaging (MRI) per RECIST 1.1 criteria. Target lesions may be located in a previously irradiated field if there is documented (radiographic) disease progression at that site;
8. Eastern Cooperative Oncology Group (ECOG) performance status of 1;
9. Anticipated life expectancy of at least 3 months;
10. Adequate organ and bone marrow function as defined below:
  Hemoglobin ≥9.0 g/dL (NOTE: patients who have received transfusions for hemoglobin <9.0 g/dL within 14 days prior to screening laboratory evaluation are not eligible)
  Absolute neutrophil count $1.5 \times 10^9$/L
  Platelet count ≥75,000/mm$^3$
  Glomerular filtration rate (GFR) >30 mL/min/1.73 m$^2$
  Total bilirubin ≤1.5×ULN (if liver metastases ≤3×ULN), with the exception of patients diagnosed with clinically confirmed Gilbert's syndrome
  AST) and ALT ≤3×ULN or ≤5×ULN, if liver metastases
  Alkaline phosphatase ≤2.5×ULN (or ≤5.0×ULN, if liver or bone metastases)
  Not meeting criteria for Hy's law (ALT and/or AST >3×ULN and bilirubin >2×ULN);
11. Willing and able to comply with clinic visits and study-related procedures; and
12. Provide informed consent signed by study patient or legally acceptable representative.

Exclusion Criteria: A patient who meets any of the following criteria will be excluded from the study:

1. Expansion cohort(s) only: Patients who have never smoked, defined as smoking 100 cigarettes in a lifetime;
2. Active or untreated brain metastases or spinal cord compression. Patients are eligible if central nervous system (CNS) metastases are adequately treated and patients have neurologically returned to baseline (except for residual signs or symptoms related to the CNS treatment) for at least 2 weeks prior to enrollment. Patients must be off (immunosuppressive doses of) corticosteroid therapy;
3. Expansion cohort(s) only: Patients with tumors tested positive for EGFR and ALK gene mutations or ROS1 fusions. All patients should have tumor evaluated for EGFR mutations, ALK rearrangement, and ROS1 fusions;
4. Radiation therapy within 2 weeks prior to enrollment and not recovered to baseline from any AE due to radiation;
5. Patients who received prior treatment with an anti-CTLA-4 antibody;
6. Encephalitis, meningitis, or uncontrolled seizures in the year prior to informed consent;
7. History of interstitial lung disease (e.g., idiopathic pulmonary fibrosis, organizing pneumonia) or active, noninfectious pneumonitis that required immune-suppressive doses of glucocorticoids to assist with management. A history of radiation pneumonitis in the radiation field is permitted as long as pneumonitis resolved months prior to enrollment;
8. Ongoing or recent evidence of significant autoimmune disease that required treatment with systemic immunosuppressive treatments, which may suggest risk for immune-related treatment-emergent adverse events (irTEAEs). The following are not exclusionary: vitiligo, childhood asthma that has resolved, type I diabetes, residual hypothyroidism that required only hormone replacement or psoriasis that does not require systemic treatment;
9. Patients with a condition requiring corticosteroid therapy (>10 mg prednisone/day or equivalent) within 14 days of randomization. Physiologic replacement doses are allowed even if they are >10 mg of prednisone/day or equivalent, as long as they are not being administered for immunosuppressive intent. Inhaled or topical steroids are permitted, provided that they are not for treatment of an autoimmune disorder;
10. Expansion cohort(s) only: Another malignancy that is progressing or requires treatment, with the exception of non-melanomatous skin cancer that has undergone potentially curative therapy, or in situ cervical carcinoma or any other tumor that has been treated, and the patient is deemed to be in complete remission for at least 2 years prior to study entry, and no additional therapy is required during the study period;
11. Uncontrolled infection with human immunodeficiency virus, hepatitis B or hepatitis C infection; or diagnosis of immunodeficiency;
Notes:
Patients will be tested for hepatitis C virus (HCV) and hepatitis B virus (HBV) at screening;
Patients with known HIV infection who have controlled infection (undetectable viral load (HIV RNA PCR) and CD4 count above 350 either spontaneously or on a stable antiviral regimen) are permitted. For patients with controlled HIV infection, monitoring will be performed per local standards;
Patients with hepatitis B (HepBsAg+) who have controlled infection (serum hepatitis B virus DNA PCR that is below the limit of detection AND receiving anti-viral therapy for hepatitis B) are permitted. Patients with controlled infections must undergo periodic monitoring of HBV DNA. Patients must remain on anti-viral therapy for at least 6 months beyond the last dose of investigational study drug;
Patients who are hepatitis C virus antibody positive (HCV Ab+) who have controlled infection (undetectable HCV RNA by PCR either spontaneously or in response to a successful prior course of anti-HCV therapy) are permitted.
12. Active infection requiring systemic therapy within 14 days prior to start of study drug;
13. Treatment-related immune-mediated AEs from immune-modulatory agents (including but not limited to anti-PD1/PD-L1 therapy, other checkpoint inhibitor therapies, and PI3K-δ inhibitors) that have not resolved to baseline at least 3 months prior to initiation of treatment with study therapy. Patients are excluded from treatment with cemiplimab if they experienced immune-mediated AEs related to prior treatment with a blocker of the PD-1/PD-L1 pathway that required permanent discontinuation of the agent, regardless of time of occurrence. NOTE: patients who experienced hypothyroidism or type I diabetes mellitus of any grade who are controlled with hormone replacement are permitted;
14. Previous treatment with idelalisib (ZYDELIG®) at any time;
15. Currently receiving treatment in another study, or has participated in a study of an investigational agent and received treatment, or used an investigational device within 4 weeks of first dose of study therapy, or received treatment with an approved systemic therapy within 3 weeks of first dose of study therapy, or has received any previous systemic therapy within 5 half-lives of first dose of study therapy, whichever is longer (with the exception of anti-PD-1/PD-L1 therapy). Patients previously treated with bevacizumab, cetuximab, rituximab or other non-immunomodulatory antibodies with half-lives longer than 7 days are permitted after a discussion with the sponsor if at least 28 days have elapsed since last treatment. For anti-PD-1/PD-L1 experienced patients, prior anti-PD-1/PD-L1 therapy cannot have been given within 3 weeks of first dose of study therapy, regardless of half-life or approval status of the drug;
16. Receipt of a live vaccine within 30 days of planned start of study medication;
17. Major surgery or significant traumatic injury within 4 weeks prior to first dose;
18. Known sensitivity to doxycycline or similar compounds (ie, tetracyclines);
19. Documented allergic or hypersensitivity response to any protein therapeutics (e.g., recombinant proteins, vaccines, intravenous immune globulins, monoclonal antibodies, receptor traps);
20. Known psychiatric or substance abuse disorder that would interfere with participation with the requirements of the study, including current use of illicit drugs;
21. Prior allogeneic stem cell transplant;
22. Any medical condition that in the opinion of the investigator would make participation in the study not in the best interest of the patient;
23. Pregnant or breastfeeding women;
24. Positive serum hCG pregnancy test at the baseline (cycle 1 day 1, prior to dosing) visit;
25. Sexually active men and women of childbearing potential* who are unwilling to practice highly effective contraception prior to the initial dose/start of the first treatment, during the study, and for at least 6 months after the last dose. Highly effective contraceptive measures include:
  stable use of combined (estrogen and progestogen containing) hormonal contraception (oral, intravaginal, transdermal) or progestogen-only hormonal contraception (oral, injectable, implantable) associated with inhibition of ovulation initiated 2 or more menstrual cycles prior to screening;
  intrauterine device (IUD); intrauterine hormone-releasing system (IUS);
  bilateral tubal ligation;
  vasectomized partner;
  and or sexual abstinence†, ‡.

*Postmenopausal women must be amenorrheic for at least 12 months in order not to be considered of childbearing potential. Pregnancy testing and contraception are not required for women with documented hysterectomy or tubal ligation.

†Sexual abstinence is considered a highly effective method only if defined as refraining from heterosexual intercourse during the entire period of risk associated with the study treatments. ‡Periodic abstinence (calendar, symptothermal, post-ovulation methods), withdrawal (coitus interruptus), spermicides only, and lactational amenorrhoea method (LAM) are not acceptable methods of contraception. Female condom and male condom should not be used together;

26. Member of the clinical site study team and/or his/her immediate family.

Treatments

REGN4659: 3 dose levels (25, 75, and 250 mg IV fixed dose) will be investigated at various schedules (Q3W, Q6W, Q12W).

Cemiplimab: 2 dose levels (350 and 1050 mg IV fixed dose) administered Q3W.

Primary Endpoints

In the Dose Escalation Phase: Rate of DLTs, treatment emergent adverse events (TEAEs), irAEs, serious adverse events (SAEs), deaths, laboratory abnormalities (grade 3 or higher per Common Terminology Criteria for Adverse Events [CTCAE]).

In the Dose Expansion Phase: Objective response rate (ORR) based on Response Evaluation Criteria in Solid Tumors (RECIST) 1.1, and rate of TEAEs, irAEs, SAEs, deaths, laboratory abnormalities (grade 3 or higher per CTCAE).

Secondary Endpoints

Tumor measurement based on multiple response criteria including: (i) ORR based on RECIST 1.1 (dose escalation), (ii) ORR based on immune-based therapy Response Evaluation Criteria (iRECIST), (iii) best overall response (BOR), duration of response (DOR), disease control rate, and progression-free survival (PFS) based on RECIST 1.1, iRECIST, and (iv) Overall survival (OS).

Quantitation of % change in absolute ICOS+CD4 T-cells and other markers of activation via flow cytometry within each dose cohort.

Procedures and Assessments

The safety and tolerability of REGN4659 and cemiplimab will be monitored by clinical assessment of AEs and by repeated measurements of clinical evaluation including vital signs (temperature, blood pressure, pulse, and respiration), physical examinations (complete and limited), 12-lead electrocardiograms (ECGs), and laboratory assessments including standard hematology, chemistry, and urinalysis.

Anti-tumor activity will be assessed by CT/MRI.

Blood samples for the determination of functional REGN4659 and functional cemiplimab in serum and anti-drug antibodies (anti-REGN4659 or anti-cemiplimab) samples will be collected.

Serum, plasma, peripheral blood mononuclear cells (PBMCs), and tumor biopsies will be collected for analysis of biomarkers. A genomic DNA sample will be collected. Speculated pharmacodynamic, predictive and prognostic biomarkers related to REGN4659 and cemiplimab treatment exposure, clinical activity, or underlying disease will be investigated in serum, plasma, PBMCs, and tumor tissue.

Statistical Plan

Dose Escalation Phase: There is no formal statistical hypothesis for the dose escalation phase of the study; the analyses of this phase will be descriptive and exploratory in nature. Approximately 35 DLT-evaluable patients are planned based on a modified 3+3 design ("4+3") for each dose-escalation cohort (cohort 1*, 2*, 2, 3 and 4*). Twelve patients are planned for cohort 5 and 6 (6 patients per cohort). The actual sample size of these dose escalation cohorts will depend on DLTs documented, resultant cohort sizes, and the number of dose levels implemented.

Dose Expansion Phase: For each expansion cohort in patients with NSCLC who are anti-PD-1/PD-L1 immunotherapy experienced and have progressed while receiving anti-PD-1/PD-L1 therapy, as there is few efficacy data available in these patients, sponsor believes any measurable ORR better than 5% represents a clinical meaningful treatment effect. The sample size of 27 patients for each expansion cohort is determined using Simon 2-stage Minimax design with 1-sided significant level of 5% and power of 80%.

Primary Efficacy Analysis: Best overall response determined by RECIST 1.1 for expansion cohort will be summarized using descriptive statistics, along with 2-sided 95% confidence interval.

The ORR will be summarized by descriptive statistics, along with 95% confidence interval. Patients who are not evaluable for the BOR will be considered as nonresponders.

For the expansion cohort, if the number of responders is greater than or equal to the minimum number of responders specified in the Simon 2-stage design, the treatment is considered as effective and worthy of further investigation.

The secondary analyses of efficacy include ORR as measured by iRECIST, DOR, rate of disease control and PFS. Those secondary efficacy endpoints will be summarized descriptively by dose escalation and expansion cohorts.

Safety observations and measurements including drug exposure, AEs, laboratory data, and vital signs will be summarized and presented in tables and listings.

For the dose escalation phase: DLTs observed during the DLT evaluation period will be summarized by dose cohort.

Results

In the dose escalation phase, REGN4659 and cemiplimab will be well tolerated alone and in combination in treatment-experienced patients with NSCLC. In the dose expansion phase, REGN4659 will be well tolerated in combination with cemiplimab and will demonstrate measurable anti-tumor responses in anti-PD-1/PD-1 immunotherapy experienced patients with NSCLC.

Exemplary Embodiments

The present invention also relates to the following items:

Item 1. An antibody or antigen-binding fragment thereof that binds human cytotoxic T-lymphocyte-associated protein 4 (CTLA-4) and blocks the interaction between hCTLA-4 and ligand B7-1 and/or ligand B7-2.

Item 2. The antibody or antigen-binding fragment of item 1 that induces T-cell activation.

Item 3. The antibody or antigen-binding fragment of item 2, wherein the T-cell is a cytotoxic T-cell.

Item 4. The antibody or antigen-binding fragment of item 2 or 3, wherein the T-cell is a tumor infiltrating lymphocyte.

Item 5. The antibody or antigen-binding fragment of any one of items 1-4, wherein the antibody or antigen-binding fragment binds monkey CTLA-4.

Item 6. The antibody or antigen-binding fragment of any one of items 1-5, wherein the antibody or antigen-binding fragment binds CTLA-4-expressing cells with an EC50 of less than 5 nM.

Item 7. The antibody or antigen-binding fragment of any one of items 1-6, wherein the antibody or antigen-binding fragment binds CTLA-4 expressing cells with an EC50 of less than 1 nM.

Item 8. The antibody or antigen-binding fragment of any one of items 1-7, wherein the antibody or antigen-binding fragment binds human CTLA-4 expressing cells with an EC50 of less than 0.5 nM.

Item 9. The antibody or antigen-binding fragment of any one of item 1-8 that binds monkey CTLA-4 expressing cells with an EC50 of less than 0.5 nM.

Item 10. The antibody or antigen-binding fragment of any one of items 1-9 that is a fully human antibody.

Item 11. The antibody or antigen-binding fragment of any one of items 1-10, wherein the antibody or antigen-binding fragment thereof competes for binding to human CTLA-4 with a reference antibody comprising an HCVR/LCVR amino acid sequence pair selected from the group consisting of: (a) SEQ ID NOs: 2 and 10, (b) SEQ ID NOs: 18 and 26, (c) SEQ ID NOs: 34 and 42, (d) SEQ ID NOs: 50 and 58, (e) SEQ ID NOs: 66 and 74, (f) SEQ ID NOs: 82 and 90, (g) SEQ ID NOs: 98 and 106, (h) SEQ ID NOs: 114 and 122, (i) SEQ ID NOs: 130 and 138, (j) SEQ ID NOs: 146 and 154, (k) SEQ ID NOs: 162 and 170, (l) SEQ ID NOs: 178 and 186, (m) SEQ ID NOs: 194 and 202, (n) SEQ ID NOs: 210 and 218, (o) SEQ ID NOs: 226 and 234, (p) SEQ ID NOs: 242 and 250, (q) SEQ ID NOs: 258 and 266, (r) SEQ ID NOs: 274 and 282, (s) SEQ ID NOs: 290 and 298, (t) SEQ ID NOs: 306 and 298, (u) SEQ ID NOs: 314 and 322, (v) SEQ ID NOs: 330 and 338, (w) SEQ ID NOs: 346 and 354, (x) SEQ ID NOs: 362 and 370, (y) SEQ ID NOs: 378 and 386, (z) SEQ ID NOs: 394 and 402, (a') SEQ ID NOs: 410 and 418, (b') SEQ ID NOs: 426 and 434, (c') SEQ ID NOs: 442 and 450, (d') SEQ ID NOs: 458 and 466, (e') SEQ ID NOs: 474 and 482, and (f') SEQ ID NOs: 490 and 498.

Item 12. The antibody or antigen-binding fragment of any one of items 1-11, wherein the antibody or antigen-binding fragment thereof binds to the same epitope on human CTLA-4 as a reference antibody comprising an HCVR/LCVR amino acid sequence pair selected from the group consisting of: (a) SEQ ID NOs: 2 and 10, (b) SEQ ID NOs: 18 and 26, (c) SEQ ID NOs: 34 and 42, (d) SEQ ID NOs: 50 and 58, (e) SEQ ID NOs: 66 and 74, (f) SEQ ID NOs: 82 and 90, (g) SEQ ID NOs: 98 and 106, (h) SEQ ID NOs: 114 and 122, (i) SEQ ID NOs: 130 and 138, (j) SEQ ID NOs: 146 and 154, (k) SEQ ID NOs: 162 and 170, (l) SEQ ID NOs: 178 and 186, (m) SEQ ID NOs: 194 and 202, (n) SEQ ID NOs: 210 and 218, (o) SEQ ID NOs: 226 and 234, (p) SEQ ID NOs: 242 and 250, (q) SEQ ID NOs: 258 and 266, (r) SEQ ID NOs: 274 and 282, (s) SEQ ID NOs: 290 and 298, (t) SEQ ID NOs: 306 and 298, (u) SEQ ID NOs: 314 and 322, (v) SEQ ID NOs: 330 and 338, (w) SEQ ID NOs: 346 and 354, (x) SEQ ID NOs: 362 and 370, (y) SEQ ID NOs: 378 and 386, (z) SEQ ID NOs: 394 and 402, (a') SEQ ID NOs: 410 and 418, (b') SEQ ID NOs: 426 and 434, (c') SEQ ID NOs: 442 and 450, (d') SEQ ID NOs: 458 and 466, (e') SEQ ID NOs: 474 and 482, and (f') SEQ ID NOs: 490 and 498.

Item 13. The antibody or antigen-binding fragment of any one of items 1-12, wherein the antibody or antigen-binding fragment comprises: (a) the complementarity determining regions (CDRs) of a heavy chain variable region (HCVR) having an amino acid sequence selected from the group consisting of SEQ ID NOs: 2, 18, 34, 50, 66, 82, 98, 114, 130, 146, 162, 178, 194, 210, 226, 242, 258, 274, 290, 306, 314, 330, 346, 362, 378, 394, 410, 426, 442, 458, 474, and 490; and (b) the CDRs of a light chain variable region (LCVR) having an amino acid sequence selected from the group consisting of SEQ ID NOs: 10, 26, 42, 58, 74, 90, 106, 122, 138, 154, 170, 186, 202, 218, 234, 250, 266, 282, 298, 322, 338, 354, 370, 386, 402, 418, 434, 450, 466, 482, and 498.

Item 14. The antibody or antigen-binding fragment of any one of items 1-13, wherein the antibody or antigen-binding fragment comprises the heavy and light chain CDRs of a HCVR/LCVR amino acid sequence pair selected from the group consisting of: (a) SEQ ID NOs: 2 and 10, (b) SEQ ID NOs: 18 and 26, (c) SEQ ID NOs: 34 and 42, (d) SEQ ID NOs: 50 and 58, (e) SEQ ID NOs: 66 and 74, (f) SEQ ID NOs: 82 and 90, (g) SEQ ID NOs: 98 and 106, (h) SEQ ID NOs: 114 and 122, (i) SEQ ID NOs: 130 and 138, (j) SEQ ID NOs: 146 and 154, (k) SEQ ID NOs: 162 and 170, (l) SEQ ID NOs: 178 and 186, (m) SEQ ID NOs: 194 and 202, (n) SEQ ID NOs: 210 and 218, (o) SEQ ID NOs: 226 and 234, (p) SEQ ID NOs: 242 and 250, (q) SEQ ID NOs: 258 and 266, (r) SEQ ID NOs: 274 and 282, (s) SEQ ID NOs: 290 and 298, (t) SEQ ID NOs: 306 and 298, (u) SEQ ID NOs: 314 and 322, (v) SEQ ID NOs: 330 and 338, (w) SEQ ID NOs: 346 and 354, (x) SEQ ID NOs: 362 and 370, (y) SEQ ID NOs: 378 and 386, (z) SEQ ID NOs: 394 and 402, (a') SEQ ID NOs: 410 and 418, (b') SEQ ID NOs: 426 and 434, (c') SEQ ID NOs: 442 and 450, (d') SEQ ID NOs: 458 and 466, (e') SEQ ID NOs: 474 and 482, and (f') SEQ ID NOs: 490 and 498.

Item 15. The antibody or antigen-binding fragment of any one of items 1-14, wherein the antibody or antigen-binding fragment comprises comprises HCDR1, HCDR2, HCDR3, LCDR1, LCDR2 and LCDR3 domains selected from the group consisting of: (a) SEQ ID NOs: 4, 6, 8, 12, 14 and 16 respectively; (b) SEQ ID NOs: 20, 22, 24, 28, 30 and 32 respectively; (c) SEQ ID NOs: 36, 38, 40, 44, 46 and 48 respectively; (d) SEQ ID NOs: 52, 54, 56, 60, 62 and 64 respectively; (e) SEQ ID NOs: 68, 70, 72, 76, 78 and 80 respectively; (f) SEQ ID NOs: 84, 86, 88, 92, 94 and 96 respectively; (g) SEQ ID NOs: 100, 102, 104, 108, 110 and 112 respectively; (h) SEQ ID NOs: 116, 118, 120, 124, 126 and 128 respectively; (i) SEQ ID NOs: 132, 134, 136, 140, 142 and 144 respectively; (j) SEQ ID NOs: 148, 150, 152, 156, 158 and 160 respectively; (k) SEQ ID NOs: 164, 166, 168, 172, 174 and 176 respectively; (l) SEQ ID NOs: 180, 182, 184, 188, 190 and 192 respectively; (m) SEQ ID NOs: 196, 198, 200, 204, 206 and 208 respectively; (n) SEQ ID NOs: 212, 214, 216, 220, 222 and 224 respectively; (o) SEQ ID NOs: 228, 230, 232, 236, 238 and 240 respectively; (p) SEQ ID NOs: 244, 246, 248, 252, 254 and 256 respectively; (q) SEQ ID NOs: 260, 262, 264, 268, 270 and 272 respectively; (r) SEQ ID NOs: 276, 278, 280, 284, 286 and 288 respectively; (s) SEQ ID NOs: 292, 294, 296, 300, 302 and 304 respectively; (t) SEQ ID NOs: 308, 310, 312, 300, 302 and 304 respectively; (u) SEQ ID NOs: 316, 318, 320, 324, 326 and 328 respectively; (v) SEQ ID NOs: 332, 334, 336, 340, 342 and 344 respectively; (w) SEQ ID NOs: 348, 350, 352, 356, 358 and 360 respectively; (x) SEQ ID NOs: 364, 366, 368, 372, 374 and 376 respectively; (y) SEQ ID NOs: 380, 382, 384, 388, 390 and 392 respectively; (z) SEQ ID NOs: 396, 398, 400, 404, 406 and 408 respectively; (a') SEQ ID NOs: 412, 414, 416, 420, 422 and 424 respectively; (b') SEQ ID NOs: 428, 430, 432, 436, 438 and 440 respectively; (c') SEQ ID NOs: 444, 446, 448, 452, 454 and 456 respectively; (d') SEQ ID NOs: 460, 462, 464, 468, 470 and 472 respectively; (e') SEQ ID NOs: 476, 478, 480, 484, 486 and 488 respectively; and (f') SEQ ID NOs: 492, 494, 496, 500, 502 and 504 respectively.

Item 16. The antibody or antigen-binding fragment of any one of items 1-15, wherein the antibody or antigen-binding fragment comprises a HCVR/LCVR amino acid sequence pair selected from the group consisting of: (a) SEQ ID NOs: 2 and 10, (b) SEQ ID NOs: 18 and 26, (c) SEQ ID NOs: 34 and 42, (d) SEQ ID NOs: 50 and 58, (e) SEQ ID NOs: 66 and 74, (f) SEQ ID NOs: 82 and 90, (g) SEQ ID NOs: 98 and 106, (h) SEQ ID NOs: 114 and 122, (i) SEQ ID NOs: 130 and 138, (j) SEQ ID NOs: 146 and 154, (k) SEQ ID NOs: 162 and 170, (l) SEQ ID NOs: 178 and 186, (m) SEQ ID NOs: 194 and 202, (n) SEQ ID NOs: 210 and 218, (o) SEQ ID NOs: 226 and 234, (p) SEQ ID NOs: 242 and 250, (q) SEQ ID NOs: 258 and 266, (r) SEQ ID NOs: 274 and 282, (s) SEQ ID NOs: 290 and 298, (t) SEQ ID NOs: 306 and 298, (u) SEQ ID NOs: 314 and 322, (v) SEQ ID NOs: 330 and 338, (w) SEQ ID NOs: 346 and 354, (x) SEQ ID NOs: 362 and 370, (y) SEQ ID NOs: 378 and 386, (z) SEQ ID NOs: 394 and 402, (a') SEQ ID NOs: 410 and 418, (b') SEQ ID NOs: 426 and 434, (c') SEQ ID NOs: 442 and 450, (d') SEQ ID NOs: 458 and 466, (e') SEQ ID NOs: 474 and 482, and (f') SEQ ID NOs: 490 and 498.

Item 17. An anti-CTLA-4 antibody or antigen-binding fragment thereof comprising: (a) the complementarity determining regions (CDRs) of a heavy chain variable region (HCVR) having an amino acid sequence selected from the group consisting of SEQ ID NOs: 2, 18, 34, 50, 66, 82, 98, 114, 130, 146, 162, 178, 194, 210, 226, 242, 258, 274, 290, 306, 314, 330, 346, 362, 378, 394, 410, 426, 442, 458, 474, and 490; and (b) the CDRs of a light chain variable region (LCVR) having an amino acid sequence selected from the group consisting of SEQ ID NOs: 10, 26, 42, 58, 74, 90, 106, 122, 138, 154, 170, 186, 202, 218, 234, 250, 266, 282, 298, 322, 338, 354, 370, 386, 402, 418, 434, 450, 466, 482, and 498.

Item 18. The antibody or antigen-binding fragment of item 17, wherein the antibody comprises the heavy and light chain CDRs of a HCVR/LCVR amino acid sequence pair selected from the group consisting of: (a) SEQ ID NOs: 2 and 10, (b) SEQ ID NOs: 18 and 26, (c) SEQ ID NOs: 34 and 42, (d) SEQ ID NOs: 50 and 58, (e) SEQ ID NOs: 66 and 74, (f) SEQ ID NOs: 82 and 90, (g) SEQ ID NOs: 98 and 106, (h) SEQ ID NOs: 114 and 122, (i) SEQ ID NOs: 130 and 138, (j) SEQ ID NOs: 146 and 154, (k) SEQ ID NOs: 162 and 170, (l) SEQ ID NOs: 178 and 186, (m) SEQ ID NOs: 194 and 202, (n) SEQ ID NOs: 210 and 218, (o) SEQ ID NOs: 226 and 234, (p) SEQ ID NOs: 242 and 250, (q) SEQ ID NOs: 258 and 266, (r) SEQ ID NOs: 274 and 282, (s) SEQ ID NOs: 290 and 298, (t) SEQ ID NOs: 306 and 298, (u) SEQ ID NOs: 314 and 322, (v) SEQ ID NOs: 330 and 338, (w) SEQ ID NOs: 346 and 354, (x) SEQ ID NOs: 362 and 370, (y) SEQ ID NOs: 378 and 386, (z) SEQ ID NOs: 394 and 402, (a') SEQ ID NOs: 410 and 418, (b') SEQ ID NOs: 426 and 434, (c') SEQ ID NOs: 442 and 450, (d') SEQ ID NOs: 458 and 466, (e') SEQ ID NOs: 474 and 482, and (f') SEQ ID NOs: 490 and 498.

Item 19. The antibody or antigen-binding fragment of item 17 or 18, wherein the antibody or antigen-binding fragment comprises HCDR1, HCDR2, HCDR3, LCDR1, LCDR2 and LCDR3 domains selected from the group consisting of: (a) SEQ ID NOs: 4, 6, 8, 12, 14 and 16 respectively; (b) SEQ ID NOs: 20, 22, 24, 28, 30 and 32 respectively; (c) SEQ ID NOs: 36, 38, 40, 44, 46 and 48 respectively; (d) SEQ ID NOs: 52, 54, 56, 60, 62 and 64 respectively; (e) SEQ ID NOs: 68, 70, 72, 76, 78 and 80 respectively; (f) SEQ ID NOs: 84, 86, 88, 92, 94 and 96 respectively; (g) SEQ ID NOs: 100, 102, 104, 108, 110 and 112 respectively; (h) SEQ ID NOs: 116, 118, 120, 124, 126 and 128 respectively; (i) SEQ ID NOs: 132, 134, 136, 140, 142 and 144 respectively; (j) SEQ ID NOs: 148, 150, 152, 156, 158 and 160 respectively; (k) SEQ ID NOs: 164, 166, 168, 172, 174 and 176 respectively; (l) SEQ ID NOs: 180, 182, 184, 188, 190 and 192 respectively; (m) SEQ ID NOs: 196, 198, 200, 204, 206 and 208 respectively; (n) SEQ ID NOs: 212, 214, 216, 220, 222 and 224 respectively; (o) SEQ ID NOs: 228, 230, 232, 236, 238 and 240 respectively; (p) SEQ ID NOs: 244, 246, 248, 252, 254 and 256 respectively; (q) SEQ ID NOs: 260, 262, 264, 268, 270 and 272 respectively; (r) SEQ ID NOs: 276, 278, 280, 284, 286 and 288 respectively; (s) SEQ ID NOs: 292, 294, 296, 300, 302 and 304 respectively; (t) SEQ ID NOs: 308, 310, 312, 300, 302 and 304 respectively; (u) SEQ ID NOs: 316, 318, 320, 324, 326 and 328 respectively; (v) SEQ ID NOs: 332, 334, 336, 340, 342 and 344 respectively; (w) SEQ ID NOs: 348, 350, 352, 356, 358 and 360 respectively; (x) SEQ ID NOs: 364, 366, 368, 372, 374 and 376 respectively; (y) SEQ ID NOs: 380, 382, 384, 388, 390 and 392 respectively; (z) SEQ ID NOs: 396, 398, 400, 404, 406 and 408 respectively; (a') SEQ ID NOs: 412, 414, 416, 420, 422 and 424 respectively; (b') SEQ ID NOs: 428, 430, 432, 436, 438 and 440 respectively; (c') SEQ ID NOs: 444, 446, 448, 452, 454 and 456 respectively; (d') SEQ ID NOs: 460, 462, 464, 468, 470 and 472 respectively; (e') SEQ ID NOs: 476, 478, 480, 484, 486 and 488 respectively; and (f') SEQ ID NOs: 492, 494, 496, 500, 502 and 504 respectively.

Item 20. The antibody or antigen-binding fragment of any one of items 17-19, wherein the antibody or antigen-binding fragment comprises a HCVR/LCVR amino acid sequence pair selected from the group consisting of: (a) SEQ ID NOs: 2 and 10, (b) SEQ ID NOs: 18 and 26, (c) SEQ ID NOs: 34 and 42, (d) SEQ ID NOs: 50 and 58, (e) SEQ ID NOs: 66 and 74, (f) SEQ ID NOs: 82 and 90, (g) SEQ ID NOs: 98 and 106, (h) SEQ ID NOs: 114 and 122, (i) SEQ ID NOs: 130 and 138, (j) SEQ ID NOs: 146 and 154, (k) SEQ ID NOs: 162 and 170, (l) SEQ ID NOs: 178 and 186, (m) SEQ ID NOs: 194 and 202, (n) SEQ ID NOs: 210 and 218, (o) SEQ ID NOs: 226 and 234, (p) SEQ ID NOs: 242 and 250, (q) SEQ ID NOs: 258 and 266, (r) SEQ ID NOs: 274 and 282, (s) SEQ ID NOs: 290 and 298, (t) SEQ ID NOs: 306 and 298, (u) SEQ ID NOs: 314 and 322, (v) SEQ ID NOs: 330 and 338, (w) SEQ ID NOs: 346 and 354, (x) SEQ ID NOs: 362 and 370, (y) SEQ ID NOs: 378 and 386, (z) SEQ ID NOs: 394 and 402, (a') SEQ ID NOs: 410 and 418, (b') SEQ ID NOs: 426 and 434, (c') SEQ ID NOs: 442 and 450, (d') SEQ ID NOs: 458 and 466, (e') SEQ ID NOs: 474 and 482, and (f') SEQ ID NOs: 490 and 498.

Item 21. The antibody or antigen-binding fragment of any one of items 17-20, wherein the antibody comprises a heavy chain comprising the amino acid sequence of SEQ ID NO: 509 and a light chain comprising the amino acid sequence of SEQ ID NO: 510.

Item 22. A pharmaceutical composition comprising an antibody or antigen-binding fragment thereof of any one of items 1-21 and a pharmaceutically acceptable carrier or diluent.

Item 23. An isolated polynucleotide molecule comprising a polynucleotide sequence that encodes a HCVR of an antibody as set forth in any one of items 1-21.

Item 24. An isolated polynucleotide molecule comprising a polynucleotide sequence that encodes a LCVR of an antibody as set forth in any one of items 1-21.

Item 25. A vector comprising the polynucleotide of item 23 and/or the polynucleotide of item 24.

Item 26. A host cell expressing the vector of item 25.

Item 27. The antibody or antigen-binding fragment thereof of any one of items 1-21, or the pharmaceutical composition of item 22, for use for inhibiting growth of a tumor or a tumor cell in a subject in need thereof.

Item 28. The antibody or antigen-binding fragment thereof, or the pharmaceutical composition, for the use according to item 27, wherein the tumor is a primary or a recurrent tumor.

Item 29. The antibody or antigen-binding fragment thereof, or the pharmaceutical composition, for the use according to item 27, wherein the tumor is an established tumor.

Item 30. The antibody or antigen-binding fragment thereof, or the pharmaceutical composition, for the use according to any one of items 27-29, wherein the tumor is present in a subject with a disease or disorder selected from the group consisting of blood cancer, brain cancer, renal cell cancer, ovarian cancer, bladder cancer, prostate cancer, skin cancer, kidney cancer, cervical cancer, stomach cancer, pancreatic cancer, breast cancer, hepatic cell carcinoma, bone cancer, colon cancer, non-small-cell lung cancer, squamous cell carcinoma of head and neck, colorectal cancer, mesothelioma, B cell lymphoma, myeloma, and melanoma.

Item 31. The antibody or antigen-binding fragment thereof, or the pharmaceutical composition, for the use according to any one of items 27-30, wherein the antibody or antigen-binding fragment thereof or the pharmaceutical composition is administered to the subject as an initial dose followed by one or more secondary doses, wherein each secondary dose is administered 1 to 12 weeks after the immediately preceding dose.

Item 32. The antibody or antigen-binding fragment thereof, or the pharmaceutical composition, for the use according to item 31, wherein the antibody or antigen-binding fragment thereof or the pharmaceutical composition is administered to the subject at a dose of about 25-600 mg.

Item 33. The antibody or antigen-binding fragment thereof, or the pharmaceutical composition, for the use according to any one of items 27-32, wherein the antibody or antigen-binding fragment thereof is administered to the subject in combination with a second therapeutic agent.

Item 34. The antibody or antigen-binding fragment thereof, or the pharmaceutical composition, for the use according to item 33, wherein the second therapeutic agent is selected from the group consisting of a LAG3 inhibitor, an antibody to a tumor specific antigen, an antibody to a virally-infected-cell antigen, a PD-1 inhibitor, a PD-L1 inhibitor, a CD20 inhibitor, a bispecific antibody against CD20 and CD3, a dietary supplement such as an antioxidant, a VEGF antagonist, a cancer vaccine, a chemotherapeutic agent, a cytotoxic agent, radiation, surgery, and any other therapy useful for ameliorating at least one symptom associated with the disease or disorder.

Item 35. The antibody or antigen-binding fragment thereof, or the pharmaceutical composition, for the use according to item 33 or 34, wherein the second therapeutic agent is a PD-1 inhibitor.

Item 36. The antibody or antigen-binding fragment thereof, or the pharmaceutical composition, for the use according to any one of items 33-35, wherein the PD-1 inhibitor is cemiplimab, nivolumab or pembrolizumab.

Item 37. The antibody or antigen-binding fragment thereof, or the pharmaceutical composition, for the use according to item 36, wherein the PD-1 inhibitor is administered at a dose of 1, 3 or 10 mg/kg of the subject's body weight.

Item 38. The antibody or antigen-binding fragment thereof, or the pharmaceutical composition, for the use according to any one of items 33-35, wherein the PD-1 inhibitor is administered at a dose of 50-1200 mg.

Item 39. The antibody or antigen-binding fragment thereof, or the pharmaceutical composition, for the use according to any one of items 27-38, wherein the antibody or antigen-binding fragment thereof or the pharmaceutical composition is administered subcutaneously, intravenously, intratumorally, peritumorally, intradermally, intraperitoneally, orally, intramuscularly or intracranially.

Item 40. The antibody or antigen-binding fragment thereof of any one of items 1-21, or the pharmaceutical composition of item 22, for use in the treatment of a disease or disorder that is treatable by antagonizing CTLA-4 in a subject in need thereof.

Item 41. The antibody or antigen-binding fragment thereof, or the pharmaceutical composition, for the use according to item 40, wherein the disease or disorder is a chronic viral infection caused by a virus selected from the group consisting of human immunodeficiency virus (HIV), hepatitis C virus (HCV), hepatitis B virus (HBV), human papilloma virus (HPV), lymphocytic choriomeningitis virus (LCMV) and simian immunodeficiency virus (SIV).

Item 42. The antibody or antigen-binding fragment thereof, or the pharmaceutical composition, for the use according to item 40, wherein the disease or disorder is selected from the group consisting of blood cancer, brain cancer, renal cell cancer, ovarian cancer, bladder cancer, skin cancer, cervical cancer, stomach cancer, kidney cancer, prostate cancer, breast cancer, hepatic cell carcinoma, bone cancer, colon cancer, non-small-cell lung cancer, squamous cell carcinoma of head and neck, colorectal cancer, mesothelioma, B cell lymphoma, and melanoma.

Item 43. A method of producing an anti-CTLA-4 antibody or antigen-binding fragment thereof, comprising growing the host cell of item 26 under conditions permitting production of the antibody or antigen-binding fragment thereof, and recovering the antibody or antigen-binding fragment thereof so produced.

Item 44. The method of item 43, further comprising formulating the antibody or antigen-binding fragment thereof as a pharmaceutical composition comprising an acceptable carrier.

Item 45. An anti-CTLA-4 antibody or antigen-biding fragment thereof for use in combination with an anti-PD-1 antibody in the treatment of non-small cell lung cancer in a subject in need thereof.

Item 46. The anti-CTLA-4 antibody or antigen-binding fragment thereof for the use according to item 45, wherein the anti-CTLA-4 antibody or antigen-binding fragment thereof is an antibody or an antigen-binding fragment thereof as claimed in any one of items 1-21.

Item 47. The antibody or antigen-binding fragment thereof for the use according to item 45 or 46, wherein the anti-CTLA-4 antibody comprises the CDRs of a HCVR comprising the amino acid sequence of SEQ ID NO: 194 and the CDRs of a LCVR comprising the amino acid sequence of SEQ ID NO: 202.

Item 48. The antibody or antigen-binding fragment thereof for the use according to any one of items 45-47, wherein the anti-CTLA-4 antibody comprises a HCDR1 of sequence SEQ ID NO: 196, a HCDR2 of sequence SEQ ID NO: 198, a HCDR3 of sequence SEQ ID NO: 200, a LCDR1 of sequence SEQ ID NO: 204, a LCDR2 of sequence SEQ ID NO: 206, and a LCDR3 of sequence SEQ ID NO: 208.

Item 49. The antibody or antigen-binding fragment thereof for the use according to any one of items 45-48, wherein the anti-CTLA-4 antibody comprises a HCVR comprising the amino acid sequence of SEQ ID NO: 194, and a LCVR comprising the amino acid sequence of SEQ ID NO: 202.

Item 50. The antibody or antigen-binding fragment thereof for the use according to any one of items 45-49, wherein the anti-CTLA-4 antibody comprises a human IgG1 heavy chain constant region.

Item 51. The antibody or antigen-binding fragment thereof for the use according to any one of items 45-50, wherein the anti-CTLA-4 antibody comprises a heavy chain comprising the amino acid sequence of SEQ ID NO: 509 and a light chain of amino acid sequence of SEQ ID NO: 510.

Item 52. The antibody or antigen-binding fragment thereof for the use according to any one of items 45-51, wherein the anti-PD-1 antibody is cemiplimab.

Item 53. The antibody or antigen-binding fragment thereof for the use according to any one of items 45-52, wherein the anti-CTLA-4 antibody or antigen-binding fragment thereof is administered at a dose of 25-600 mg.

Item 54. The antibody or antigen-binding fragment thereof for the use according to any one of items 45-53, wherein the anti-PD-1 antibody is administered at a dose of 50-1200 mg.

Item 55. The antibody or antigen-binding fragment thereof for the use according to any one of items 45-54, wherein the anti-CTLA-4 antibody or antigen-binding fragment thereof is administered as an initial dose, followed by one or more secondary doses, wherein each secondary dose is administered 1 to 12 weeks after the immediately preceding dose.

Item 56. The antibody or antigen-binding fragment thereof for the use according to any one of items 45-55, wherein the non-small cell lung cancer (NSCLC) is advanced or metastatic NSCLC.

Item 57. The pharmaceutical composition of Item 22 for use in combination with an anti-PD-1 antibody in the treatment of non-small cell lung cancer in a subject in need thereof The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A pair of polynucleotide molecules encoding a heavy chain variable region (HCVR) and a light chain variable region (LCVR), respectively, of an antibody or antigen-binding fragment thereof that binds specifically to cytotoxic T-lymphocyte-associated protein 4 (CTLA-4), wherein the HCVR comprises three heavy chain complementarity determining regions (HCDR1, HCDR2 and HCDR3), wherein the HCDR1 comprises the amino acid sequence of SEQ ID NO: 196, the HCDR2 comprises the amino acid sequence of SEQ ID NO: 198, and the HCDR3 comprises the amino acid sequence of SEQ ID NO: 200, and the LCVR comprises three light chain complementarity determining regions (LCDR1, LCDR2 and LCDR3), wherein the LCDR1 comprises the amino acid sequence of SEQ ID NO: 204, the LCDR2 comprises the amino acid sequence of SEQ ID NO: 206, and the LCDR3 comprises the amino acid sequence of SEQ ID NO: 208.

2. The pair of polynucleotide molecules of claim 1, wherein the HCVR comprises the amino acid sequence of SEQ ID NO: 194.

3. The pair of polynucleotide molecules of claim 1, wherein the polynucleotide comprises an HCDR1 nucleic acid sequence set forth in SEQ ID NO: 195, an HCDR2 nucleic acid sequence set forth in SEQ ID NO: 197, and an HCDR3 nucleic acid sequence set forth in SEQ ID NO: 199.

4. The pair of polynucleotide molecules of claim 1, wherein the polynucleotide comprises the nucleic acid sequence of SEQ ID NO: 193.

5. The pair of polynucleotide molecules of claim 1, further encoding an immunoglobulin heavy chain constant region of the antibody.

6. The pair of polynucleotide molecules of claim 5, wherein the immunoglobulin heavy chain constant region is a human IgG1 constant region.

7. The pair of polynucleotide molecules of claim 6, wherein the polynucleotide encodes a heavy chain of the antibody comprising the amino acid sequence of SEQ ID NO: 509.

8. A recombinant expression vector comprising the pair of polynucleotide molecules of claim 1.

9. An isolated host cell comprising the vector of claim 8.

10. The pair of polynucleotide molecules of claim 1, wherein the LCVR comprises the amino acid sequence of SEQ ID NO: 202.

11. The pair of polynucleotide molecules of claim 1, wherein the polynucleotide comprises an LCDR1 nucleic acid sequence set forth in SEQ ID NO: 203, an LCDR2 nucleic acid sequence set forth in SEQ ID NO: 205, and an LCDR3 nucleic acid sequence set forth in SEQ ID NO: 207.

12. The pair of polynucleotide molecules of claim 1, wherein the polynucleotide comprises the nucleic acid sequence of SEQ ID NO: 201.

13. The pair of polynucleotide molecules of claim 1, further encoding an immunoglobulin light chain constant region of the antibody.

14. The pair of polynucleotide molecules of claim 13, wherein the immunoglobulin light chain constant region is a human kappa constant region.

15. The pair of polynucleotide molecules of claim 14, wherein the polynucleotide encodes a light chain of the antibody comprising the amino acid sequence of SEQ ID NO: 510.

16. A pair of recombinant expression vectors comprising the pair of polynucleotide molecules, respectively, of claim 1.

17. An isolated host cell comprising the pair of vectors of claim 16.

18. An isolated host cell comprising a first polynucleotide encoding a heavy chain variable region (HCVR) of an antibody or antigen-binding fragment thereof that binds specifically to cytotoxic T-lymphocyte-associated protein 4 (CTLA-4), wherein the HCVR comprises three heavy chain complementarity determining regions (HCDR1, HCDR2 and HCDR3), wherein the HCDR1 comprises the amino acid sequence of SEQ ID NO: 196, the HCDR2 comprises the amino acid sequence of SEQ ID NO: 198, and the HCDR3 comprises the amino acid sequence of SEQ ID NO: 200, and a second polynucleotide encoding a light chain variable region (LCVR) of an antibody or antigen-binding fragment thereof that binds specifically to cytotoxic T-lymphocyte-associated protein 4 (CTLA-4), wherein the LCVR comprises three light chain complementarity determining regions (LCDR1, LCDR2 and LCDR3), wherein the LCDR1 comprises the amino acid sequence of SEQ ID NO: 204, the LCDR2 comprises the amino acid sequence of SEQ ID NO: 206, and the LCDR3 comprises the amino acid sequence of SEQ ID NO: 208.

19. The isolated host cell of claim 18, wherein the first polynucleotide encodes a heavy chain of the antibody comprising the amino acid sequence of SEQ ID NO: 509, and the second polynucleotide encodes a light chain of the antibody comprising the amino acid sequence of SEQ ID NO: 510.

20. A method of producing an anti-CTLA-4 antibody or antigen-binding fragment thereof by culturing the isolated host cell of claim 18 under conditions permitting production of the antibody or antigen-binding fragment, and recovering the antibody or antigen-binding fragment so produced.

21. The method of claim 20, wherein the isolated host cell is a CHO cell.

* * * * *

SEQUENCE LISTING

```
<160> NUMBER OF SEQ ID NOS: 510

<210> SEQ ID NO 1
<211> LENGTH: 351
<212> TYPE: DNA
<213> ORGANISM: Artificial Sequence
<220> FEATURE:
<223> OTHER INFORMATION: synthetic

<400> SEQUENCE: 1
caggttcagc tggtgcagtc tggagctgag gtgaagaagc ctggggcctc agtgaaggtc      60
tcctgcaagg cttctgatta cacctttacc agctatggta tcagctgggt gcgacaggcc    120
cctggacaag gcttgagtg gatgggctgg atcagcgttt acaatggtaa tataaactat    180
gcacagaagt tcaagggcag agtcaccatg accagacaca tccacgag cactgcctac      240 atggagctga ggagcctgag atctgacgac atggccgtgt attactgtgc gagagtgacc    300
caattcggta tggacgtctg gggccaaggg accacggtca ccgtctcctc a              351

<210> SEQ ID NO 2
<211> LENGTH: 117
<212> TYPE: PRT
<213> ORGANISM: Artificial Sequence
<220> FEATURE:
<223> OTHER INFORMATION: synthetic

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Asp Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Val Tyr Asn Gly Asn Ile Asn Tyr Ala Gln Lys Phe
    50                  55                  60

Lys Gly Arg Val Thr Met Thr Thr Asp Thr Ser Thr Ser Thr Ala Tyr
65                  70                  75                  80
```

```
Met Glu Leu Arg Ser Leu Arg Ser Asp Asp Met Ala Val Tyr Tyr Cys
                 85                  90                  95

Ala Arg Val Thr Gln Phe Gly Met Asp Val Trp Gly Gln Gly Thr Thr
            100                 105                 110

Val Thr Val Ser Ser
            115

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
gattacacct ttaccagcta tggt                                              24

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Asp Tyr Thr Phe Thr Ser Tyr Gly
1               5

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
atcagcgttt acaatggtaa tata                                              24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ile Ser Val Tyr Asn Gly Asn Ile
1               5

<210> SEQ ID NO 7
<211> LENGTH: 30
<212> TYPE: DNA
<213> ORGANISM: Artificial Sequence
<220> FEATURE:
<223> OTHER INFORMATION: synthetic

<400> SEQUENCE: 7
gcgagagtga cccaattcgg tatggacgtc                                        30

<210> SEQ ID NO 8
<211> LENGTH: 10
<212> TYPE: PRT
<213> ORGANISM: Artificial Sequence
<220> FEATURE:
<223> OTHER INFORMATION: synthetic
```

<400> SEQUENCE: 8

Ala Arg Val Thr Gln Phe Gly Met Asp Val
1               5                   10

<210> SEQ ID NO 9
<211> LENGTH: 321
<212> TYPE: DNA
<213> ORGANISM: Artificial Sequence
<220> FEATURE:
<223> OTHER INFORMATION: synthetic

<400> SEQUENCE: 9

```
gacatccaga tgacccagtc tccatcctcc ctgtctgcat ctgtaggaga cagagtcacc      60
atcacttgcc gggcaagtca gagcattagt agtaatttaa attggtatca gcagaatcca     120
gggaaagccc ctaagctcct gatctatact acatccagtt tgcaaggtgg ggtcccatca     180
aggttcagtg gcagtggatc tgggacagat ttcactctca ccatcagcag tctacaacct     240
gaagattttg caacttacta ctgtcaacag agtttcagga ccccattcac tttcggccct     300
gggaccaaag tggatatcaa a                                                321
```

<210> SEQ ID NO 10
<211> LENGTH: 107
<212> TYPE: PRT
<213> ORGANISM: Artificial Sequence
<220> FEATURE:
<223> OTHER INFORMATION: synthetic

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Asn
            20                  25                  30

Leu Asn Trp Tyr Gln Gln Asn Pro Gly Lys Ala Pro Lys Leu Leu Ile
        35                  40                  45

Tyr Thr Thr Ser Ser Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Arg Thr Pro Phe
                85                  90                  95

Thr Phe Gly Pro Gly Thr Lys Val Asp Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
cagagcatta gtagtaat                                                    18

<210> SEQ ID NO 12
<211> LENGTH: 6
<212> TYPE: PRT
<213> ORGANISM: Artificial Sequence
<220> FEATURE:
<223> OTHER INFORMATION: synthetic

```
<400> SEQUENCE: 12

Gln Ser Ile Ser Ser Asn
1               5

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 actacatcc                                                                  9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Thr Thr Ser
1

<210> SEQ ID NO 15
<211> LENGTH: 27
<212> TYPE: DNA
<213> ORGANISM: Artificial Sequence
<220> FEATURE:
<223> OTHER INFORMATION: synthetic

<400> SEQUENCE: 15
caacagagtt tcaggacccc attcact                                             27

<210> SEQ ID NO 16
<211> LENGTH: 9
<212> TYPE: PRT
<213> ORGANISM: Artificial Sequence
<220> FEATURE:
<223> OTHER INFORMATION: synthetic

<400> SEQUENCE: 16

Gln Gln Ser Phe Arg Thr Pro Phe Thr
1               5

<210> SEQ ID NO 17
<211> LENGTH: 384
<212> TYPE: DNA
<213> ORGANISM: Artificial Sequence
<220> FEATURE:
<223> OTHER INFORMATION: synthetic

<400> SEQUENCE: 17
gaggtgcagc tggtggagtc tggggaggc ttggtccagc ctgggggtc cctgaaactc          60 tcctgtgcag cctctgggtt caccttcagt ggctctgcta tgcactgggt ccgccaggct       120
tccgggaaag gctggagtg gttggccgt attagaggca aagctaatag tttcgcgaca         180
gcatattctg cgtcggtgaa aggcaggttc accatctcca gagatgactc aaagaacacg       240
gcgtctctgc aaatgaacag cctgagaacc gaagacacgg ccgtgtattt tgtactaga        300 gaggatcagc agttggtacg tccatactac taccactacg gtatggacgt ctggggccaa       360
gggaccacgg tcaccgtctc ctca                                              384
```

<210> SEQ ID NO 18
<211> LENGTH: 128
<212> TYPE: PRT
<213> ORGANISM: Artificial Sequence
<220> FEATURE:
<223> OTHER INFORMATION: synthetic

<400> SEQUENCE: 18

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Gly Lys Ala Asn Ser Phe Ala Thr Ala Tyr Ser Ala
    50                  55                  60

Ser Val Lys Gly Arg Phe Thr Ile Ser Arg Asp Asp Ser Lys Asn Thr
65                  70                  75                  80

Ala Ser Leu Gln Met Asn Ser Leu Arg Thr Glu Asp Thr Ala Val Tyr
                85                  90                  95

Phe Cys Thr Arg Glu Asp Gln Gln Leu Val Arg Pro Tyr Tyr Tyr His
            100                 105                 110

Tyr Gly Met Asp Val Trp Gly Gln Gly Thr Thr Val Thr Val Ser Ser
        115                 120                 125
```

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
gggttcacct tcagtggctc tgct                                     24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

```
Gly Phe Thr Phe Ser Gly Ser Ala
1               5
```

<210> SEQ ID NO 21
<211> LENGTH: 30
<212> TYPE: DNA
<213> ORGANISM: Artificial Sequence
<220> FEATURE:
<223> OTHER INFORMATION: synthetic

<400> SEQUENCE: 21
attagaggca aagctaatag tttcgcgaca                               30

<210> SEQ ID NO 22
<211> LENGTH: 10
<212> TYPE: PRT
<213> ORGANISM: Artificial Sequence
<220> FEATURE:
<223> OTHER INFORMATION: synthetic

<400> SEQUENCE: 22

Ile Arg Gly Lys Ala Asn Ser Phe Ala Thr
1               5                   10

<210> SEQ ID NO 23
<211> LENGTH: 57
<212> TYPE: DNA
<213> ORGANISM: Artificial Sequence
<220> FEATURE:
<223> OTHER INFORMATION: synthetic

<400> SEQUENCE: 23
actagagagg atcagcagtt ggtacgtcca tactactacc actacggtat ggacgtc    57

<210> SEQ ID NO 24
<211> LENGTH: 19
<212> TYPE: PRT
<213> ORGANISM: Artificial Sequence
<220> FEATURE:
<223> OTHER INFORMATION: synthetic

<400> SEQUENCE: 24

Thr Arg Glu Asp Gln Gln Leu Val Arg Pro Tyr Tyr Tyr His Tyr Gly
1               5                   10                  15

Met Asp Val

<210> SEQ ID NO 25
<211> LENGTH: 321
<212> TYPE: DNA
<213> ORGANISM: Artificial Sequence
<220> FEATURE:
<223> OTHER INFORMATION: synthetic

<400> SEQUENCE: 25
gacatccaga tgacccagtc tccatcctcc ctgtctgcat ctgtaggaga cagagtcacc     60
atcacttgcc ggacaagtca gagcattacc aactatttaa attggtatca gcagaaacca    120
gggaaagccc ctaagctcct gatctatgct acagccagtt tgcaaagtgg ggtcccatca    180
aggttcagtg gcagtggatc tgagacagat ttcactctca ccatcagcag tctgcaacct    240
gaagattttg caacttacta ctgtcaacag agttacagta ccccgctcac tttcggcgga    300
gggaccaagg tggagatcaa a                                              321

<210> SEQ ID NO 26
<211> LENGTH: 107
<212> TYPE: PRT
<213> ORGANISM: Artificial Sequence
<220> FEATURE:
<223> OTHER INFORMATION: synthetic

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Thr Asn Tyr
                20                  25                  30

Leu Asn Trp Tyr Gln Gln Lys Pro Gly Lys Ala Pro Lys Leu Leu Ile
            35                  40                  45

Tyr Ala Thr Ala Ser Leu Gln Ser Gly Val Pro Ser Arg Phe Ser Gly
        50                  55                  60

Ser Gly Ser Glu Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
            85                  90                  95
Thr Phe Gly Gly Gly Thr Lys Val Glu Ile Lys
        100                 105

<210> SEQ ID NO 27
<211> LENGTH: 18
<212> TYPE: DNA
<213> ORGANISM: Artificial Sequence
<220> FEATURE:
<223> OTHER INFORMATION: synthetic

<400> SEQUENCE: 27
cagagcatta ccaactat                                             18

<210> SEQ ID NO 28
<211> LENGTH: 6
<212> TYPE: PRT
<213> ORGANISM: Artificial Sequence
<220> FEATURE:
<223> OTHER INFORMATION: synthetic

<400> SEQUENCE: 28

Gln Ser Ile Thr Asn Tyr
1               5

<210> SEQ ID NO 29
<211> LENGTH: 9
<212> TYPE: DNA
<213> ORGANISM: Artificial Sequence
<220> FEATURE:
<223> OTHER INFORMATION: synthetic

<400> SEQUENCE: 29 gctacagcc                                                        9

<210> SEQ ID NO 30
<211> LENGTH: 3
<212> TYPE: PRT
<213> ORGANISM: Artificial Sequence
<220> FEATURE:
<223> OTHER INFORMATION: synthetic

<400> SEQUENCE: 30

Ala Thr Ala
1

<210> SEQ ID NO 31
<211> LENGTH: 27
<212> TYPE: DNA
<213> ORGANISM: Artificial Sequence
<220> FEATURE:
<223> OTHER INFORMATION: synthetic

<400> SEQUENCE: 31
caacagagtt acagtacccc gctcact                                   27

<210> SEQ ID NO 32
<211> LENGTH: 9
<212> TYPE: PRT
<213> ORGANISM: Artificial Sequence
<220> FEATURE:
<223> OTHER INFORMATION: synthetic

<400> SEQUENCE: 32

Gln Gln Ser Tyr Ser Thr Pro Leu Thr

<210> SEQ ID NO 33
<211> LENGTH: 369
<212> TYPE: DNA
<213> ORGANISM: Artificial Sequence
<220> FEATURE:
<223> OTHER INFORMATION: synthetic

<400> SEQUENCE: 33

```
cagatcacct tgaaggagtc tggtcctacg ctggtgaaac ccacacagac cctcacgctg      60
acctgcacct tctctgggtt ctcactcagc actagtggag tgggtgtggg ctggatccgt     120
cagtccccag gaagggccct ggagtggctg gcactcattt attggaatga tcatgagcgc     180
tatagtccat ctctgaagag caggctcacc attaccaagg acacctccaa aaacctggtt     240
gtcctcgcaa tggccaacat ggaccccgtg acacagcca catatttctg tgcacacaga      300
aacatcgaat atagaaggtc gtacttcttt gactactggg gtcagggaac cctggtcacc     360
gtctcctca                                                              369
```

<210> SEQ ID NO 34
<211> LENGTH: 123
<212> TYPE: PRT
<213> ORGANISM: Artificial Sequence
<220> FEATURE:
<223> OTHER INFORMATION: synthetic

<400> SEQUENCE: 34

Gln Ile Thr Leu Lys Glu Ser Gly Pro Thr Leu Val Lys Pro Thr Gln
1               5                   10                  15
Thr Leu Thr Leu Thr Cys Thr Phe Ser Gly Phe Ser Leu Ser Thr Ser
            20                  25                  30
Gly Val Gly Val Gly Trp Ile Arg Gln Ser Pro Gly Arg Ala Leu Glu
        35                  40                  45
Trp Leu Ala Leu Ile Tyr Trp Asn Asp His Glu Arg Tyr Ser Pro Ser
    50                  55                  60
Leu Lys Ser Arg Leu Thr Ile Thr Lys Asp Thr Ser Lys Asn Leu Val
65                  70                  75                  80
Val Leu Ala Met Ala Asn Met Asp Pro Val Asp Thr Ala Thr Tyr Phe
                85                  90                  95
Cys Ala His Arg Asn Ile Glu Tyr Arg Arg Ser Tyr Phe Phe Asp Tyr
            100                 105                 110
Trp Gly Gln Gly Thr Leu Val Thr Val Ser Ser
        115                 120

<210> SEQ ID NO 35
<211> LENGTH: 30
<212> TYPE: DNA
<213> ORGANISM: Artificial Sequence
<220> FEATURE:
<223> OTHER INFORMATION: synthetic

<400> SEQUENCE: 35

```
gggttctcac tcagcactag tggagtgggt                                       30
```

<210> SEQ ID NO 36
<211> LENGTH: 10
<212> TYPE: PRT
<213> ORGANISM: Artificial Sequence
<220> FEATURE:
<223> OTHER INFORMATION: synthetic

<400> SEQUENCE: 36

Gly Phe Ser Leu Ser Thr Ser Gly Val Gly
1               5                   10

<210> SEQ ID NO 37
<211> LENGTH: 21
<212> TYPE: DNA
<213> ORGANISM: Artificial Sequence
<220> FEATURE:
<223> OTHER INFORMATION: synthetic

<400> SEQUENCE: 37
atttattgga atgatcatga g                                          21

<210> SEQ ID NO 38
<211> LENGTH: 7
<212> TYPE: PRT
<213> ORGANISM: Artificial Sequence
<220> FEATURE:
<223> OTHER INFORMATION: synthetic

<400> SEQUENCE: 38

Ile Tyr Trp Asn Asp His Glu
1               5

<210> SEQ ID NO 39
<211> LENGTH: 45
<212> TYPE: DNA
<213> ORGANISM: Artificial Sequence
<220> FEATURE:
<223> OTHER INFORMATION: synthetic

<400> SEQUENCE: 39
gcacacagaa acatcgaata tagaaggtcg tacttctttg actac               45

<210> SEQ ID NO 40
<211> LENGTH: 15
<212> TYPE: PRT
<213> ORGANISM: Artificial Sequence
<220> FEATURE:
<223> OTHER INFORMATION: synthetic

<400> SEQUENCE: 40

Ala His Arg Asn Ile Glu Tyr Arg Arg Ser Tyr Phe Phe Asp Tyr
1               5                   10                  15

<210> SEQ ID NO 41
<211> LENGTH: 321
<212> TYPE: DNA
<213> ORGANISM: Artificial Sequence
<220> FEATURE:
<223> OTHER INFORMATION: synthetic

<400> SEQUENCE: 41
gacatccaga tgacccagtc tccatcttcc gtgtctgcat ctgtaagaga cagagtcacc    60
gtcacttgtc gggcgagtca ggatattaac aactggttag cctggtatca gcagaaacca   120
gggaaagccc ctaaactcct gatctatgct gcatccagtt tacaaagtgg ggtcccatca   180
aggttcagcg gcagtggatc tgggacagat ttcactctca ccatcagcag cctgcagcct   240
gaagattttg caacttacta ttgtcaacag gctaacactt tcccattcac tttcggccct   300
gggaccaaag tggatatcaa a                                             321

```
<210> SEQ ID NO 42
<211> LENGTH: 107
<212> TYPE: PRT
<213> ORGANISM: Artificial Sequence
<220> FEATURE:
<223> OTHER INFORMATION: synthetic

<400> SEQUENCE: 42
```

Asp Ile Gln Met Thr Gln Ser Pro Ser Ser Val Ser Ala Ser Val Arg
1               5                   10                  15

Asp Arg Val Thr Val Thr Cys Arg Ala Ser Gln Asp Ile Asn Asn Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Thr Phe Pro Phe
                85                  90                  95

Thr Phe Gly Pro Gly Thr Lys Val Asp Ile Lys
            100                 105

```
<210> SEQ ID NO 43
<211> LENGTH: 18
<212> TYPE: DNA
<213> ORGANISM: Artificial Sequence
<220> FEATURE:
<223> OTHER INFORMATION: synthetic

<400> SEQUENCE: 43
caggatatta acaactgg                                              18

<210> SEQ ID NO 44
<211> LENGTH: 6
<212> TYPE: PRT
<213> ORGANISM: Artificial Sequence
<220> FEATURE:
<223> OTHER INFORMATION: synthetic

<400> SEQUENCE: 44
```

Gln Asp Ile Asn Asn Trp
1               5

```
<210> SEQ ID NO 45
<211> LENGTH: 9
<212> TYPE: DNA
<213> ORGANISM: Artificial Sequence
<220> FEATURE:
<223> OTHER INFORMATION: synthetic

<400> SEQUENCE: 45 gctgcatcc                                                         9

<210> SEQ ID NO 46
<211> LENGTH: 3
<212> TYPE: PRT
<213> ORGANISM: Artificial Sequence
<220> FEATURE:
<223> OTHER INFORMATION: synthetic

<400> SEQUENCE: 46
```

Ala Ala Ser
1

<210> SEQ ID NO 47
<211> LENGTH: 27
<212> TYPE: DNA
<213> ORGANISM: Artificial Sequence
<220> FEATURE:
<223> OTHER INFORMATION: synthetic

<400> SEQUENCE: 47
caacaggcta acactttccc attcact                                              27

<210> SEQ ID NO 48
<211> LENGTH: 9
<212> TYPE: PRT
<213> ORGANISM: Artificial Sequence
<220> FEATURE:
<223> OTHER INFORMATION: synthetic

<400> SEQUENCE: 48

Gln Gln Ala Asn Thr Phe Pro Phe Thr
1               5

<210> SEQ ID NO 49
<211> LENGTH: 354
<212> TYPE: DNA
<213> ORGANISM: Artificial Sequence
<220> FEATURE:
<223> OTHER INFORMATION: synthetic

<400> SEQUENCE: 49
caggtgcagc tgcaggagtc gggcccagga ctggtgaagc cttcggagac cctgtccctc          60
acctgcactg tctctggtgg ctccatcaat agttattact ggacctggat ccggcagccc         120
ccagggaagg gactggagtg gattggatat gtctattaca gtgggagcac acctacaac          180 ccctccctca agagtcgagt caccatatca gtagacacgt ccaagaacca gttcttcctg         240
aacctgaact ctgtgaccgc tgcggaaacg gccgtgtatt actgtgcgag agggacactg         300
gggtactacg gtatggacgt ctggggccaa gggaccacgg tcaccgtctc ctca              354

<210> SEQ ID NO 50
<211> LENGTH: 118
<212> TYPE: PRT
<213> ORGANISM: Artificial Sequence
<220> FEATURE:
<223> OTHER INFORMATION: synthetic

<400> SEQUENCE: 50

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Ser Tyr
            20                  25                  30

Tyr Trp Thr Trp Ile Arg Gln Pro Pro Gly Lys Gly Leu Glu Trp Ile
        35                  40                  45

Gly Tyr Val Tyr Tyr Ser Gly Ser Thr Thr Tyr Asn Pro Ser Leu Lys
    50                  55                  60

Ser Arg Val Thr Ile Ser Val Asp Thr Ser Lys Asn Gln Phe Phe Leu
65                  70                  75                  80

Asn Leu Asn Ser Val Thr Ala Ala Glu Thr Ala Val Tyr Tyr Cys Ala
                85                  90                  95

Arg Gly Thr Leu Gly Tyr Tyr Gly Met Asp Val Trp Gly Gln Gly Thr
            100                 105                 110

Thr Val Thr Val Ser Ser
         115

<210> SEQ ID NO 51
<211> LENGTH: 24
<212> TYPE: DNA
<213> ORGANISM: Artificial Sequence
<220> FEATURE:
<223> OTHER INFORMATION: synthetic

<400> SEQUENCE: 51
ggtggctcca tcaatagtta ttac                                    24

<210> SEQ ID NO 52
<211> LENGTH: 8
<212> TYPE: PRT
<213> ORGANISM: Artificial Sequence
<220> FEATURE:
<223> OTHER INFORMATION: synthetic

<400> SEQUENCE: 52

Gly Gly Ser Ile Asn Ser Tyr Tyr
1               5

<210> SEQ ID NO 53
<211> LENGTH: 21
<212> TYPE: DNA
<213> ORGANISM: Artificial Sequence
<220> FEATURE:
<223> OTHER INFORMATION: synthetic

<400> SEQUENCE: 53
gtctattaca gtgggagcac c                                       21

<210> SEQ ID NO 54
<211> LENGTH: 7
<212> TYPE: PRT
<213> ORGANISM: Artificial Sequence
<220> FEATURE:
<223> OTHER INFORMATION: synthetic

<400> SEQUENCE: 54

Val Tyr Tyr Ser Gly Ser Thr
1               5

<210> SEQ ID NO 55
<211> LENGTH: 36
<212> TYPE: DNA
<213> ORGANISM: Artificial Sequence
<220> FEATURE:
<223> OTHER INFORMATION: synthetic

<400> SEQUENCE: 55
gcgagaggga cactggggta ctacggtatg gacgtc                       36

<210> SEQ ID NO 56
<211> LENGTH: 12
<212> TYPE: PRT
<213> ORGANISM: Artificial Sequence
<220> FEATURE:
<223> OTHER INFORMATION: synthetic

<400> SEQUENCE: 56

Ala Arg Gly Thr Leu Gly Tyr Tyr Gly Met Asp Val
1               5                   10

<210> SEQ ID NO 57
<211> LENGTH: 324
<212> TYPE: DNA
<213> ORGANISM: Artificial Sequence
<220> FEATURE:
<223> OTHER INFORMATION: synthetic

<400> SEQUENCE: 57

```
gaaattgtgt tgacgcagtc tccaggcacc ctgtctttgt ctccagggga aagagccacc      60
ctctcctgca gggccagtca gagttttagc aacaactact tagcctggta ccagcagaaa     120
cctggccagg ctcccaggct cctcatctat ggtacatcca tcagggccac tggcatccca     180
gacaggttca gtggcagtgg gtctgggaca gacttcactc tcgccatcag cagactggag     240
cctgaagatt ttgcagtgta ttattgtcag cagtatggta ggtcacctct cactttcggc     300
ggagggacca aggtggagat caaa                                            324
```

<210> SEQ ID NO 58
<211> LENGTH: 108
<212> TYPE: PRT
<213> ORGANISM: Artificial Sequence
<220> FEATURE:
<223> OTHER INFORMATION: synthetic

<400> SEQUENCE: 58

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Phe Ser Asn Asn
            20                  25                  30

Tyr Leu Ala Trp Tyr Gln Gln Lys Pro Gly Gln Ala Pro Arg Leu Leu
        35                  40                  45

Ile Tyr Gly Thr Ser Ile Arg Ala Thr Gly Ile Pro Asp Arg Phe Ser
    50                  55                  60

Gly Ser Gly Ser Gly Thr Asp Phe Thr Leu Ala Ile Ser Arg Leu Glu
65                  70                  75                  80

Pro Glu Asp Phe Ala Val Tyr Tyr Cys Gln Gln Tyr Gly Arg Ser Pro
                85                  90                  95

Leu Thr Phe Gly Gly Gly Thr Lys Val Glu Ile Lys
            100                 105

<210> SEQ ID NO 59
<211> LENGTH: 21
<212> TYPE: DNA
<213> ORGANISM: Artificial Sequence
<220> FEATURE:
<223> OTHER INFORMATION: synthetic

<400> SEQUENCE: 59

```
cagagtttta gcaacaacta c                                                21
```

<210> SEQ ID NO 60
<211> LENGTH: 7
<212> TYPE: PRT
<213> ORGANISM: Artificial Sequence
<220> FEATURE:
<223> OTHER INFORMATION: synthetic

<400> SEQUENCE: 60

Gln Ser Phe Ser Asn Asn Tyr
1               5

<210> SEQ ID NO 61

```
<211> LENGTH: 9
<212> TYPE: DNA
<213> ORGANISM: Artificial Sequence
<220> FEATURE:
<223> OTHER INFORMATION: synthetic

<400> SEQUENCE: 61 ggtacatcc                                                                 9

<210> SEQ ID NO 62
<211> LENGTH: 3
<212> TYPE: PRT
<213> ORGANISM: Artificial Sequence
<220> FEATURE:
<223> OTHER INFORMATION: synthetic

<400> SEQUENCE: 62

Gly Thr Ser
1

<210> SEQ ID NO 63
<211> LENGTH: 27
<212> TYPE: DNA
<213> ORGANISM: Artificial Sequence
<220> FEATURE:
<223> OTHER INFORMATION: synthetic

<400> SEQUENCE: 63
cagcagtatg gtaggtcacc tctcact                                            27

<210> SEQ ID NO 64
<211> LENGTH: 9
<212> TYPE: PRT
<213> ORGANISM: Artificial Sequence
<220> FEATURE:
<223> OTHER INFORMATION: synthetic

<400> SEQUENCE: 64

Gln Gln Tyr Gly Arg Ser Pro Leu Thr
1               5

<210> SEQ ID NO 65
<211> LENGTH: 354
<212> TYPE: DNA
<213> ORGANISM: Artificial Sequence
<220> FEATURE:
<223> OTHER INFORMATION: synthetic

<400> SEQUENCE: 65
caggtgcagc tggtggagtc tgggggaggc gtggtccagc ctggggaggtc cctgagactc        60 tcctgtgcag cgtctggatt caccttcagt agttatggca tgaactgggt ccgccaggct       120
ccaggcaagg ggctggagtg ggtggcagtt acatgtatg atggaagtaa taaacattat        180
gcagactccg tgaagggccg attcaccatc tccagagaca attccaagaa cacgctgtat       240
ctgcaaatgt acagcctgag agccgaggac acggctatgt attattgtgt gagagggggg       300 caccctcggcg ctttttgatat ctggggccaa gggacaatgg tcaccgtctc ttca           354

<210> SEQ ID NO 66
<211> LENGTH: 118
<212> TYPE: PRT
<213> ORGANISM: Artificial Sequence
<220> FEATURE:
<223> OTHER INFORMATION: synthetic

<400> SEQUENCE: 66
```

```
Gln Val Gln Leu Val Glu Ser Gly Gly Val Val Gln Pro Gly Arg
 1               5                  10                  15
Ser Leu Arg Leu Ser Cys Ala Ala Ser Gly Phe Thr Phe Ser Ser Tyr
             20                  25                  30
Gly Met Asn Trp Val Arg Gln Ala Pro Gly Lys Gly Leu Glu Trp Val
         35                  40                  45
Ala Val Thr Trp Tyr Asp Gly Ser Asn Lys His Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Tyr Ser Leu Arg Ala Glu Asp Thr Ala Met Tyr Tyr Cys
                 85                  90                  95
Val Arg Gly Gly His Leu Gly Ala Phe Asp Ile Trp Gly Gln Gly Thr
             100                 105                 110
Met Val Thr Val Ser Ser
            115
```

<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67
ggattcacct tcagtagtta tggc                                    24

<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68

```
Gly Phe Thr Phe Ser Ser Tyr Gly
 1               5
```

<210> SEQ ID NO 69
<211> LENGTH: 24
<212> TYPE: DNA
<213> ORGANISM: Artificial Sequence
<220> FEATURE:
<223> OTHER INFORMATION: synthetic

<400> SEQUENCE: 69
acatggtatg atggaagtaa taaa                                    24

<210> SEQ ID NO 70
<211> LENGTH: 8
<212> TYPE: PRT
<213> ORGANISM: Artificial Sequence
<220> FEATURE:
<223> OTHER INFORMATION: synthetic

<400> SEQUENCE: 70

```
Thr Trp Tyr Asp Gly Ser Asn Lys
 1               5
```

<210> SEQ ID NO 71
<211> LENGTH: 33
<212> TYPE: DNA

```
<213> ORGANISM: Artificial Sequence
<220> FEATURE:
<223> OTHER INFORMATION: synthetic

<400> SEQUENCE: 71
gtgagagggg ggcacctcgg cgcttttgat atc                               33

<210> SEQ ID NO 72
<211> LENGTH: 11
<212> TYPE: PRT
<213> ORGANISM: Artificial Sequence
<220> FEATURE:
<223> OTHER INFORMATION: synthetic

<400> SEQUENCE: 72

Val Arg Gly Gly His Leu Gly Ala Phe Asp Ile
1               5                   10

<210> SEQ ID NO 73
<211> LENGTH: 321
<212> TYPE: DNA
<213> ORGANISM: Artificial Sequence
<220> FEATURE:
<223> OTHER INFORMATION: synthetic

<400> SEQUENCE: 73
gaaattgtgt tgacgcagtc tccaggcacc ctgtctttgt ctccagggga aagagccacc    60
ctctcctgca gggccagtca gagtgttagc agctacttag cctggtacca gcagaaacct   120
ggccaggctc ccaggctcct catctatggt gcatccagca gggccactgg catcccagac   180
aggttcagtg gcggtgggtc tgggacagac ttcactctca ccatcagcag actggagcct   240
gaagattttg cagtgtatta ctgtcagcag tatggtagct caccattcac tttcggccct   300
gggaccaaag tggatatcaa a                                            321

<210> SEQ ID NO 74
<211> LENGTH: 107
<212> TYPE: PRT
<213> ORGANISM: Artificial Sequence
<220> FEATURE:
<223> OTHER INFORMATION: synthetic

<400> SEQUENCE: 74

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Gly Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Phe
                85                  90                  95

Thr Phe Gly Pro Gly Thr Lys Val Asp Ile Lys
            100                 105

<210> SEQ ID NO 75
<211> LENGTH: 18
<212> TYPE: DNA
<213> ORGANISM: Artificial Sequence
```

<220> FEATURE:
<223> OTHER INFORMATION: synthetic

<400> SEQUENCE: 75
cagagtgtta gcagctac                    18

<210> SEQ ID NO 76
<211> LENGTH: 6
<212> TYPE: PRT
<213> ORGANISM: Artificial Sequence
<220> FEATURE:
<223> OTHER INFORMATION: synthetic

<400> SEQUENCE: 76

Gln Ser Val Ser Ser Tyr
1               5

<210> SEQ ID NO 77
<211> LENGTH: 9
<212> TYPE: DNA
<213> ORGANISM: Artificial Sequence
<220> FEATURE:
<223> OTHER INFORMATION: synthetic

<400> SEQUENCE: 77 ggtgcatcc                    9

<210> SEQ ID NO 78
<211> LENGTH: 3
<212> TYPE: PRT
<213> ORGANISM: Artificial Sequence
<220> FEATURE:
<223> OTHER INFORMATION: synthetic

<400> SEQUENCE: 78

Gly Ala Ser
1

<210> SEQ ID NO 79
<211> LENGTH: 27
<212> TYPE: DNA
<213> ORGANISM: Artificial Sequence
<220> FEATURE:
<223> OTHER INFORMATION: synthetic

<400> SEQUENCE: 79
cagcagtatg gtagctcacc attcact                    27

<210> SEQ ID NO 80
<211> LENGTH: 9
<212> TYPE: PRT
<213> ORGANISM: Artificial Sequence
<220> FEATURE:
<223> OTHER INFORMATION: synthetic

<400> SEQUENCE: 80

Gln Gln Tyr Gly Ser Ser Pro Phe Thr
1               5

<210> SEQ ID NO 81
<211> LENGTH: 363
<212> TYPE: DNA
<213> ORGANISM: Artificial Sequence
<220> FEATURE:
<223> OTHER INFORMATION: synthetic

<400> SEQUENCE: 81

```
caggtccagc tggtgcagtc tggggctgag gtgaagaagc ctggggcctc agtgaaggtc    60
tcctgcaagg cttctggata caccttcacc gactactata tacactgggt gcgacaggcc   120
cctggacagg gcttgagtg atggggtgg atcaaccta acaatggtgt ctcaaattat   180
```

```
<220> FEATURE:
<223> OTHER INFORMATION: synthetic

<400> SEQUENCE: 85
atcaacccta acaatggtgt ctca                                              24

<210> SEQ ID NO 86
<211> LENGTH: 8
<212> TYPE: PRT
<213> ORGANISM: Artificial Sequence
<220> FEATURE:
<223> OTHER INFORMATION: synthetic

<400> SEQUENCE: 86

Ile Asn Pro Asn Asn Gly Val Ser
1               5

<210> SEQ ID NO 87
<211> LENGTH: 42
<212> TYPE: DNA
<213> ORGANISM: Artificial Sequence
<220> FEATURE:
<223> OTHER INFORMATION: synthetic

<400> SEQUENCE: 87
gcgagagaga gggctagctg gactacaac ggtgtggacg tc                           42

<210> SEQ ID NO 88
<211> LENGTH: 14
<212> TYPE: PRT
<213> ORGANISM: Artificial Sequence
<220> FEATURE:
<223> OTHER INFORMATION: synthetic

<400> SEQUENCE: 88

Ala Arg Glu Arg Ala Ser Trp Asp Tyr Asn Gly Val Asp Val
1               5                   10

<210> SEQ ID NO 89
<211> LENGTH: 336
<212> TYPE: DNA
<213> ORGANISM: Artificial Sequence
<220> FEATURE:
<223> OTHER INFORMATION: synthetic

<400> SEQUENCE: 89
gatattgtga tgactcagtc tccactctcc ctgcccgtca cccctggaga gccggcctcc        60
atctcctgca ggtctagtca gagcctcctg catagtaatg gatacagcta tttggattgg       120
tacctgcaga agccagggca gtctccacaa ctcctgatct atttgggttc taatcgggcc       180
tccggggtcc ctgacaggtt cagtggcagt ggatcaggca cagattttac actgaaaatc       240
agcagagtgg aggctgagga tgttggggtt tattactgca tgcaaggtct acaacctccg       300
aacacttttg gccaggggac caagctggag atcaaa                                 336

<210> SEQ ID NO 90
<211> LENGTH: 112
<212> TYPE: PRT
<213> ORGANISM: Artificial Sequence
<220> FEATURE:
<223> OTHER INFORMATION: synthetic

<400> SEQUENCE: 90

Asp Ile Val Met Thr Gln Ser Pro Leu Ser Leu Pro Val Thr Pro Gly
1               5                   10                  15
```

Glu Pro Ala Ser Ile Ser Cys Arg Ser Ser Gln Ser Leu Leu His Ser
            20                  25                  30

Asn Gly Tyr Ser Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Gln Pro Pro Asn Thr Phe Gly Gln Gly Thr Lys Leu Glu Ile Lys
            100                 105                 110

<210> SEQ ID NO 91
<211> LENGTH: 33
<212> TYPE: DNA
<213> ORGANISM: Artificial Sequence
<220> FEATURE:
<223> OTHER INFORMATION: synthetic

<400> SEQUENCE: 91
cagagcctcc tgcatagtaa tggatacagc tat                          33

<210> SEQ ID NO 92
<211> LENGTH: 11
<212> TYPE: PRT
<213> ORGANISM: Artificial Sequence
<220> FEATURE:
<223> OTHER INFORMATION: synthetic

<400> SEQUENCE: 92

Gln Ser Leu Leu His Ser Asn Gly Tyr Ser Tyr
1               5                   10

<210> SEQ ID NO 93
<211> LENGTH: 9
<212> TYPE: DNA
<213> ORGANISM: Artificial Sequence
<220> FEATURE:
<223> OTHER INFORMATION: synthetic

<400> SEQUENCE: 93 ttgggttct                                                     9

<210> SEQ ID NO 94
<211> LENGTH: 3
<212> TYPE: PRT
<213> ORGANISM: Artificial Sequence
<220> FEATURE:
<223> OTHER INFORMATION: synthetic

<400> SEQUENCE: 94

Leu Gly Ser
1

<210> SEQ ID NO 95
<211> LENGTH: 27
<212> TYPE: DNA
<213> ORGANISM: Artificial Sequence
<220> FEATURE:
<223> OTHER INFORMATION: synthetic

<400> SEQUENCE: 95
atgcaaggtc tacaacctcc gaacact                                                    27

<210> SEQ ID NO 96
<211> LENGTH: 9
<212> TYPE: PRT
<213> ORGANISM: Artificial Sequence
<220> FEATURE:
<223> OTHER INFORMATION: synthetic

<400> SEQUENCE: 96

Met Gln Gly Leu Gln Pro Pro Asn Thr
1               5

<210> SEQ ID NO 97
<211> LENGTH: 354
<212> TYPE: DNA
<213> ORGANISM: Artificial Sequence
<220> FEATURE:
<223> OTHER INFORMATION: synthetic

<400> SEQUENCE: 97
cagctgcagc tgcaggagtc gggcccagga ctagtgaagc cttcggagac cctgtccctc      60
acctgtattg tctctggtgg ctccaccagc agtaacactt actactgggg ctggatccgt     120
cagcccccag ggaagggtct ggaatggatt gggactatcc attatagtgg gaaccoctac    180 tacgacccgt ccctcaagag tcgagtcacc atatccgtag acacgtccaa gaaccacttc     240
tccctgaagc tgaactctgt gaccgccgca gacacggctg tttattactg tacgagacag     300
tacattaact tctttgactt ctggggccag ggaaccctgg tcaccgtctc ctca           354

<210> SEQ ID NO 98
<211> LENGTH: 118
<212> TYPE: PRT
<213> ORGANISM: Artificial Sequence
<220> FEATURE:
<223> OTHER INFORMATION: synthetic

<400> SEQUENCE: 98

Gln Leu Gln Leu Gln Glu Ser Gly Pro Gly Leu Val Lys Pro Ser Glu
1               5                   10                  15

Thr Leu Ser Leu Thr Cys Ile Val Ser Gly Gly Ser Thr Ser Ser Asn
                20                  25                  30

Thr Tyr Tyr Trp Gly Trp Ile Arg Gln Pro Pro Gly Lys Gly Leu Glu
            35                  40                  45

Trp Ile Gly Thr Ile His Tyr Ser Gly Asn Pro Tyr Tyr Asp Pro Ser
        50                  55                  60

Leu Lys Ser Arg Val Thr Ile Ser Val Asp Thr Ser Lys Asn His Phe
65                  70                  75                  80

Ser Leu Lys Leu Asn Ser Val Thr Ala Ala Asp Thr Ala Val Tyr Tyr
                85                  90                  95

Cys Thr Arg Gln Tyr Ile Asn Phe Phe Asp Phe Trp Gly Gln Gly Thr
            100                 105                 110

Leu Val Thr Val Ser Ser
        115

<210> SEQ ID NO 99
<211> LENGTH: 30
<212> TYPE: DNA
<213> ORGANISM: Artificial Sequence
<220> FEATURE:
<223> OTHER INFORMATION: synthetic

<400> SEQUENCE: 99
ggtggctcca ccagcagtaa cacttactac                              30

<210> SEQ ID NO 100
<211> LENGTH: 10
<212> TYPE: PRT
<213> ORGANISM: Artificial Sequence
<220> FEATURE:
<223> OTHER INFORMATION: synthetic

<400> SEQUENCE: 100

Gly Gly Ser Thr Ser Ser Asn Thr Tyr Tyr
1               5                   10

<210> SEQ ID NO 101
<211> LENGTH: 21
<212> TYPE: DNA
<213> ORGANISM: Artificial Sequence
<220> FEATURE:
<223> OTHER INFORMATION: synthetic

<400> SEQUENCE: 101
atccattata gtgggaaccc c                                       21

<210> SEQ ID NO 102
<211> LENGTH: 7
<212> TYPE: PRT
<213> ORGANISM: Artificial Sequence
<220> FEATURE:
<223> OTHER INFORMATION: synthetic

<400> SEQUENCE: 102

Ile His Tyr Ser Gly Asn Pro
1               5

<210> SEQ ID NO 103
<211> LENGTH: 30
<212> TYPE: DNA
<213> ORGANISM: Artificial Sequence
<220> FEATURE:
<223> OTHER INFORMATION: synthetic

<400> SEQUENCE: 103
acgagacagt acattaactt ctttgacttc                              30

<210> SEQ ID NO 104
<211> LENGTH: 10
<212> TYPE: PRT
<213> ORGANISM: Artificial Sequence
<220> FEATURE:
<223> OTHER INFORMATION: synthetic

<400> SEQUENCE: 104

Thr Arg Gln Tyr Ile Asn Phe Phe Asp Phe
1               5                   10

<210> SEQ ID NO 105
<211> LENGTH: 321
<212> TYPE: DNA
<213> ORGANISM: Artificial Sequence
<220> FEATURE:
<223> OTHER INFORMATION: synthetic

<400> SEQUENCE: 105
gaaattgtgt tgacacagtc tccagccacc ctgtctttgt ctccagggga aagagtcact    60

```
ctctcctgca gggccagtca gagtattagc agatacttag cctggtatca acagaaacct    120
ggccaggctc ccagggtcct catttatgat gcatccaaca gggccactga catcccagcc    180
aggttcagtg gcagtgggtc tgggacagac ttcactctca ccatcagcag tctagagcct    240
gaagattttg cagtttatta ctgtcagcag cgtagcaatt ggcctatcac cttcggccaa    300
gggacacgac tggagattaa a                                              321
```

<210> SEQ ID NO 106
<211> LENGTH: 107
<212> TYPE: PRT
<213> ORGANISM: Artificial Sequence
<220> FEATURE:
<223> OTHER INFORMATION: synthetic

<400> SEQUENCE: 106

```
Glu Ile Val Leu Thr Gln Ser Pro Ala Thr Leu Ser Leu Ser Pro Gly
1               5                   10                  15

Glu Arg Val Thr Leu Ser Cys Arg Ala Ser Gln Ser Ile Ser Arg Tyr
            20                  25                  30

Leu Ala Trp Tyr Gln Gln Lys Pro Gly Gln Ala Pro Arg Val Leu Ile
        35                  40                  45

Tyr Asp Ala Ser Asn Arg Ala Thr Asp Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105
```

<210> SEQ ID NO 107
<211> LENGTH: 18
<212> TYPE: DNA
<213> ORGANISM: Artificial Sequence
<220> FEATURE:
<223> OTHER INFORMATION: synthetic

<400> SEQUENCE: 107

```
cagagtatta gcagatac                                                   18
```

<210> SEQ ID NO 108
<211> LENGTH: 6
<212> TYPE: PRT
<213> ORGANISM: Artificial Sequence
<220> FEATURE:
<223> OTHER INFORMATION: synthetic

<400> SEQUENCE: 108

```
Gln Ser Ile Ser Arg Tyr
1               5
```

<210> SEQ ID NO 109
<211> LENGTH: 9
<212> TYPE: DNA
<213> ORGANISM: Artificial Sequence
<220> FEATURE:
<223> OTHER INFORMATION: synthetic

<400> SEQUENCE: 109

```
gatgcatcc                                                              9
```

<210> SEQ ID NO 110
<211> LENGTH: 3
<212> TYPE: PRT
<213> ORGANISM: Artificial Sequence
<220> FEATURE:
<223> OTHER INFORMATION: synthetic

<400> SEQUENCE: 110

Asp Ala Ser
1

<210> SEQ ID NO 111
<211> LENGTH: 27
<212> TYPE: DNA
<213> ORGANISM: Artificial Sequence
<220> FEATURE:
<223> OTHER INFORMATION: synthetic

<400> SEQUENCE: 111
cagcagcgta gcaattggcc tatcacc                                          27

<210> SEQ ID NO 112
<211> LENGTH: 9
<212> TYPE: PRT
<213> ORGANISM: Artificial Sequence
<220> FEATURE:
<223> OTHER INFORMATION: synthetic

<400> SEQUENCE: 112

Gln Gln Arg Ser Asn Trp Pro Ile Thr
1               5

<210> SEQ ID NO 113
<211> LENGTH: 363
<212> TYPE: DNA
<213> ORGANISM: Artificial Sequence
<220> FEATURE:
<223> OTHER INFORMATION: synthetic

<400> SEQUENCE: 113
caggtgcagc tggtggagtc tgggggaggc gtggtccagc ctggagggtc cctgagactc        60
tcctgtgcag cctctggact caccttcagt tactatggca tgcactgggt ccgccaggct       120
ccaggcaagg ggctggagtg ggtggcagtt atatcatatg atggaagtaa taaatattat       180
gcagactccg tgaagggccg attcaccatc tccagagaca attccaagaa cacgctgtat       240
ctgcaaatga acagcctgag agctgaggac gcggctgtgt attactgtgc gaaagatttg       300
gggggggacg actactacgg tatggacgtc tggggccaag ggaccacggt caccgtctcc       360
tca                                                                    363

<210> SEQ ID NO 114
<211> LENGTH: 121
<212> TYPE: PRT
<213> ORGANISM: Artificial Sequence
<220> FEATURE:
<223> OTHER INFORMATION: synthetic

<400> SEQUENCE: 114

Gln Val Gln Leu Val Glu Ser Gly Gly Gly Val Val Gln Pro Gly Arg
1               5                   10                  15

Ser Leu Arg Leu Ser Cys Ala Ala Ser Gly Leu Thr Phe Ser Tyr Tyr
            20                  25                  30

Gly Met His Trp Val Arg Gln Ala Pro Gly Lys Gly Leu Glu Trp Val
        35                  40                  45

```
Ala Val Ile Ser Tyr Asp Gly Ser Asn Lys Tyr Tyr Ala Asp Ser Val
        50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Ala Ala Val Tyr Tyr Cys
                 85                  90                  95
Ala Lys Asp Leu Gly Gly Asp Asp Tyr Tyr Gly Met Asp Val Trp Gly
            100                 105                 110
Gln Gly Thr Thr Val Thr Val Ser Ser
            115                 120

<210> SEQ ID NO 115
<211> LENGTH: 24
<212> TYPE: DNA
<213> ORGANISM: Artificial Sequence
<220> FEATURE:
<223> OTHER INFORMATION: synthetic

<400> SEQUENCE: 115
ggactcacct tcagttacta tggc                                          24

<210> SEQ ID NO 116
<211> LENGTH: 8
<212> TYPE: PRT
<213> ORGANISM: Artificial Sequence
<220> FEATURE:
<223> OTHER INFORMATION: synthetic

<400> SEQUENCE: 116

Gly Leu Thr Phe Ser Tyr Tyr Gly
 1               5

<210> SEQ ID NO 117
<211> LENGTH: 24
<212> TYPE: DNA
<213> ORGANISM: Artificial Sequence
<220> FEATURE:
<223> OTHER INFORMATION: synthetic

<400> SEQUENCE: 117
atatcatatg atggaagtaa taaa                                          24

<210> SEQ ID NO 118
<211> LENGTH: 8
<212> TYPE: PRT
<213> ORGANISM: Artificial Sequence
<220> FEATURE:
<223> OTHER INFORMATION: synthetic

<400> SEQUENCE: 118

Ile Ser Tyr Asp Gly Ser Asn Lys
 1               5

<210> SEQ ID NO 119
<211> LENGTH: 42
<212> TYPE: DNA
<213> ORGANISM: Artificial Sequence
<220> FEATURE:
<223> OTHER INFORMATION: synthetic

<400> SEQUENCE: 119
gcgaaagatt tggggggga cgactactac ggtatggacg tc                       42
```

```
<210> SEQ ID NO 120
<211> LENGTH: 14
<212> TYPE: PRT
<213> ORGANISM: Artificial Sequence
<220> FEATURE:
<223> OTHER INFORMATION: synthetic

<400> SEQUENCE: 120

Ala Lys Asp Leu Gly Gly Asp Asp Tyr Tyr Gly Met Asp Val
1               5                   10

<210> SEQ ID NO 121
<211> LENGTH: 324
<212> TYPE: DNA
<213> ORGANISM: Artificial Sequence
<220> FEATURE:
<223> OTHER INFORMATION: synthetic

<400> SEQUENCE: 121
gaaattgtgt tgacgcagtc tccaggcacc ctgtctttgt ctccagggga aagagccacc      60
ctctcctgca gggccagtca gagtgttagc agaacctact tagcctggta ccagcagaaa     120
cctggccagg ctcccaggct cctcatctat ggtgcattca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccgta cactttggc      300 caggggacca agctggagat caaa                                             324

<210> SEQ ID NO 122
<211> LENGTH: 108
<212> TYPE: PRT
<213> ORGANISM: Artificial Sequence
<220> FEATURE:
<223> OTHER INFORMATION: synthetic

<400> SEQUENCE: 122

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Thr
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
            100                 105

<210> SEQ ID NO 123
<211> LENGTH: 21
<212> TYPE: DNA
<213> ORGANISM: Artificial Sequence
<220> FEATURE:
<223> OTHER INFORMATION: synthetic

<400> SEQUENCE: 123
cagagtgtta gcagaaccta c                                                21

<210> SEQ ID NO 124
```

```
<211> LENGTH: 7
<212> TYPE: PRT
<213> ORGANISM: Artificial Sequence
<220> FEATURE:
<223> OTHER INFORMATION: synthetic

<400> SEQUENCE: 124

Gln Ser Val Ser Arg Thr Tyr
1               5

<210> SEQ ID NO 125
<211> LENGTH: 9
<212> TYPE: DNA
<213> ORGANISM: Artificial Sequence
<220> FEATURE:
<223> OTHER INFORMATION: synthetic

<400> SEQUENCE: 125 ggtgcattc                                                                  9

<210> SEQ ID NO 126
<211> LENGTH: 3
<212> TYPE: PRT
<213> ORGANISM: Artificial Sequence
<220> FEATURE:
<223> OTHER INFORMATION: synthetic

<400> SEQUENCE: 126

Gly Ala Phe
1

<210> SEQ ID NO 127
<211> LENGTH: 27
<212> TYPE: DNA
<213> ORGANISM: Artificial Sequence
<220> FEATURE:
<223> OTHER INFORMATION: synthetic

<400> SEQUENCE: 127
cagcagtatg gtagctcacc gtacact                                             27

<210> SEQ ID NO 128
<211> LENGTH: 9
<212> TYPE: PRT
<213> ORGANISM: Artificial Sequence
<220> FEATURE:
<223> OTHER INFORMATION: synthetic

<400> SEQUENCE: 128

Gln Gln Tyr Gly Ser Ser Pro Tyr Thr
1               5

<210> SEQ ID NO 129
<211> LENGTH: 366
<212> TYPE: DNA
<213> ORGANISM: Artificial Sequence
<220> FEATURE:
<223> OTHER INFORMATION: synthetic

<400> SEQUENCE: 129
caggtgcagc tggtggagtc tgggggaggc ttggtcaagc ctggagggtc cctgagactc         60
tcctgtgcag cctctggatt caccttcagt gactactaca tgacctggat ccgccaggct        120
ccagggaagg ggctggagtg ggtttcatac attagtagta gtggtggtaa catattctac        180
gcagactctg tgaagggccg attcaccatc tccagggaca cgccaagaa ctcactgtat        240
```

```
ctgcaaatga acagcctgag aggcgaggac acggccgtgt attactgtgc gagaggtctg    300
gaaccctacc actactatta cggtatggac gtctggggcc aagggaccac ggtcaccgtc    360
tcctca                                                                366
```

<210> SEQ ID NO 130
<211> LENGTH: 122
<212> TYPE: PRT
<213> ORGANISM: Artificial Sequence
<220> FEATURE:
<223> OTHER INFORMATION: synthetic

<400> SEQUENCE: 130

```
Gln Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asp Tyr
            20                  25                  30
Tyr Met Thr Trp Ile Arg Gln Ala Pro Gly Lys Gly Leu Glu Trp Val
        35                  40                  45
Ser Tyr Ile Ser Ser Gly Gly Asn Ile Phe Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Gly Glu Asp Thr Ala Val Tyr Tyr Cys
                85                  90                  95
Ala Arg Gly Leu Glu Pro Tyr His Tyr Tyr Tyr Gly Met Asp Val Trp
            100                 105                 110
Gly Gln Gly Thr Thr Val Thr Val Ser Ser
        115                 120
```

<210> SEQ ID NO 131
<211> LENGTH: 24
<212> TYPE: DNA
<213> ORGANISM: Artificial Sequence
<220> FEATURE:
<223> OTHER INFORMATION: synthetic

<400> SEQUENCE: 131

```
ggattcacct tcagtgacta ctac                                            24
```

<210> SEQ ID NO 132
<211> LENGTH: 8
<212> TYPE: PRT
<213> ORGANISM: Artificial Sequence
<220> FEATURE:
<223> OTHER INFORMATION: synthetic

<400> SEQUENCE: 132

```
Gly Phe Thr Phe Ser Asp Tyr Tyr
1               5
```

<210> SEQ ID NO 133
<211> LENGTH: 24
<212> TYPE: DNA
<213> ORGANISM: Artificial Sequence
<220> FEATURE:
<223> OTHER INFORMATION: synthetic

<400> SEQUENCE: 133

```
attagtagta gtggtggtaa cata                                            24
```

<210> SEQ ID NO 134

<211> LENGTH: 8
<212> TYPE: PRT
<213> ORGANISM: Artificial Sequence
<220> FEATURE:
<223> OTHER INFORMATION: synthetic

<400> SEQUENCE: 134

Ile Ser Ser Ser Gly Gly Asn Ile
1               5

<210> SEQ ID NO 135
<211> LENGTH: 45
<212> TYPE: DNA
<213> ORGANISM: Artificial Sequence
<220> FEATURE:
<223> OTHER INFORMATION: synthetic

<400> SEQUENCE: 135
gcgagaggtc tggaacccta ccactactat tacggtatgg acgtc          45

<210> SEQ ID NO 136
<211> LENGTH: 15
<212> TYPE: PRT
<213> ORGANISM: Artificial Sequence
<220> FEATURE:
<223> OTHER INFORMATION: synthetic

<400> SEQUENCE: 136

Ala Arg Gly Leu Glu Pro Tyr His Tyr Tyr Tyr Gly Met Asp Val
1               5                   10                  15

<210> SEQ ID NO 137
<211> LENGTH: 321
<212> TYPE: DNA
<213> ORGANISM: Artificial Sequence
<220> FEATURE:
<223> OTHER INFORMATION: synthetic

<400> SEQUENCE: 137
gacatccaga tgacccagtc tccatcctcc ctgtctgcat ctgttggaga cagagtcacc    60
atcacttgcc aggcgagtca ggacattagt aattatttaa attggtatca gcagaaacca   120
gggaaagccc ctaaactcct gatctacgat gcatccaatt tggaaacagg ggtcccatca   180
aggttcagtg gaagtggatc tgggacagat tttactttca ccatcagcag cctgcagcct   240
gaagatattg caacatattt ctgtcaacac tatgataatc tcccattcac tttcggccct   300
gggaccaaag tggatatcaa a                                             321

<210> SEQ ID NO 138
<211> LENGTH: 107
<212> TYPE: PRT
<213> ORGANISM: Artificial Sequence
<220> FEATURE:
<223> OTHER INFORMATION: synthetic

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Tyr Asp Asn Leu Pro Phe
            85                  90                  95

Thr Phe Gly Pro Gly Thr Lys Val Asp Ile Lys
            100                 105

<210> SEQ ID NO 139
<211> LENGTH: 18
<212> TYPE: DNA
<213> ORGANISM: Artificial Sequence
<220> FEATURE:
<223> OTHER INFORMATION: synthetic

<400> SEQUENCE: 139
caggacatta gtaattat                                                    18

<210> SEQ ID NO 140
<211> LENGTH: 6
<212> TYPE: PRT
<213> ORGANISM: Artificial Sequence
<220> FEATURE:
<223> OTHER INFORMATION: synthetic

<400> SEQUENCE: 140

Gln Asp Ile Ser Asn Tyr
1               5

<210> SEQ ID NO 141
<211> LENGTH: 9
<212> TYPE: DNA
<213> ORGANISM: Artificial Sequence
<220> FEATURE:
<223> OTHER INFORMATION: synthetic

<400> SEQUENCE: 141 gatgcatcc                                                               9

<210> SEQ ID NO 142
<211> LENGTH: 3
<212> TYPE: PRT
<213> ORGANISM: Artificial Sequence
<220> FEATURE:
<223> OTHER INFORMATION: synthetic

<400> SEQUENCE: 142

Asp Ala Ser
1

<210> SEQ ID NO 143
<211> LENGTH: 27
<212> TYPE: DNA
<213> ORGANISM: Artificial Sequence
<220> FEATURE:
<223> OTHER INFORMATION: synthetic

<400> SEQUENCE: 143
caacactatg ataatctccc attcact                                          27

<210> SEQ ID NO 144
<211> LENGTH: 9
<212> TYPE: PRT
<213> ORGANISM: Artificial Sequence
<220> FEATURE:
<223> OTHER INFORMATION: synthetic

<400> SEQUENCE: 144

Gln His Tyr Asp Asn Leu Pro Phe Thr
1               5

<210> SEQ ID NO 145
<211> LENGTH: 369
<212> TYPE: DNA
<213> ORGANISM: Artificial Sequence
<220> FEATURE:
<223> OTHER INFORMATION: synthetic

<400> SEQUENCE: 145

```
gaggtgcagc tggtggagtc tgggggaggc ttggtacagc ctgggggtc cctgagactc      60
tcctgtgcag cctctggatt caccttgagt aattatgtca tgacctgggt ccgccaggct     120
ccagggaagg ggctggagtg ggtctcagct attagtggta gaggtggtaa ttcatatat     180
gcagactccg tgaagggccg gttcagcatt tccaggacc attccaagaa cacgctgtat     240
ctgcaagtga acagcctgag agccgaggac acggccgtat attactgtgc gaaagccgaa     300
cgtggataca gttatggctt caactggttc gaccctggg gccagggaac cctggtcacc     360
gtctcctca                                                            369
```

<210> SEQ ID NO 146
<211> LENGTH: 123
<212> TYPE: PRT
<213> ORGANISM: Artificial Sequence
<220> FEATURE:
<223> OTHER INFORMATION: synthetic

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Asn Tyr
            20                  25                  30

Val Met Thr Trp Val Arg Gln Ala Pro Gly Lys Gly Leu Glu Trp Val
        35                  40                  45

Ser Ala Ile Ser Gly Arg Gly Gly Asn Ser Tyr Tyr Ala Asp Ser Val
    50                  55                  60

Lys Gly Arg Phe Ser Ile Ser Arg Asp His Ser Lys Asn Thr Leu Tyr
65                  70                  75                  80

Leu Gln Val Asn Ser Leu Arg Ala Glu Asp Thr Ala Val Tyr Tyr Cys
                85                  90                  95

Ala Lys Ala Glu Arg Gly Tyr Ser Tyr Gly Phe Asn Trp Phe Asp Pro
            100                 105                 110

Trp Gly Gln Gly Thr Leu Val Thr Val Ser Ser
        115                 120

<210> SEQ ID NO 147
<211> LENGTH: 24
<212> TYPE: DNA
<213> ORGANISM: Artificial Sequence
<220> FEATURE:
<223> OTHER INFORMATION: synthetic

<400> SEQUENCE: 147
ggattcacct tgagtaatta tgtc                                            24

<210> SEQ ID NO 148
<211> LENGTH: 8

<210> SEQ ID NO 148
<211> LENGTH: 7
<212> TYPE: PRT
<213> ORGANISM: Artificial Sequence
<220> FEATURE:
<223> OTHER INFORMATION: synthetic

<400> SEQUENCE: 148

Gly Phe Thr Leu Ser Asn Tyr Val
1               5

<210> SEQ ID NO 149
<211> LENGTH: 24
<212> TYPE: DNA
<213> ORGANISM: Artificial Sequence
<220> FEATURE:
<223> OTHER INFORMATION: synthetic

<400> SEQUENCE: 149
attagtggta gaggtggtaa ttca                                          24

<210> SEQ ID NO 150
<211> LENGTH: 8
<212> TYPE: PRT
<213> ORGANISM: Artificial Sequence
<220> FEATURE:
<223> OTHER INFORMATION: synthetic

<400> SEQUENCE: 150

Ile Ser Gly Arg Gly Gly Asn Ser
1               5

<210> SEQ ID NO 151
<211> LENGTH: 48
<212> TYPE: DNA
<213> ORGANISM: Artificial Sequence
<220> FEATURE:
<223> OTHER INFORMATION: synthetic

<400> SEQUENCE: 151
gcgaaagccg aacgtggata cagttatggc ttcaactggt tcgacccc              48

<210> SEQ ID NO 152
<211> LENGTH: 16
<212> TYPE: PRT
<213> ORGANISM: Artificial Sequence
<220> FEATURE:
<223> OTHER INFORMATION: synthetic

<400> SEQUENCE: 152

Ala Lys Ala Glu Arg Gly Tyr Ser Tyr Gly Phe Asn Trp Phe Asp Pro
1               5                   10                  15

<210> SEQ ID NO 153
<211> LENGTH: 321
<212> TYPE: DNA
<213> ORGANISM: Artificial Sequence
<220> FEATURE:
<223> OTHER INFORMATION: synthetic

<400> SEQUENCE: 153
gacatccaga tgacccagtc tccatcttcc gtgtctgcat ctgcaggaga cagagtcacc    60
atcacttgtc gggcgagtca gggtattagc agctggttag cctggtatca gcagaaacca   120
gggaaagccc ctaagctcct gatctatgct gcatccagtt tgcaaagtgg ggtcccatca   180
aggttcagcg gcagtggatc tgggacagat ttcactctca ccatcagcag cctgcagcct   240
gaagattttg catcttacta ttgtcaacag ggtaacaatt tcccgctcac tttcggcgga   300
gggaccaagg tggagatcaa a                                                 321

<210> SEQ ID NO 154
<211> LENGTH: 107
<212> TYPE: PRT
<213> ORGANISM: Artificial Sequence
<220> FEATURE:
<223> OTHER INFORMATION: synthetic

<400> SEQUENCE: 154

Asp Ile Gln Met Thr Gln Ser Pro Ser Ser Val Ser Ala Ser Ala Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Gly Asn Asn Phe Pro Leu
                85                  90                  95

Thr Phe Gly Gly Gly Thr Lys Val Glu Ile Lys
            100                 105

<210> SEQ ID NO 155
<211> LENGTH: 18
<212> TYPE: DNA
<213> ORGANISM: Artificial Sequence
<220> FEATURE:
<223> OTHER INFORMATION: synthetic

<400> SEQUENCE: 155
cagggtatta gcagctgg                                                      18

<210> SEQ ID NO 156
<211> LENGTH: 6
<212> TYPE: PRT
<213> ORGANISM: Artificial Sequence
<220> FEATURE:
<223> OTHER INFORMATION: synthetic

<400> SEQUENCE: 156

Gln Gly Ile Ser Ser Trp
1               5

<210> SEQ ID NO 157
<211> LENGTH: 9
<212> TYPE: DNA
<213> ORGANISM: Artificial Sequence
<220> FEATURE:
<223> OTHER INFORMATION: synthetic

<400> SEQUENCE: 157 gctgcatcc                                                                 9

<210> SEQ ID NO 158
<211> LENGTH: 3
<212> TYPE: PRT
<213> ORGANISM: Artificial Sequence
<220> FEATURE:
<223> OTHER INFORMATION: synthetic

<400> SEQUENCE: 158

Ala Ala Ser
1

<210> SEQ ID NO 159
<211> LENGTH: 27
<212> TYPE: DNA
<213> ORGANISM: Artificial Sequence
<220> FEATURE:
<223> OTHER INFORMATION: synthetic

<400> SEQUENCE: 159
caacagggta acaatttccc gctcact                                            27

<210> SEQ ID NO 160
<211> LENGTH: 9
<212> TYPE: PRT
<213> ORGANISM: Artificial Sequence
<220> FEATURE:
<223> OTHER INFORMATION: synthetic

<400> SEQUENCE: 160

Gln Gln Gly Asn Asn Phe Pro Leu Thr
1               5

<210> SEQ ID NO 161
<211> LENGTH: 360
<212> TYPE: DNA
<213> ORGANISM: Artificial Sequence
<220> FEATURE:
<223> OTHER INFORMATION: synthetic

<400> SEQUENCE: 161
caggtgcagc tggtggagtc tgggggaggc gtggtccagc ctgggaggtc cctgagactc        60
tcctgtgcag cgtctggatt caccttcagt acctatggca tgcactgggt ccgccaggct       120
ccaggcaagg ggctggagtg ggtgacagtt atatggtatg atggaaataa taaatactat       180
gcagactccg tgaagggccg attcaccatc tccagagaca attccaagaa cacgctgtat       240
ctgcaaatga acaacctgag agccgaggat acggctttat actactgtgc gagaggaggt       300
gggaggttat cgtactatca tgactactgg ggccagggaa ccctggtcac cgtctcctca       360

<210> SEQ ID NO 162
<211> LENGTH: 120
<212> TYPE: PRT
<213> ORGANISM: Artificial Sequence
<220> FEATURE:
<223> OTHER INFORMATION: synthetic

<400> SEQUENCE: 162

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Thr Val Ile Trp Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Leu Tyr Tyr Cys
                85                  90                  95

Ala Arg Gly Gly Gly Arg Leu Ser Tyr Tyr His Asp Tyr Trp Gly Gln
            100                 105                 110

Gly Thr Leu Val Thr Val Ser Ser
        115                 120

<210> SEQ ID NO 163
<211> LENGTH: 24
<212> TYPE: DNA
<213> ORGANISM: Artificial Sequence
<220> FEATURE:
<223> OTHER INFORMATION: synthetic

<400> SEQUENCE: 163
ggattcacct tcagtaccta tggc                                          24

<210> SEQ ID NO 164
<211> LENGTH: 8
<212> TYPE: PRT
<213> ORGANISM: Artificial Sequence
<220> FEATURE:
<223> OTHER INFORMATION: synthetic

<400> SEQUENCE: 164

Gly Phe Thr Phe Ser Thr Tyr Gly
1               5

<210> SEQ ID NO 165
<211> LENGTH: 24
<212> TYPE: DNA
<213> ORGANISM: Artificial Sequence
<220> FEATURE:
<223> OTHER INFORMATION: synthetic

<400> SEQUENCE: 165
atatggtatg atggaaataa taaa                                          24

<210> SEQ ID NO 166
<211> LENGTH: 8
<212> TYPE: PRT
<213> ORGANISM: Artificial Sequence
<220> FEATURE:
<223> OTHER INFORMATION: synthetic

<400> SEQUENCE: 166

Ile Trp Tyr Asp Gly Asn Asn Lys
1               5

<210> SEQ ID NO 167
<211> LENGTH: 39
<212> TYPE: DNA
<213> ORGANISM: Artificial Sequence
<220> FEATURE:
<223> OTHER INFORMATION: synthetic

<400> SEQUENCE: 167
gcgagaggag gtgggaggtt atcgtactat catgactac                          39

<210> SEQ ID NO 168
<211> LENGTH: 13
<212> TYPE: PRT
<213> ORGANISM: Artificial Sequence
<220> FEATURE:
<223> OTHER INFORMATION: synthetic

<400> SEQUENCE: 168

Ala Arg Gly Gly Gly Arg Leu Ser Tyr Tyr His Asp Tyr
1               5                   10

<210> SEQ ID NO 169
<211> LENGTH: 321
<212> TYPE: DNA
<213> ORGANISM: Artificial Sequence
<220> FEATURE:
<223> OTHER INFORMATION: synthetic

<400> SEQUENCE: 169
gacatccaga tgacccagtc tccatcctcc ctgtctgcat ctgtaggaga cagagtcacc    60
atcacttgcc gggcaagtca gagcattagc accttttta attggtatca gcagaaacca   120
gggaaagccc ctaacctcct gatctatggt acatccagtt tgcaaagtgg ggtcccatca   180
aggttcagtg gcagtggatc tgggacagat ttcactctca ccatcagcag tctgcaacct   240
gaagattttg cagcttacta ctgtcaacag acttacagta ccccattcac tttcggccct   300
gggaccaaag tggatatcaa a                                             321

<210> SEQ ID NO 170
<211> LENGTH: 107
<212> TYPE: PRT
<213> ORGANISM: Artificial Sequence
<220> FEATURE:
<223> OTHER INFORMATION: synthetic

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Phe
            20                  25                  30

Leu Asn Trp Tyr Gln Gln Lys Pro Gly Lys Ala Pro Asn Leu Leu Ile
        35                  40                  45

Tyr Gly Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ala Tyr Tyr Cys Gln Gln Thr Tyr Ser Thr Pro Phe
                85                  90                  95

Thr Phe Gly Pro Gly Thr Lys Val Asp Ile Lys
            100                 105

<210> SEQ ID NO 171
<211> LENGTH: 18
<212> TYPE: DNA
<213> ORGANISM: Artificial Sequence
<220> FEATURE:
<223> OTHER INFORMATION: synthetic

<400> SEQUENCE: 171
cagagcatta gcaccttt                                                  18

<210> SEQ ID NO 172
<211> LENGTH: 6
<212> TYPE: PRT
<213> ORGANISM: Artificial Sequence
<220> FEATURE:
<223> OTHER INFORMATION: synthetic

<400> SEQUENCE: 172

Gln Ser Ile Ser Thr Phe

<210> SEQ ID NO 173
<211> LENGTH: 9
<212> TYPE: DNA
<213> ORGANISM: Artificial Sequence
<220> FEATURE:
<223> OTHER INFORMATION: synthetic

<400> SEQUENCE: 173 ggtacatcc                                                                                                9

<210> SEQ ID NO 174
<211> LENGTH: 3
<212> TYPE: PRT
<213> ORGANISM: Artificial Sequence
<220> FEATURE:
<223> OTHER INFORMATION: synthetic

<400> SEQUENCE: 174

Gly Thr Ser
1

<210> SEQ ID NO 175
<211> LENGTH: 27
<212> TYPE: DNA
<213> ORGANISM: Artificial Sequence
<220> FEATURE:
<223> OTHER INFORMATION: synthetic

<400> SEQUENCE: 175
caacagactt acagtacccc attcact                                                                           27

<210> SEQ ID NO 176
<211> LENGTH: 9
<212> TYPE: PRT
<213> ORGANISM: Artificial Sequence
<220> FEATURE:
<223> OTHER INFORMATION: synthetic

<400> SEQUENCE: 176

Gln Gln Thr Tyr Ser Thr Pro Phe Thr
1               5

<210> SEQ ID NO 177
<211> LENGTH: 357
<212> TYPE: DNA
<213> ORGANISM: Artificial Sequence
<220> FEATURE:
<223> OTHER INFORMATION: synthetic

<400> SEQUENCE: 177
caggttcagc tggtgcagtc tggagctgag gtgaagatgt ctggggcctc agtgagggtc       60
tcctgcaagg cttctggtta ccctttacc agctatggta ttagctggat gcgacaggcc      120
cctggacaag gcttgagtg gatgggatgg atcaccgctt acaatggtaa ctcaaactat      180
gcacagaagc tccagggcag agtcaccatg accacagaca catccacggg cacagcctac      240
atggagttga ggagcctgac atctgacgac acggccgtgt attactgtgc gagaaggggg      300
gactaccttg gggttttttcc ctactgggc cagggaaccc tggtcaccgt ctcctca        357

<210> SEQ ID NO 178
<211> LENGTH: 119
<212> TYPE: PRT
<213> ORGANISM: Artificial Sequence
<220> FEATURE:
<223> OTHER INFORMATION: synthetic

<400> SEQUENCE: 178

Gln Val Gln Leu Val Gln Ser Gly Ala Glu Val Lys Met Ser Gly Ala
1               5                   10                  15

Ser Val Arg Val Ser Cys Lys Ala Ser Gly Tyr Thr Phe Thr Ser Tyr
            20                  25                  30

Gly Ile Ser Trp Met Arg Gln Ala Pro Gly Gln Gly Leu Glu Trp Met
        35                  40                  45

Gly Trp Ile Thr Ala Tyr Asn Gly Asn Ser Asn Tyr Ala Gln Lys Leu
    50                  55                  60

Gln Gly Arg Val Thr Met Thr Thr Asp Thr Ser Thr Gly Thr Ala Tyr
65                  70                  75                  80

Met Glu Leu Arg Ser Leu Thr Ser Asp Asp Thr Ala Val Tyr Tyr Cys
                85                  90                  95

Ala Arg Arg Gly Asp Tyr Leu Gly Val Phe Pro Tyr Trp Gly Gln Gly
            100                 105                 110

Thr Leu Val Thr Val Ser Ser
        115

<210> SEQ ID NO 179
<211> LENGTH: 24
<212> TYPE: DNA
<213> ORGANISM: Artificial Sequence
<220> FEATURE:
<223> OTHER INFORMATION: synthetic

<400> SEQUENCE: 179
ggttacacct ttaccagcta tggt                                       24

<210> SEQ ID NO 180
<211> LENGTH: 8
<212> TYPE: PRT
<213> ORGANISM: Artificial Sequence
<220> FEATURE:
<223> OTHER INFORMATION: synthetic

<400> SEQUENCE: 180

Gly Tyr Thr Phe Thr Ser Tyr Gly
1               5

<210> SEQ ID NO 181
<211> LENGTH: 24
<212> TYPE: DNA
<213> ORGANISM: Artificial Sequence
<220> FEATURE:
<223> OTHER INFORMATION: synthetic

<400> SEQUENCE: 181
atcaccgctt acaatggtaa ctca                                       24

<210> SEQ ID NO 182
<211> LENGTH: 8
<212> TYPE: PRT
<213> ORGANISM: Artificial Sequence
<220> FEATURE:
<223> OTHER INFORMATION: synthetic

<400> SEQUENCE: 182

Ile Thr Ala Tyr Asn Gly Asn Ser
1               5

<210> SEQ ID NO 183
<211> LENGTH: 36
<212> TYPE: DNA
<213> ORGANISM: Artificial Sequence
<220> FEATURE:
<223> OTHER INFORMATION: synthetic

<400> SEQUENCE: 183
gcgagaaggg gggactacct tggggttttt ccctac                                    36

<210> SEQ ID NO 184
<211> LENGTH: 12
<212> TYPE: PRT
<213> ORGANISM: Artificial Sequence
<220> FEATURE:
<223> OTHER INFORMATION: synthetic

<400> SEQUENCE: 184

Ala Arg Arg Gly Asp Tyr Leu Gly Val Phe Pro Tyr
1               5                   10

<210> SEQ ID NO 185
<211> LENGTH: 321
<212> TYPE: DNA
<213> ORGANISM: Artificial Sequence
<220> FEATURE:
<223> OTHER INFORMATION: synthetic

<400> SEQUENCE: 185
gacatccaga tgacccagtc tccatcctcc ctgtctgcat ctgtaggaga cagagtcacc          60
atcacttgcc gggcaagtca gagcattagt agctatttaa attggtatca acagaaacca         120
gggaaagccc ctaacctcct gatctatact gcatccagtt tgcaaagtgg ggtcccatca         180
aggttcagtg gcagtggatc tgggacagac ttcactctca ccatcagcag tctgcaacct         240
gaagattttg caacttacta ctgtcaacag agttacagtt ccccccctca cttcggcgga         300
gggaccaagg tggagatcaa a                                                   321

<210> SEQ ID NO 186
<211> LENGTH: 107
<212> TYPE: PRT
<213> ORGANISM: Artificial Sequence
<220> FEATURE:
<223> OTHER INFORMATION: synthetic

<400> SEQUENCE: 186

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Asn Leu Leu Ile
        35                  40                  45

Tyr Thr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Pro Leu
                85                  90                  95

Thr Phe Gly Gly Gly Thr Lys Val Glu Ile Lys
            100                 105

```
<210> SEQ ID NO 187
<211> LENGTH: 18
<212> TYPE: DNA
<213> ORGANISM: Artificial Sequence
<220> FEATURE:
<223> OTHER INFORMATION: synthetic

<400> SEQUENCE: 187
cagagcatta gtagctat                                                 18

<210> SEQ ID NO 188
<211> LENGTH: 6
<212> TYPE: PRT
<213> ORGANISM: Artificial Sequence
<220> FEATURE:
<223> OTHER INFORMATION: synthetic

<400> SEQUENCE: 188

Gln Ser Ile Ser Ser Tyr
1               5

<210> SEQ ID NO 189
<211> LENGTH: 9
<212> TYPE: DNA
<213> ORGANISM: Artificial Sequence
<220> FEATURE:
<223> OTHER INFORMATION: synthetic

<400> SEQUENCE: 189 actgcatcc                                                            9

<210> SEQ ID NO 190
<211> LENGTH: 3
<212> TYPE: PRT
<213> ORGANISM: Artificial Sequence
<220> FEATURE:
<223> OTHER INFORMATION: synthetic

<400> SEQUENCE: 190

Thr Ala Ser
1

<210> SEQ ID NO 191
<211> LENGTH: 27
<212> TYPE: DNA
<213> ORGANISM: Artificial Sequence
<220> FEATURE:
<223> OTHER INFORMATION: synthetic

<400> SEQUENCE: 191
caacagagtt acagttcccc cctcact                                       27

<210> SEQ ID NO 192
<211> LENGTH: 9
<212> TYPE: PRT
<213> ORGANISM: Artificial Sequence
<220> FEATURE:
<223> OTHER INFORMATION: synthetic

<400> SEQUENCE: 192

Gln Gln Ser Tyr Ser Ser Pro Leu Thr
1               5

<210> SEQ ID NO 193
<211> LENGTH: 348
<212> TYPE: DNA
<213> ORGANISM: Artificial Sequence
```

<220> FEATURE:
<223> OTHER INFORMATION: synthetic

<400> SEQUENCE: 193

```
gaggtgcagc tggtggagtc tgggggaggc ttggtacagc ctggagggtc cctgagactc      60
tcctgtgcag cctctggatt caccttcagt aattatgaga tgagctgggt ccgccaggct     120
ccagggaagg gctggagtg gtttcatcc attagaacta gtggtactac caaatactac      180
gcagactcta tgaagggccg attcaccatc tccagagaca cgccaagaa ctcactgtat      240
ctgcaaatga acagcctgag agccgaggac acggctgttt attactgtgc gggagggggt     300
acgttcctcc actactgggg ccagggaacc ctggtcaccg tctcctca                  348
```

<210> SEQ ID NO 194
<211> LENGTH: 116
<212> TYPE: PRT
<213> ORGANISM: Artificial Sequence
<220> FEATURE:
<223> OTHER INFORMATION: synthetic

<400> SEQUENCE: 194

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Glu Met Ser Trp Val Arg Gln Ala Pro Gly Lys Gly Leu Glu Trp Val
        35                  40                  45

Ser Ser Ile Arg Thr Ser Gly Thr Thr Lys Tyr Tyr Ala Asp Ser Met
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Gly Gly Gly Thr Phe Leu His Tyr Trp Gly Gln Gly Thr Leu Val
            100                 105                 110

Thr Val Ser Ser
        115
```

<210> SEQ ID NO 195
<211> LENGTH: 24
<212> TYPE: DNA
<213> ORGANISM: Artificial Sequence
<220> FEATURE:
<223> OTHER INFORMATION: synthetic

<400> SEQUENCE: 195

```
ggattcacct tcagtaatta tgag                                             24
```

<210> SEQ ID NO 196
<211> LENGTH: 8
<212> TYPE: PRT
<213> ORGANISM: Artificial Sequence
<220> FEATURE:
<223> OTHER INFORMATION: synthetic

<400> SEQUENCE: 196

```
Gly Phe Thr Phe Ser Asn Tyr Glu
1               5
```

<210> SEQ ID NO 197
<211> LENGTH: 24

<210> SEQ ID NO 198
<211> LENGTH: 8
<212> TYPE: DNA
<213> ORGANISM: Artificial Sequence
<220> FEATURE:
<223> OTHER INFORMATION: synthetic

<400> SEQUENCE: 197
attagaacta gtggtactac caaa                                            24

<210> SEQ ID NO 198
<211> LENGTH: 8
<212> TYPE: PRT
<213> ORGANISM: Artificial Sequence
<220> FEATURE:
<223> OTHER INFORMATION: synthetic

<400> SEQUENCE: 198

Ile Arg Thr Ser Gly Thr Thr Lys
1               5

<210> SEQ ID NO 199
<211> LENGTH: 27
<212> TYPE: DNA
<213> ORGANISM: Artificial Sequence
<220> FEATURE:
<223> OTHER INFORMATION: synthetic

<400> SEQUENCE: 199
gcgggagggg gtacgttcct ccactac                                         27

<210> SEQ ID NO 200
<211> LENGTH: 9
<212> TYPE: PRT
<213> ORGANISM: Artificial Sequence
<220> FEATURE:
<223> OTHER INFORMATION: synthetic

<400> SEQUENCE: 200

Ala Gly Gly Gly Thr Phe Leu His Tyr
1               5

<210> SEQ ID NO 201
<211> LENGTH: 324
<212> TYPE: DNA
<213> ORGANISM: Artificial Sequence
<220> FEATURE:
<223> OTHER INFORMATION: synthetic

<400> SEQUENCE: 201
gacatccaga tgacccagtc tccatcttcc gtgtctgcgt ctgtaggaga cagagtcacc      60
atcacttgtc gggcgagtca gggtattgcc agctatttag cctggtatca gcagaaacca     120
gggaaagccc ctaagctcct gatttatgct gcatccagtt tgcaaactgg ggtcccatca     180
aggttcagcg gcagtggata tgggacagat ttcactctca ccatcagcag cctgcagcct     240
gaagattttg caacttacta ttgtcaacag gctaagagtt tccccatgta cacttttggc     300
caggggacca agctggagat caaa                                            324

<210> SEQ ID NO 202
<211> LENGTH: 108
<212> TYPE: PRT
<213> ORGANISM: Artificial Sequence
<220> FEATURE:
<223> OTHER INFORMATION: synthetic

<400> SEQUENCE: 202

-continued

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ala Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Thr Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Ala Lys Ser Phe Pro Met
                85                  90                  95

Tyr Thr Phe Gly Gln Gly Thr Lys Leu Glu Ile Lys
            100                 105
```

<210> SEQ ID NO 203
<211> LENGTH: 18
<212> TYPE: DNA
<213> ORGANISM: Artificial Sequence
<220> FEATURE:
<223> OTHER INFORMATION: synthetic

<400> SEQUENCE: 203
cagggtattg ccagctat                                              18

<210> SEQ ID NO 204
<211> LENGTH: 6
<212> TYPE: PRT
<213> ORGANISM: Artificial Sequence
<220> FEATURE:
<223> OTHER INFORMATION: synthetic

<400> SEQUENCE: 204

```
Gln Gly Ile Ala Ser Tyr
1               5
```

<210> SEQ ID NO 205
<211> LENGTH: 9
<212> TYPE: DNA
<213> ORGANISM: Artificial Sequence
<220> FEATURE:
<223> OTHER INFORMATION: synthetic

<400> SEQUENCE: 205 gctgcatcc                                                         9

<210> SEQ ID NO 206
<211> LENGTH: 3
<212> TYPE: PRT
<213> ORGANISM: Artificial Sequence
<220> FEATURE:
<223> OTHER INFORMATION: synthetic

<400> SEQUENCE: 206

```
Ala Ala Ser
1
```

<210> SEQ ID NO 207
<211> LENGTH: 30
<212> TYPE: DNA
<213> ORGANISM: Artificial Sequence
<220> FEATURE:
<223> OTHER INFORMATION: synthetic

<400> SEQUENCE: 207
caacaggcta agagtttccc catgtacact                                          30

<210> SEQ ID NO 208
<211> LENGTH: 10
<212> TYPE: PRT
<213> ORGANISM: Artificial Sequence
<220> FEATURE:
<223> OTHER INFORMATION: synthetic

<400> SEQUENCE: 208

Gln Gln Ala Lys Ser Phe Pro Met Tyr Thr
1               5                   10

<210> SEQ ID NO 209
<211> LENGTH: 366
<212> TYPE: DNA
<213> ORGANISM: Artificial Sequence
<220> FEATURE:
<223> OTHER INFORMATION: synthetic

<400> SEQUENCE: 209
caggtgcagc tgcaggagtc gggcccagga ctggtgaagc cttcacagac cctgtccctc        60
acctgcactg tctctggtgg ctccatcacc agtggtggtt actactggag ctggatccgc       120
cagcacccag ggaagggcct ggagtggatt ggatacatct tttacagtgg gatcaccaac       180
tacaacccgt ccctcaagag tcgagttacc atatcagtag acacgtctaa gaaccagttc       240
tccctgaaac tgacctctgt gactgccgcg gacacggccg tgtattactg tgcgacgtat       300
aacagcctcc gactctacta cggtatggac gtctggggcc aagggaccac ggtcaccgtc       360
tcctca                                                                  366

<210> SEQ ID NO 210
<211> LENGTH: 122
<212> TYPE: PRT
<213> ORGANISM: Artificial Sequence
<220> FEATURE:
<223> OTHER INFORMATION: synthetic

<400> SEQUENCE: 210

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Phe Tyr Ser Gly Ile Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Thr Ser Val Thr Ala Ala Asp Thr Ala Val Tyr Tyr
                85                  90                  95

Cys Ala Thr Tyr Asn Ser Leu Arg Leu Tyr Tyr Gly Met Asp Val Trp
            100                 105                 110

Gly Gln Gly Thr Thr Val Thr Val Ser Ser
        115                 120

<210> SEQ ID NO 211
<211> LENGTH: 30
<212> TYPE: DNA

<213> ORGANISM: Artificial Sequence
<220> FEATURE:
<223> OTHER INFORMATION: synthetic

<400> SEQUENCE: 211
ggtggctcca tcaccagtgg tggttactac                                           30

<210> SEQ ID NO 212
<211> LENGTH: 10
<212> TYPE: PRT
<213> ORGANISM: Artificial Sequence
<220> FEATURE:
<223> OTHER INFORMATION: synthetic

<400> SEQUENCE: 212

Gly Gly Ser Ile Thr Ser Gly Gly Tyr Tyr
1               5                   10

<210> SEQ ID NO 213
<211> LENGTH: 21
<212> TYPE: DNA
<213> ORGANISM: Artificial Sequence
<220> FEATURE:
<223> OTHER INFORMATION: synthetic

<400> SEQUENCE: 213
atcttttaca gtgggatcac c                                                    21

<210> SEQ ID NO 214
<211> LENGTH: 7
<212> TYPE: PRT
<213> ORGANISM: Artificial Sequence
<220> FEATURE:
<223> OTHER INFORMATION: synthetic

<400> SEQUENCE: 214

Ile Phe Tyr Ser Gly Ile Thr
1               5

<210> SEQ ID NO 215
<211> LENGTH: 42
<212> TYPE: DNA
<213> ORGANISM: Artificial Sequence
<220> FEATURE:
<223> OTHER INFORMATION: synthetic

<400> SEQUENCE: 215
gcgacgtata acagcctccg actctactac ggtatggacg tc                             42

<210> SEQ ID NO 216
<211> LENGTH: 14
<212> TYPE: PRT
<213> ORGANISM: Artificial Sequence
<220> FEATURE:
<223> OTHER INFORMATION: synthetic

<400> SEQUENCE: 216

Ala Thr Tyr Asn Ser Leu Arg Leu Tyr Tyr Gly Met Asp Val
1               5                   10

<210> SEQ ID NO 217
<211> LENGTH: 336
<212> TYPE: DNA
<213> ORGANISM: Artificial Sequence
<220> FEATURE:
<223> OTHER INFORMATION: synthetic -continued

<400> SEQUENCE: 217

```
gatgttgtga tgacccagtc tccactctcc ctgcccgtca tccttggaca gccggcctcc    60
atctcctgca ggtctagtca aagcctcgta tacggtgatg aaacaccta cttgaattgg   120 tttcagcaga ggccaggcca atctccaagg cgactaattt ataaggtttc taaccgggac   180
tctggggtcc cagacagatt cagcggcagt gggtcaggca ctgatttcac actgaaaatc   240
agcagggtgg aggctgagga tgttggggtt tattactgca tgcaaagtac acactggccg   300
ctcactttcg gcggagggac caaggtggag atcaaa                             336
```

<210> SEQ ID NO 218
<211> LENGTH: 112
<212> TYPE: PRT
<213> ORGANISM: Artificial Sequence
<220> FEATURE:
<223> OTHER INFORMATION: synthetic

<400> SEQUENCE: 218

```
Asp Val Val Met Thr Gln Ser Pro Leu Ser Leu Pro Val Ile Leu Gly
1               5                   10                  15

Gln Pro Ala Ser Ile Ser Cys Arg Ser Ser Gln Ser Leu Val Tyr Gly
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Thr His Trp Pro Leu Thr Phe Gly Gly Gly Thr Lys Val Glu Ile Lys
            100                 105                 110
```

<210> SEQ ID NO 219
<211> LENGTH: 33
<212> TYPE: DNA
<213> ORGANISM: Artificial Sequence
<220> FEATURE:
<223> OTHER INFORMATION: synthetic

<400> SEQUENCE: 219

```
caaagcctcg tatacggtga tggaaacacc tac                                33
```

<210> SEQ ID NO 220
<211> LENGTH: 11
<212> TYPE: PRT
<213> ORGANISM: Artificial Sequence
<220> FEATURE:
<223> OTHER INFORMATION: synthetic

<400> SEQUENCE: 220

```
Gln Ser Leu Val Tyr Gly Asp Gly Asn Thr Tyr
1               5                   10
```

<210> SEQ ID NO 221
<211> LENGTH: 9
<212> TYPE: DNA
<213> ORGANISM: Artificial Sequence
<220> FEATURE:
<223> OTHER INFORMATION: synthetic

<400> SEQUENCE: 221 aaggtttct                                                                          9

<210> SEQ ID NO 222
<211> LENGTH: 3
<212> TYPE: PRT
<213> ORGANISM: Artificial Sequence
<220> FEATURE:
<223> OTHER INFORMATION: synthetic

<400> SEQUENCE: 222

Lys Val Ser
1

<210> SEQ ID NO 223
<211> LENGTH: 27
<212> TYPE: DNA
<213> ORGANISM: Artificial Sequence
<220> FEATURE:
<223> OTHER INFORMATION: synthetic

<400> SEQUENCE: 223
atgcaaagta cacactggcc gctcact                                                     27

<210> SEQ ID NO 224
<211> LENGTH: 9
<212> TYPE: PRT
<213> ORGANISM: Artificial Sequence
<220> FEATURE:
<223> OTHER INFORMATION: synthetic

<400> SEQUENCE: 224

Met Gln Ser Thr His Trp Pro Leu Thr
1               5

<210> SEQ ID NO 225
<211> LENGTH: 360
<212> TYPE: DNA
<213> ORGANISM: Artificial Sequence
<220> FEATURE:
<223> OTHER INFORMATION: synthetic

<400> SEQUENCE: 225
gaggtgcagc tggtggagtc tgggggaggc ttggtccagc ctggagggtc cctgagactc         60
gcctgtgcag cctctggatt caccttcagt gactattaca tggactgggt ccgccaggtt        120
ccagggaagg ggctggagtg ggttggccgt tctagagaca agctaacag tttcaccaca         180 gaatacgtcg cgtctgtgaa aggtagattc accatctcac gagaagattc aaagaactca        240
gtgtatctgc aaatgaacag cctgaaaacc gaagacacgg ccgtgtatta ctgtgctaga        300
acaaattacg attttccctt ggacgtctgg ggccaaggga ccacggtcac cgtctcctca        360

<210> SEQ ID NO 226
<211> LENGTH: 120
<212> TYPE: PRT
<213> ORGANISM: Artificial Sequence
<220> FEATURE:
<223> OTHER INFORMATION: synthetic

<400> SEQUENCE: 226

Glu Val Gln Leu Val Glu Ser Gly Gly Gly Leu Val Gln Pro Gly Gly
1               5                   10                  15

Ser Leu Arg Leu Ala Cys Ala Ala Ser Gly Phe Thr Phe Ser Asp Tyr
            20                  25                  30

```
Tyr Met Asp Trp Val Arg Gln Val Pro Gly Lys Gly Leu Glu Trp Val
         35                  40                  45
Gly Arg Ser Arg Asp Lys Ala Asn Ser Phe Thr Thr Glu Tyr Val Ala
 50                  55                  60
Ser Val Lys Gly Arg Phe Thr Ile Ser Arg Glu Asp Ser Lys Asn Ser
 65                  70                  75                  80
Val Tyr Leu Gln Met Asn Ser Leu Lys Thr Glu Asp Thr Ala Val Tyr
                 85                  90                  95
Tyr Cys Ala Arg Thr Asn Tyr Asp Phe Ser Leu Asp Val Trp Gly Gln
                100                 105                 110
Gly Thr Thr Val Thr Val Ser Ser
        115                 120
```

<210> SEQ ID NO 227
<211> LENGTH: 24
<212> TYPE: DNA
<213> ORGANISM: Artificial Sequence
<220> FEATURE:
<223> OTHER INFORMATION: synthetic

<400> SEQUENCE: 227
ggattcacct tcagtgacta ttac                                      24

<210> SEQ ID NO 228
<211> LENGTH: 8
<212> TYPE: PRT
<213> ORGANISM: Artificial Sequence
<220> FEATURE:
<223> OTHER INFORMATION: synthetic

<400> SEQUENCE: 228

```
Gly Phe Thr Phe Ser Asp Tyr Tyr
 1               5
```

<210> SEQ ID NO 229
<211> LENGTH: 30
<212> TYPE: DNA
<213> ORGANISM: Artificial Sequence
<220> FEATURE:
<223> OTHER INFORMATION: synthetic

<400> SEQUENCE: 229
tctagagaca aagctaacag tttcaccaca                                30

<210> SEQ ID NO 230
<211> LENGTH: 10
<212> TYPE: PRT
<213> ORGANISM: Artificial Sequence
<220> FEATURE:
<223> OTHER INFORMATION: synthetic

<400> SEQUENCE: 230

```
Ser Arg Asp Lys Ala Asn Ser Phe Thr Thr
 1               5                  10
```

<210> SEQ ID NO 231
<211> LENGTH: 33
<212> TYPE: DNA
<213> ORGANISM: Artificial Sequence
<220> FEATURE:
<223> OTHER INFORMATION: synthetic

<400> SEQUENCE: 231
gctagaacaa attacgattt ttccttggac gtc                            33

<210> SEQ ID NO 232
<211> LENGTH: 11
<212> TYPE: PRT
<213> ORGANISM: Artificial Sequence
<220> FEATURE:
<223> OTHER INFORMATION: synthetic

<400> SEQUENCE: 232

Ala Arg Thr Asn Tyr Asp Phe Ser Leu Asp Val
1               5                   10

<210> SEQ ID NO 233
<211> LENGTH: 321
<212> TYPE: DNA
<213> ORGANISM: Artificial Sequence
<220> FEATURE:
<223> OTHER INFORMATION: synthetic

<400> SEQUENCE: 233
gacatccaga tgacccagtc tccatcctca ctgtctgcat ctgtaggaga cagagtcacc      60
atcacttgtc gggcgagtca ggacattaac aattatttag cctggtttca gcagaaacca    120
gggaacgccc ctaagtccct gatctatgct gcatccagtt tgcaaagtgg ggtcccatca    180
aagttcagcg gcagtggatc tgggacagac ttcactctca ccatcagcag cctgcagcct    240
gaagattttg caacttatta ctgccaacaa tatagtactt acccgatcac cttcggccaa    300
gggacacgac tggagattaa a                                              321

<210> SEQ ID NO 234
<211> LENGTH: 107
<212> TYPE: PRT
<213> ORGANISM: Artificial Sequence
<220> FEATURE:
<223> OTHER INFORMATION: synthetic

<400> SEQUENCE: 234

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
                20                  25                  30

Leu Ala Trp Phe Gln Gln Lys Pro Gly Asn Ala Pro Lys Ser Leu Ile
            35                  40                  45

Tyr Ala Ala Ser Ser Leu Gln Ser Gly Val Pro Ser Lys Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Tyr Pro Ile
                85                  90                  95

Thr Phe Gly Gln Gly Thr Arg Leu Glu Ile Lys
            100                 105

<210> SEQ ID NO 235
<211> LENGTH: 18
<212> TYPE: DNA
<213> ORGANISM: Artificial Sequence
<220> FEATURE:
<223> OTHER INFORMATION: synthetic

<400> SEQUENCE: 235
caggacatta acaattat                                                   18

```
<210> SEQ ID NO 236
<211> LENGTH: 6
<212> TYPE: PRT
<213> ORGANISM: Artificial Sequence
<220> FEATURE:
<223> OTHER INFORMATION: synthetic

<400> SEQUENCE: 236

Gln Asp Ile Asn Asn Tyr
1               5

<210> SEQ ID NO 237
<211> LENGTH: 9
<212> TYPE: DNA
<213> ORGANISM: Artificial Sequence
<220> FEATURE:
<223> OTHER INFORMATION: synthetic

<400> SEQUENCE: 237 gctgcatcc                                                              9

<210> SEQ ID NO 238
<211> LENGTH: 3
<212> TYPE: PRT
<213> ORGANISM: Artificial Sequence
<220> FEATURE:
<223> OTHER INFORMATION: synthetic

<400> SEQUENCE: 238

Ala Ala Ser
1

<210> SEQ ID NO 239
<211> LENGTH: 27
<212> TYPE: DNA
<213> ORGANISM: Artificial Sequence
<220> FEATURE:
<223> OTHER INFORMATION: synthetic

<400> SEQUENCE: 239
caacaatata gtacttaccc gatcacc                                         27

<210> SEQ ID NO 240
<211> LENGTH: 9
<212> TYPE: PRT
<213> ORGANISM: Artificial Sequence
<220> FEATURE:
<223> OTHER INFORMATION: synthetic

<400> SEQUENCE: 240

Gln Gln Tyr Ser Thr Tyr Pro Ile Thr
1               5

<210> SEQ ID NO 241
<211> LENGTH: 354
<212> TYPE: DNA
<213> ORGANISM: Artificial Sequence
<220> FEATURE:
<223> OTHER INFORMATION: synthetic

<400> SEQUENCE: 241
caggtgcagc tgcaggagtc gggcccagga ctggtgaagc cttcggagac cctgtccctc      60
acctgtactg tctctggtgg ctccatcagt agttaccact ggagctggat ccggcagcct     120
ctagggaagg gactggagtg gattgggtat atctattaca gtgggagcac caattacaac     180
```

```
ccctccctca agagtcgggt caccatatca gtagacacgt ccaaaaacca gttctccctg    240
aagctgagct ctgtgaccgc tgcggatacg ccgtgtatt  actgtgcgag aggggggtagc    300 agcatctggc cctttgacta ctggggccag ggaaccctgg tcaccgtctc ctca           354
```

<210> SEQ ID NO 242
<211> LENGTH: 118
<212> TYPE: PRT
<213> ORGANISM: Artificial Sequence
<220> FEATURE:
<223> OTHER INFORMATION: synthetic

<400> SEQUENCE: 242

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

His Trp Ser Trp Ile Arg Gln Pro Leu Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Ser Ser Ile Trp Pro Phe Asp Tyr Trp Gly Gln Gly Thr
            100                 105                 110

Leu Val Thr Val Ser Ser
        115
```

<210> SEQ ID NO 243
<211> LENGTH: 24
<212> TYPE: DNA
<213> ORGANISM: Artificial Sequence
<220> FEATURE:
<223> OTHER INFORMATION: synthetic

<400> SEQUENCE: 243

```
ggtggctcca tcagtagtta ccac                                             24
```

<210> SEQ ID NO 244
<211> LENGTH: 8
<212> TYPE: PRT
<213> ORGANISM: Artificial Sequence
<220> FEATURE:
<223> OTHER INFORMATION: synthetic

<400> SEQUENCE: 244

```
Gly Gly Ser Ile Ser Ser Tyr His
1               5
```

<210> SEQ ID NO 245
<211> LENGTH: 21
<212> TYPE: DNA
<213> ORGANISM: Artificial Sequence
<220> FEATURE:
<223> OTHER INFORMATION: synthetic

<400> SEQUENCE: 245

```
atctattaca gtgggagcac c                                                21
```

<210> SEQ ID NO 246

```
<211> LENGTH: 7
<212> TYPE: PRT
<213> ORGANISM: Artificial Sequence
<220> FEATURE:
<223> OTHER INFORMATION: synthetic

<400> SEQUENCE: 246

Ile Tyr Tyr Ser Gly Ser Thr
1               5

<210> SEQ ID NO 247
<211> LENGTH: 36
<212> TYPE: DNA
<213> ORGANISM: Artificial Sequence
<220> FEATURE:
<223> OTHER INFORMATION: synthetic

<400> SEQUENCE: 247
gcgagagggg gtagcagcat ctggcccttt gactac                              36

<210> SEQ ID NO 248
<211> LENGTH: 12
<212> TYPE: PRT
<213> ORGANISM: Artificial Sequence
<220> FEATURE:
<223> OTHER INFORMATION: synthetic

<400> SEQUENCE: 248

Ala Arg Gly Gly Ser Ser Ile Trp Pro Phe Asp Tyr
1               5                   10

<210> SEQ ID NO 249
<211> LENGTH: 321
<212> TYPE: DNA
<213> ORGANISM: Artificial Sequence
<220> FEATURE:
<223> OTHER INFORMATION: synthetic

<400> SEQUENCE: 249
gacatccaga tgacccagtc tccttccacc ctgtctgcat ctgtaggaga cagagtcacc     60
atcacttgtc gggccagtca gagtattagt agctggttgg cctggtatca gcagaaatca    120
gggaaagccc ctaaactcct gatctctaag gcgtctactt tagaaagtgg ggtcccatca    180
aggttcagcg gcagtggatc tgggacagaa ttcactctca ccatcagcag cctgcagcct    240
gatgattttg caacttatta ctgccaacag tataatattt attcgtggac gttcggccaa    300
gggaccaagg tggaaatcaa a                                              321

<210> SEQ ID NO 250
<211> LENGTH: 107
<212> TYPE: PRT
<213> ORGANISM: Artificial Sequence
<220> FEATURE:
<223> OTHER INFORMATION: synthetic

<400> SEQUENCE: 250

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Ser Gly Lys Ala Pro Lys Leu Leu Ile
        35                  40                  45

Ser Lys Ala Ser Thr Leu Glu Ser Gly Val Pro Ser Arg Phe Ser Gly
    50                  55                  60
```

```
Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ile Tyr Ser Trp
                85                  90                  95

Thr Phe Gly Gln Gly Thr Lys Val Glu Ile Lys
            100                 105

<210> SEQ ID NO 251
<211> LENGTH: 18
<212> TYPE: DNA
<213> ORGANISM: Artificial Sequence
<220> FEATURE:
<223> OTHER INFORMATION: synthetic

<400> SEQUENCE: 251
cagagtatta gtagctgg                                                       18

<210> SEQ ID NO 252
<211> LENGTH: 6
<212> TYPE: PRT
<213> ORGANISM: Artificial Sequence
<220> FEATURE:
<223> OTHER INFORMATION: synthetic

<400> SEQUENCE: 252

Gln Ser Ile Ser Ser Trp
1               5

<210> SEQ ID NO 253
<211> LENGTH: 9
<212> TYPE: DNA
<213> ORGANISM: Artificial Sequence
<220> FEATURE:
<223> OTHER INFORMATION: synthetic

<400> SEQUENCE: 253 aaggcgtct                                                                  9

<210> SEQ ID NO 254
<211> LENGTH: 3
<212> TYPE: PRT
<213> ORGANISM: Artificial Sequence
<220> FEATURE:
<223> OTHER INFORMATION: synthetic

<400> SEQUENCE: 254

Lys Ala Ser
1

<210> SEQ ID NO 255
<211> LENGTH: 27
<212> TYPE: DNA
<213> ORGANISM: Artificial Sequence
<220> FEATURE:
<223> OTHER INFORMATION: synthetic

<400> SEQUENCE: 255
caacagtata atatttattc gtggacg                                             27

<210> SEQ ID NO 256
<211> LENGTH: 9
<212> TYPE: PRT
<213> ORGANISM: Artificial Sequence
<220> FEATURE:
<223> OTHER INFORMATION: synthetic
```

<400> SEQUENCE: 256

Gln Gln Tyr Asn Ile Tyr Ser Trp Thr
1               5

<210> SEQ ID NO 257
<211> LENGTH: 360
<212> TYPE: DNA
<213> ORGANISM: Artificial Sequence
<220> FEATURE:
<223> OTHER INFORMATION: synthetic

<400> SEQUENCE: 257

```
cagatcacct tgaaggagtc tggtcctacg ctggtgaaac ccacacagac cctcacgctg      60
acctgcacct ctctccgggtt ctcactcagc actagtggag tgggtgtggg ctggatccgt    120
cagcccccag gagtggccct ggagtggctt gcactcattt attggaatga tgataaacgc    180
ttcagcccat ctctgaagag tcggctcacc atcaccaaag acacctccaa aaaccaggtg    240
gtccttacaa tgaccaacat ggaccctgtg acacagcca catattactg tgcacacagg     300
agacttggac tatactactt tgactactgg ggccagggaa ccctggtcac cgtctcctca    360
```

<210> SEQ ID NO 258
<211> LENGTH: 120
<212> TYPE: PRT
<213> ORGANISM: Artificial Sequence
<220> FEATURE:
<223> OTHER INFORMATION: synthetic

<400> SEQUENCE: 258

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Val Ala Leu Glu
        35                  40                  45

Trp Leu Ala Leu Ile Tyr Trp Asn Asp Asp Lys Arg Phe Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Arg Leu Gly Leu Tyr Tyr Phe Asp Tyr Trp Gly Gln
            100                 105                 110

Gly Thr Leu Val Thr Val Ser Ser
        115                 120

<210> SEQ ID NO 259
<211> LENGTH: 30
<212> TYPE: DNA
<213> ORGANISM: Artificial Sequence
<220> FEATURE:
<223> OTHER INFORMATION: synthetic

<400> SEQUENCE: 259

```
gggttctcac tcagcactag tggagtgggt                                       30
```

<210> SEQ ID NO 260
<211> LENGTH: 10
<212> TYPE: PRT
<213> ORGANISM: Artificial Sequence

```
<220> FEATURE:
<223> OTHER INFORMATION: synthetic

<400> SEQUENCE: 260

Gly Phe Ser Leu Ser Thr Ser Gly Val Gly
1               5                   10

<210> SEQ ID NO 261
<211> LENGTH: 21
<212> TYPE: DNA
<213> ORGANISM: Artificial Sequence
<220> FEATURE:
<223> OTHER INFORMATION: synthetic

<400> SEQUENCE: 261
atttattgga atgatgataa a                                          21

<210> SEQ ID NO 262
<211> LENGTH: 7
<212> TYPE: PRT
<213> ORGANISM: Artificial Sequence
<220> FEATURE:
<223> OTHER INFORMATION: synthetic

<400> SEQUENCE: 262

Ile Tyr Trp Asn Asp Asp Lys
1               5

<210> SEQ ID NO 263
<211> LENGTH: 36
<212> TYPE: DNA
<213> ORGANISM: Artificial Sequence
<220> FEATURE:
<223> OTHER INFORMATION: synthetic

<400> SEQUENCE: 263
gcacacagga gacttggact atactacttt gactac                          36

<210> SEQ ID NO 264
<211> LENGTH: 12
<212> TYPE: PRT
<213> ORGANISM: Artificial Sequence
<220> FEATURE:
<223> OTHER INFORMATION: synthetic

<400> SEQUENCE: 264

Ala His Arg Arg Leu Gly Leu Tyr Tyr Phe Asp Tyr
1               5                   10

<210> SEQ ID NO 265
<211> LENGTH: 321
<212> TYPE: DNA
<213> ORGANISM: Artificial Sequence
<220> FEATURE:
<223> OTHER INFORMATION: synthetic

<400> SEQUENCE: 265
gacatccagt tgacccagtc tccatccttc ctgtctgcat ctgtaggaga cagagtcacc     60
atcacttgct gggccagtca gggcattagc agttatttag cctggtatca gcaaaaacca    120
gggaaagccc ctaagctcct gatctatgct gcatccactt tgcaaagtgg ggtcccatca    180
aggttcagcg gcagtggatc tgggacagaa ttcactctca caatcagcag cctgcagcct    240
gaagattttg caacttatta ctgtcaacag gttcatattt acccattcac tttcggccct    300
gggaccaaag tggatatcaa a                                             321
```

<210> SEQ ID NO 266
<211> LENGTH: 107
<212> TYPE: PRT
<213> ORGANISM: Artificial Sequence
<220> FEATURE:
<223> OTHER INFORMATION: synthetic

<400> SEQUENCE: 266

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Val His Ile Tyr Pro Phe
                85                  90                  95

Thr Phe Gly Pro Gly Thr Lys Val Asp Ile Lys
            100                 105

<210> SEQ ID NO 267
<211> LENGTH: 18
<212> TYPE: DNA
<213> ORGANISM: Artificial Sequence
<220> FEATURE:
<223> OTHER INFORMATION: synthetic

<400> SEQUENCE: 267
cagggcatta gcagttat                                              18

<210> SEQ ID NO 268
<211> LENGTH: 6
<212> TYPE: PRT
<213> ORGANISM: Artificial Sequence
<220> FEATURE:
<223> OTHER INFORMATION: synthetic

<400> SEQUENCE: 268

Gln Gly Ile Ser Ser Tyr
1               5

<210> SEQ ID NO 269
<211> LENGTH: 9
<212> TYPE: DNA
<213> ORGANISM: Artificial Sequence
<220> FEATURE:
<223> OTHER INFORMATION: synthetic

<400> SEQUENCE: 269 gctgcatcc                                                         9

<210> SEQ ID NO 270
<211> LENGTH: 3
<212> TYPE: PRT
<213> ORGANISM: Artificial Sequence
<220> FEATURE:
<223> OTHER INFORMATION: synthetic

<400> SEQUENCE: 270

Ala Ala Ser
1

<210> SEQ ID NO 271
<211> LENGTH: 27
<212> TYPE: DNA
<213> ORGANISM: Artificial Sequence
<220> FEATURE:
<223> OTHER INFORMATION: synthetic

<400> SEQUENCE: 271
caacaggttc atatttaccc attcact        27

<210> SEQ ID NO 272
<211> LENGTH: 9
<212> TYPE: PRT
<213> ORGANISM: Artificial Sequence
<220> FEATURE:
<223> OTHER INFORMATION: synthetic

<400> SEQUENCE: 272

Gln Gln Val His Ile Tyr Pro Phe Thr
1               5

<210> SEQ ID NO 273
<211> LENGTH: 366
<212> TYPE: DNA
<213> ORGANISM: Artificial Sequence
<220> FEATURE:
<223> OTHER INFORMATION: synthetic

<400> SEQUENCE: 273
caggttcagc tggtgcagtc tggagctgag gtgaagaagc ctggggcctc agtgaaggtc        60
tcctgcaagg cttctggtta caccctaagc agctatggta tcagctgggt gcgacaggcc       120
cctggacaag gacttgagtg gatggggtgg atcagcgctt acaatggaaa cacaaactat       180
gctcagaagc tccagggtag actcaccatg accacagaca catccacgag cacagcctac       240
atggagctga ggagcctgag atctgacgac acggccgtat attattgttc gagagacggg       300
ccctttaaga tatccttttt cggtatggac gtctggggcc aagggaccac ggtcaccgtc       360
tcctca                                                                 366

<210> SEQ ID NO 274
<211> LENGTH: 122
<212> TYPE: PRT
<213> ORGANISM: Artificial Sequence
<220> FEATURE:
<223> OTHER INFORMATION: synthetic

<400> SEQUENCE: 274

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Ser Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Leu Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ser Arg Asp Gly Pro Phe Lys Ile Ser Phe Phe Gly Met Asp Val Trp
            100                 105                 110

Gly Gln Gly Thr Thr Val Thr Val Ser Ser
        115                 120

<210> SEQ ID NO 275
<211> LENGTH: 24
<212> TYPE: DNA
<213> ORGANISM: Artificial Sequence
<220> FEATURE:
<223> OTHER INFORMATION: synthetic

<400> SEQUENCE: 275
ggttacaccc taagcagcta tggt                                      24

<210> SEQ ID NO 276
<211> LENGTH: 8
<212> TYPE: PRT
<213> ORGANISM: Artificial Sequence
<220> FEATURE:
<223> OTHER INFORMATION: synthetic

<400> SEQUENCE: 276

Gly Tyr Thr Leu Ser Ser Tyr Gly
1               5

<210> SEQ ID NO 277
<211> LENGTH: 24
<212> TYPE: DNA
<213> ORGANISM: Artificial Sequence
<220> FEATURE:
<223> OTHER INFORMATION: synthetic

<400> SEQUENCE: 277
atcagcgctt acaatggaaa caca                                      24

<210> SEQ ID NO 278
<211> LENGTH: 8
<212> TYPE: PRT
<213> ORGANISM: Artificial Sequence
<220> FEATURE:
<223> OTHER INFORMATION: synthetic

<400> SEQUENCE: 278

Ile Ser Ala Tyr Asn Gly Asn Thr
1               5

<210> SEQ ID NO 279
<211> LENGTH: 45
<212> TYPE: DNA
<213> ORGANISM: Artificial Sequence
<220> FEATURE:
<223> OTHER INFORMATION: synthetic

<400> SEQUENCE: 279
tcgagagacg ggccctttaa gatatccttt ttcggtatgg acgtc                45

<210> SEQ ID NO 280
<211> LENGTH: 15
<212> TYPE: PRT
<213> ORGANISM: Artificial Sequence
<220> FEATURE:
<223> OTHER INFORMATION: synthetic

<400> SEQUENCE: 280

Ser Arg Asp Gly Pro Phe Lys Ile Ser Phe Phe Gly Met Asp Val
1               5                   10                  15

<210> SEQ ID NO 281
<211> LENGTH: 324
<212> TYPE: DNA
<213> ORGANISM: Artificial Sequence
<220> FEATURE:
<223> OTHER INFORMATION: synthetic

<400> SEQUENCE: 281

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta ccccctccgat caccttcggc   300
caagggacac gactggagat taaa                                           324
```

<210> SEQ ID NO 282
<211> LENGTH: 108
<212> TYPE: PRT
<213> ORGANISM: Artificial Sequence
<220> FEATURE:
<223> OTHER INFORMATION: synthetic

<400> SEQUENCE: 282

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 283
<211> LENGTH: 18
<212> TYPE: DNA
<213> ORGANISM: Artificial Sequence
<220> FEATURE:
<223> OTHER INFORMATION: synthetic

<400> SEQUENCE: 283

```
cagagcatta gcagctat                                                   18
```

<210> SEQ ID NO 284
<211> LENGTH: 6
<212> TYPE: PRT
<213> ORGANISM: Artificial Sequence
<220> FEATURE:
<223> OTHER INFORMATION: synthetic

<400> SEQUENCE: 284

Gln Ser Ile Ser Ser Tyr

<210> SEQ ID NO 285
<211> LENGTH: 9
<212> TYPE: DNA
<213> ORGANISM: Artificial Sequence
<220> FEATURE:
<223> OTHER INFORMATION: synthetic

<400> SEQUENCE: 285 gctgcatcc                                                                 9

<210> SEQ ID NO 286
<211> LENGTH: 3
<212> TYPE: PRT
<213> ORGANISM: Artificial Sequence
<220> FEATURE:
<223> OTHER INFORMATION: synthetic

<400> SEQUENCE: 286

Ala Ala Ser
1

<210> SEQ ID NO 287
<211> LENGTH: 30
<212> TYPE: DNA
<213> ORGANISM: Artificial Sequence
<220> FEATURE:
<223> OTHER INFORMATION: synthetic

<400> SEQUENCE: 287
caacagagtt acagtacccc tccgatcacc                                         30

<210> SEQ ID NO 288
<211> LENGTH: 10
<212> TYPE: PRT
<213> ORGANISM: Artificial Sequence
<220> FEATURE:
<223> OTHER INFORMATION: synthetic

<400> SEQUENCE: 288

Gln Gln Ser Tyr Ser Thr Pro Pro Ile Thr
1               5                   10

<210> SEQ ID NO 289
<211> LENGTH: 354
<212> TYPE: DNA
<213> ORGANISM: Artificial Sequence
<220> FEATURE:
<223> OTHER INFORMATION: synthetic

<400> SEQUENCE: 289
caggtgcagc tggtggagtc tgggggaggc gaggtccagc tggggaggtc cctgagactc         60
tcctgtgcag cgtctggatt caccttcagt agctatggca tgcactgggt ccgccaggct        120
ccaggcaagg ggctggagtg ggtggcagtt atatggtatg atggaaggaa taaacactat        180
gtagattccg tgaagggccg attcaccatc tccagagaca attccaagaa cacggtgtat        240
ctgcaaatga acagcctgag agccgaggac tcggctgtgt attattgtgt gagaggggggg       300 cagctcggcg ctttttgatta ctggggccag gggaccctgg tcaccgtctc ctca             354

<210> SEQ ID NO 290
<211> LENGTH: 118
<212> TYPE: PRT
<213> ORGANISM: Artificial Sequence

```
<220> FEATURE:
<223> OTHER INFORMATION: synthetic

<400> SEQUENCE: 290

Gln Val Gln Leu Val Glu Ser Gly Gly Gly Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Arg Asn Lys His Tyr Val Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Ser Ala Val Tyr Tyr Cys
                85                  90                  95

Val Arg Gly Gly Gln Leu Gly Ala Phe Asp Tyr Trp Gly Gln Gly Thr
            100                 105                 110

Leu Val Thr Val Ser Ser
        115

<210> SEQ ID NO 291
<211> LENGTH: 24
<212> TYPE: DNA
<213> ORGANISM: Artificial Sequence
<220> FEATURE:
<223> OTHER INFORMATION: synthetic

<400> SEQUENCE: 291
ggattcacct tcagtagcta tggc                                      24

<210> SEQ ID NO 292
<211> LENGTH: 8
<212> TYPE: PRT
<213> ORGANISM: Artificial Sequence
<220> FEATURE:
<223> OTHER INFORMATION: synthetic

<400> SEQUENCE: 292

Gly Phe Thr Phe Ser Ser Tyr Gly
1               5

<210> SEQ ID NO 293
<211> LENGTH: 24
<212> TYPE: DNA
<213> ORGANISM: Artificial Sequence
<220> FEATURE:
<223> OTHER INFORMATION: synthetic

<400> SEQUENCE: 293
atatggtatg atggaaggaa taaa                                      24

<210> SEQ ID NO 294
<211> LENGTH: 8
<212> TYPE: PRT
<213> ORGANISM: Artificial Sequence
<220> FEATURE:
<223> OTHER INFORMATION: synthetic

<400> SEQUENCE: 294

Ile Trp Tyr Asp Gly Arg Asn Lys
1               5
```

<210> SEQ ID NO 295
<211> LENGTH: 33
<212> TYPE: DNA
<213> ORGANISM: Artificial Sequence
<220> FEATURE:
<223> OTHER INFORMATION: synthetic

<400> SEQUENCE: 295
gtgagagggg ggcagctcgg cgcttttgat tac                                   33

<210> SEQ ID NO 296
<211> LENGTH: 11
<212> TYPE: PRT
<213> ORGANISM: Artificial Sequence
<220> FEATURE:
<223> OTHER INFORMATION: synthetic

<400> SEQUENCE: 296

Val Arg Gly Gly Gln Leu Gly Ala Phe Asp Tyr
1               5                   10

<210> SEQ ID NO 297
<211> LENGTH: 324
<212> TYPE: DNA
<213> ORGANISM: Artificial Sequence
<220> FEATURE:
<223> OTHER INFORMATION: synthetic

<400> SEQUENCE: 297
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccttg gacgttcggc     300
caagggacca aggtggaaat caaa                                            324

<210> SEQ ID NO 298
<211> LENGTH: 108
<212> TYPE: PRT
<213> ORGANISM: Artificial Sequence
<220> FEATURE:
<223> OTHER INFORMATION: synthetic

<400> SEQUENCE: 298

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

```
<210> SEQ ID NO 299
<211> LENGTH: 21
<212> TYPE: DNA
<213> ORGANISM: Artificial Sequence
<220> FEATURE:
<223> OTHER INFORMATION: synthetic

<400> SEQUENCE: 299
cagagtgtta gcagcagcta c                                              21

<210> SEQ ID NO 300
<211> LENGTH: 7
<212> TYPE: PRT
<213> ORGANISM: Artificial Sequence
<220> FEATURE:
<223> OTHER INFORMATION: synthetic

<400> SEQUENCE: 300

Gln Ser Val Ser Ser Ser Tyr
1               5

<210> SEQ ID NO 301
<211> LENGTH: 9
<212> TYPE: DNA
<213> ORGANISM: Artificial Sequence
<220> FEATURE:
<223> OTHER INFORMATION: synthetic

<400> SEQUENCE: 301 ggtgcatcc                                                             9

<210> SEQ ID NO 302
<211> LENGTH: 3
<212> TYPE: PRT
<213> ORGANISM: Artificial Sequence
<220> FEATURE:
<223> OTHER INFORMATION: synthetic

<400> SEQUENCE: 302

Gly Ala Ser
1

<210> SEQ ID NO 303
<211> LENGTH: 27
<212> TYPE: DNA
<213> ORGANISM: Artificial Sequence
<220> FEATURE:
<223> OTHER INFORMATION: synthetic

<400> SEQUENCE: 303
cagcagtatg gtagctcacc ttggacg                                        27

<210> SEQ ID NO 304
<211> LENGTH: 9
<212> TYPE: PRT
<213> ORGANISM: Artificial Sequence
<220> FEATURE:
<223> OTHER INFORMATION: synthetic

<400> SEQUENCE: 304

Gln Gln Tyr Gly Ser Ser Pro Trp Thr
1               5

<210> SEQ ID NO 305
<211> LENGTH: 354
<212> TYPE: DNA
<213> ORGANISM: Artificial Sequence
```

<220> FEATURE:
<223> OTHER INFORMATION: synthetic

<400> SEQUENCE: 305

```
caggtgcagc tggtggagtc tgggggaggc gtggtccagc ctggagggtc cctgagactc    60
tcctgtgcag cgtctggatt cacctccagt agctatggca ttcactgggt ccgccaggct   120
ccaggcaagg gctggagtg gtggcagtt atatggtatg atggaagtaa taaatactat    180
gcagactccg tgaagggccg attcaccatc tccagagaca attccaagaa cacactgtat   240
ctgcaaatga acagcctgag agccgaggac acggctgtgt attactgtgc gagagggggt   300
ccgtggggtg cttttgatat ctggggccaa gggacaatgg tcaccgtctc ttca         354
```

<210> SEQ ID NO 306
<211> LENGTH: 118
<212> TYPE: PRT
<213> ORGANISM: Artificial Sequence
<220> FEATURE:
<223> OTHER INFORMATION: synthetic

<400> SEQUENCE: 306

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Ser Ser Ser Tyr
            20                  25                  30

Gly Ile His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Pro Trp Gly Ala Phe Asp Ile Trp Gly Gln Gly Thr
            100                 105                 110

Met Val Thr Val Ser Ser
        115
```

<210> SEQ ID NO 307
<211> LENGTH: 24
<212> TYPE: DNA
<213> ORGANISM: Artificial Sequence
<220> FEATURE:
<223> OTHER INFORMATION: synthetic

<400> SEQUENCE: 307

```
ggattcacct ccagtagcta tggc                                            24
```

<210> SEQ ID NO 308
<211> LENGTH: 8
<212> TYPE: PRT
<213> ORGANISM: Artificial Sequence
<220> FEATURE:
<223> OTHER INFORMATION: synthetic

<400> SEQUENCE: 308

```
Gly Phe Thr Ser Ser Ser Tyr Gly
1               5
```

<210> SEQ ID NO 309
<211> LENGTH: 24

<212> TYPE: DNA
<213> ORGANISM: Artificial Sequence
<220> FEATURE:
<223> OTHER INFORMATION: synthetic

<400> SEQUENCE: 309
atatggtatg atggaagtaa taaa                                           24

<210> SEQ ID NO 310
<211> LENGTH: 8
<212> TYPE: PRT
<213> ORGANISM: Artificial Sequence
<220> FEATURE:
<223> OTHER INFORMATION: synthetic

<400> SEQUENCE: 310

Ile Trp Tyr Asp Gly Ser Asn Lys
1               5

<210> SEQ ID NO 311
<211> LENGTH: 33
<212> TYPE: DNA
<213> ORGANISM: Artificial Sequence
<220> FEATURE:
<223> OTHER INFORMATION: synthetic

<400> SEQUENCE: 311
gcgagagggg gtccgtgggg tgcttttgat atc                                 33

<210> SEQ ID NO 312
<211> LENGTH: 11
<212> TYPE: PRT
<213> ORGANISM: Artificial Sequence
<220> FEATURE:
<223> OTHER INFORMATION: synthetic

<400> SEQUENCE: 312

Ala Arg Gly Gly Pro Trp Gly Ala Phe Asp Ile
1               5                   10

<210> SEQ ID NO 313
<211> LENGTH: 366
<212> TYPE: DNA
<213> ORGANISM: Artificial Sequence
<220> FEATURE:
<223> OTHER INFORMATION: synthetic

<400> SEQUENCE: 313
caggtacagt tgcatgagtc ggggccagga ctggtgaagc cttcacagac cctgtccctc    60
acctgcagtg tctctggtgg ctccatcagt aatggtggtt actactggag ttggatccgc   120
cagcacccag gcagggcct ggagtggatt ggatacatct attatattgg gaacacatac    180
tacaatccgt cccttgagag tcgagttacc atgtcaattg acacgtctaa gaaccagttc   240
tccctaaaac tgagctctgt gactgccgcg gacacggcca tatactactg tgcgcgacag   300
gagttcgtcc cggcgctga atatttccta cactggggcc agggcatcct ggtcaccgtc   360
tcctca                                                              366

<210> SEQ ID NO 314
<211> LENGTH: 122
<212> TYPE: PRT
<213> ORGANISM: Artificial Sequence
<220> FEATURE:
<223> OTHER INFORMATION: synthetic -continued

<400> SEQUENCE: 314

Gln Val Gln Leu His Glu Ser Gly Pro Gly Leu Val Lys Pro Ser Gln
1               5                   10                  15

Thr Leu Ser Leu Thr Cys Ser Val Ser Gly Ser Ile Ser Asn Gly
            20                  25                  30

Gly Tyr Tyr Trp Ser Trp Ile Arg Gln His Pro Gly Gln Gly Leu Glu
        35                  40                  45

Trp Ile Gly Tyr Ile Tyr Tyr Ile Gly Asn Thr Tyr Tyr Asn Pro Ser
    50                  55                  60

Leu Glu Ser Arg Val Thr Met Ser Ile Asp Thr Ser Lys Asn Gln Phe
65                  70                  75                  80

Ser Leu Lys Leu Ser Ser Val Thr Ala Ala Asp Thr Ala Ile Tyr Tyr
                85                  90                  95

Cys Ala Arg Gln Glu Phe Val Pro Gly Ala Glu Tyr Phe Leu His Trp
            100                 105                 110

Gly Gln Gly Ile Leu Val Thr Val Ser Ser
        115                 120

<210> SEQ ID NO 315
<211> LENGTH: 30
<212> TYPE: DNA
<213> ORGANISM: Artificial Sequence
<220> FEATURE:
<223> OTHER INFORMATION: synthetic

<400> SEQUENCE: 315
ggtggctcca tcagtaatgg tggttactac                                  30

<210> SEQ ID NO 316
<211> LENGTH: 10
<212> TYPE: PRT
<213> ORGANISM: Artificial Sequence
<220> FEATURE:
<223> OTHER INFORMATION: synthetic

<400> SEQUENCE: 316

Gly Gly Ser Ile Ser Asn Gly Gly Tyr Tyr
1               5                   10

<210> SEQ ID NO 317
<211> LENGTH: 21
<212> TYPE: DNA
<213> ORGANISM: Artificial Sequence
<220> FEATURE:
<223> OTHER INFORMATION: synthetic

<400> SEQUENCE: 317
atctattata ttgggaacac a                                           21

<210> SEQ ID NO 318
<211> LENGTH: 7
<212> TYPE: PRT
<213> ORGANISM: Artificial Sequence
<220> FEATURE:
<223> OTHER INFORMATION: synthetic

<400> SEQUENCE: 318

Ile Tyr Tyr Ile Gly Asn Thr
1               5

<210> SEQ ID NO 319
<211> LENGTH: 42

-continued

```
<212> TYPE: DNA
<213> ORGANISM: Artificial Sequence
<220> FEATURE:
<223> OTHER INFORMATION: synthetic

<400> SEQUENCE: 319
gcgcgacagg agttcgtccc gggcgctgaa tatttcctac ac              42

<210> SEQ ID NO 320
<211> LENGTH: 14
<212> TYPE: PRT
<213> ORGANISM: Artificial Sequence
<220> FEATURE:
<223> OTHER INFORMATION: synthetic

<400> SEQUENCE: 320

Ala Arg Gln Glu Phe Val Pro Gly Ala Glu Tyr Phe Leu His
1               5                   10

<210> SEQ ID NO 321
<211> LENGTH: 324
<212> TYPE: DNA
<213> ORGANISM: Artificial Sequence
<220> FEATURE:
<223> OTHER INFORMATION: synthetic

<400> SEQUENCE: 321
gacatccgga tgacccagtc tccatcctcc ctgtctgcat ctgttggaga cagagtcacc      60
atcacctgcc gggcaagtca gaccgttaac acctttttaa attggtatca acagaaacca     120
gggaaagccc ctaaactcct gatctttggt gcgtccagtt tgcaaagtgg ggtcccatca     180
cggttcagtg gcagtggatc tgggacagat ttcactctca ccatcagcgg tctacagcct     240
gaagactttg caatttatta ctgtcagcag agttacagtg tccctccgat caccttcggc     300
caagggacac gactggagat tgaa                                             324

<210> SEQ ID NO 322
<211> LENGTH: 108
<212> TYPE: PRT
<213> ORGANISM: Artificial Sequence
<220> FEATURE:
<223> OTHER INFORMATION: synthetic

<400> SEQUENCE: 322

Asp Ile Arg Met Thr Gln Ser Pro Ser Ser Leu Ser Ala Ser Val Gly
1               5                   10                  15

Asp Arg Val Thr Ile Thr Cys Arg Ala Ser Gln Thr Val Asn Thr Phe
                20                  25                  30

Leu Asn Trp Tyr Gln Gln Lys Pro Gly Lys Ala Pro Lys Leu Leu Ile
            35                  40                  45

Phe Gly Ala Ser Ser Leu Gln Ser Gly Val Pro Ser Arg Phe Ser Gly
        50                  55                  60

Ser Gly Ser Gly Thr Asp Phe Thr Leu Thr Ile Ser Gly Leu Gln Pro
65                  70                  75                  80

Glu Asp Phe Ala Ile Tyr Tyr Cys Gln Gln Ser Tyr Ser Val Pro Pro
                85                  90                  95

Ile Thr Phe Gly Gln Gly Thr Arg Leu Glu Ile Glu
            100                 105

<210> SEQ ID NO 323
<211> LENGTH: 18
<212> TYPE: DNA
```

```
<213> ORGANISM: Artificial Sequence
<220> FEATURE:
<223> OTHER INFORMATION: synthetic

<400> SEQUENCE: 323
cagaccgtta acaccttt                                               18

<210> SEQ ID NO 324
<211> LENGTH: 6
<212> TYPE: PRT
<213> ORGANISM: Artificial Sequence
<220> FEATURE:
<223> OTHER INFORMATION: synthetic

<400> SEQUENCE: 324

Gln Thr Val Asn Thr Phe
1               5

<210> SEQ ID NO 325
<211> LENGTH: 9
<212> TYPE: DNA
<213> ORGANISM: Artificial Sequence
<220> FEATURE:
<223> OTHER INFORMATION: synthetic

<400> SEQUENCE: 325 ggtgcgtcc                                                          9

<210> SEQ ID NO 326
<211> LENGTH: 3
<212> TYPE: PRT
<213> ORGANISM: Artificial Sequence
<220> FEATURE:
<223> OTHER INFORMATION: synthetic

<400> SEQUENCE: 326

Gly Ala Ser
1

<210> SEQ ID NO 327
<211> LENGTH: 30
<212> TYPE: DNA
<213> ORGANISM: Artificial Sequence
<220> FEATURE:
<223> OTHER INFORMATION: synthetic

<400> SEQUENCE: 327
cagcagagtt acagtgtccc tccgatcacc                                  30

<210> SEQ ID NO 328
<211> LENGTH: 10
<212> TYPE: PRT
<213> ORGANISM: Artificial Sequence
<220> FEATURE:
<223> OTHER INFORMATION: synthetic

<400> SEQUENCE: 328

Gln Gln Ser Tyr Ser Val Pro Pro Ile Thr
1               5                   10

<210> SEQ ID NO 329
<211> LENGTH: 366
<212> TYPE: DNA
<213> ORGANISM: Artificial Sequence
<220> FEATURE:
<223> OTHER INFORMATION: synthetic
```

<400> SEQUENCE: 329

```
gaagtgcagc tggtggagtc tgggggaggc ttggtacagc ctggcaggtc cctgagactc    60
tcctgtgcag gcactggatt catctttgat gactatgcca tgcactgggt ccggcaagct   120
ccagggaagg gcctggagtg ggtctcaggt attagttgga acagtaatag tttaggctat   180
gcggactctg tgaagggccg attcaccatc tccagagaca acgccaagaa atccctgtat   240
ttgcaaatga gcagtctgag agctgaggac acggccttgt attactgtgt aaaagatgta   300
actagactgg aactacgagg atttcttgac tattggggcc agggaaccca ggtcaccgtc   360
tcttca                                                              366
```

<210> SEQ ID NO 330
<211> LENGTH: 122
<212> TYPE: PRT
<213> ORGANISM: Artificial Sequence
<220> FEATURE:
<223> OTHER INFORMATION: synthetic

<400> SEQUENCE: 330

```
Glu Val Gln Leu Val Glu Ser Gly Gly Gly Leu Val Gln Pro Gly Arg
1               5                   10                  15

Ser Leu Arg Leu Ser Cys Ala Gly Thr Gly Phe Ile Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Asn Ser Leu Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Ser Ser Leu Arg Ala Glu Asp Thr Ala Leu Tyr Tyr Cys
                85                  90                  95

Val Lys Asp Val Thr Arg Leu Glu Leu Arg Gly Phe Leu Asp Tyr Trp
            100                 105                 110

Gly Gln Gly Thr Gln Val Thr Val Ser Ser
        115                 120
```

<210> SEQ ID NO 331
<211> LENGTH: 24
<212> TYPE: DNA
<213> ORGANISM: Artificial Sequence
<220> FEATURE:
<223> OTHER INFORMATION: synthetic

<400> SEQUENCE: 331

```
ggattcatct ttgatgacta tgcc                                           24
```

<210> SEQ ID NO 332
<211> LENGTH: 8
<212> TYPE: PRT
<213> ORGANISM: Artificial Sequence
<220> FEATURE:
<223> OTHER INFORMATION: synthetic

<400> SEQUENCE: 332

```
Gly Phe Ile Phe Asp Asp Tyr Ala
1               5
```

<210> SEQ ID NO 333
<211> LENGTH: 24
<212> TYPE: DNA

```
<213> ORGANISM: Artificial Sequence
<220> FEATURE:
<223> OTHER INFORMATION: synthetic

<400> SEQUENCE: 333
attagttgga acagtaatag ttta                                            24

<210> SEQ ID NO 334
<211> LENGTH: 8
<212> TYPE: PRT
<213> ORGANISM: Artificial Sequence
<220> FEATURE:
<223> OTHER INFORMATION: synthetic

<400> SEQUENCE: 334

Ile Ser Trp Asn Ser Asn Ser Leu
1               5

<210> SEQ ID NO 335
<211> LENGTH: 45
<212> TYPE: DNA
<213> ORGANISM: Artificial Sequence
<220> FEATURE:
<223> OTHER INFORMATION: synthetic

<400> SEQUENCE: 335
gtaaaagatg taactagact ggaactacga ggatttcttg actat                     45

<210> SEQ ID NO 336
<211> LENGTH: 15
<212> TYPE: PRT
<213> ORGANISM: Artificial Sequence
<220> FEATURE:
<223> OTHER INFORMATION: synthetic

<400> SEQUENCE: 336

Val Lys Asp Val Thr Arg Leu Glu Leu Arg Gly Phe Leu Asp Tyr
1               5                   10                  15

<210> SEQ ID NO 337
<211> LENGTH: 321
<212> TYPE: DNA
<213> ORGANISM: Artificial Sequence
<220> FEATURE:
<223> OTHER INFORMATION: synthetic

<400> SEQUENCE: 337
gacatccaga tgacccagtc tccatcctcc ctgtctgcat ctgtgggaga cagagtcacc     60
atcacttgcc gggcaagtca ggacattaga aatgatttag gctggcatca gcagaaatca    120
gggaaagccc ctaagagcct gatctatgct gcatccagtt tgcaaagtgg ggccccatca    180
aggttcagcg gcagtggatc tgggacagaa ttcactctca caatcagcag cctgcagcct    240
gaagattctg caacttatta ctgtctacag caaaatagtt accctccgac gttcggccaa    300
gggaccaagg tggaaatcaa a                                              321

<210> SEQ ID NO 338
<211> LENGTH: 107
<212> TYPE: PRT
<213> ORGANISM: Artificial Sequence
<220> FEATURE:
<223> OTHER INFORMATION: synthetic

<400> SEQUENCE: 338

Asp Ile Gln Met Thr Gln Ser Pro Ser Ser Leu Ser Ala Ser Val Gly
```

```
            1               5                  10                  15
Asp Arg Val Thr Ile Thr Cys Arg Ala Ser Gln Asp Ile Arg Asn Asp
            20                  25                  30

Leu Gly Trp His Gln Gln Lys Ser Gly Lys Ala Pro Lys Ser Leu Ile
            35                  40                  45

Tyr Ala Ala Ser Ser Leu Gln Ser Gly Ala Pro Ser Arg Phe Ser Gly
            50                  55                  60

Ser Gly Ser Gly Thr Glu Phe Thr Leu Thr Ile Ser Ser Leu Gln Pro
65                      70                  75                  80

Glu Asp Ser Ala Thr Tyr Tyr Cys Leu Gln Gln Asn Ser Tyr Pro Pro
                85                  90                  95

Thr Phe Gly Gln Gly Thr Lys Val Glu Ile Lys
            100                 105
```

<210> SEQ ID NO 339
<211> LENGTH: 18
<212> TYPE: DNA
<213> ORGANISM: Artificial Sequence
<220> FEATURE:
<223> OTHER INFORMATION: synthetic

<400> SEQUENCE: 339
caggacatta gaaatgat                                                 18

<210> SEQ ID NO 340
<211> LENGTH: 6
<212> TYPE: PRT
<213> ORGANISM: Artificial Sequence
<220> FEATURE:
<223> OTHER INFORMATION: synthetic

<400> SEQUENCE: 340

Gln Asp Ile Arg Asn Asp
1               5

<210> SEQ ID NO 341
<211> LENGTH: 9
<212> TYPE: DNA
<213> ORGANISM: Artificial Sequence
<220> FEATURE:
<223> OTHER INFORMATION: synthetic

<400> SEQUENCE: 341 gctgcatcc                                                           9

<210> SEQ ID NO 342
<211> LENGTH: 3
<212> TYPE: PRT
<213> ORGANISM: Artificial Sequence
<220> FEATURE:
<223> OTHER INFORMATION: synthetic

<400> SEQUENCE: 342

Ala Ala Ser
1

<210> SEQ ID NO 343
<211> LENGTH: 27
<212> TYPE: DNA
<213> ORGANISM: Artificial Sequence
<220> FEATURE:
<223> OTHER INFORMATION: synthetic

<400> SEQUENCE: 343
ctacagcaaa atagttaccc tccgacg      27

<210> SEQ ID NO 344
<211> LENGTH: 9
<212> TYPE: PRT
<213> ORGANISM: Artificial Sequence
<220> FEATURE:
<223> OTHER INFORMATION: synthetic

<400> SEQUENCE: 344

Leu Gln Gln Asn Ser Tyr Pro Pro Thr
1               5

<210> SEQ ID NO 345
<211> LENGTH: 354
<212> TYPE: DNA
<213> ORGANISM: Artificial Sequence
<220> FEATURE:
<223> OTHER INFORMATION: synthetic

<400> SEQUENCE: 345
gatagacaga tggtggagtc tgggggaggc gtggtccagc ctgggaggtc cctgagactc      60
tcctgtatag cgtctggatt catcatcagt agatatggca tgcattgggt ccgccaggct     120
ccaggcaagg ggctggagtg ggtggcagtt atatggtatg atggaagaaa taaaaactat     180
gcagactccg tgaagggccg attcaccatc tccagagaca attccaagaa cacgttatat     240
ctggaaatga acagcctgag agccgaggac acggctgtgt attactgtgg gagagttcac     300
caatttgggg cttttgatat ctggggccaa gggacaatgg tcaccgtctc ttca           354

<210> SEQ ID NO 346
<211> LENGTH: 118
<212> TYPE: PRT
<213> ORGANISM: Artificial Sequence
<220> FEATURE:
<223> OTHER INFORMATION: synthetic

<400> SEQUENCE: 346

Asp Arg Gln Met Val Glu Ser Gly Gly Gly Val Val Gln Pro Gly Arg
1               5                   10                  15

Ser Leu Arg Leu Ser Cys Ile Ala Ser Gly Phe Ile Ile Ser Arg Tyr
            20                  25                  30

Gly Met His Trp Val Arg Gln Ala Pro Gly Lys Gly Leu Glu Trp Val
        35                  40                  45

Ala Val Ile Trp Tyr Asp Gly Arg Asn Lys Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ala Glu Asp Thr Ala Val Tyr Tyr Cys
                85                  90                  95

Gly Arg Val His Gln Phe Gly Ala Phe Asp Ile Trp Gly Gln Gly Thr
            100                 105                 110

Met Val Thr Val Ser Ser
        115

<210> SEQ ID NO 347
<211> LENGTH: 24
<212> TYPE: DNA
<213> ORGANISM: Artificial Sequence
<220> FEATURE:
<223> OTHER INFORMATION: synthetic

```
<400> SEQUENCE: 347
ggattcatca tcagtagata tggc                                              24

<210> SEQ ID NO 348
<211> LENGTH: 8
<212> TYPE: PRT
<213> ORGANISM: Artificial Sequence
<220> FEATURE:
<223> OTHER INFORMATION: synthetic

<400> SEQUENCE: 348

Gly Phe Ile Ile Ser Arg Tyr Gly
1               5

<210> SEQ ID NO 349
<211> LENGTH: 24
<212> TYPE: DNA
<213> ORGANISM: Artificial Sequence
<220> FEATURE:
<223> OTHER INFORMATION: synthetic

<400> SEQUENCE: 349
atatggtatg atggaagaaa taaa                                              24

<210> SEQ ID NO 350
<211> LENGTH: 8
<212> TYPE: PRT
<213> ORGANISM: Artificial Sequence
<220> FEATURE:
<223> OTHER INFORMATION: synthetic

<400> SEQUENCE: 350

Ile Trp Tyr Asp Gly Arg Asn Lys
1               5

<210> SEQ ID NO 351
<211> LENGTH: 33
<212> TYPE: DNA
<213> ORGANISM: Artificial Sequence
<220> FEATURE:
<223> OTHER INFORMATION: synthetic

<400> SEQUENCE: 351
gggagagttc accaatttgg ggcttttgat atc                                    33

<210> SEQ ID NO 352
<211> LENGTH: 11
<212> TYPE: PRT
<213> ORGANISM: Artificial Sequence
<220> FEATURE:
<223> OTHER INFORMATION: synthetic

<400> SEQUENCE: 352

Gly Arg Val His Gln Phe Gly Ala Phe Asp Ile
1               5                   10

<210> SEQ ID NO 353
<211> LENGTH: 324
<212> TYPE: DNA
<213> ORGANISM: Artificial Sequence
<220> FEATURE:
<223> OTHER INFORMATION: synthetic

<400> SEQUENCE: 353
gaaattgtgt tgacgcagtc tccagacacc ctgtctttgt ctccagggga aagagccacc       60
```

```
ctctcctgca gggccagtca gagtgttagc agcagcttct tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag caatatggta ggtcaccttg gacgttcggc    300
caagggacca aggtggcaat caaa                                           324
```

<210> SEQ ID NO 354
<211> LENGTH: 108
<212> TYPE: PRT
<213> ORGANISM: Artificial Sequence
<220> FEATURE:
<223> OTHER INFORMATION: synthetic

<400> SEQUENCE: 354

```
Glu Ile Val Leu Thr Gln Ser Pro Asp Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Pro
                85                  90                  95

Trp Thr Phe Gly Gln Gly Thr Lys Val Ala Ile Lys
            100                 105
```

<210> SEQ ID NO 355
<211> LENGTH: 21
<212> TYPE: DNA
<213> ORGANISM: Artificial Sequence
<220> FEATURE:
<223> OTHER INFORMATION: synthetic

<400> SEQUENCE: 355

```
cagagtgtta gcagcagctt c                                               21
```

<210> SEQ ID NO 356
<211> LENGTH: 7
<212> TYPE: PRT
<213> ORGANISM: Artificial Sequence
<220> FEATURE:
<223> OTHER INFORMATION: synthetic

<400> SEQUENCE: 356

```
Gln Ser Val Ser Ser Ser Phe
1               5
```

<210> SEQ ID NO 357
<211> LENGTH: 9
<212> TYPE: DNA
<213> ORGANISM: Artificial Sequence
<220> FEATURE:
<223> OTHER INFORMATION: synthetic

<400> SEQUENCE: 357

```
ggtgcatcc                                                              9
```

<210> SEQ ID NO 358
<211> LENGTH: 3
<212> TYPE: PRT
<213> ORGANISM: Artificial Sequence
<220> FEATURE:
<223> OTHER INFORMATION: synthetic

<400> SEQUENCE: 358

Gly Ala Ser
1

<210> SEQ ID NO 359
<211> LENGTH: 27
<212> TYPE: DNA
<213> ORGANISM: Artificial Sequence
<220> FEATURE:
<223> OTHER INFORMATION: synthetic

<400> SEQUENCE: 359
cagcaatatg gtaggtcacc ttggacg                                        27

<210> SEQ ID NO 360
<211> LENGTH: 9
<212> TYPE: PRT
<213> ORGANISM: Artificial Sequence
<220> FEATURE:
<223> OTHER INFORMATION: synthetic

<400> SEQUENCE: 360

Gln Gln Tyr Gly Arg Ser Pro Trp Thr
1               5

<210> SEQ ID NO 361
<211> LENGTH: 363
<212> TYPE: DNA
<213> ORGANISM: Artificial Sequence
<220> FEATURE:
<223> OTHER INFORMATION: synthetic

<400> SEQUENCE: 361
caggtgcagc tgcaggagtc gggcccagga ctggtgaagc cttcacagac cctgtccctc     60
acctgcactg tttccggtgg ctccatcaac aatggtggtc actactggac ctggatccgg    120
caacacccag ggaagggcct agaatggatt gggtacattt attatattgg gaccacttat    180 acaatccgt ccctcgagag tcgactttcc ctatcagtgg acacgtctaa gaatcagttc     240
tccctgaagc tgagctctgt gactgccgcg gacacggcca tttattactg tgcgagaagc    300
agtttatcag tgtctgaggc ttttgatgtc tggggccaag ggacaatggt caccgtctct    360
tca                                                                 363

<210> SEQ ID NO 362
<211> LENGTH: 121
<212> TYPE: PRT
<213> ORGANISM: Artificial Sequence
<220> FEATURE:
<223> OTHER INFORMATION: synthetic

<400> SEQUENCE: 362

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Asn Gly
            20                  25                  30

Gly His Tyr Trp Thr Trp Ile Arg Gln His Pro Gly Lys Gly Leu Glu

```
                    35                  40                  45
Trp Ile Gly Tyr Ile Tyr Tyr Ile Gly Thr Thr Tyr Tyr Asn Pro Ser
         50                  55                  60

Leu Glu Ser Arg Leu Ser Leu Ser Val Asp Thr Ser Lys Asn Gln Phe
 65                  70                  75                  80

Ser Leu Lys Leu Ser Ser Val Thr Ala Ala Asp Thr Ala Ile Tyr Tyr
                 85                  90                  95

Cys Ala Arg Ser Ser Leu Ser Val Ser Glu Ala Phe Asp Val Trp Gly
            100                 105                 110

Gln Gly Thr Met Val Thr Val Ser Ser
        115                 120
```

<210> SEQ ID NO 363
<211> LENGTH: 30
<212> TYPE: DNA
<213> ORGANISM: Artificial Sequence
<220> FEATURE:
<223> OTHER INFORMATION: synthetic

<400> SEQUENCE: 363
ggtggctcca tcaacaatgg tggtcactac                                      30

<210> SEQ ID NO 364
<211> LENGTH: 10
<212> TYPE: PRT
<213> ORGANISM: Artificial Sequence
<220> FEATURE:
<223> OTHER INFORMATION: synthetic

<400> SEQUENCE: 364

```
Gly Gly Ser Ile Asn Asn Gly Gly His Tyr
 1               5                  10
```

<210> SEQ ID NO 365
<211> LENGTH: 21
<212> TYPE: DNA
<213> ORGANISM: Artificial Sequence
<220> FEATURE:
<223> OTHER INFORMATION: synthetic

<400> SEQUENCE: 365
atttattata ttgggaccac t                                               21

<210> SEQ ID NO 366
<211> LENGTH: 7
<212> TYPE: PRT
<213> ORGANISM: Artificial Sequence
<220> FEATURE:
<223> OTHER INFORMATION: synthetic

<400> SEQUENCE: 366

```
Ile Tyr Tyr Ile Gly Thr Thr
 1               5
```

<210> SEQ ID NO 367
<211> LENGTH: 39
<212> TYPE: DNA
<213> ORGANISM: Artificial Sequence
<220> FEATURE:
<223> OTHER INFORMATION: synthetic

<400> SEQUENCE: 367
gcgagaagca gtttatcagt gtctgaggct tttgatgtc                            39

```
<210> SEQ ID NO 368
<211> LENGTH: 13
<212> TYPE: PRT
<213> ORGANISM: Artificial Sequence
<220> FEATURE:
<223> OTHER INFORMATION: synthetic

<400> SEQUENCE: 368

Ala Arg Ser Ser Leu Ser Val Ser Glu Ala Phe Asp Val
1               5                   10

<210> SEQ ID NO 369
<211> LENGTH: 324
<212> TYPE: DNA
<213> ORGANISM: Artificial Sequence
<220> FEATURE:
<223> OTHER INFORMATION: synthetic

<400> SEQUENCE: 369
gacatccaga tgacccagtc tccatcctcc ctgtctgcat ctgtaggaga cagaatcacc      60
atcacttgcc gggggagtca gaacattggc agcttttta gttggtatca acagagacca     120
gggaaggccc ctaaactcct aatctttggt gcatacaatt tgcaaggtgg ggtcccatca     180
aggttcagtg gcagtggatc cgggacagat ttcactctca ccatcagtag tctgcaacct     240
gaagattttg caacttactt ctgtcagcag agttatagta cccctccgat caccttcggc     300
caagggacac gactggagat taaa                                            324

<210> SEQ ID NO 370
<211> LENGTH: 108
<212> TYPE: PRT
<213> ORGANISM: Artificial Sequence
<220> FEATURE:
<223> OTHER INFORMATION: synthetic

<400> SEQUENCE: 370

Asp Ile Gln Met Thr Gln Ser Pro Ser Ser Leu Ser Ala Ser Val Gly
1               5                   10                  15

Asp Arg Ile Thr Ile Thr Cys Arg Gly Ser Gln Asn Ile Gly Ser Phe
            20                  25                  30

Leu Ser Trp Tyr Gln Gln Arg Pro Gly Lys Ala Pro Lys Leu Leu Ile
        35                  40                  45

Phe Gly Ala Tyr Asn Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 371
<211> LENGTH: 18
<212> TYPE: DNA
<213> ORGANISM: Artificial Sequence
<220> FEATURE:
<223> OTHER INFORMATION: synthetic

<400> SEQUENCE: 371
cagaacattg gcagcttt                                                    18
```

<210> SEQ ID NO 372
<211> LENGTH: 6
<212> TYPE: PRT
<213> ORGANISM: Artificial Sequence
<220> FEATURE:
<223> OTHER INFORMATION: synthetic

<400> SEQUENCE: 372

Gln Asn Ile Gly Ser Phe
1               5

<210> SEQ ID NO 373
<211> LENGTH: 9
<212> TYPE: DNA
<213> ORGANISM: Artificial Sequence
<220> FEATURE:
<223> OTHER INFORMATION: synthetic

<400> SEQUENCE: 373 ggtgcatac                                                                9

<210> SEQ ID NO 374
<211> LENGTH: 3
<212> TYPE: PRT
<213> ORGANISM: Artificial Sequence
<220> FEATURE:
<223> OTHER INFORMATION: synthetic

<400> SEQUENCE: 374

Gly Ala Tyr
1

<210> SEQ ID NO 375
<211> LENGTH: 30
<212> TYPE: DNA
<213> ORGANISM: Artificial Sequence
<220> FEATURE:
<223> OTHER INFORMATION: synthetic

<400> SEQUENCE: 375
cagcagagtt atagtacccc tccgatcacc                                         30

<210> SEQ ID NO 376
<211> LENGTH: 10
<212> TYPE: PRT
<213> ORGANISM: Artificial Sequence
<220> FEATURE:
<223> OTHER INFORMATION: synthetic

<400> SEQUENCE: 376

Gln Gln Ser Tyr Ser Thr Pro Pro Ile Thr
1               5                   10

<210> SEQ ID NO 377
<211> LENGTH: 363
<212> TYPE: DNA
<213> ORGANISM: Artificial Sequence
<220> FEATURE:
<223> OTHER INFORMATION: synthetic

<400> SEQUENCE: 377
caggtgcagc tgcaggagtc gggcccagga ctggtgaggc cttcacagac cctgtccctc        60
acctgcactg tctctggtgg ctccatcagc aatggtggtt actattggac ctggatccgc       120
caaaacccag ggaagggcct agaatggatt ggatacatct attacattgg gaccacctac       180
tacaacccgt ccctcgagag tcgactttcc ctatcagtag acacgtctaa gaaccagttc       240

-continued

```
tccctgaagc tgacctctgt gactgccgcg gacacggccg tttattactg tgcgagaagc      300
agtttagcag tgtctgaggc ttttgatatc tggggccaag ggacaatggt caccgtctct      360
tca                                                                    363
```

<210> SEQ ID NO 378
<211> LENGTH: 121
<212> TYPE: PRT
<213> ORGANISM: Artificial Sequence
<220> FEATURE:
<223> OTHER INFORMATION: synthetic

<400> SEQUENCE: 378

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Gly Ser Ile Ser Asn Gly
            20                  25                  30

Gly Tyr Tyr Trp Thr Trp Ile Arg Gln Asn Pro Gly Lys Gly Leu Glu
        35                  40                  45

Trp Ile Gly Tyr Ile Tyr Tyr Ile Gly Thr Thr Tyr Tyr Asn Pro Ser
    50                  55                  60

Leu Glu Ser Arg Leu Ser Leu Ser Val Asp Thr Ser Lys Asn Gln Phe
65                  70                  75                  80

Ser Leu Lys Leu Thr Ser Val Thr Ala Ala Asp Thr Ala Val Tyr Tyr
                85                  90                  95

Cys Ala Arg Ser Ser Leu Ala Val Ser Glu Ala Phe Asp Ile Trp Gly
            100                 105                 110

Gln Gly Thr Met Val Thr Val Ser Ser
        115                 120
```

<210> SEQ ID NO 379
<211> LENGTH: 30
<212> TYPE: DNA
<213> ORGANISM: Artificial Sequence
<220> FEATURE:
<223> OTHER INFORMATION: synthetic

<400> SEQUENCE: 379

```
ggtggctcca tcagcaatgg tggttactat                                        30
```

<210> SEQ ID NO 380
<211> LENGTH: 10
<212> TYPE: PRT
<213> ORGANISM: Artificial Sequence
<220> FEATURE:
<223> OTHER INFORMATION: synthetic

<400> SEQUENCE: 380

```
Gly Gly Ser Ile Ser Asn Gly Gly Tyr Tyr
1               5                   10
```

<210> SEQ ID NO 381
<211> LENGTH: 21
<212> TYPE: DNA
<213> ORGANISM: Artificial Sequence
<220> FEATURE:
<223> OTHER INFORMATION: synthetic

<400> SEQUENCE: 381

```
atctattaca ttgggaccac c                                                 21
```

```
<210> SEQ ID NO 382
<211> LENGTH: 7
<212> TYPE: PRT
<213> ORGANISM: Artificial Sequence
<220> FEATURE:
<223> OTHER INFORMATION: synthetic

<400> SEQUENCE: 382

Ile Tyr Tyr Ile Gly Thr Thr
1               5

<210> SEQ ID NO 383
<211> LENGTH: 39
<212> TYPE: DNA
<213> ORGANISM: Artificial Sequence
<220> FEATURE:
<223> OTHER INFORMATION: synthetic

<400> SEQUENCE: 383
gcgagaagca gtttagcagt gtctgaggct tttgatatc                            39

<210> SEQ ID NO 384
<211> LENGTH: 13
<212> TYPE: PRT
<213> ORGANISM: Artificial Sequence
<220> FEATURE:
<223> OTHER INFORMATION: synthetic

<400> SEQUENCE: 384

Ala Arg Ser Ser Leu Ala Val Ser Glu Ala Phe Asp Ile
1               5                   10

<210> SEQ ID NO 385
<211> LENGTH: 324
<212> TYPE: DNA
<213> ORGANISM: Artificial Sequence
<220> FEATURE:
<223> OTHER INFORMATION: synthetic

<400> SEQUENCE: 385
gacatccaga tgacccagtc tccatcctcc ctgtctgcat ctgtaggcga cagattcacc      60
atcacttgcc gggcgagtca gagcattggc agcttttta gttggtatca gcagaaacca     120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacaata cccctccgat caccttcggc    300
caagggacac gactggagat taaa                                           324

<210> SEQ ID NO 386
<211> LENGTH: 108
<212> TYPE: PRT
<213> ORGANISM: Artificial Sequence
<220> FEATURE:
<223> OTHER INFORMATION: synthetic

<400> SEQUENCE: 386

Asp Ile Gln Met Thr Gln Ser Pro Ser Ser Leu Ser Ala Ser Val Gly
1               5                   10                  15

Asp Arg Phe Thr Ile Thr Cys Arg Ala Ser Gln Ser Ile Gly Ser Phe
            20                  25                  30

Leu Ser Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
```

```
                50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Asn Thr Pro Pro
                 85                  90                  95

Ile Thr Phe Gly Gln Gly Thr Arg Leu Glu Ile Lys
            100                 105
```

<210> SEQ ID NO 387
<211> LENGTH: 18
<212> TYPE: DNA
<213> ORGANISM: Artificial Sequence
<220> FEATURE:
<223> OTHER INFORMATION: synthetic

<400> SEQUENCE: 387
cagagcattg gcagcttt                                           18

<210> SEQ ID NO 388
<211> LENGTH: 6
<212> TYPE: PRT
<213> ORGANISM: Artificial Sequence
<220> FEATURE:
<223> OTHER INFORMATION: synthetic

<400> SEQUENCE: 388

```
Gln Ser Ile Gly Ser Phe
 1               5
```

<210> SEQ ID NO 389
<211> LENGTH: 9
<212> TYPE: DNA
<213> ORGANISM: Artificial Sequence
<220> FEATURE:
<223> OTHER INFORMATION: synthetic

<400> SEQUENCE: 389 gctgcatcc                                                      9

<210> SEQ ID NO 390
<211> LENGTH: 3
<212> TYPE: PRT
<213> ORGANISM: Artificial Sequence
<220> FEATURE:
<223> OTHER INFORMATION: synthetic

<400> SEQUENCE: 390

```
Ala Ala Ser
 1
```

<210> SEQ ID NO 391
<211> LENGTH: 30
<212> TYPE: DNA
<213> ORGANISM: Artificial Sequence
<220> FEATURE:
<223> OTHER INFORMATION: synthetic

<400> SEQUENCE: 391
caacagagtt acaataccccc tccgatcacc                             30

<210> SEQ ID NO 392
<211> LENGTH: 10
<212> TYPE: PRT
<213> ORGANISM: Artificial Sequence
<220> FEATURE:

<223> OTHER INFORMATION: synthetic

<400> SEQUENCE: 392

Gln Gln Ser Tyr Asn Thr Pro Pro Ile Thr
1               5                   10

<210> SEQ ID NO 393
<211> LENGTH: 363
<212> TYPE: DNA
<213> ORGANISM: Artificial Sequence
<220> FEATURE:
<223> OTHER INFORMATION: synthetic

<400> SEQUENCE: 393
caggtgcagc tggtgcaatc tgggactgag gtgaagaggc ctggggcctc agtgaaggtc      60
tcctgcaagg cttctggatt caccttcacc ggctattata tatactgggt gcgacaggcc     120
cctggagagg ggcttgagtg gatggggtgg atcaaccctc acagtggtgg cacaaaatac     180
gcacagaagt tcagggcag ggtcaccctg accaggaca cgtccatcaa tacagcctac       240
ctggacctga tcagtctgcg atctgacgac acggccgtat attactgtgc gagaatcggg     300
ggtgggggct actcttccta ctttgactac tggggccagg gaaccctggt caccgtctcc     360
tca                                                                  363

<210> SEQ ID NO 394
<211> LENGTH: 121
<212> TYPE: PRT
<213> ORGANISM: Artificial Sequence
<220> FEATURE:
<223> OTHER INFORMATION: synthetic

<400> SEQUENCE: 394

Gln Val Gln Leu Val Gln Ser Gly Thr Glu Val Lys Arg Pro Gly Ala
1               5                   10                  15

Ser Val Lys Val Ser Cys Lys Ala Ser Gly Phe Thr Phe Thr Gly Tyr
            20                  25                  30

Tyr Ile Tyr Trp Val Arg Gln Ala Pro Gly Glu Gly Leu Glu Trp Met
        35                  40                  45

Gly Trp Ile Asn Pro His Ser Gly Gly Thr Lys Tyr Ala Gln Lys Phe
    50                  55                  60

Gln Gly Arg Val Thr Leu Thr Arg Asp Thr Ser Ile Asn Thr Ala Tyr
65                  70                  75                  80

Leu Asp Leu Ile Ser Leu Arg Ser Asp Asp Thr Ala Val Tyr Tyr Cys
                85                  90                  95

Ala Arg Ile Gly Gly Gly Tyr Ser Ser Tyr Phe Asp Tyr Trp Gly
            100                 105                 110

Gln Gly Thr Leu Val Thr Val Ser Ser
        115                 120

<210> SEQ ID NO 395
<211> LENGTH: 24
<212> TYPE: DNA
<213> ORGANISM: Artificial Sequence
<220> FEATURE:
<223> OTHER INFORMATION: synthetic

<400> SEQUENCE: 395
ggattcacct tcaccggcta ttat                                            24

<210> SEQ ID NO 396

```
<211> LENGTH: 8
<212> TYPE: PRT
<213> ORGANISM: Artificial Sequence
<220> FEATURE:
<223> OTHER INFORMATION: synthetic

<400> SEQUENCE: 396

Gly Phe Thr Phe Thr Gly Tyr Tyr
1               5

<210> SEQ ID NO 397
<211> LENGTH: 24
<212> TYPE: DNA
<213> ORGANISM: Artificial Sequence
<220> FEATURE:
<223> OTHER INFORMATION: synthetic

<400> SEQUENCE: 397
atcaaccctc acagtggtgg caca                                              24

<210> SEQ ID NO 398
<211> LENGTH: 8
<212> TYPE: PRT
<213> ORGANISM: Artificial Sequence
<220> FEATURE:
<223> OTHER INFORMATION: synthetic

<400> SEQUENCE: 398

Ile Asn Pro His Ser Gly Gly Thr
1               5

<210> SEQ ID NO 399
<211> LENGTH: 42
<212> TYPE: DNA
<213> ORGANISM: Artificial Sequence
<220> FEATURE:
<223> OTHER INFORMATION: synthetic

<400> SEQUENCE: 399
gcgagaatcg ggggtggggg ctactcttcc tactttgact ac                          42

<210> SEQ ID NO 400
<211> LENGTH: 14
<212> TYPE: PRT
<213> ORGANISM: Artificial Sequence
<220> FEATURE:
<223> OTHER INFORMATION: synthetic

<400> SEQUENCE: 400

Ala Arg Ile Gly Gly Gly Gly Tyr Ser Ser Tyr Phe Asp Tyr
1               5                   10

<210> SEQ ID NO 401
<211> LENGTH: 324
<212> TYPE: DNA
<213> ORGANISM: Artificial Sequence
<220> FEATURE:
<223> OTHER INFORMATION: synthetic

<400> SEQUENCE: 401
gacatccaac tgacccagtc tccatcttcc ctgtctgcat ctgtaggaga cagagtcacc        60
atcacttgcc gggcaagtca gactattagt acctatttaa attggtatca gcagaaacca       120
gggaatgccc ctaaactcct gatctatgct gcatccagtt tgcaaagtgg ggtcccatca       180
aggttcagtg gcagaggatc tgggacagat ttcactctca ccatcagcag tctccaacct       240
```

```
gaagattttg ccacttacta ctgtcaacag ggttacacta ccccctccgat caccttcggc    300 caagggacac gactggagat taaa                                            324
```

<210> SEQ ID NO 402
<211> LENGTH: 108
<212> TYPE: PRT
<213> ORGANISM: Artificial Sequence
<220> FEATURE:
<223> OTHER INFORMATION: synthetic

<400> SEQUENCE: 402

```
Asp Ile Gln Leu Thr Gln Ser Pro Ser Leu Ser Ala Ser Val Gly
1               5                   10                  15

Asp Arg Val Thr Ile Thr Cys Arg Ala Ser Gln Thr Ile Ser Thr Tyr
            20                  25                  30

Leu Asn Trp Tyr Gln Gln Lys Pro Gly Asn Ala Pro Lys Leu Leu Ile
        35                  40                  45

Tyr Ala Ala Ser Ser Leu Gln Ser Gly Val Pro Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Thr Pro Pro
                85                  90                  95

Ile Thr Phe Gly Gln Gly Thr Arg Leu Glu Ile Lys
            100                 105
```

<210> SEQ ID NO 403
<211> LENGTH: 18
<212> TYPE: DNA
<213> ORGANISM: Artificial Sequence
<220> FEATURE:
<223> OTHER INFORMATION: synthetic

<400> SEQUENCE: 403

```
cagactatta gtacctat                                                   18
```

<210> SEQ ID NO 404
<211> LENGTH: 6
<212> TYPE: PRT
<213> ORGANISM: Artificial Sequence
<220> FEATURE:
<223> OTHER INFORMATION: synthetic

<400> SEQUENCE: 404

```
Gln Thr Ile Ser Thr Tyr
1               5
```

<210> SEQ ID NO 405
<211> LENGTH: 9
<212> TYPE: DNA
<213> ORGANISM: Artificial Sequence
<220> FEATURE:
<223> OTHER INFORMATION: synthetic

<400> SEQUENCE: 405

```
gctgcatcc                                                             9
```

<210> SEQ ID NO 406
<211> LENGTH: 3
<212> TYPE: PRT
<213> ORGANISM: Artificial Sequence
<220> FEATURE:
<223> OTHER INFORMATION: synthetic

<400> SEQUENCE: 406

Ala Ala Ser
1

<210> SEQ ID NO 407
<211> LENGTH: 30
<212> TYPE: DNA
<213> ORGANISM: Artificial Sequence
<220> FEATURE:
<223> OTHER INFORMATION: synthetic

<400> SEQUENCE: 407
caacagggtt acactacccc tccgatcacc                                      30

<210> SEQ ID NO 408
<211> LENGTH: 10
<212> TYPE: PRT
<213> ORGANISM: Artificial Sequence
<220> FEATURE:
<223> OTHER INFORMATION: synthetic

<400> SEQUENCE: 408

Gln Gln Gly Tyr Thr Thr Pro Pro Ile Thr
1               5                   10

<210> SEQ ID NO 409
<211> LENGTH: 363
<212> TYPE: DNA
<213> ORGANISM: Artificial Sequence
<220> FEATURE:
<223> OTHER INFORMATION: synthetic

<400> SEQUENCE: 409
gaggtgcagc tgttggaatc tgggggaggc ttggtacagc ctggggggtc cctgagactc     60
tcctgtgcag cctctggatt cacctttagc agctatgcca tgagctgggt ccgccaggct    120
ccagggaagg ggctggagtg ggtctcagat attagtggta gtggtcttag cacatactac    180
gcagactccg tgaagggccg gttcgccatc tccagagaca attccaagaa catgttgtat    240
ctgcaaatga acaggctgag agccgaggac acggccgtct attactgtgc gaaagagccc    300
tctcactgga acggtgaagc gtttgatatt tggggccaag ggacaatggt caccgtctct    360
tca                                                                  363

<210> SEQ ID NO 410
<211> LENGTH: 121
<212> TYPE: PRT
<213> ORGANISM: Artificial Sequence
<220> FEATURE:
<223> OTHER INFORMATION: synthetic

<400> SEQUENCE: 410

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Ser Gly Ser Gly Leu Ser Thr Tyr Tyr Ala Asp Ser Val
    50                  55                  60

Lys Gly Arg Phe Ala Ile Ser Arg Asp Asn Ser Lys Asn Met Leu Tyr
65                  70                  75                  80

Leu Gln Met Asn Arg Leu Arg Ala Glu Asp Thr Ala Val Tyr Tyr Cys
            85                  90                  95

Ala Lys Glu Pro Ser His Trp Asn Gly Glu Ala Phe Asp Ile Trp Gly
            100                 105                 110

Gln Gly Thr Met Val Thr Val Ser Ser
        115                 120

<210> SEQ ID NO 411
<211> LENGTH: 24
<212> TYPE: DNA
<213> ORGANISM: Artificial Sequence
<220> FEATURE:
<223> OTHER INFORMATION: synthetic

<400> SEQUENCE: 411
ggattcacct ttagcagcta tgcc                                        24

<210> SEQ ID NO 412
<211> LENGTH: 8
<212> TYPE: PRT
<213> ORGANISM: Artificial Sequence
<220> FEATURE:
<223> OTHER INFORMATION: synthetic

<400> SEQUENCE: 412

Gly Phe Thr Phe Ser Ser Tyr Ala
1               5

<210> SEQ ID NO 413
<211> LENGTH: 24
<212> TYPE: DNA
<213> ORGANISM: Artificial Sequence
<220> FEATURE:
<223> OTHER INFORMATION: synthetic

<400> SEQUENCE: 413
attagtggta gtggtcttag caca                                        24

<210> SEQ ID NO 414
<211> LENGTH: 8
<212> TYPE: PRT
<213> ORGANISM: Artificial Sequence
<220> FEATURE:
<223> OTHER INFORMATION: synthetic

<400> SEQUENCE: 414

Ile Ser Gly Ser Gly Leu Ser Thr
1               5

<210> SEQ ID NO 415
<211> LENGTH: 42
<212> TYPE: DNA
<213> ORGANISM: Artificial Sequence
<220> FEATURE:
<223> OTHER INFORMATION: synthetic

<400> SEQUENCE: 415
gcgaaagagc cctctcactg gaacggtgaa gcgtttgata tt                    42

<210> SEQ ID NO 416
<211> LENGTH: 14
<212> TYPE: PRT
<213> ORGANISM: Artificial Sequence
<220> FEATURE:
<223> OTHER INFORMATION: synthetic

<400> SEQUENCE: 416

Ala Lys Glu Pro Ser His Trp Asn Gly Glu Ala Phe Asp Ile
1               5                   10

<210> SEQ ID NO 417
<211> LENGTH: 321
<212> TYPE: DNA
<213> ORGANISM: Artificial Sequence
<220> FEATURE:
<223> OTHER INFORMATION: synthetic

<400> SEQUENCE: 417
gacatccaga tgacccagtc tccatcttcc gtgtctgcat ctgtaggaga cagagtcacc      60
atcacttgtc gggcgagtca ggatattagc agttggttag cctggtatca gcagaaacca     120
gggaaagccc ctaaactcct gatctatact acagccaatt tacaaagtgg ggtcccatcc     180
aggttcagcg gcagtggatc tgggacagat ttcactctca ccatcagcag cctgcagtct     240
gaagattttg caacttacta ttgtcaacag gctaacagtt tcccattcac tttcggctct     300
gggaccaaag tggatatcaa a                                                321

<210> SEQ ID NO 418
<211> LENGTH: 107
<212> TYPE: PRT
<213> ORGANISM: Artificial Sequence
<220> FEATURE:
<223> OTHER INFORMATION: synthetic

<400> SEQUENCE: 418

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Gln Lys Pro Gly Lys Ala Pro Lys Leu Leu Ile
        35                  40                  45

Tyr Thr Thr Ala Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Thr Tyr Tyr Cys Gln Gln Ala Asn Ser Phe Pro Phe
                85                  90                  95

Thr Phe Gly Ser Gly Thr Lys Val Asp Ile Lys
            100                 105

<210> SEQ ID NO 419
<211> LENGTH: 18
<212> TYPE: DNA
<213> ORGANISM: Artificial Sequence
<220> FEATURE:
<223> OTHER INFORMATION: synthetic

<400> SEQUENCE: 419
caggatatta gcagttgg                                                    18

<210> SEQ ID NO 420
<211> LENGTH: 6
<212> TYPE: PRT
<213> ORGANISM: Artificial Sequence
<220> FEATURE:
<223> OTHER INFORMATION: synthetic

<400> SEQUENCE: 420

Gln Asp Ile Ser Ser Trp
1               5

<210> SEQ ID NO 421
<211> LENGTH: 9
<212> TYPE: DNA
<213> ORGANISM: Artificial Sequence
<220> FEATURE:
<223> OTHER INFORMATION: synthetic

<400> SEQUENCE: 421 actacagcc                                                          9

<210> SEQ ID NO 422
<211> LENGTH: 3
<212> TYPE: PRT
<213> ORGANISM: Artificial Sequence
<220> FEATURE:
<223> OTHER INFORMATION: synthetic

<400> SEQUENCE: 422

Thr Thr Ala
1

<210> SEQ ID NO 423
<211> LENGTH: 27
<212> TYPE: DNA
<213> ORGANISM: Artificial Sequence
<220> FEATURE:
<223> OTHER INFORMATION: synthetic

<400> SEQUENCE: 423
caacaggcta acagtttccc attcact                                     27

<210> SEQ ID NO 424
<211> LENGTH: 9
<212> TYPE: PRT
<213> ORGANISM: Artificial Sequence
<220> FEATURE:
<223> OTHER INFORMATION: synthetic

<400> SEQUENCE: 424

Gln Gln Ala Asn Ser Phe Pro Phe Thr
1               5

<210> SEQ ID NO 425
<211> LENGTH: 366
<212> TYPE: DNA
<213> ORGANISM: Artificial Sequence
<220> FEATURE:
<223> OTHER INFORMATION: synthetic

<400> SEQUENCE: 425
cagctgcaac tgcaggagtc gggcccagga ctggtgaagc cttcggagac cctgtccttc    60
acctgcactg tctctggtgg ctccatcagt agtaattatt actactgggg ctgggtccgc   120
cagtccccgg ggaagggact ggagtggatc gggagtatct atcacactgg gaacgcctac   180
gacaatccgt ccctcaagag tcgagtcacc atttccgtag acacgtccaa gaatcagttc   240
tccctgaacc tgaactctgt gaccgccgca gacacggcta tttattattg tgcgagacat   300
catagcagtt cgtcctggtg gtacttcgat gtctggggcc gtggcaccct ggtcattgtc   360
tcctca                                                             366

<210> SEQ ID NO 426
<211> LENGTH: 122
<212> TYPE: PRT
<213> ORGANISM: Artificial Sequence
<220> FEATURE:
<223> OTHER INFORMATION: synthetic

<400> SEQUENCE: 426

Gln Leu Gln Leu Gln Glu Ser Gly Pro Gly Leu Val Lys Pro Ser Glu
1               5                   10                  15
Thr Leu Ser Phe Thr Cys Thr Val Ser Gly Gly Ser Ile Ser Ser Asn
            20                  25                  30
Tyr Tyr Tyr Trp Gly Trp Val Arg Gln Ser Pro Gly Lys Gly Leu Glu
        35                  40                  45
Trp Ile Gly Ser Ile Tyr His Thr Gly Asn Ala Tyr Asp Asn Pro Ser
    50                  55                  60
Leu Lys Ser Arg Val Thr Ile Ser Val Asp Thr Ser Lys Asn Gln Phe
65                  70                  75                  80
Ser Leu Asn Leu Asn Ser Val Thr Ala Ala Asp Thr Ala Ile Tyr Tyr
                85                  90                  95
Cys Ala Arg His His Ser Ser Ser Trp Tyr Phe Asp Val Trp
            100                 105                 110
Gly Arg Gly Thr Leu Val Ile Val Ser Ser
        115                 120

<210> SEQ ID NO 427
<211> LENGTH: 30
<212> TYPE: DNA
<213> ORGANISM: Artificial Sequence
<220> FEATURE:
<223> OTHER INFORMATION: synthetic

<400> SEQUENCE: 427
ggtggctcca tcagtagtaa ttattactac                                    30

<210> SEQ ID NO 428
<211> LENGTH: 10
<212> TYPE: PRT
<213> ORGANISM: Artificial Sequence
<220> FEATURE:
<223> OTHER INFORMATION: synthetic

<400> SEQUENCE: 428

Gly Gly Ser Ile Ser Ser Asn Tyr Tyr Tyr
1               5                   10

<210> SEQ ID NO 429
<211> LENGTH: 21
<212> TYPE: DNA
<213> ORGANISM: Artificial Sequence
<220> FEATURE:
<223> OTHER INFORMATION: synthetic

<400> SEQUENCE: 429
atctatcaca ctgggaacgc c                                             21

<210> SEQ ID NO 430
<211> LENGTH: 7
<212> TYPE: PRT
<213> ORGANISM: Artificial Sequence
<220> FEATURE:
<223> OTHER INFORMATION: synthetic

```
<400> SEQUENCE: 430

Ile Tyr His Thr Gly Asn Ala
1               5

<210> SEQ ID NO 431
<211> LENGTH: 42
<212> TYPE: DNA
<213> ORGANISM: Artificial Sequence
<220> FEATURE:
<223> OTHER INFORMATION: synthetic

<400> SEQUENCE: 431
gcgagacatc atagcagttc gtcctggtgg tacttcgatg tc                          42

<210> SEQ ID NO 432
<211> LENGTH: 14
<212> TYPE: PRT
<213> ORGANISM: Artificial Sequence
<220> FEATURE:
<223> OTHER INFORMATION: synthetic

<400> SEQUENCE: 432

Ala Arg His His Ser Ser Ser Ser Trp Trp Tyr Phe Asp Val
1               5                   10

<210> SEQ ID NO 433
<211> LENGTH: 324
<212> TYPE: DNA
<213> ORGANISM: Artificial Sequence
<220> FEATURE:
<223> OTHER INFORMATION: synthetic

<400> SEQUENCE: 433
gaaattgtgt tgacgcagtc tccagacacc ctgtctttgt ctccagggga aagagccacc       60
ctctcctgca gggccagtca gactgttagc aacagccact tagcctggta ccagcagaaa      120
cctggccagg ctcccaggct cctcatctat ggtacatcca gcagggccac tggcatccca      180
gacaggttca gtggcagtgg gtctgggacc gacttctctc tcaccatcat cagactggag      240
cctgacgatt ttgcagtata tttctgtcag cagcatgaaa gttcacctcc cacttttggc      300 caggggggcca agctcgagat caaa                                             324

<210> SEQ ID NO 434
<211> LENGTH: 108
<212> TYPE: PRT
<213> ORGANISM: Artificial Sequence
<220> FEATURE:
<223> OTHER INFORMATION: synthetic

<400> SEQUENCE: 434

Glu Ile Val Leu Thr Gln Ser Pro Asp Thr Leu Ser Leu Ser Pro Gly
1               5                   10                  15

Glu Arg Ala Thr Leu Ser Cys Arg Ala Ser Gln Thr Val Ser Asn Ser
            20                  25                  30

His Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
    50                  55                  60

Gly Ser Gly Ser Gly Thr Asp Phe Ser Leu Thr Ile Ile Arg Leu Glu
65                  70                  75                  80

Pro Asp Asp Phe Ala Val Tyr Phe Cys Gln Gln His Glu Ser Ser Pro
                85                  90                  95
```

```
Pro Thr Phe Gly Gln Gly Ala Lys Leu Glu Ile Lys
            100                 105
```

<210> SEQ ID NO 435
<211> LENGTH: 21
<212> TYPE: DNA
<213> ORGANISM: Artificial Sequence
<220> FEATURE:
<223> OTHER INFORMATION: synthetic

<400> SEQUENCE: 435
cagactgtta gcaacagcca c                                    21

<210> SEQ ID NO 436
<211> LENGTH: 7
<212> TYPE: PRT
<213> ORGANISM: Artificial Sequence
<220> FEATURE:
<223> OTHER INFORMATION: synthetic

<400> SEQUENCE: 436

```
Gln Thr Val Ser Asn Ser His
1               5
```

<210> SEQ ID NO 437
<211> LENGTH: 9
<212> TYPE: DNA
<213> ORGANISM: Artificial Sequence
<220> FEATURE:
<223> OTHER INFORMATION: synthetic

<400> SEQUENCE: 437 ggtacatcc                                                   9

<210> SEQ ID NO 438
<211> LENGTH: 3
<212> TYPE: PRT
<213> ORGANISM: Artificial Sequence
<220> FEATURE:
<223> OTHER INFORMATION: synthetic

<400> SEQUENCE: 438

```
Gly Thr Ser
1
```

<210> SEQ ID NO 439
<211> LENGTH: 27
<212> TYPE: DNA
<213> ORGANISM: Artificial Sequence
<220> FEATURE:
<223> OTHER INFORMATION: synthetic

<400> SEQUENCE: 439
cagcagcatg aaagttcacc tcccact                               27

<210> SEQ ID NO 440
<211> LENGTH: 9
<212> TYPE: PRT
<213> ORGANISM: Artificial Sequence
<220> FEATURE:
<223> OTHER INFORMATION: synthetic

<400> SEQUENCE: 440

```
Gln Gln His Glu Ser Ser Pro Pro Thr
1               5
```

<210> SEQ ID NO 441
<211> LENGTH: 363
<212> TYPE: DNA
<213> ORGANISM: Artificial Sequence
<220> FEATURE:
<223> OTHER INFORMATION: synthetic

<400> SEQUENCE: 441

```
caggtgcagc tggtggagtc tgggggaggc gtggtccagc ctggagggtc cctgagactc      60
tcctgtgcag cctctggaat caccttcagt agctatggca tgcactgggt ccgccaggct     120
ccaggcaagg ggctggagtg ggtggcactc acatcatatg atggaagtaa aaaatactat     180
tcagactccg tgaagggccg attcaccatc tccagagaca attccaagaa cacgctgtat     240
ctgcaaatga acagtctgag acctgaggac acggctgtgt attactgtgc gaaagataaa     300
gggggagacg actactacgg tatggacgtc tggggccaag gaccacggt caccgtctcc     360 tca                                                                   363
```

<210> SEQ ID NO 442
<211> LENGTH: 121
<212> TYPE: PRT
<213> ORGANISM: Artificial Sequence
<220> FEATURE:
<223> OTHER INFORMATION: synthetic

<400> SEQUENCE: 442

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Ile Thr Phe Ser Ser Tyr
             20                  25                  30

Gly Met His Trp Val Arg Gln Ala Pro Gly Lys Gly Leu Glu Trp Val
         35                  40                  45

Ala Leu Thr Ser Tyr Asp Gly Ser Lys Lys Tyr Tyr Ser Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Lys Asp Lys Gly Gly Asp Asp Tyr Tyr Gly Met Asp Val Trp Gly
            100                 105                 110

Gln Gly Thr Thr Val Thr Val Ser Ser
        115                 120
```

<210> SEQ ID NO 443
<211> LENGTH: 24
<212> TYPE: DNA
<213> ORGANISM: Artificial Sequence
<220> FEATURE:
<223> OTHER INFORMATION: synthetic

<400> SEQUENCE: 443

```
ggaatcacct tcagtagcta tggc                                             24
```

<210> SEQ ID NO 444
<211> LENGTH: 8
<212> TYPE: PRT
<213> ORGANISM: Artificial Sequence
<220> FEATURE:
<223> OTHER INFORMATION: synthetic

<400> SEQUENCE: 444

Gly Ile Thr Phe Ser Ser Tyr Gly
1               5

<210> SEQ ID NO 445
<211> LENGTH: 24
<212> TYPE: DNA
<213> ORGANISM: Artificial Sequence
<220> FEATURE:
<223> OTHER INFORMATION: synthetic

<400> SEQUENCE: 445
acatcatatg atggaagtaa aaaa                                              24

<210> SEQ ID NO 446
<211> LENGTH: 8
<212> TYPE: PRT
<213> ORGANISM: Artificial Sequence
<220> FEATURE:
<223> OTHER INFORMATION: synthetic

<400> SEQUENCE: 446

Thr Ser Tyr Asp Gly Ser Lys Lys
1               5

<210> SEQ ID NO 447
<211> LENGTH: 42
<212> TYPE: DNA
<213> ORGANISM: Artificial Sequence
<220> FEATURE:
<223> OTHER INFORMATION: synthetic

<400> SEQUENCE: 447
gcgaaagata aggggggaga cgactactac ggtatggacg tc                          42

<210> SEQ ID NO 448
<211> LENGTH: 14
<212> TYPE: PRT
<213> ORGANISM: Artificial Sequence
<220> FEATURE:
<223> OTHER INFORMATION: synthetic

<400> SEQUENCE: 448

Ala Lys Asp Lys Gly Gly Asp Asp Tyr Tyr Gly Met Asp Val
1               5                   10

<210> SEQ ID NO 449
<211> LENGTH: 324
<212> TYPE: DNA
<213> ORGANISM: Artificial Sequence
<220> FEATURE:
<223> OTHER INFORMATION: synthetic

<400> SEQUENCE: 449
gaaattgtgt tgacgcagtc tccaggcacc ctgtctttgt ctccagggga aagagccacc       60
ctctcctgca gggccagtca gtggattagc agcagctact tagcctggta ccagcagaaa      120
cctggccagg ctcccaggct cctcatctat ggtgctttca gcagggcccc tggcatccca      180
ggcaggttca gtggcagtgg gtctgggaca gacttcactc tcaccatcag cagactggag      240
cctgaagatt ttgcagtgta ttactgtcag cagtatggta gttcaccgta cacttttggc      300
caggggacca agctggagat caat                                             324

<210> SEQ ID NO 450
<211> LENGTH: 108

```
<212> TYPE: PRT
<213> ORGANISM: Artificial Sequence
<220> FEATURE:
<223> OTHER INFORMATION: synthetic

<400> SEQUENCE: 450

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Trp Ile Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Pro Gly Ile Pro Gly Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Asn
            100                 105

<210> SEQ ID NO 451
<211> LENGTH: 21
<212> TYPE: DNA
<213> ORGANISM: Artificial Sequence
<220> FEATURE:
<223> OTHER INFORMATION: synthetic

<400> SEQUENCE: 451
cagtggatta gcagcagcta c                                        21

<210> SEQ ID NO 452
<211> LENGTH: 7
<212> TYPE: PRT
<213> ORGANISM: Artificial Sequence
<220> FEATURE:
<223> OTHER INFORMATION: synthetic

<400> SEQUENCE: 452

Gln Trp Ile Ser Ser Ser Tyr
1               5

<210> SEQ ID NO 453
<211> LENGTH: 9
<212> TYPE: DNA
<213> ORGANISM: Artificial Sequence
<220> FEATURE:
<223> OTHER INFORMATION: synthetic

<400> SEQUENCE: 453 ggtgctttc                                                       9

<210> SEQ ID NO 454
<211> LENGTH: 3
<212> TYPE: PRT
<213> ORGANISM: Artificial Sequence
<220> FEATURE:
<223> OTHER INFORMATION: synthetic

<400> SEQUENCE: 454

Gly Ala Phe
1
```

```
<210> SEQ ID NO 455
<211> LENGTH: 27
<212> TYPE: DNA
<213> ORGANISM: Artificial Sequence
<220> FEATURE:
<223> OTHER INFORMATION: synthetic

<400> SEQUENCE: 455
cagcagtatg gtagttcacc gtacact                                         27

<210> SEQ ID NO 456
<211> LENGTH: 9
<212> TYPE: PRT
<213> ORGANISM: Artificial Sequence
<220> FEATURE:
<223> OTHER INFORMATION: synthetic

<400> SEQUENCE: 456

Gln Gln Tyr Gly Ser Ser Pro Tyr Thr
1               5

<210> SEQ ID NO 457
<211> LENGTH: 366
<212> TYPE: DNA
<213> ORGANISM: Artificial Sequence
<220> FEATURE:
<223> OTHER INFORMATION: synthetic

<400> SEQUENCE: 457
caggttcaac tggtgcagtc tggagctgag gtgaagaagc ctggggcctc agtgaaggtc     60
tcctgtaaga cttctggtta cacctttacc aacaatggta tcagctgggt gcgacaggtc    120
cctggacaag gcttgagtg gatgggatgg atcagccctt ataatggtaa tacaaagtat    180
gcacagaagt tccagggcag agtcaccatg accacagaca tcgacgac tacagtctac     240 atggacgtga ggagcctgag atctgacgac acggccgttt atttctgtgc gagagatggg   300
cccattacga tctcctactt cggtatggac gtctggggcc aagggaccac ggtcaccgtc   360
tcctca                                                              366

<210> SEQ ID NO 458
<211> LENGTH: 122
<212> TYPE: PRT
<213> ORGANISM: Artificial Sequence
<220> FEATURE:
<223> OTHER INFORMATION: synthetic

<400> SEQUENCE: 458

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Asn Asn
            20                  25                  30

Gly Ile Ser Trp Val Arg Gln Val Pro Gly Gln Gly Leu Glu Trp Met
        35                  40                  45

Gly Trp Ile Ser Pro Tyr Asn Gly Asn Thr Lys Tyr Ala Gln Lys Phe
    50                  55                  60

Gln Gly Arg Val Thr Met Thr Thr Asp Thr Ser Thr Thr Val Tyr
65                  70                  75                  80

Met Asp Val Arg Ser Leu Arg Ser Asp Asp Thr Ala Val Tyr Phe Cys
                85                  90                  95

Ala Arg Asp Gly Pro Ile Thr Ile Ser Tyr Phe Gly Met Asp Val Trp
            100                 105                 110
```

Gly Gln Gly Thr Thr Val Thr Val Ser Ser
        115                 120

<210> SEQ ID NO 459
<211> LENGTH: 24
<212> TYPE: DNA
<213> ORGANISM: Artificial Sequence
<220> FEATURE:
<223> OTHER INFORMATION: synthetic

<400> SEQUENCE: 459 ggttacaccct ttaccaacaa tggt                                    24

<210> SEQ ID NO 460
<211> LENGTH: 8
<212> TYPE: PRT
<213> ORGANISM: Artificial Sequence
<220> FEATURE:
<223> OTHER INFORMATION: synthetic

<400> SEQUENCE: 460

Gly Tyr Thr Phe Thr Asn Asn Gly
1               5

<210> SEQ ID NO 461
<211> LENGTH: 24
<212> TYPE: DNA
<213> ORGANISM: Artificial Sequence
<220> FEATURE:
<223> OTHER INFORMATION: synthetic

<400> SEQUENCE: 461 atcagcccctt ataatggtaa taca                                    24

<210> SEQ ID NO 462
<211> LENGTH: 8
<212> TYPE: PRT
<213> ORGANISM: Artificial Sequence
<220> FEATURE:
<223> OTHER INFORMATION: synthetic

<400> SEQUENCE: 462

Ile Ser Pro Tyr Asn Gly Asn Thr
1               5

<210> SEQ ID NO 463
<211> LENGTH: 45
<212> TYPE: DNA
<213> ORGANISM: Artificial Sequence
<220> FEATURE:
<223> OTHER INFORMATION: synthetic

<400> SEQUENCE: 463
gcgagagatg ggcccattac gatctcctac ttcggtatgg acgtc              45

<210> SEQ ID NO 464
<211> LENGTH: 15
<212> TYPE: PRT
<213> ORGANISM: Artificial Sequence
<220> FEATURE:
<223> OTHER INFORMATION: synthetic

<400> SEQUENCE: 464

Ala Arg Asp Gly Pro Ile Thr Ile Ser Tyr Phe Gly Met Asp Val
1               5                   10                  15

<210> SEQ ID NO 465
<211> LENGTH: 324
<212> TYPE: DNA
<213> ORGANISM: Artificial Sequence
<220> FEATURE:
<223> OTHER INFORMATION: synthetic

<400> SEQUENCE: 465

```
gacatccaga tgacccagtc tccgtcctcc ctgtctgcat ctgtaggaga cagagtcacc    60
atcacttgcc gggcaagtca gagtattagc acctatttaa attggtatca gcagaaacca   120
gggaaagccc ctaaactcct gatctatgct gcatccactt tgcaaagtgg ggtcccatca   180
aggttcggtg cagtggatc tgggacagac ttcactctca ccgtcagcag tctgcaacct   240
gaagattttg caacttacta ctgtcaacag agttacagta cccctccgat caccttcggc   300
caagggacac gactggagat taat                                         324
```

<210> SEQ ID NO 466
<211> LENGTH: 108
<212> TYPE: PRT
<213> ORGANISM: Artificial Sequence
<220> FEATURE:
<223> OTHER INFORMATION: synthetic

<400> SEQUENCE: 466

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Gly Gly
    50                  55                  60

Ser Gly Ser Gly Thr Asp Phe Thr Leu Thr Val Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Asn
            100                 105

<210> SEQ ID NO 467
<211> LENGTH: 18
<212> TYPE: DNA
<213> ORGANISM: Artificial Sequence
<220> FEATURE:
<223> OTHER INFORMATION: synthetic

<400> SEQUENCE: 467

```
cagagtatta gcacctat                                                 18
```

<210> SEQ ID NO 468
<211> LENGTH: 6
<212> TYPE: PRT
<213> ORGANISM: Artificial Sequence
<220> FEATURE:
<223> OTHER INFORMATION: synthetic

<400> SEQUENCE: 468

Gln Ser Ile Ser Thr Tyr
1               5

<210> SEQ ID NO 469

-continued

<211> LENGTH: 9
<212> TYPE: DNA
<213> ORGANISM: Artificial Sequence
<220> FEATURE:
<223> OTHER INFORMATION: synthetic

<400> SEQUENCE: 469 gctgcatcc                                                                9

<210> SEQ ID NO 470
<211> LENGTH: 3
<212> TYPE: PRT
<213> ORGANISM: Artificial Sequence
<220> FEATURE:
<223> OTHER INFORMATION: synthetic

<400> SEQUENCE: 470

Ala Ala Ser
1

<210> SEQ ID NO 471
<211> LENGTH: 30
<212> TYPE: DNA
<213> ORGANISM: Artificial Sequence
<220> FEATURE:
<223> OTHER INFORMATION: synthetic

<400> SEQUENCE: 471
caacagagtt acagtacccc tccgatcacc                                         30

<210> SEQ ID NO 472
<211> LENGTH: 10
<212> TYPE: PRT
<213> ORGANISM: Artificial Sequence
<220> FEATURE:
<223> OTHER INFORMATION: synthetic

<400> SEQUENCE: 472

Gln Gln Ser Tyr Ser Thr Pro Pro Ile Thr
1               5                   10

<210> SEQ ID NO 473
<211> LENGTH: 354
<212> TYPE: DNA
<213> ORGANISM: Artificial Sequence
<220> FEATURE:
<223> OTHER INFORMATION: synthetic

<400> SEQUENCE: 473
caggtacaac tggtggagtc tggggggaggc gtggtccagc ctggggaggtc cctgagactc       60 tcctgtgcag cgtctggatt caccgtcaat agatatggca tacactgggt ccgccaggct       120
ccaggcaagg ggctggagtg ggtggcagtt acatgtatg atggaagaaa taaatacttt       180
gccgactccg tgaagggccg attctccttc tccagagaca gttccacgaa cacgttgtat       240
ctgcaaatga acagtctgag agccgaggac acggctgtat attactgtgc gagggggga       300 ttgtttggat actttgacta ctggggccag ggaaccctgg tcaccgtctc ctca            354

<210> SEQ ID NO 474
<211> LENGTH: 118
<212> TYPE: PRT
<213> ORGANISM: Artificial Sequence
<220> FEATURE:
<223> OTHER INFORMATION: synthetic

<400> SEQUENCE: 474

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Val Asn Arg Tyr
                20                  25                  30

Gly Ile His Trp Val Arg Gln Ala Pro Gly Lys Gly Leu Glu Trp Val
            35                  40                  45

Ala Val Thr Trp Tyr Asp Gly Arg Asn Lys Tyr Phe Ala Asp Ser Val
        50                  55                  60

Lys Gly Arg Phe Ser Phe Ser Arg Asp Ser Ser Thr Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Phe Gly Tyr Phe Asp Tyr Trp Gly Gln Gly Thr
            100                 105                 110

Leu Val Thr Val Ser Ser
            115

<210> SEQ ID NO 475
<211> LENGTH: 24
<212> TYPE: DNA
<213> ORGANISM: Artificial Sequence
<220> FEATURE:
<223> OTHER INFORMATION: synthetic

<400> SEQUENCE: 475
ggattcaccg tcaatagata tggc                                        24

<210> SEQ ID NO 476
<211> LENGTH: 8
<212> TYPE: PRT
<213> ORGANISM: Artificial Sequence
<220> FEATURE:
<223> OTHER INFORMATION: synthetic

<400> SEQUENCE: 476

Gly Phe Thr Val Asn Arg Tyr Gly
1               5

<210> SEQ ID NO 477
<211> LENGTH: 24
<212> TYPE: DNA
<213> ORGANISM: Artificial Sequence
<220> FEATURE:
<223> OTHER INFORMATION: synthetic

<400> SEQUENCE: 477
acatggtatg atggaagaaa taaa                                        24

<210> SEQ ID NO 478
<211> LENGTH: 8
<212> TYPE: PRT
<213> ORGANISM: Artificial Sequence
<220> FEATURE:
<223> OTHER INFORMATION: synthetic

<400> SEQUENCE: 478

Thr Trp Tyr Asp Gly Arg Asn Lys
1               5

<210> SEQ ID NO 479
<211> LENGTH: 33
<212> TYPE: DNA

<213> ORGANISM: Artificial Sequence
<220> FEATURE:
<223> OTHER INFORMATION: synthetic

<400> SEQUENCE: 479

```
gcgaggggggg gattgtttgg atactttgac tac                        33
```

<210> SEQ ID NO 480
<211> LENGTH: 11
<212> TYPE: PRT
<213> ORGANISM: Artificial Sequence
<220> FEATURE:
<223> OTHER INFORMATION: synthetic

<400> SEQUENCE: 480

```
Ala Arg Gly Gly Leu Phe Gly Tyr Phe Asp Tyr
1               5                   10
```

<210> SEQ ID NO 481
<211> LENGTH: 324
<212> TYPE: DNA
<213> ORGANISM: Artificial Sequence
<220> FEATURE:
<223> OTHER INFORMATION: synthetic

<400> SEQUENCE: 481

```
gaaattgtgt tgacgcagtc tccagacacc ctgtctttgt ctccagggga aagagccacc    60
ctctcctgca gggccagtca gagtgttgcc ggcagctact tagcctggta ccagcagaaa   120
cctggccagg ctcccagact cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta cctcaccttg gacgttcggc   300
caggggacca aggtggaaat caca                                          324
```

<210> SEQ ID NO 482
<211> LENGTH: 108
<212> TYPE: PRT
<213> ORGANISM: Artificial Sequence
<220> FEATURE:
<223> OTHER INFORMATION: synthetic

<400> SEQUENCE: 482

```
Glu Ile Val Leu Thr Gln Ser Pro Asp Thr Leu Ser Leu Ser Pro Gly
1               5                   10                  15

Glu Arg Ala Thr Leu Ser Cys Arg Ala Ser Gln Ser Val Ala Gly Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Pro
                85                  90                  95

Trp Thr Phe Gly Gln Gly Thr Lys Val Glu Ile Thr
            100                 105
```

<210> SEQ ID NO 483
<211> LENGTH: 21
<212> TYPE: DNA
<213> ORGANISM: Artificial Sequence
<220> FEATURE:
<223> OTHER INFORMATION: synthetic

<400> SEQUENCE: 483
cagagtgttg ccggcagcta c                                    21

<210> SEQ ID NO 484
<211> LENGTH: 7
<212> TYPE: PRT
<213> ORGANISM: Artificial Sequence
<220> FEATURE:
<223> OTHER INFORMATION: synthetic

<400> SEQUENCE: 484

Gln Ser Val Ala Gly Ser Tyr
1               5

<210> SEQ ID NO 485
<211> LENGTH: 9
<212> TYPE: DNA
<213> ORGANISM: Artificial Sequence
<220> FEATURE:
<223> OTHER INFORMATION: synthetic

<400> SEQUENCE: 485 ggtgcatcc                                                   9

<210> SEQ ID NO 486
<211> LENGTH: 3
<212> TYPE: PRT
<213> ORGANISM: Artificial Sequence
<220> FEATURE:
<223> OTHER INFORMATION: synthetic

<400> SEQUENCE: 486

Gly Ala Ser
1

<210> SEQ ID NO 487
<211> LENGTH: 27
<212> TYPE: DNA
<213> ORGANISM: Artificial Sequence
<220> FEATURE:
<223> OTHER INFORMATION: synthetic

<400> SEQUENCE: 487
cagcagtatg gtacctcacc ttggacg                              27

<210> SEQ ID NO 488
<211> LENGTH: 9
<212> TYPE: PRT
<213> ORGANISM: Artificial Sequence
<220> FEATURE:
<223> OTHER INFORMATION: synthetic

<400> SEQUENCE: 488

Gln Gln Tyr Gly Thr Ser Pro Trp Thr
1               5

<210> SEQ ID NO 489
<211> LENGTH: 354
<212> TYPE: DNA
<213> ORGANISM: Artificial Sequence
<220> FEATURE:
<223> OTHER INFORMATION: synthetic

<400> SEQUENCE: 489

```
caggtgcagt tggtggagtc tgggggaggc gtggtccagc ctgggaggtc cctgagactc    60
tcctgtgcag cgtctggatt caccttcagt agctatggca tacactgggt ccgccaggct   120
ccaggcaagg ggctggagtg ggtggcagtt atatggtatg gtggaaataa taaatactat   180
gcagactccg tgaagggccg attcaccatc tccagagaca attccaagaa cacgctgtat   240
ctgcaaatga acagcctgag agccgaggac acggctttat atcactgtgc gagaagtggg   300
aacttcggtg cttttgatat ctggggccaa gggacaatgg tcaccgtctc ttca         354
```

<210> SEQ ID NO 490
<211> LENGTH: 118
<212> TYPE: PRT
<213> ORGANISM: Artificial Sequence
<220> FEATURE:
<223> OTHER INFORMATION: synthetic

<400> SEQUENCE: 490

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Ile His Trp Val Arg Gln Ala Pro Gly Lys Gly Leu Glu Trp Val
        35                  40                  45

Ala Val Ile Trp Tyr Gly Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr His Cys
                85                  90                  95

Ala Arg Ser Gly Asn Phe Gly Ala Phe Asp Ile Trp Gly Gln Gly Thr
            100                 105                 110

Met Val Thr Val Ser Ser
        115
```

<210> SEQ ID NO 491
<211> LENGTH: 24
<212> TYPE: DNA
<213> ORGANISM: Artificial Sequence
<220> FEATURE:
<223> OTHER INFORMATION: synthetic

<400> SEQUENCE: 491

```
ggattcacct tcagtagcta tggc                                           24
```

<210> SEQ ID NO 492
<211> LENGTH: 8
<212> TYPE: PRT
<213> ORGANISM: Artificial Sequence
<220> FEATURE:
<223> OTHER INFORMATION: synthetic

<400> SEQUENCE: 492

```
Gly Phe Thr Phe Ser Ser Tyr Gly
1               5
```

<210> SEQ ID NO 493
<211> LENGTH: 24
<212> TYPE: DNA
<213> ORGANISM: Artificial Sequence
<220> FEATURE:
<223> OTHER INFORMATION: synthetic

<400> SEQUENCE: 493
atatggtatg gtggaaataa taaa 24

<210> SEQ ID NO 494
<211> LENGTH: 8
<212> TYPE: PRT
<213> ORGANISM: Artificial Sequence
<220> FEATURE:
<223> OTHER INFORMATION: synthetic

<400> SEQUENCE: 494

Ile Trp Tyr Gly Gly Asn Asn Lys
1               5

<210> SEQ ID NO 495
<211> LENGTH: 33
<212> TYPE: DNA
<213> ORGANISM: Artificial Sequence
<220> FEATURE:
<223> OTHER INFORMATION: synthetic

<400> SEQUENCE: 495
gcgagaagtg ggaacttcgg tgcttttgat atc 33

<210> SEQ ID NO 496
<211> LENGTH: 11
<212> TYPE: PRT
<213> ORGANISM: Artificial Sequence
<220> FEATURE:
<223> OTHER INFORMATION: synthetic

<400> SEQUENCE: 496

Ala Arg Ser Gly Asn Phe Gly Ala Phe Asp Ile
1               5                   10

<210> SEQ ID NO 497
<211> LENGTH: 321
<212> TYPE: DNA
<213> ORGANISM: Artificial Sequence
<220> FEATURE:
<223> OTHER INFORMATION: synthetic

<400> SEQUENCE: 497
gaaattgtgt tgacgcagtc tccaggcacc ctgtctttgt ctccagggga aagagccacc     60
ctctcctgca gggccagtca gagtgttagc agctacttag cctggtacca gcagaaacct    120
ggccaggctc ccaggctcct catctatggt gcatccagca gggccactgg catcccagac    180
aggttcagtg gcagtgggtc tgggacagac ttcattctca ccatcaacag actggagcct    240
gaagattttg cagtctatta ctgtcagcac tatggtaact caccttggac gttcggccaa    300
gggaccaagg tggaaatcaa a                                              321

<210> SEQ ID NO 498
<211> LENGTH: 107
<212> TYPE: PRT
<213> ORGANISM: Artificial Sequence
<220> FEATURE:
<223> OTHER INFORMATION: synthetic

<400> SEQUENCE: 498

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr

```
                    20                  25                  30
Leu Ala Trp Tyr Gln Gln Lys Pro Gly Gln Ala Pro Arg Leu Leu Ile
            35                  40                  45

Tyr Gly Ala Ser Ser Arg Ala Thr Gly Ile Pro Asp Arg Phe Ser Gly
    50                  55                  60

Ser Gly Ser Gly Thr Asp Phe Ile Leu Thr Ile Asn Arg Leu Glu Pro
65                  70                  75                  80

Glu Asp Phe Ala Val Tyr Tyr Cys Gln His Tyr Gly Asn Ser Pro Trp
                85                  90                  95

Thr Phe Gly Gln Gly Thr Lys Val Glu Ile Lys
            100                 105
```

<210> SEQ ID NO 499
<211> LENGTH: 18
<212> TYPE: DNA
<213> ORGANISM: Artificial Sequence
<220> FEATURE:
<223> OTHER INFORMATION: synthetic

<400> SEQUENCE: 499
cagagtgtta gcagctac                                                 18

<210> SEQ ID NO 500
<211> LENGTH: 6
<212> TYPE: PRT
<213> ORGANISM: Artificial Sequence
<220> FEATURE:
<223> OTHER INFORMATION: synthetic

<400> SEQUENCE: 500

```
Gln Ser Val Ser Ser Tyr
1               5
```

<210> SEQ ID NO 501
<211> LENGTH: 9
<212> TYPE: DNA
<213> ORGANISM: Artificial Sequence
<220> FEATURE:
<223> OTHER INFORMATION: synthetic

<400> SEQUENCE: 501 ggtgcatcc                                                            9

<210> SEQ ID NO 502
<211> LENGTH: 3
<212> TYPE: PRT
<213> ORGANISM: Artificial Sequence
<220> FEATURE:
<223> OTHER INFORMATION: synthetic

<400> SEQUENCE: 502

```
Gly Ala Ser
1
```

<210> SEQ ID NO 503
<211> LENGTH: 27
<212> TYPE: DNA
<213> ORGANISM: Artificial Sequence
<220> FEATURE:
<223> OTHER INFORMATION: synthetic

<400> SEQUENCE: 503
cagcactatg gtaactcacc ttggacg                                       27

```
<210> SEQ ID NO 504
<211> LENGTH: 9
<212> TYPE: PRT
<213> ORGANISM: Artificial Sequence
<220> FEATURE:
<223> OTHER INFORMATION: synthetic

<400> SEQUENCE: 504

Gln His Tyr Gly Asn Ser Pro Trp Thr
1               5

<210> SEQ ID NO 505
<211> LENGTH: 223
<212> TYPE: PRT
<213> ORGANISM: Artificial Sequence
<220> FEATURE:
<223> OTHER INFORMATION: hCTLA-4 NP_005205.2

<400> SEQUENCE: 505

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220

<210> SEQ ID NO 506
<211> LENGTH: 154
<212> TYPE: PRT
<213> ORGANISM: Artificial Sequence
<220> FEATURE:
<223> OTHER INFORMATION: hCTLA-4-mmH (aa K36-D161 of NP_005205.2 with
      C-terminal myc-myc-hexahistidine tag)

<400> SEQUENCE: 506

Lys Ala Met His Val Ala Gln Pro Ala Val Val Leu Ala Ser Ser Arg
1               5                   10                  15
```

```
Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu Pro Cys Pro Asp Ser Asp Glu Gln
        115                 120                 125

Lys Leu Ile Ser Glu Glu Asp Leu Gly Gly Glu Gln Lys Leu Ile Ser
    130                 135                 140

Glu Glu Asp Leu His His His His His His
145                 150
```

<210> SEQ ID NO 507
<211> LENGTH: 154
<212> TYPE: PRT
<213> ORGANISM: Artificial Sequence
<220> FEATURE:
<223> OTHER INFORMATION: MfCTLA-4-mmH (aa K36-D161 of XP_005574071.1
      with C-terminal myc-myc-hexahistidine tag)

<400> SEQUENCE: 507

```
Lys Ala Met His Val Ala Gln Pro Ala Val Val Leu Ala Asn Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Met Gly Ile Gly Asn Gly Thr
            100                 105                 110

Gln Ile Tyr Val Ile Asp Pro Glu Pro Cys Pro Asp Ser Asp Glu Gln
        115                 120                 125

Lys Leu Ile Ser Glu Glu Asp Leu Gly Gly Glu Gln Lys Leu Ile Ser
    130                 135                 140

Glu Glu Asp Leu His His His His His His
145                 150
```

<210> SEQ ID NO 508
<211> LENGTH: 359
<212> TYPE: PRT
<213> ORGANISM: Artificial Sequence
<220> FEATURE:
<223> OTHER INFORMATION: hCTLA-4-mFc
      dimeric hCTLA-4 ectodomain (aa K36-D161 of
      NP_005205.2) with C-terminal mouse Fcgamma domain
      (aa E98-K330 of P01863)

<400> SEQUENCE: 508

```
Lys Ala Met His Val Ala Gln Pro Ala Val Leu Ala Ser Ser Arg
1               5                   10                  15

Gly Ile Ala Ser Phe Val Cys Glu Tyr Ala Ser Pro Gly Lys Ala Thr
                20                  25                  30

Glu Val Arg Val Thr Val Leu Arg Gln Ala Asp Ser Gln Val Thr Glu
            35                  40                  45

Val Cys Ala Ala Thr Tyr Met Met Gly Asn Glu Leu Thr Phe Leu Asp
        50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Leu Gly Ile Gly Asn Gly Thr
                100                 105                 110

Gln Ile Tyr Val Ile Asp Pro Glu Pro Cys Pro Asp Ser Asp Glu Pro
            115                 120                 125

Arg Gly Pro Thr Ile Lys Pro Cys Pro Pro Cys Lys Cys Pro Ala Pro
130                 135                 140

Asn Leu Leu Gly Gly Pro Ser Val Phe Ile Phe Pro Pro Lys Ile Lys
145                 150                 155                 160

Asp Val Leu Met Ile Ser Leu Ser Pro Ile Val Thr Cys Val Val Val
                165                 170                 175

Asp Val Ser Glu Asp Asp Pro Asp Val Gln Ile Ser Trp Phe Val Asn
            180                 185                 190

Asn Val Glu Val His Thr Ala Gln Thr Gln Thr His Arg Glu Asp Tyr
        195                 200                 205

Asn Ser Thr Leu Arg Val Val Ser Ala Leu Pro Ile Gln His Gln Asp
    210                 215                 220

Trp Met Ser Gly Lys Glu Phe Lys Cys Lys Val Asn Asn Lys Asp Leu
225                 230                 235                 240

Pro Ala Pro Ile Glu Arg Thr Ile Ser Lys Pro Lys Gly Ser Val Arg
                245                 250                 255

Ala Pro Gln Val Tyr Val Leu Pro Pro Pro Glu Glu Glu Met Thr Lys
            260                 265                 270

Lys Gln Val Thr Leu Thr Cys Met Val Thr Asp Phe Met Pro Glu Asp
        275                 280                 285

Ile Tyr Val Glu Trp Thr Asn Asn Gly Lys Thr Glu Leu Asn Tyr Lys
    290                 295                 300

Asn Thr Glu Pro Val Leu Asp Ser Asp Gly Ser Tyr Phe Met Tyr Ser
305                 310                 315                 320

Lys Leu Arg Val Glu Lys Lys Asn Trp Val Arg Asn Ser Tyr Ser
                325                 330                 335

Cys Ser Val Val His Glu Gly Leu His Asn His His Thr Thr Lys Ser
            340                 345                 350

Phe Ser Arg Thr Pro Gly Lys
        355
```

<210> SEQ ID NO 509
<211> LENGTH: 446
<212> TYPE: PRT
<213> ORGANISM: Artificial Sequence
<220> FEATURE:
<223> OTHER INFORMATION: R4659: HC

```
<400> SEQUENCE: 509

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Glu Met Ser Trp Val Arg Gln Ala Pro Gly Lys Gly Leu Glu Trp Val
        35                  40                  45

Ser Ser Ile Arg Thr Ser Gly Thr Thr Lys Tyr Tyr Ala Asp Ser Met
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Gly Gly Gly Thr Phe Leu His Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415
```

```
Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 510
<211> LENGTH: 215
<212> TYPE: PRT
<213> ORGANISM: Artificial Sequence
<220> FEATURE:
<223> OTHER INFORMATION: R4659: LC

<400> SEQUENCE: 510

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ala Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Thr Gly Val Pro Ser Arg Phe Ser Gly
50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Ala Lys Ser Phe Pro Met
                85                  90                  95

Tyr Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```